US007829673B2

(12) United States Patent
De Weers et al.

(10) Patent No.: US 7,829,673 B2
(45) Date of Patent: Nov. 9, 2010

(54) ANTIBODIES AGAINST CD38 FOR TREATMENT OF MULTIPLE MYELOMA

(75) Inventors: Michel De Weers, Houten (NL); Yvo Graus, Odijk (NL); Judith Oprins, Bunnik (NL); Paul Parren, Odijk (NL); Jan Van De Winkel, Zeist (NL); Martine Van Vugt, Houten (NL)

(73) Assignee: Genmab A/S, Copenhagen (DK)

( * ) Notice: Subject to any disclaimer, the term of this patent is extended or adjusted under 35 U.S.C. 154(b) by 157 days.

(21) Appl. No.: 11/886,932

(22) PCT Filed: Mar. 23, 2006

(86) PCT No.: PCT/DK2006/000166

§ 371 (c)(1),
(2), (4) Date: Sep. 21, 2007

(87) PCT Pub. No.: WO2006/099875

PCT Pub. Date: Sep. 28, 2006

(65) Prior Publication Data

US 2009/0148449 A1 Jun. 11, 2009

Related U.S. Application Data

(60) Provisional application No. 60/667,579, filed on Apr. 1, 2005, provisional application No. 60/696,163, filed on Jul. 1, 2005, provisional application No. 60/728,561, filed on Oct. 20, 2005.

(30) Foreign Application Priority Data

Mar. 23, 2005 (DK) ............................... 2005 00429

(51) Int. Cl.
*C07K 16/00* (2006.01)
*C07K 17/00* (2006.01)
*C07K 17/14* (2006.01)
*C12P 21/08* (2006.01)
*A61K 39/395* (2006.01)
*A61K 39/00* (2006.01)

(52) U.S. Cl. .............. 530/387.1; 530/387.2; 530/387.9; 530/391.1; 424/130.1; 424/131.1; 424/139.1; 424/172.1; 424/178.1

(58) Field of Classification Search ........................ None
See application file for complete search history.

(56) References Cited

U.S. PATENT DOCUMENTS

| 2005/0037969 A1 | 2/2005 | Lu et al. |
| 2005/0266008 A1 | 12/2005 | Graziano et al. |
| 2006/0019303 A1 | 1/2006 | Castle et al. |

FOREIGN PATENT DOCUMENTS

| WO | WO-89/08114 A1 | 9/1989 |
| WO | WO-92/01049 A2 | 1/1992 |
| WO | WO-94/17184 A1 | 8/1994 |
| WO | WO-96/16990 A1 | 6/1996 |
| WO | WO-98/16245 A1 | 4/1998 |
| WO | WO-98/16254 A1 | 4/1998 |
| WO | WO-98/50435 A1 | 11/1998 |
| WO | WO-99/62526 A2 | 12/1999 |
| WO | WO-00/06194 A2 | 2/2000 |
| WO | WO-00/40265 A1 | 7/2000 |
| WO | WO-02/06347 A1 | 1/2002 |
| WO | WO-02/32288 A2 | 4/2002 |
| WO | WO 2004058288 A1 * | 7/2004 |
| WO | WO-2005/042019 A1 | 5/2005 |
| WO | WO-2005/044855 A2 | 5/2005 |
| WO | WO-2005/103083 A2 | 11/2005 |
| WO | WO-2006/088951 A2 | 8/2006 |
| WO | WO-2006/099875 A1 | 9/2006 |
| WO | WO-2006/125640 A2 | 11/2006 |

OTHER PUBLICATIONS

Aarhus, Robert et al., "ADP-ribusyl Cyclase and CD38 Catalyze the Synthesis of a Calcium-mobilizing Metabolite from NADP," *The Journal of Biological Chemistry*, vol. 270(51):30327-30333(1995).

Antonelli, Alessandro et al., "Human Anti-CD38 Autoantibodies Raise Intracellular Calcium and Stimulate Insulin Release in Human Pancreatic Islets," *Diabetes*, vol. 50:985-991 (2001).

Bolognesi, A. et al., "CD38 as a target of IB4 mAb carrying saporin-S6: Design of an immunotoxin for ex vivo depletion of hematological CD38+ neoplasia," *Journal of Biological Regulators and Homeostatic Agents*, vol. 19:145-152 (2005).

de Weers, M. et al., "Humax-CD38, a New Human CD38 Monoclonal Antibody, Effectively Mediates Killing of Multiple Myeloma and Plasma Cell Leukemia Cells," abstract, submitted for the 16th European Congress of Immunology—ECI2006. Sep. 6-9, 2006—Paris, France.

de Weers, M. et al., "HuMax-CD38, a new human CD38 monoclonal antibody, effectively mediates killing of multiple myeloma and plasma cell leukemia cells," Poster presented at the 1st Joint Meeting of European National Societies of Immunology under auspices of EFIS, Sep. 6-9, 2006.

de Weers, Michel, "HuMax-CD38," Presentation at the Regional Myeloma Group Meeting (2007).

Donovan, K.A. et al., "Binding and internalization of an antibody engineered ant-CD38 single chain variable fragment (scFv) by human myeloma cells," *Blood*, vol. 90(10):88A (1997).

(Continued)

*Primary Examiner*—Anne M. Gussow
(74) *Attorney, Agent, or Firm*—Lahive & Cockfield, LLP; Jane E. Remillard, Esq.; Jeanne M. DiGiorgio, Esq.

(57) ABSTRACT

Isolated human monoclonal antibodies which bind to human CD38, and related antibody-based compositions and molecules, are disclosed. Also disclosed are pharmaceutical compositions comprising the human antibodies, and therapeutic and diagnostic methods for using the human antibodies.

29 Claims, 34 Drawing Sheets

OTHER PUBLICATIONS

Funaro, Ada et al., "Involvement of the multilineage CD38 molecule in a unique pathway of cell activation and proliferation," *The Journal of Immunology*, vol. 145(8):2390-2396 (1990).

Funaro, Ada et al., "Human CD38: a versatile leukocyte molecule with emerging clinical perspectives," *Fundamental and Clinical Immunology*, vol. 3(3):101-113 (1995).

Funaro, Ada et al., "Identification and characterization of an active soluble form of human CD38 in normal and pathological fluids," *International Immunology*, vol. 8(11):1643-1650 (1996).

Funaro, Ada et al., "CD38 Functions Are Regulated Through an Internalization Step," *The Journal of Immunology*, vol. 160:2238-2247 (1998).

Genmab, "Humax-CD38 Effective in Preclinical Studies," retrieved online at http://findarticles.com/p/articles/mi_hb5570/is_200512/ai_n24200986 (2005).

Goldmacher, Victor S. et al., "Anti-CD38-Blocked Ricin: An Immunotoxin for the Treatment of Multiple Myeloma," Blood, vol. 84(9):3017-3025 (1994).

Hara-Yokoyama, Miki et al., "Alteration of enzymatic properties of cell-surface antigen CD38 by agonistic anti-CD38 antibodies that prolong B cell survival and induce activation," International Immunopharmacology, vol. 8:59-70 (2008).

Howard, Maureen et al., "Formation and Hydrolysis of Cyclic ADP-Ribose Catalyzed by Lymphocyte Antigen CD38," Science, vol. 262:1056-1059 (1993).

Jackson, David G. et al., "Isolation of a cDNA Encoding the Human CD38 (T10) Molecule, a Cell Surface Glycoprotein with an Unusual Discontinuous Pattern of Expression During Lymphocyte Differentiation," The Journal of Immunology, vol. 144(7):2811-2815 (1990).

Johnson, Malisha R. et al., "Primary plasma cell leukemia: morphologic immunophenotypic, and cytogenetic featues of 4 cases treated with chemotherapy and stem cell transplantation," Annals of Diagnostic Pathology, vol. 10:263-268 (2006).

Konopleva, Marina et al., "Ligation of Cell Surface CD38 Protein with Agonistic Monoclonal Antibody Induces a Cell Growth Signal in Myeloid Leukemia Cells," The Journal of Immunology, vol. 161:4702-4708 (1998).

Konopleva, Marina et al., "CD38 in Hematopoietic Malignancies," Human CD38 and Related Molecules.Chem Immunol., vol. 75:189-206 (2000).

Malavasi, Fabio et al., "Human CD38: a glycoprotein in search of a function," Immunology Today, vol. 15(3):95-97 (1994).

Maloney, David G. et al., "Antibody Therapy for Treatment of Multiple Myeloma," Seminars in Hematology, vol. 36(1 Suppl. 3):30-33 (1999).

Mills, Charity et al., "Characterization of Monoclonal Antibodies that Inhibit CD38 ADP-Ribosyl Cyclase Activity," Poster with abstract presented at a student conference at the University of Minnesota (2007).

Parren, P.W.H.I. et al., "HuMax-CD38, a new human CD38 monoclonal antibody, effectively mediates killing of multiple myeloma and plasma cell leukemia cells," PWHI Conference Proceeding, Presentation for the CD38 meeting in Torino, Jun. 8-10, 2006.

Parren, "HuMax-CD38," Conference Proceeding, Presentation for the 23rd International Conference on Advances in the Application of Monoclonal Antibodies in Clinical Oncology, Myconos, Greece (2006).

Parren, "HuMax-CD38," Conference Proceedings, Presentation for the CD38 metting in Torino (2006).

Peipp, M. et al., "Fully Human CD38 Antibodies Efficiently Trigger ADCC and CDC of Multiple Myeloma and Plasma Cell Leukemia Cells," Conference Proceedings, Poster Presentation at the 2005 Annual Meeting of the American Society of Hematology, Dec. 12, 2005.

Peipp, Matthias et al., AN PREV200600185745, "Fully human CD38 antibodies efficiently trigger ADCC of multiple myeloma cell lines and primary tumor cells," Blood, vol. 106(11):944A, 47th Annual Meeting of the American-Society-of-Hematology (2005).

Peng, Kah-Whye et al., "Oncolytic measles viruses displaying a single-chain antibody against CD38, a myeloma cell marker," Blood, vol. 101(7):2557-2562 (2003).

Stevenson, Freda K. et al., "Preliminary Studies for an Immunotherapeutic Approach to the Treatment of Human Myeloma Using Chimeric Anti-CD38 Antibody," Blood, vol. 77(5):1071-1079 (1991).

Stevenson, George T., "CD38 as a Therapeutic Target," Mol. Med., vol. 12(11-12):345-346 (2006).

Takasawa, Shin et al., "Synthesis and Hydrolysis of Cyclic ADP-Ribose by Human Leukocyte Antigen CD38 and Inhibition of the Hydrolysis by ATP," The Journal of Biological Chemistry, vol. 268(35):26052-26054 (1993).

Vooijs, W.C. et al., "Evaluation of CD38 as Target for Immunotherapy in Multiple Myeloma," Blood, vol. 85(8):2282-2284 (1995).

Yamashita, Y. et al., "A monoclonal antibody against a murine CD38 homologue delivers a signal to B cells for prolongation of survival and protection against apoptosis in vitro: unresponsiveness of X-linked immunodeficient B cells," Immunology, vol. 85:248-255 (1995).

Zocchi, Elena et al., "A Single Protein Immunologically Identified as CD38 Displays NAD+ Glycohydrolase, ADP-Ribosyl Cyclase and Cyclic ADP-Ribose Hydrolase Activities at the Outer Surface of Human Erythrocytes," Biochemical and Biophysical Research Communications, vol. 196(3):1459-1465 (1993).

International Search Report for Application No. PCT/DK2006/000166, dated Aug. 14, 2006.

Ausiello, C.M. et al., "Functional topography of discrete domains of human CD38," *Tissue Antigens*, vol. 56:539-547 (2000).

Ellis, Jonathan H. et al., "Engineered Anti-CD38 Monoclonal Antibodies for Immunotherapy of Multiple Myeloma," *The Journal of Immunology*, vol. 155:925-937 (1995).

Hoshino, Shin-ichi et al., "Mapping of the Catalytic and Epitopic Sites of Human CD38/$NAD^+$ Glycohydrolase to a Functional Domain in the Carboxyl Terminus," *The Journal of Immunology*, vol. 158:741-747 (1997).

Written Opinion for Application No. PCT/DK2006/000166, dated Sep. 25, 2007.

Burgess, Wilson H. et al., "Possible Dissociation of the Heparin-binding and Mitogenic Activities of Heparin-binding (Acidic Fibroblast Growth Factor-1 from Its Receptor-binding Activities by Site-directed Mutagenesis of a Single Lysine Residue," *The Journal of Cell Biology*, vol. 111:2129-2138 (1990).

Casset, Florence et al., "A peptide mimetic of an anti-CD4 monoclonal antibody by rational design," *Biochemical and Biophysical Research Communications*, vol. 307:198-205 (2003).

Chen, Yvonne et al., "Selection and Analysis of an Optimized Anti-VEGF Antibody: Crystal Structure of an Affinity-matured Fab in Complex with Antigen," *J. Mol. Biol.*, vol. 293:865-881 (1999).

Holm, Patrik et al., "Functional mapping and single chain construction of the anti-cytokeratin 8 monoclonal antibody TS1," *Molecular Immunology*, vol. 44:1075-1084 (2007).

Lazar, Eliane et al., "Transforming Growth Factor α: Mutation of Aspartic Acid 47 and Leucine 48 Results in Different Biological Activities," *Molecular and Cellular Biology*, vol. 8(3):1247-1252 (1988).

Lin, Michael C. et al., "Structure-Function Relationships in Glucagon: Properties of Highly Purified Des-His-, Monoiodo-, and [Des-$Asn^{28}$, $Thr^{29}$](homoserine $lactone^{27}$)-glucagon," *Biochemistry*, vol. 14(8):1559-1563 (1975).

Rudikoff, Stuart et al., "Single amino acid substitution altering antigen-binding specificity," Proc. Natl. Acad. Sci. USA, vol. 79:1979-1983 (1982).

Schwartz, Gerald P., "A superactive insulin: [B10-Aspartic acid]insulin(human)," Proc. Natl. Acad. Sci. USA, vol. 84:6408-6411 (1987).

Skolnick, Jeffrey et al., "From genes to protein structure and function: novel applications of computational approaches in the genomic era," *TIBTECH*, vol. 18:34-39 (2000).

Vajdos, Felix F. et al., "Comprehensive Functional Maps of the Antigen-binding Site of an Anti-ErbB2 Antibody Obtained with Shotgun Scanning Mutagenesis," *J. Mol. Biol.*, vol. 320:415-428 (2002).

Wu, Herren et al., "Humanization of a Murine Monoclonal Antibody by Simultaneous Optimization of Framework and CDR Residues," *J. Mol. Biol.*, vol. 294:151-162 (1999).

Davies, Julian et al., "Affinity improvement of single antibody VH domains: residues in all three hypervariable regions affect antigen binding," *Immunotechnology*, vol. 2:169-179 (1996).

Holt, Lucy J. et al., "Domain antibodies: proteins for therapy," *Trends in Biotechnology*, vol. 21(11):484-490 (2003).

U.S. Appl. No. 11/901,953, filed Sep. 19, 2007, Michel De Weers.

U.S. Appl. No. 11/901,953, filed Apr. 3, 2009.

* cited by examiner

FIGURE 1
A:
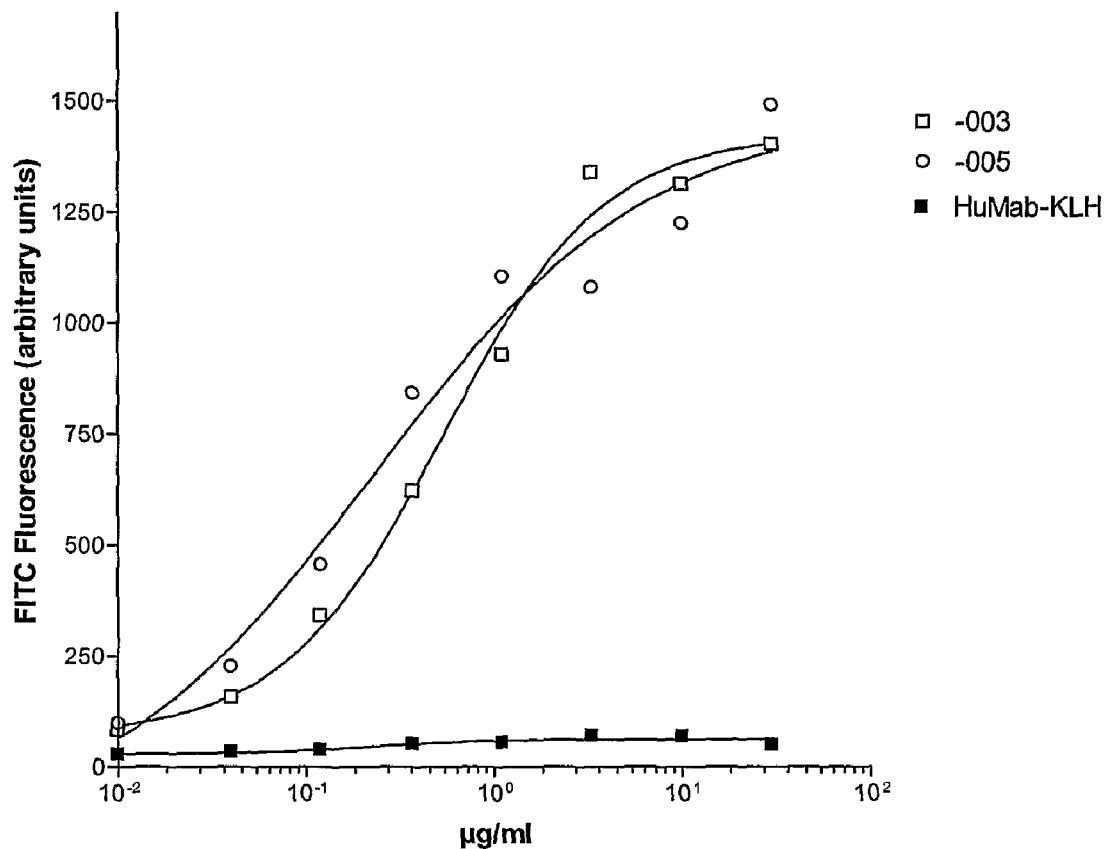
B:
Binding of -024 on CHO-CD38 cells.
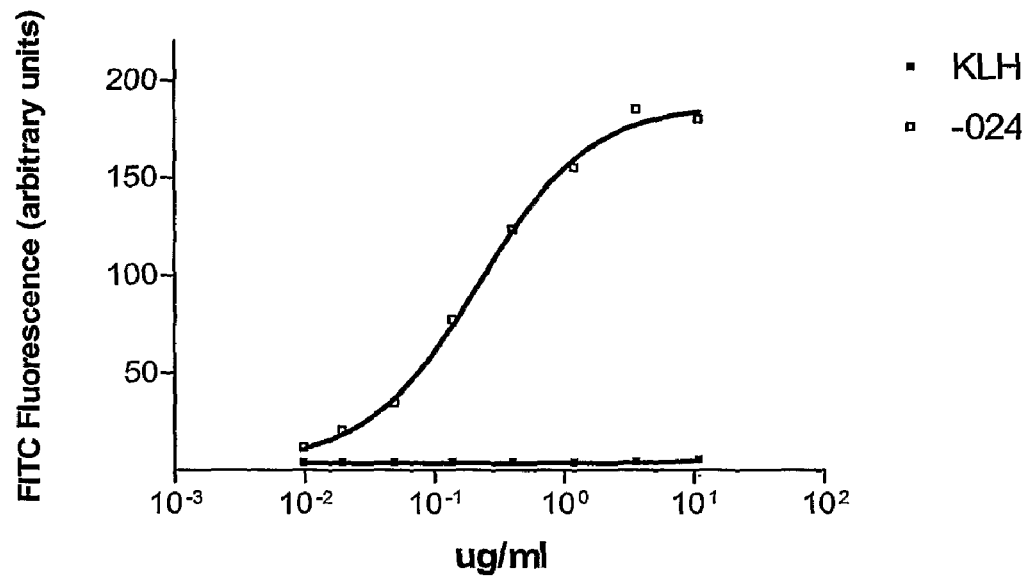

FIGURE 2
A:
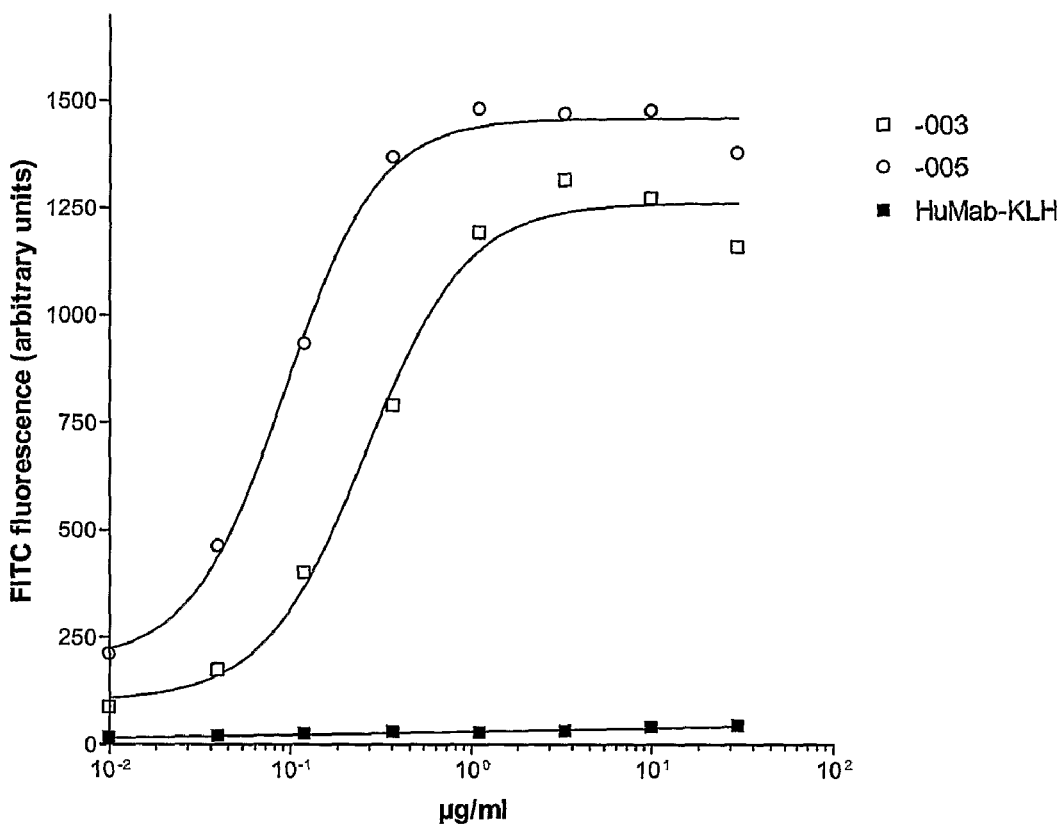
B:
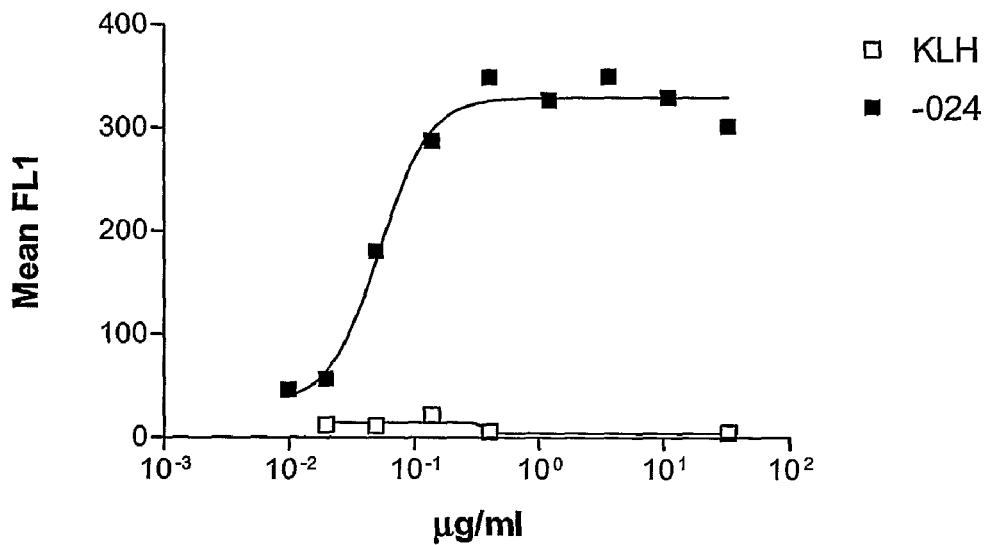

FIGURE 4
A:
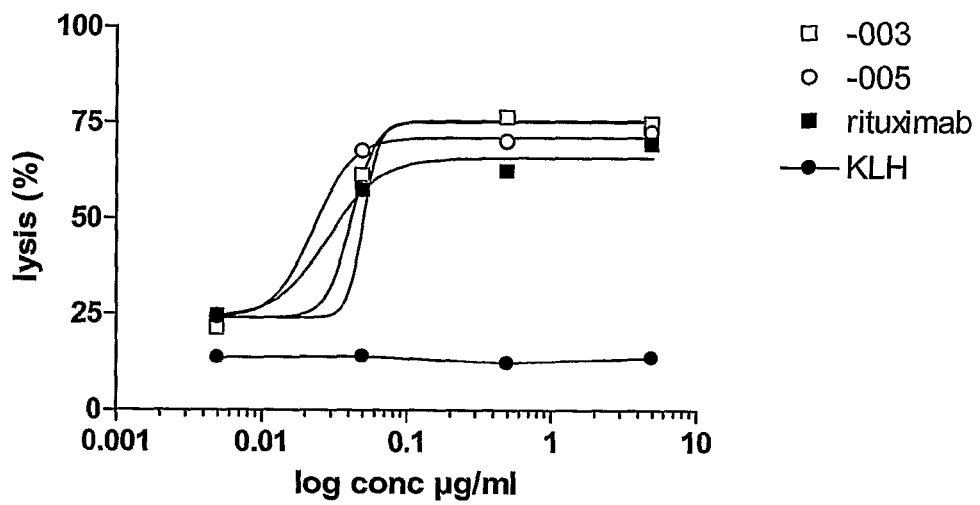
B:
ADCC on Daudi cells
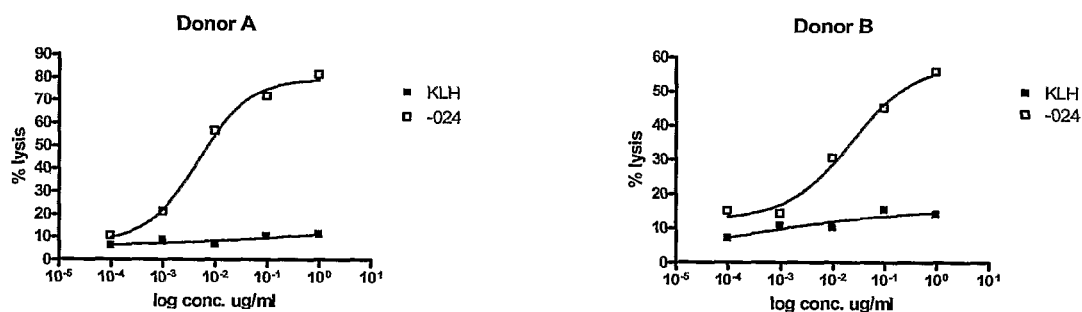

FIGURE 5
A:
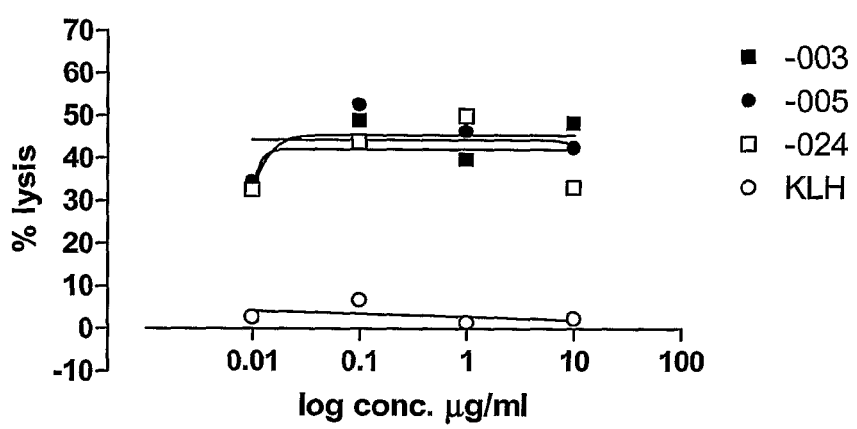
B:
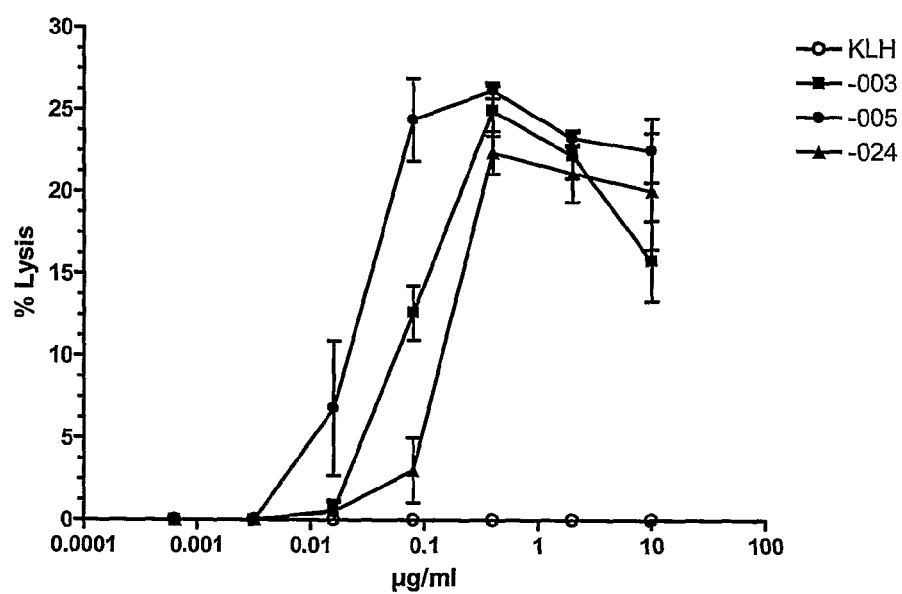

FIGURE 9
A:
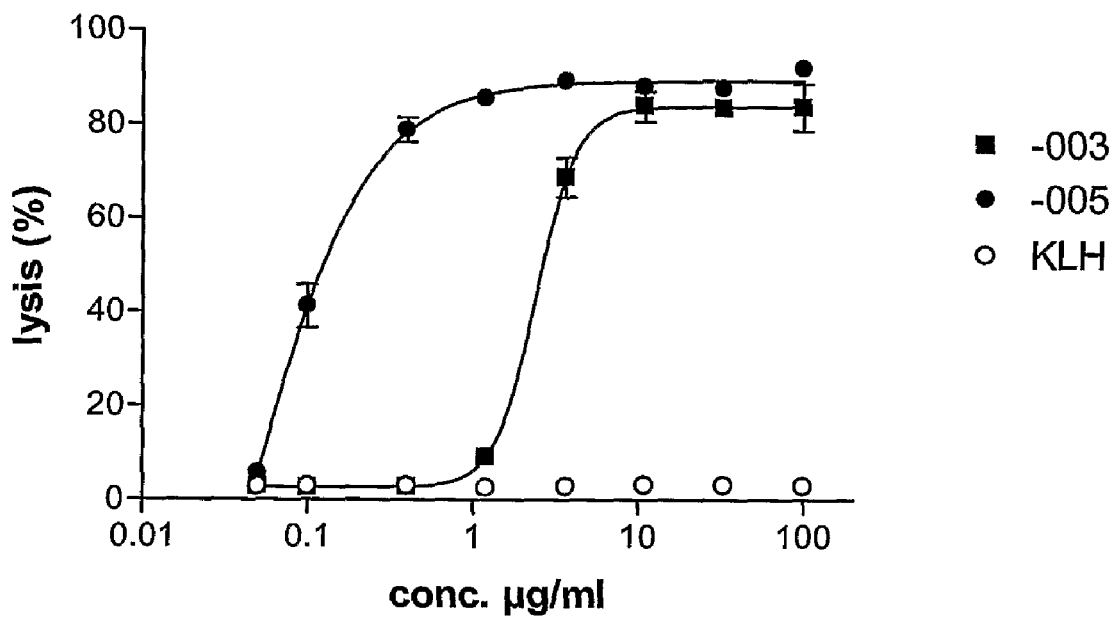
B:
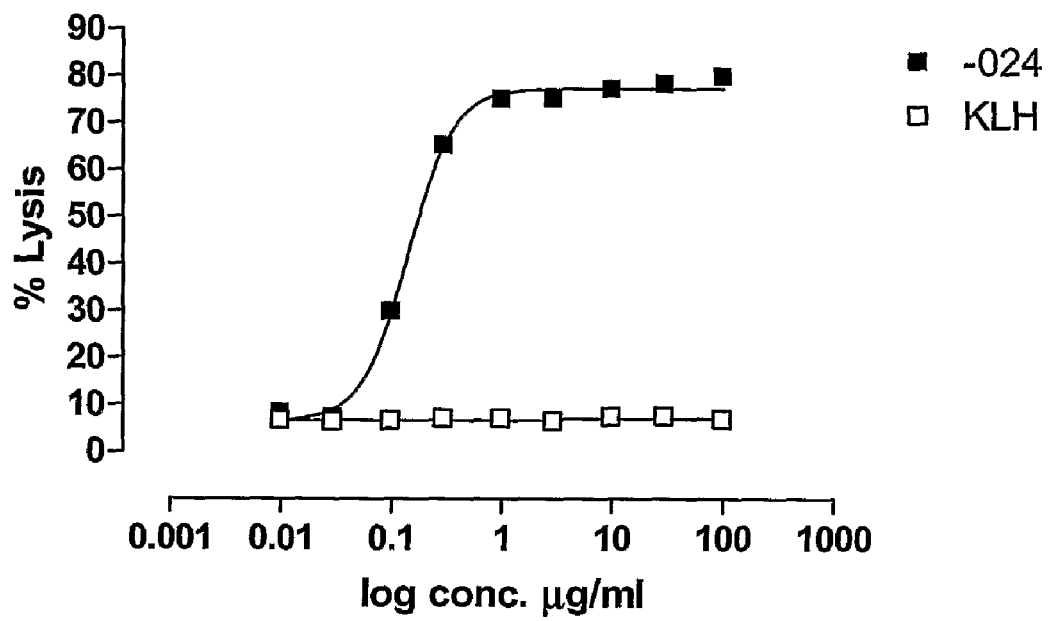

FIGURE 10
A:
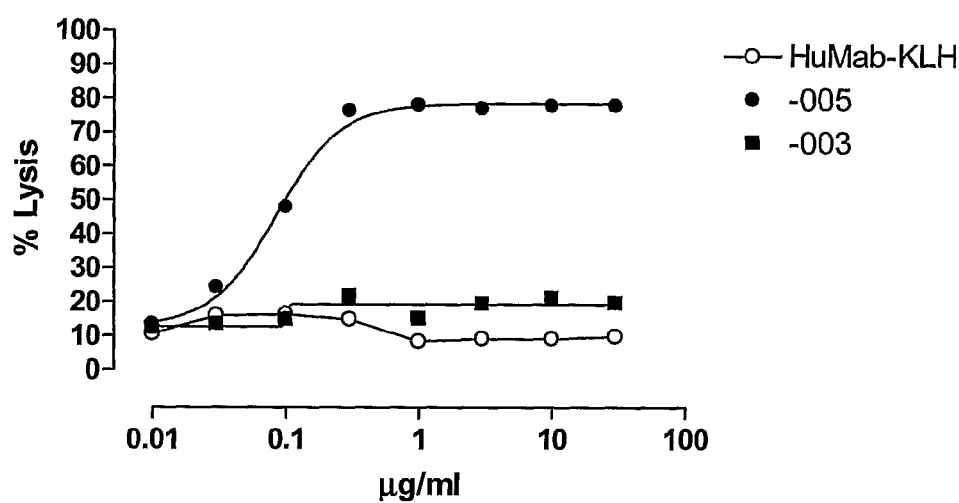
B:
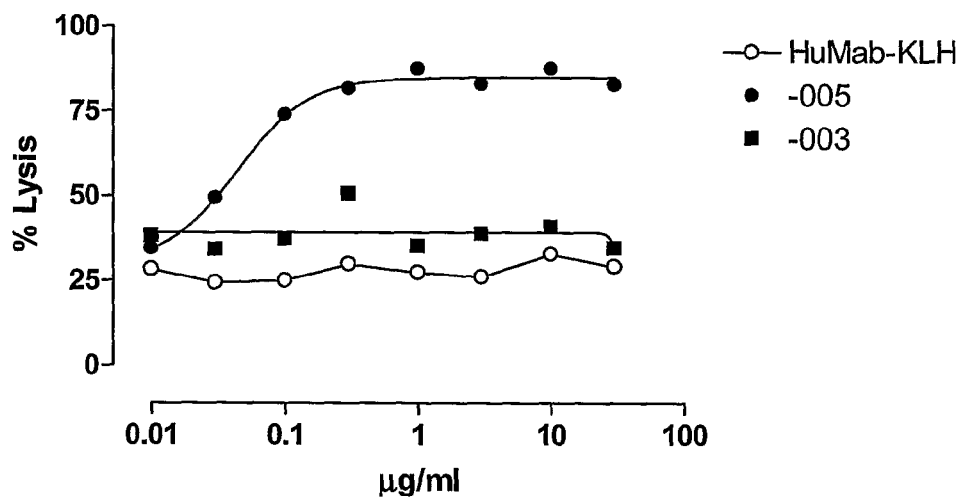

FIGURE 10
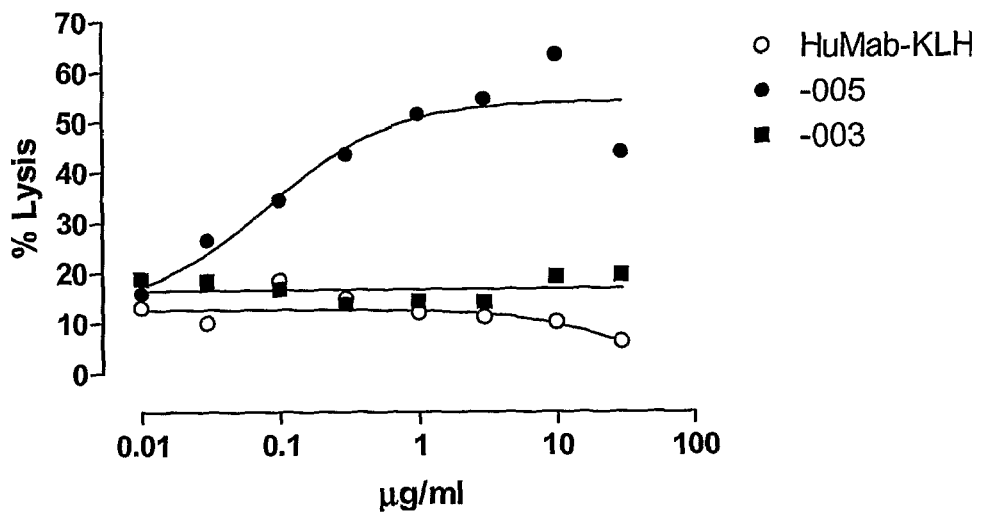
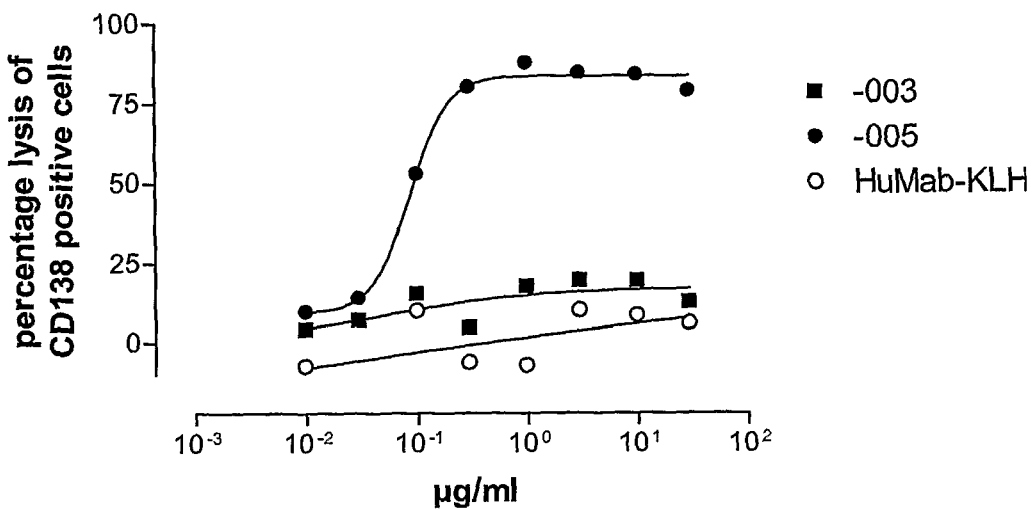

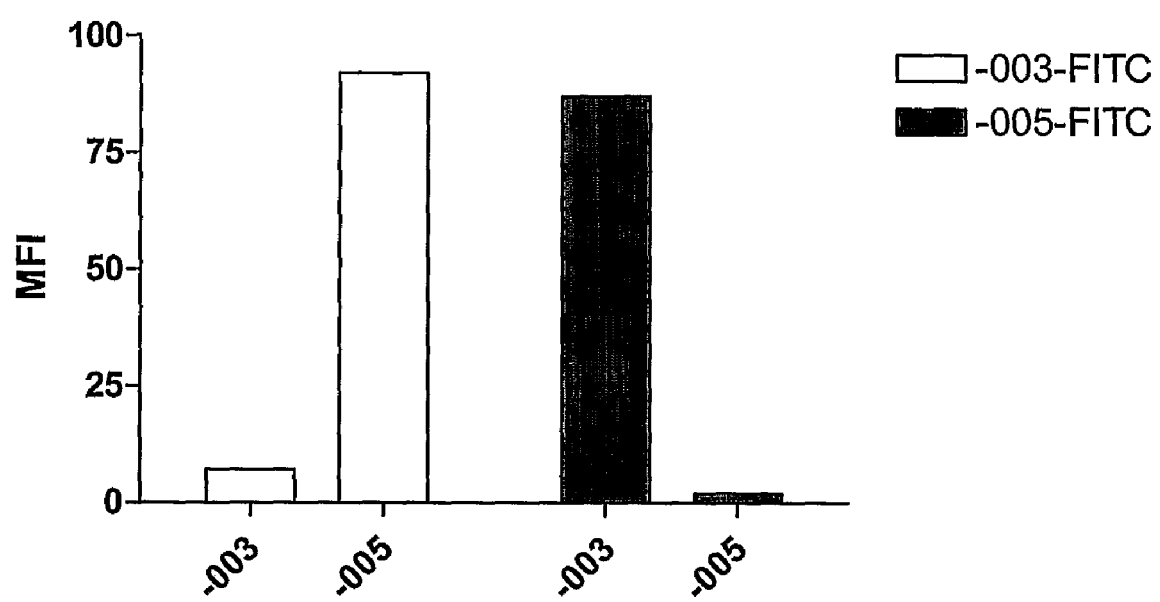

FIGURE 14
14A
14B
14C
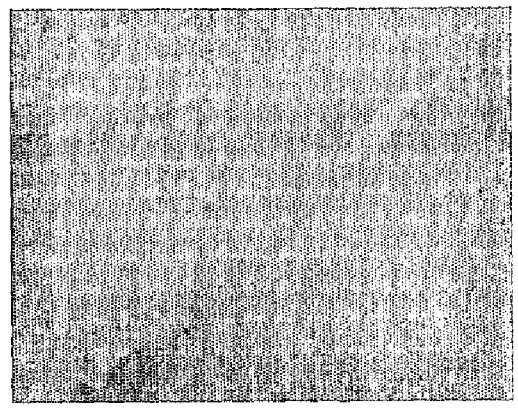
14D
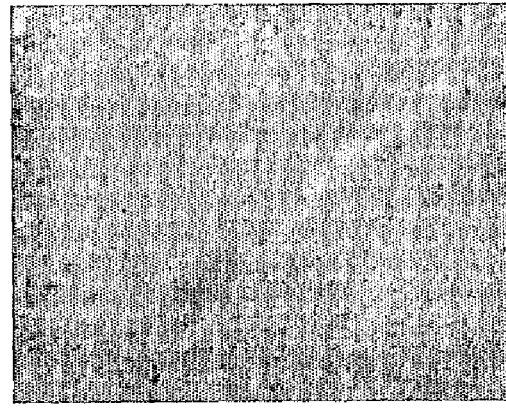
14E
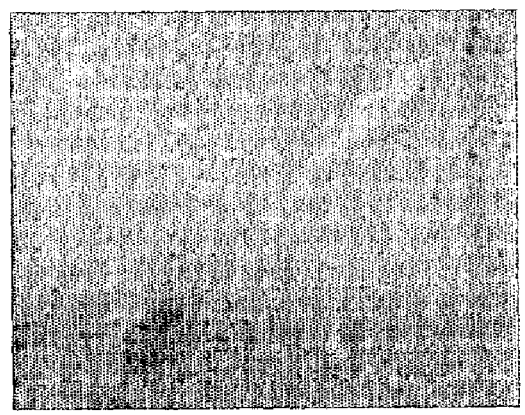

FIGURE 21
A
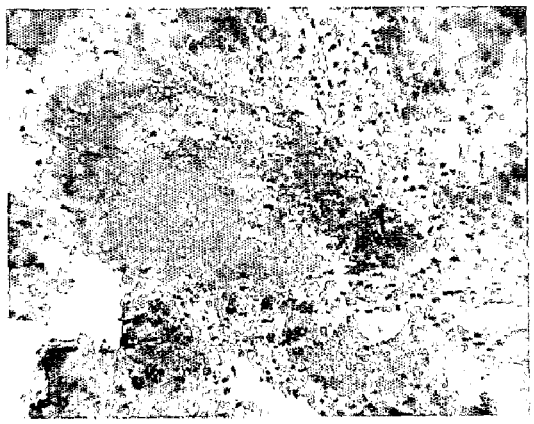
B
C
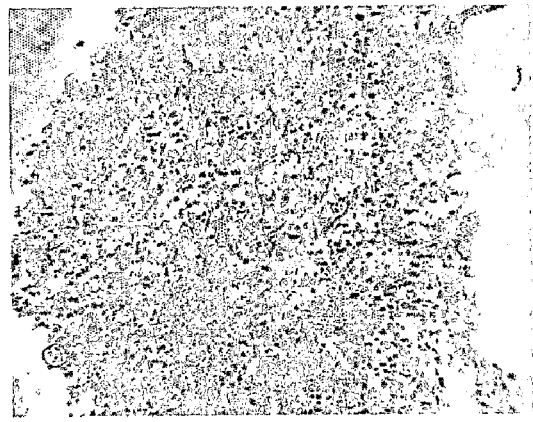

FIGURE 22
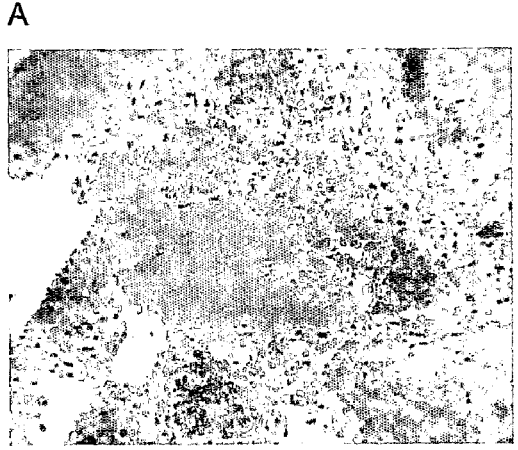
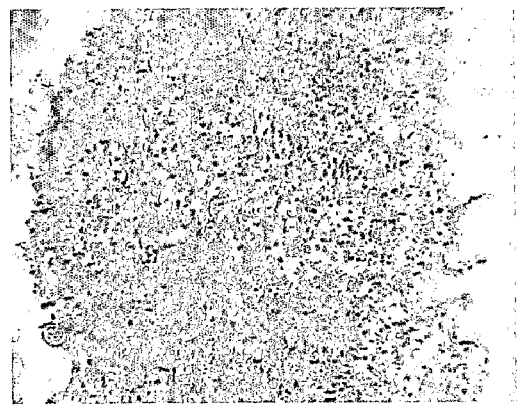

FIGURE 23
A:
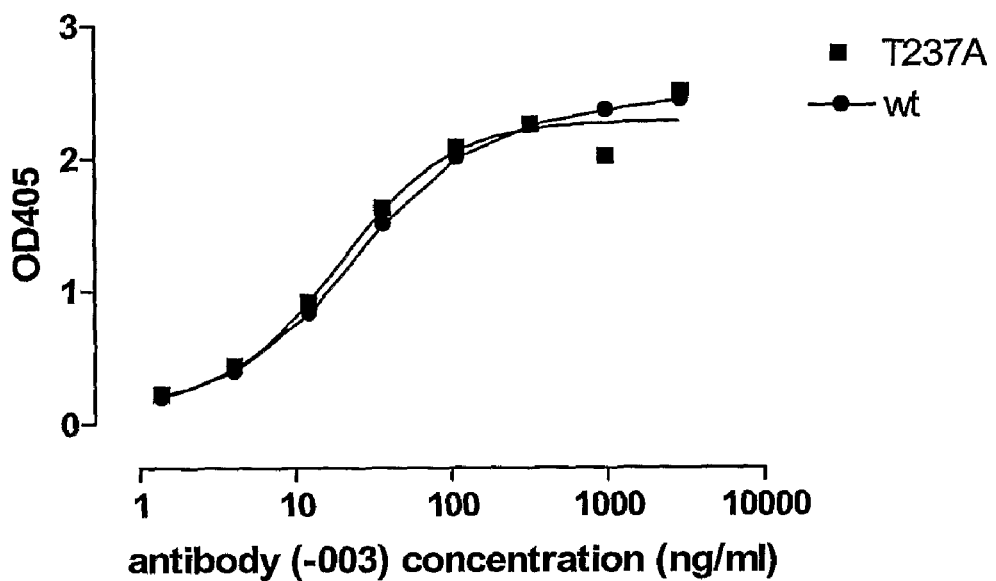
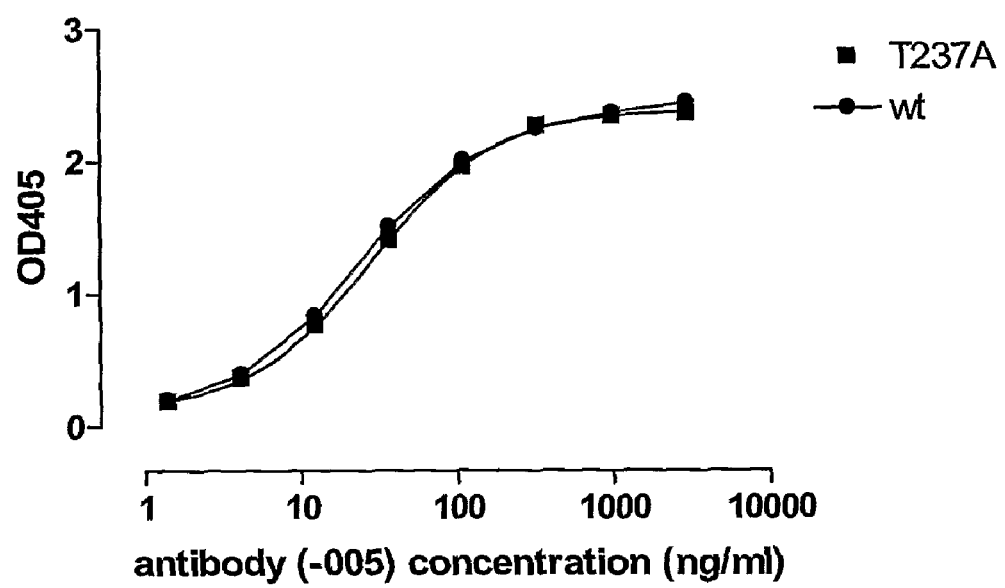

FIGURE 23
B:
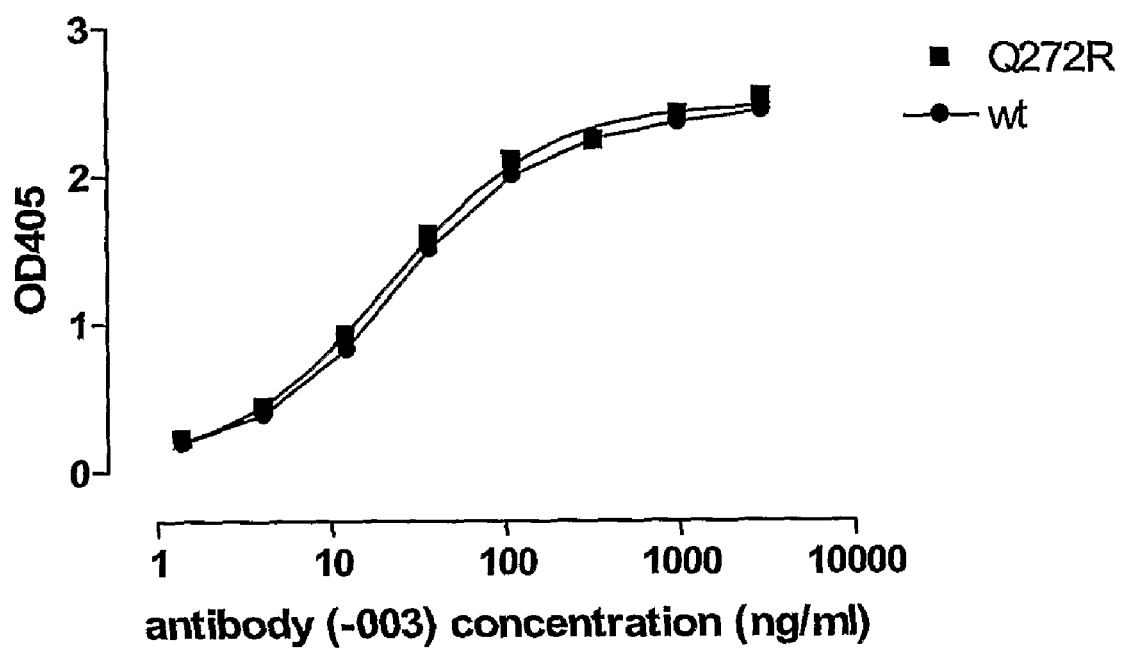
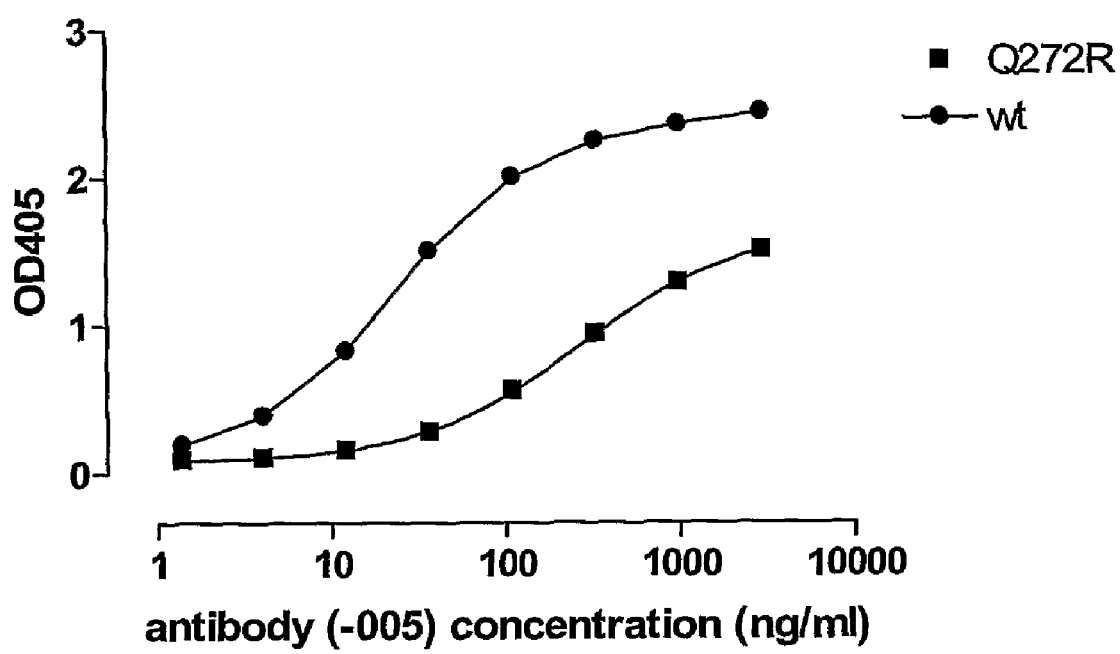

FIGURE 23
C:
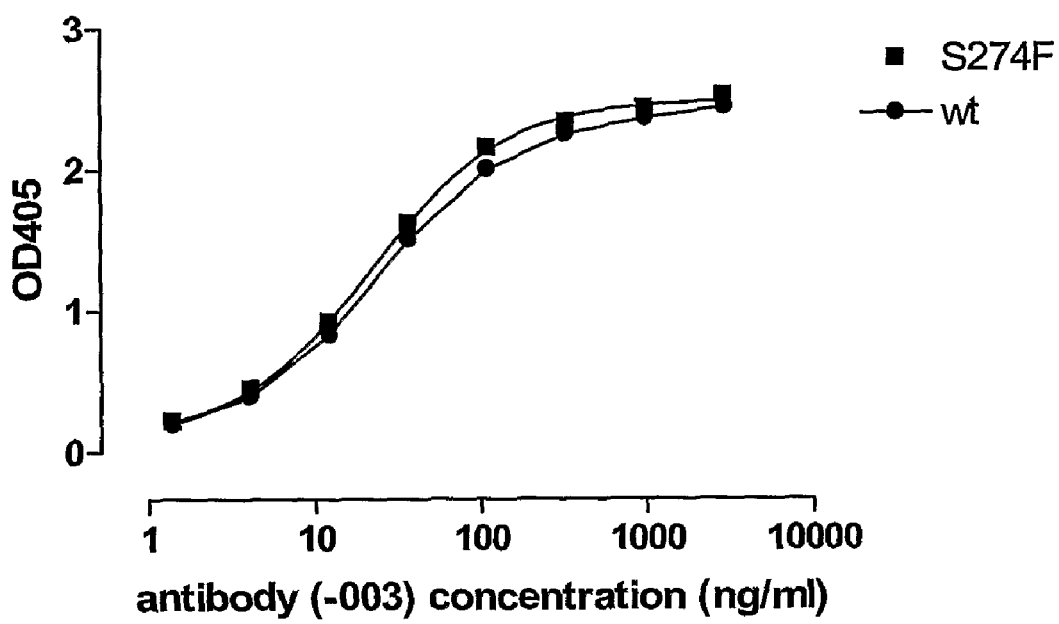
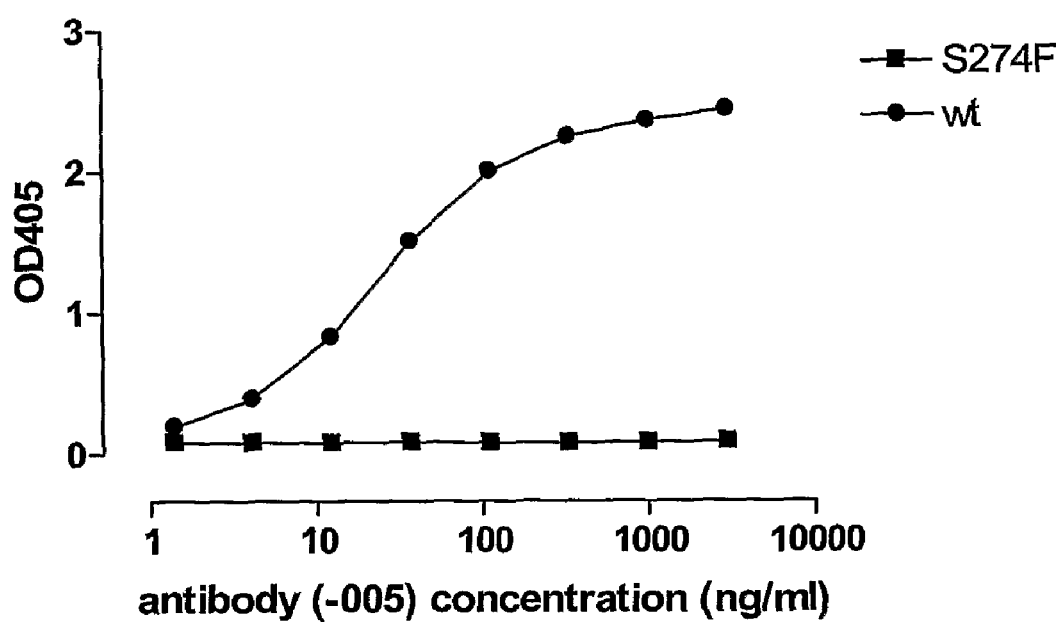

FIGURE 24
A:
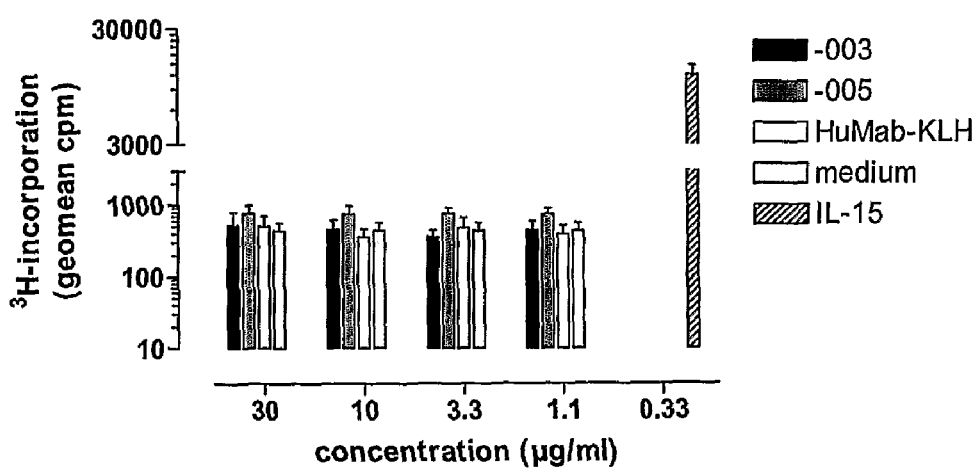
B:
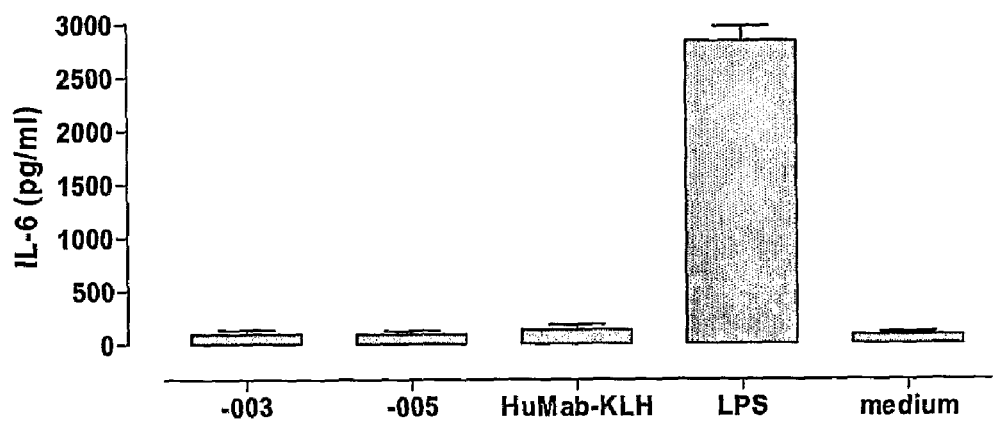
C:
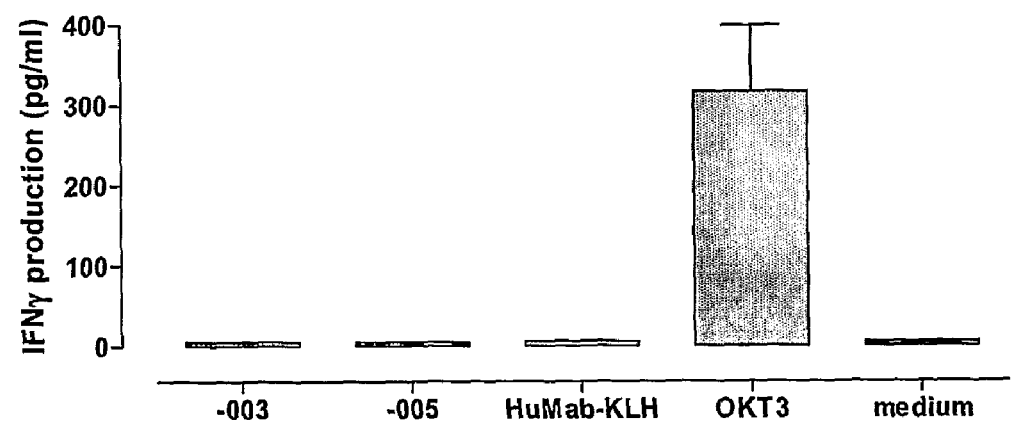

FIGURE 25
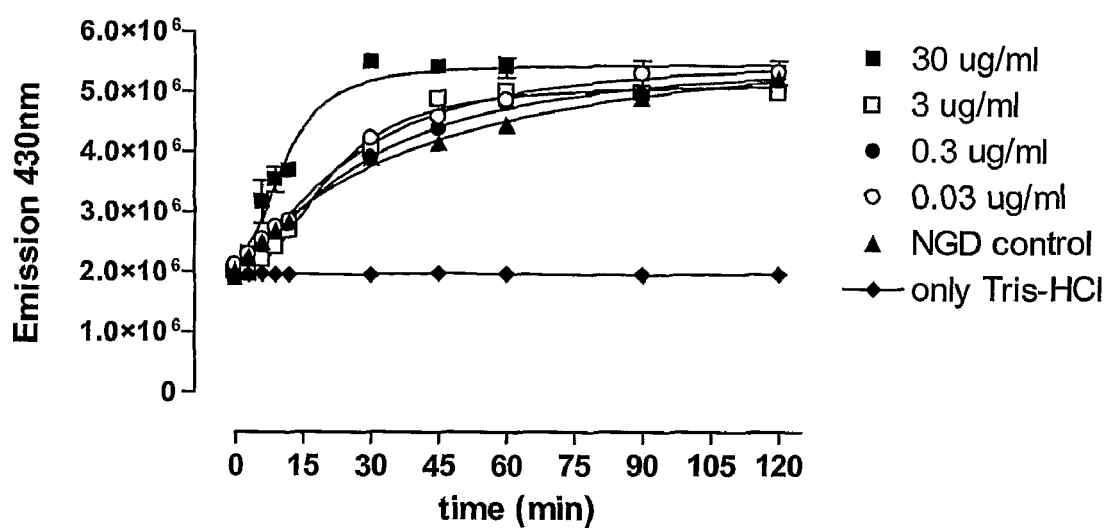
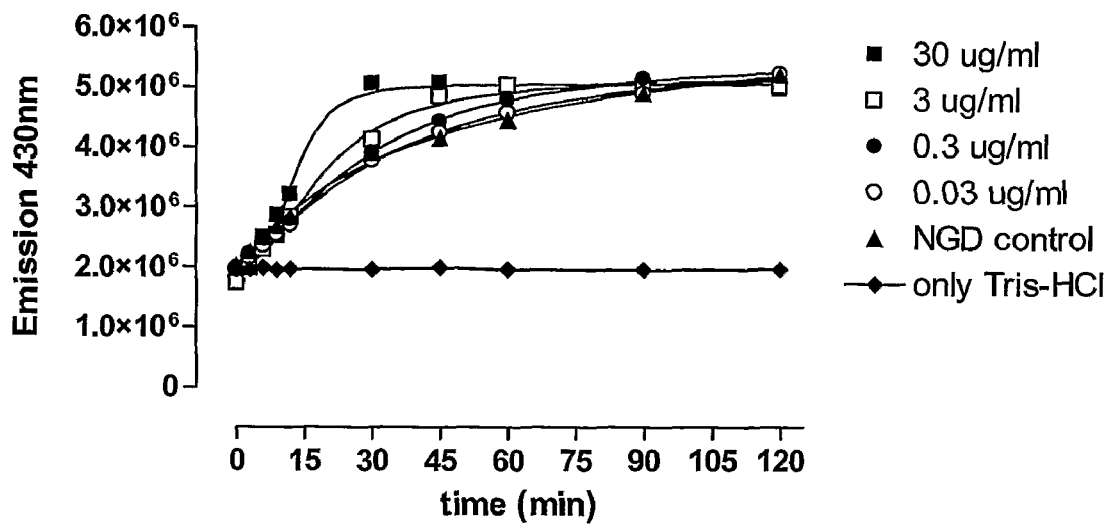

FIGURE 25
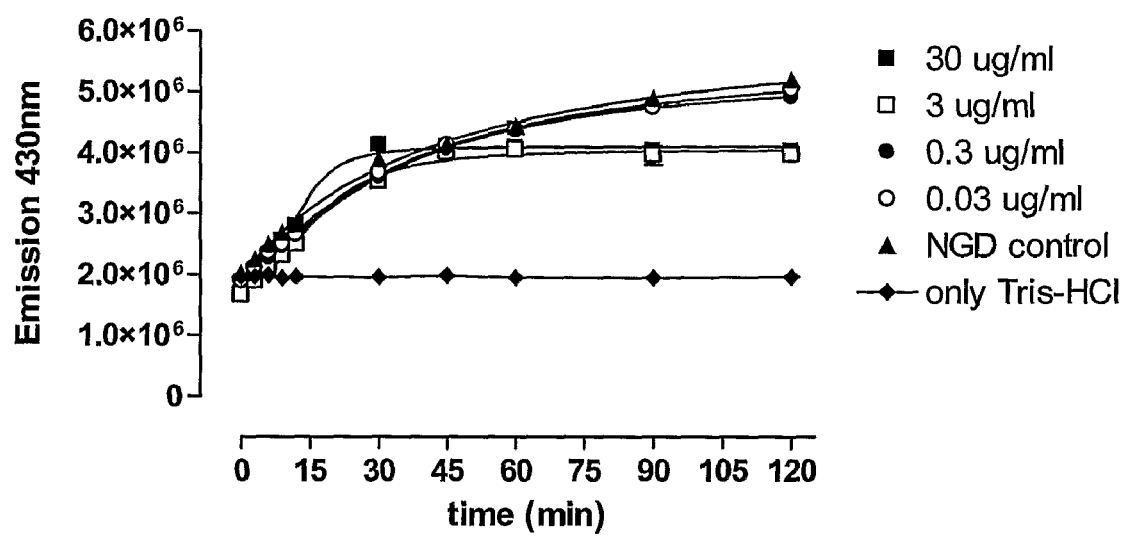
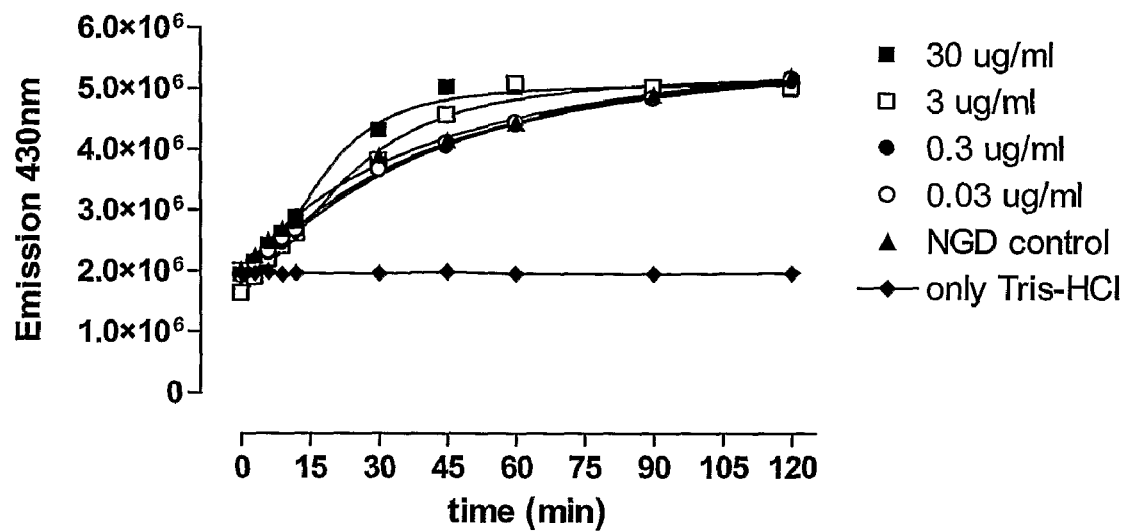

FIGURE 26
A
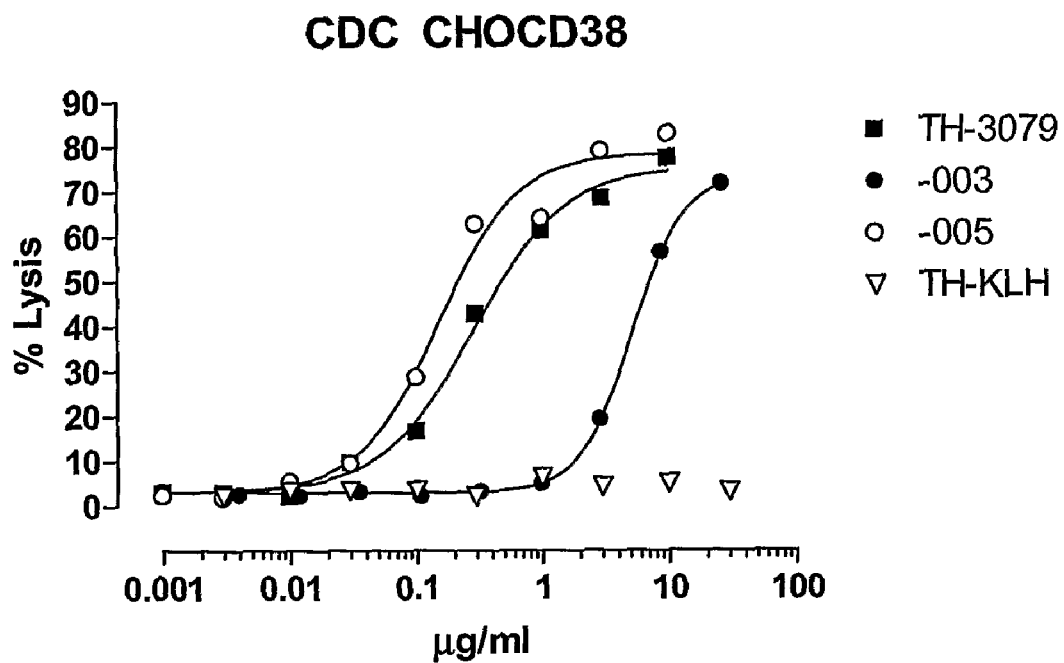
B
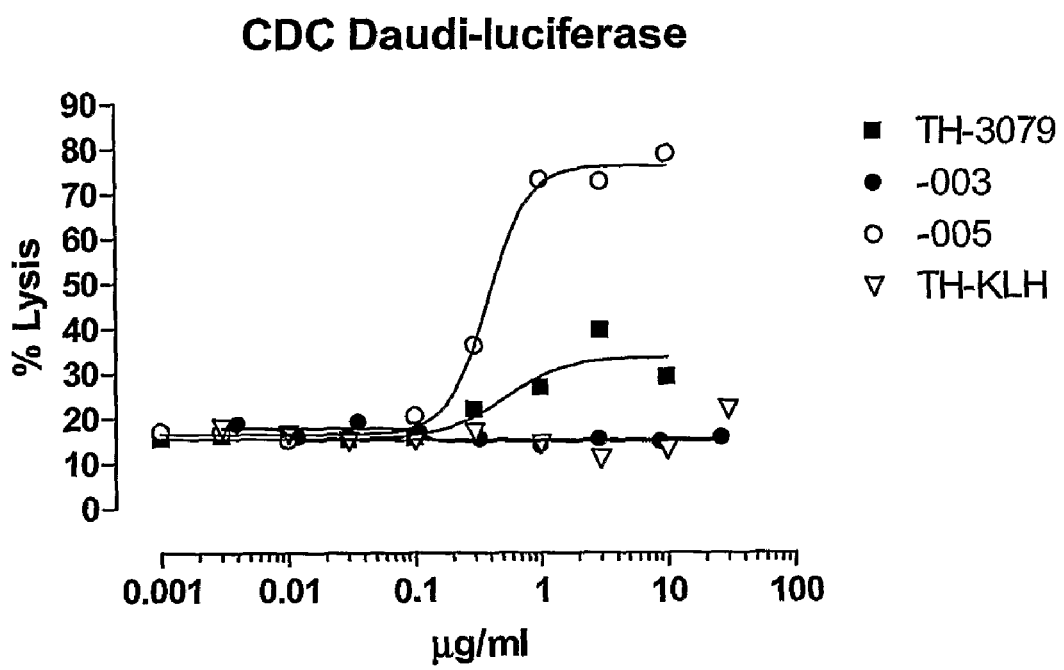

ANTIBODIES AGAINST CD38 FOR TREATMENT OF MULTIPLE MYELOMA

FIELD OF THE INVENTION

The present invention relates to antibodies binding CD38, which antibodies have specific characteristics and which are useful for treating inter alia multiple myeloma.

BACKGROUND

Multiple myeloma is a B cell malignancy characterized by the latent accumulation in bone marrow of secretory plasma cells with a low proliferative index and an extended life span. The disease ultimately attacks bones and bone marrow, resulting in multiple tumors and lesions throughout the skeletal system.

Approximately 1% of all cancers, and slightly more than 10% of all hematologic malignancies, can be attributed to multiple myeloma (MM). Incidence of MM increases in the aging population, with the median age at time of diagnosis being about 61 years.

Currently available therapies for multiple myeloma include chemotherapy, stem cell transplantation, Thalomid® (thalidomide), Velcade® (bortezomib), Aredia® (pamidronate), and Zometa® (zoledronic acid). Current treatment protocols, which include a combination of chemotherapeutic agents such as vincristine, BCNU, melphalan, cyclophosphamide, adriamycin, and prednisone or dexamethasone, yield a complete remission rate of only about 5%, and median survival is approximately 36-48 months from the time of diagnosis. Recent advances using high dose chemotherapy followed by autologous bone marrow or peripheral blood mononuclear cell transplantation have increased the complete remission rate and remission duration. Yet overall survival has only been slightly prolonged, and no evidence for a cure has been obtained. Ultimately, all MM patients relapse, even under maintenance therapy with interferon-alpha (IFN-α) alone or in combination with steroids.

Efficacy of the available chemotherapeutic treatment regimens for MM is limited by the low cell proliferation rate and development of multi-drug resistance. For more than 90% of MM patients, the disease becomes chemoresistant. As a result, alternative treatment regimens aimed at adoptive immunotherapy targeting surface antigens on plasma cells are being sought.

CD38 is an example of an antigen expressed on such malignant plasma cells, and is expressed in a variety of malignant hematological diseases, including but not restricted to multiple myeloma, B-cell chronic lymphocytic leukemia, B-cell acute lymphocytic leukemia, Waldenström macroglobulinemia, primary systemic amyloidosis, mantle-cell lymphoma, pro-lymphocytic/myelocytic leukemia, acute myeloid leukemia, chronic myeloid leukemia, follicular lymphoma, NK-cell leukemia and plasma-cell leukemia. Expression of CD38 has been described on epithelial/endothelial cells of different origin, including glandular epithelium in prostate, islet cells in pancreas, ductal epithelium in glands, including parotid gland, bronchial epithelial cells, cells in testis and ovary and tumor epithelium in colorectal adenocarcinoma. Diseases, where CD38 expression could be involved, include but is not restricted to broncho-epithelial carcinomas of the lung, breast cancer (evolving from malignant proliferation of epithelial lining in ducts and lobules of the breast), pancreatic tumors, evolving from the b-cells (insulinomas), tumors evolving from epithelium in the gut (e.g. adenocarcinoma and squamous cell carcinoma) In CNS, neuroblastomas express CD38. Other diseases include carcinoma in the prostate gland, seminomas in testis and ovarian cancers.

Normally, CD38 is expressed by hemopoietic cells, and in solid tissues. With regard to hemopoietic cells, the majority of medullary thymocytes are $CD38^+$, resting and circulating T- and B-cells are $CD38^-$, and activated cells are $CD38^+$. CD38 is also expressed on approximately 80% of resting NK cells and monocytes, and on lymph node germinal center lymphoblasts, plasma B cells and some intrafollicular cells. CD38 can also be expressed by dendritic cells. A significant proportion of normal bone marrow cells, particular precursor cells, express CD38. In addition, 50-80% of umbilical cord blood cells is $CD38^+$ and remains so in human blood for the first two to three years of life. In addition to lymphoid precursor cells, CD38 is also expressed on erythrocytes and on platelets.

With regard to solid tissues, CD38 is expressed in the gut by intra-epithelial cells and lamina propria lymphocytes, by Purkinje cells and neurofibrillary tangles in the brain, by epithelial cells in the prostate, β-cells in the pancreas, osteoclasts in the bone, retinal cells in the eye, and sarcolemma of smooth and striated muscle.

Functions ascribed to CD38 include both receptor mediation in adhesion and signaling events and (ecto-) enzymatic activity. As an ectoenzyme, CD38 uses $NAD^+$ as substrate for the formation of cyclic ADP-ribose (cADPR) and ADPR, but also of nicotinamide and nicotinic acid-adenine dinucleotide phosphate (NAADP). cADPR has been shown to act as second messenger for $Ca^{2+}$ mobilization from the endoplasmatic reticulum. In addition to signaling via $Ca^{2+}$, CD38 signaling occurs via cross-talk with antigen-receptor complexes on T and B cells or other types of receptor complexes, e.g. MHC molecules, and is in this way involved in several cellular responses, but also in switching and secretion of IgG1.

Anti-CD38 antibodies are described in the literature, for instance in Lande R, et al., Cell Immunol. 220(1), 30-8 (2002), Ausiello C M, et al., Tissue Antigens. 56(6), 539-47 (2000), and Cotner T, et al., Int J. Immunopharmacol. 3(3), 255-68 (1981). CD38 has a number of functions, which may or may not be activated by a molecule binding to CD38. For instance the mouse anti-CD38 antibody IB4 has agonistic properties in relation to CD38. IB4 is shown to induce T cell activation as indicated by $Ca^{2+}$ mobilization in Jurkat cells (Zubiaur M, et al., J. Immunol. 159(1), 193-205 (1997)), to induce significant proliferation of peripheral blood mononuclear cells (PBMCs), to induce release of significant IL-6 levels and to induce release of detectable IFN-γ levels (Lande, Zubiaur Morra, Ansiello supra).

SUMMARY OF THE INVENTION

The present invention provides an antibody binding to human CD38 encoded by (i) human light chain and human heavy chain nucleic acids comprising nucleotide sequences in their variable regions as set forth in SEQ ID No:1 and SEQ ID No:6, respectively;

(ii) human light chain and human heavy chain nucleic acids comprising nucleotide sequences in their variable regions as set forth in SEQ ID No:11 and SEQ ID No:16, respectively;

(iii) human light chain and human heavy chain nucleic acids comprising nucleotide sequences in their variable regions as set forth in SEQ ID No:21 and SEQ ID No:26, respectively; or (iv) human light chain and human heavy chain nucleic acids comprising nucleotide sequences in their variable regions, which are conservative sequence modifications of the sequences as set forth in (i), (ii) or (iii).

The present invention provides an antibody binding to human CD38 comprising a $V_H$ CDR3 having the sequence as set forth in SEQ ID No:10.

The present invention provides an antibody binding to human CD38, comprising a $V_L$ CDR3 having the sequence as set forth in SEQ ID No:5 and a $V_H$ CDR3 having the sequence as set forth in SEQ ID No:10.

The present invention provides an antibody binding to human CD38, comprising human light chain and human heavy variable regions, wherein the light chain variable region comprises a $V_L$ CDR1 having the sequence as set forth in SEQ ID No:3, a $V_L$ CDR2 having the sequence as set forth in SEQ ID No:4 and a $V_L$ CDR3 having the sequence as set forth in SEQ ID No:5, and the heavy chain variable region comprises a $V_H$ CDR1 having the sequence as set forth in SEQ ID No:8, a $V_H$ CDR2 having the sequence as set forth in SEQ ID No:9 and a $V_H$ CDR3 having the sequence as set forth in SEQ ID No:10.

The present invention provides an antibody binding to human CD38, comprising a $V_L$ region having the amino acid sequence as set forth in SEQ ID No:2.

The present invention provides an antibody binding to human CD38, comprising a $V_L$ region having at least about 90%, such as at least about 95% amino acid sequence identity to the sequence as set forth in SEQ ID No:2.

The present invention provides an antibody binding to human CD38, comprising a $V_H$ region having the amino acid sequence as set forth in SEQ ID No:7.

The present invention provides an antibody binding to human CD38, comprising a $V_H$ region comprising the amino acid sequence spanning the $V_H$ CDR1-$V_H$ CDR3 region of SEQ ID No:7.

The present invention provides an antibody binding to human CD38, comprising a $V_H$ region having at least about 90%, such as at least about 95% amino acid sequence identity to the sequence as set forth in SEQ ID No:7 or to the $V_H$ CDR1-$V_H$ CDR3 spanning region of SEQ ID No:7.

The present invention provides an antibody binding to human CD38, comprising a $V_H$ region having 1-5, such as 1-3 amino acid substitutions, deletions or additions compared to the sequence as set forth in SEQ ID No:7 or to the $V_H$ CDR1-$V_H$ CDR3 spanning region of SEQ ID No:7.

The present invention provides an antibody binding to human CD38, comprising a $V_L$ region as defined above and a $V_H$ region as defined above.

The present invention provides an antibody binding to human CD38, comprising a $V_H$ CDR3 having the sequence as set forth in SEQ ID No:20.

The present invention provides an antibody binding to human CD38, comprising a $V_L$ CDR3 having the sequence as set forth in SEQ ID No:15 and a $V_H$ CDR3 having the sequence as set forth in SEQ ID No:20.

The present invention provides an antibody binding to human CD38, comprising human light chain and human heavy variable regions, wherein the light chain variable region comprises a $V_L$ CDR1 having the sequence as set forth in SEQ ID No:13, a $V_L$ CDR2 having the sequence as set forth in SEQ ID No:14 and a $V_L$ CDR3 having the sequence as set forth in SEQ ID No:15, and the heavy chain variable region comprises a $V_H$ CDR1 having the sequence as set forth in SEQ ID No:18, a $V_H$ CDR2 having the sequence as set forth in SEQ ID No:19 and a $V_H$ CDR3 having the sequence as set forth in SEQ ID No:20.

The present invention provides an antibody binding to human CD38, comprising a $V_L$ region having the amino acid sequence as set forth in SEQ ID No:12.

The present invention provides an antibody binding to human CD38, comprising a $V_L$ region having at least about 90%, such as at least about 95% amino acid sequence identity to the sequence according to SEQ ID No:12.

The present invention provides an antibody binding to human CD38, comprising a $V_H$ region having the amino acid sequence as set forth in SEQ ID No:17.

The present invention provides an antibody binding to human CD38, comprising a $V_H$ region comprising the amino acid sequence spanning the $V_H$ CDR1-$V_H$ CDR3 region of SEQ ID No:17.

The present invention provides an antibody binding to human CD38, comprising a $V_H$ region having at least about 90%, such as at least about 95% amino acid sequence identity to the sequence as set forth in SEQ ID No:17 or to the $V_H$ CDR1-$V_H$ CDR3 spanning region of SEQ ID No:17.

The present invention provides an antibody binding to human CD38, comprising a $V_H$ region having 1-5, such as 1-3 amino acid substitutions, deletions or additions compared to the sequence as set forth in SEQ ID No:17 or to the $V_H$ CDR1-$V_H$ CDR3 spanning region of SEQ ID No:17.

The present invention provides an antibody binding to human CD38, comprising a $V_L$ region as defined above and a $V_H$ region as defined above.

The present invention provides an antibody binding to human CD38, comprising a $V_H$ CDR3 having the sequence as set forth in SEQ ID No:30.

The present invention provides an antibody binding to human CD38, comprising a $V_L$ CDR3 having the sequence as set forth in SEQ ID No:25 and a $V_H$ CDR3 having the sequence as set forth in SEQ ID No:30.

The present invention provides an antibody binding to human CD38, comprising human light chain and human heavy variable regions, wherein the light chain variable region comprises a $V_L$ CDR1 having the sequence as set forth in SEQ ID No:23, a $V_L$ CDR2 having the sequence as set forth in SEQ ID No:24 and a $V_L$ CDR3 having the sequence as set forth in SEQ ID No:25, and the heavy chain variable region comprises a $V_H$ CDR1 having the sequence as set forth in SEQ ID No:28, a $V_H$ CDR2 having the sequence as set forth in SEQ ID No:29 and a $V_H$ CDR3 having the sequence as set forth in SEQ ID No:30.

The present invention provides an antibody binding to human CD38, comprising a $V_L$ region having the amino acid sequence as set forth in SEQ ID No:22.

The present invention provides an antibody binding to human CD38, comprising a $V_L$ region having at least about 90%, such as at least about 95% amino acid sequence identity to the sequence according to SEQ ID No:22.

The present invention provides an antibody binding to human CD38, comprising a $V_H$ region having the amino acid sequence as set forth in SEQ ID No:27.

The present invention provides an antibody binding to human CD38, comprising a $V_H$ region comprising the amino acid sequence spanning the $V_H$ CDR1-$V_H$ CDR3 region of SEQ ID No:27.

The present invention provides an antibody binding to human CD38, comprising a $V_H$ region having at least about 90%, such as at least about 95% amino acid sequence identity to the sequence according to SEQ ID No:27 or to the $V_H$ CDR1-$V_H$ CDR3 spanning region of SEQ ID No:27.

The present invention provides an antibody binding to human CD38, comprising a $V_H$ region having 1-5, such as 1-3 amino acid substitutions, deletions or additions compared to the sequence as set forth in SEQ ID No:27 or to the $V_H$ CDR1-$V_H$ CDR3 spanning region of SEQ ID No:27.

The present invention provides an antibody binding to human CD38, comprising a $V_L$ region as defined above and a $V_H$ region as defined above.

The present invention provides a peptide which binds to human CD38 (SEQ ID No:31), and which does not bind to a mutant human CD38, wherein the serine residue in position 274 has been substituted with a phenylalanine residue (SEQ ID No:34), to the same degree that it binds to human CD38 (SEQ ID No:31).

The present invention provides a peptide as defined above, wherein the $EC_{50}$ of the binding of the peptide to a mutant human CD38, wherein the serine residue in position 274 has been substituted with a phenylalanine residue (SEQ ID No:34), is less than 50%, such as less than 10%, less than 5% or less than 1% of the $EC_{60}$ of the binding of the peptide to human CD38 (SEQ ID No:31).

The present invention provides a peptide which binds to human CD38 (SEQ ID No:31), and which does not bind to a mutant human CD38, wherein the glutamine residue in position 272 has been substituted with an arginine residue (SEQ ID No:33), to the same degree that it binds to human CD38 (SEQ ID No:31).

The present invention provides a peptide as defined above, wherein the $EC_{50}$ of the binding of the peptide to a mutant human CD38, wherein the glutamine residue in position 272 has been substituted with an arginine residue (SEQ ID No:33), is less than 50%, such as less than 10%, less than 5% or less than 1% of the $EC_{50}$ of the binding of the peptide to human CD38 (SEQ ID No:31).

The present invention provides a peptide as defined above, wherein said peptide binds to a mutant human CD38, wherein the threonine residue in position 237 has been substituted with an alanine residue (SEQ ID No:32), to the same degree that it binds to human CD38 (SEQ ID No:31).

The present invention provides a peptide as defined above, wherein the $EC_{50}$ of the binding of the peptide to a mutant human CD38, wherein the threonine residue in position 237 has been substituted with an alanine residue (SEQ ID No:32) corresponds to 75%-125% of the $EC_{50}$ of the binding of the peptide to human CD38 (SEQ ID No:31).

The present invention provides a peptide which binds to human CD38 (SEQ ID No:31), wherein the peptide possesses the following binding characteristics: (i) binds to a mutant human CD38, wherein the serine residue in position 274 has been substituted with a phenylalanine residue (SEQ ID No:34), to the same degree that it binds to human CD38 (SEQ ID No:31), (ii) binds to a mutant human CD38, wherein the glutamine residue in position 272 has been substituted with an arginine residue (SEQ ID No:33), to the same degree that it binds to human CD38 (SEQ ID No:31), and (iii) binds to a mutant human CD38, wherein the threonine residue in position 237 has been substituted with an alanine residue (SEQ ID No:32), to the same degree that it binds to human CD38 (SEQ ID No:31).

The present invention provides a peptide which binds to human CD38 (SEQ ID No:31), wherein the peptide possesses the following binding characteristics: (i) does not bind to a mutant human CD38, wherein the serine residue in position 274 has been substituted with a phenylalanine residue (SEQ ID No:34), to the same degree that it binds to human CD38 (SEQ ID No:31), (ii) does not bind to a mutant human CD38, wherein the glutamine residue in position 272 has been substituted with an arginine residue (SEQ ID No:33), to the same degree that it binds to human CD38 (SEQ ID No:31), (iii) binds to a mutant human CD38, wherein the threonine residue in position 237 has been substituted with an alanine residue (SEQ ID No:32), to the same degree that it binds to human CD38 (SEQ ID No:31).

The present invention provides a peptide as defined above, wherein the $EC_{50}$ is determined by use of an ELISA as described in Example 17 of the specification.

The present invention provides a peptide which competes with an antibody according to embodiment (i) above for binding to CD38. In one embodiment the competition is determined by use of an ELISA as described in Example 8 or 9 of the specification, wherein competition is defined by a signal of at least 90% as assessed by absorption, or by use of cross-blocking measurements as described in Example 7 of the specification, wherein competition is defined by a signal of at least 90% as assessed by fluorescence.

The present invention provides a peptide that specifically binds to a CD38 epitope, which epitope is also specifically bound by an antibody as defined above.

The present invention provides a peptide that specifically binds to the region SKRNIQFSCKNIYR (SEQ ID NO: 35) and the region EKVQTLEAWVIHGG (SEQ ID NO: 36) of human CD38 (SEQ ID No:31).

The present invention provides a peptide having substantially the same specific binding characteristics for binding human CD38 as an antibody as defined above.

The present invention provides a peptide binding to human CD38, which antibody possesses one or more of the following characteristics:
  (i) acts as an antagonist of CD38;
  (ii) does not induce significant proliferation of peripheral blood mononuclear cells as determined by the method described in Example 18 of the specification;
  (iii) does not induce release of significant IL-6 by human monocytes or peripheral blood mononuclear cells as determined by the method described in Example 19 of the specification;
  (iv) does not induce release of detectable IFN-γ by human T cells or peripheral blood mononuclear cells as determined by the method described in Example 20 of the specification;
  (v) is internalized by CD38 expressing cells; such as internalized by CHO-CD38 cells within 5 to 15 minutes at 37° C. by the method as described in Example 12 of the specification;
  (vi) induces ADCC; such as with an $EC_{50}$ value of below 15 ng/ml, such as below 10 ng/ml in Daudi-luc cells and with an $EC_{50}$ value of below 75 ng/ml, such as below 50 ng/ml, 30 ng/ml or 10 ng/ml in MM cells as determined by the method described in example 5 of the specification;
  (vii) induces CDC in the presence of complement; such as with an $EC_{50}$ value of below 5 µg/ml, such as below 1 µg/ml in daudi-luc or CD38-CHO cells by the method described in Example 6 of the specification;
  (viii) inhibits the synthesis of cGDPR;
  (ix) inhibits the synthesis of cADPR;
  (x) binds to human CD38 with an affinity ($K_D$) of below 10.8 M, such as in the range of from $10^{-8}$ M to $-10^{-11}$ M, for example in the range of from $7 \times 10^{-9}$ M to $-10^{-10}$ M, as determined by surface plasmon resonance as described in Example 20 of the specification.

The present invention provides a peptide as defined above, which inhibits the synthesis of cGDPR by at least 25%, such as at least 30% after 90 minutes at a concentration of 3 µg/ml as determined by spectophotometric method described in Example 24 of the specification.

The present invention provides a peptide as defined above, which inhibits the synthesis of cADPR by at least 25%, such as at least 30% after 90 minutes at a concentration of 3 µg/ml as determined by the HPLC method described in Munshi et al., J. Biol. Chem. 275, 21566-21571 (2000).

In one embodiment the peptide as defined above is a human monoclonal antibody.

The present invention provides an antibody as defined above, characterized in that it is a full length IgG1, IgG2, IgG3, IgG4, IgD, IgA, IgE, or IgM antibody, such as an IgG1 antibody, preferably an IgG1,κ antibody or an IgM antibody, preferably an IgM,κ antibody.

The present invention provides an isolated human monoclonal antibody comprising
(i) a heavy chain variable region amino acid sequence derived from a human Hv1263/3M28 ($V_H$I) germline sequence and a light chain variable region amino acid sequence derived from a human L15 (VκI) germline sequence, wherein the human antibody binds to human CD38; or
(ii) a heavy chain variable region amino acid sequence derived from a human $V_H$3-DP-47/V3-23 ($V_H$III) germline sequence and a light chain variable region amino acid sequence derived from a human L6 (VκI) germline sequence, wherein the human antibody binds to human CD38.

The present invention provides a peptide as defined above, wherein the peptide is glycosylated in a eukaryotic cell.

In one embodiment the antibody according to the invention is an antibody fragment or a single chain antibody.

The present invention provides a peptide as defined above, further comprising a chelator linker for attaching a radioisotope.

The present invention provides a peptide as defined above, which is in a substantially isolated form.

The present invention provides an isolated nucleic acid encoding a peptide as defined above.

The present invention provides an expression vector comprising a nucleic acid sequence encoding a peptide as defined above.

The present invention provides an expression vector comprising
(i) a $V_L$ nucleotide sequence of SEQ ID No:1,
(ii) a $V_H$ nucleotide sequence of SEQ ID No:6,
(iii) a $V_L$ nucleotide sequence of SEQ ID No:1 and a $V_H$ nucleotide sequence of SEQ ID No:6;
(iv) a $V_L$ nucleotide sequence of SEQ ID No:11;
(v) a $V_H$ nucleotide sequence of SEQ ID No:16;
(vi) a $V_L$ nucleotide sequence of SEQ ID No:11 and a $V_H$ nucleotide sequence of SEQ ID No:16;
(vii) a $V_L$ nucleotide sequence of SEQ ID No:21;
(viii) a $V_H$ nucleotide sequence of SEQ ID No:26; or
(ix) a $V_L$ nucleotide sequence of SEQ ID No:21 and a $V_H$ nucleotide sequence of SEQ ID No:26.

The present invention provides an expression vector as defined above, further comprising a nucleotide sequence encoding the constant region of a light chain, a heavy chain or both light and heavy chains of a human antibody.

The present invention provides an expression vector as defined above, wherein the nucleotide sequence encoding the constant region of a light chain, a heavy chain or both light and heavy chains of a human antibody encodes an IgG1 antibody.

The present invention provides a hybridoma which produces a human monoclonal anti-CD38 antibody encoded by human light chain and human heavy chain nucleic acids comprising
(i) human light chain and human heavy chain nucleic acids comprising nucleotide sequences in their variable regions as set forth in SEQ ID No:1 and SEQ ID No:6, respectively;
(ii) human light chain and human heavy chain nucleic acids comprising nucleotide sequences in their variable regions as set forth in SEQ ID No:11 and SEQ ID No:16, respectively;
(iii) human light chain and human heavy chain nucleic acids comprising nucleotide sequences in their variable regions as set forth in SEQ ID No:21 and SEQ ID No:26, respectively; or
(iv) human light chain and human heavy chain nucleic acids comprising nucleotide sequences in their variable regions, which are conservative sequence modifications of the sequences set forth in (i), (ii) or (iii).

The present invention provides a hybridoma which produces a human monoclonal anti-CD38 antibody having human heavy chain and light chain variable regions which comprise
(i) the human light chain variable amino acid sequence as set forth in SEQ ID No:2, and the human heavy chain variable amino sequence as set forth in SEQ ID No:7;
(ii) the human light chain variable amino acid sequence as set forth in SEQ ID No:12, and the human heavy chain variable amino sequence as set forth in SEQ ID No:17;
(iii) the human light chain variable amino acid sequence as set forth in SEQ ID No:22, and the human heavy chain variable amino sequence as set forth in SEQ ID No:27; or
(iv) conservative sequences modifications of the human light chain and human heavy chain variable amino acid sequences as set forth in (i), (ii) or (iii).

The present invention provides a tranfectoma which produces a human monoclonal anti-CD38 antibody encoded by human light chain and human heavy chain nucleic acids comprising
(i) human light chain and human heavy chain nucleic acids comprising nucleotide sequences in their variable regions as set forth in SEQ ID No:1 and SEQ ID No:6, respectively;
(ii) human light chain and human heavy chain nucleic acids comprising nucleotide sequences in their variable regions as set forth in SEQ ID No:11 and SEQ ID No:16, respectively;
(iii) human light chain and human heavy chain nucleic acids comprising nucleotide sequences in their variable regions as set forth in SEQ ID No:21 and SEQ ID No:26, respectively; or
(iv) human light chain and human heavy chain nucleic acids comprising nucleotide sequences in their variable regions, which are conservative sequence modifications of the sequences set forth in (i), (ii) or (iii).

The present invention provides a transfectoma which produces a human monoclonal anti-CD38 antibody having human heavy chain and light chain variable regions which comprise
(i) the human light chain variable amino acid sequence as set forth in SEQ ID No:2, and the human heavy chain variable amino sequence as set forth in SEQ ID No:7;
(ii) the human light chain variable amino acid sequence as set forth in SEQ ID No:12, and the human heavy chain variable amino sequence as set forth in SEQ ID No:17;
(iii) the human light chain variable amino acid sequence as set forth in SEQ ID No:22, and the human heavy chain variable amino sequence as set forth in SEQ ID No:27; or
(iv) conservative sequences modifications of the human light chain and human heavy chain variable amino acid sequences as set forth in (i), (ii) or (iii).

The present invention provides a eukaryotic or prokaryotic host cell which produces a peptide according as defined above.

The present invention provides a eukaryotic or prokaryotic host cell containing an expression vector as defined above.

The present invention provides a transgenic nonhuman animal or plant comprising nucleic acids encoding a human heavy chain and a human light chain, wherein the animal or plant produces a detectable amount of a peptide as defined above.

The present invention provides an immunoconjugate comprising a peptide as defined above linked to a cytotoxic agent, a radioisotope, or a drug.

The present invention provides an immunoconjugate comprising a peptide as defined above, wherein the peptide is a monomeric IgM antibody linked to a cytotoxic agent, a radioisotope, or a drug.

The present invention provides a bispecific or multispecific molecule comprising a peptide as defined above and a binding specificity for a human effector cell.

The present invention provides a bispecific or multispecific molecule comprising a peptide as defined above and a binding specificity for CD3, CD4, CD138, IL-15R, membrane bound or receptor bound TNF-α, a human Fc receptor, or membrane bound or receptor bound IL-15.

The present invention provides a pharmaceutical composition comprising a peptide as defined above or an immunoconjugate as defined above and a pharmaceutically acceptable carrier.

The present invention provides a pharmaceutical composition as defined above comprising one or more further therapeutic agents.

The present invention provides a method of inhibiting growth and/or proliferation of a cell expressing CD38, comprising administration of a peptide as defined above, an immunoconjugate as defined above, a pharmaceutical composition as defined above, or an expression vector as defined above, such that the growth and/or proliferation of the cell is inhibited.

The present invention provides a method of treating a disease or disorder involving cells expressing CD38 in a subject, which method comprises administration of a peptide as defined above, an immunoconjugate as defined above, a pharmaceutical composition as defined above, or an expression vector as defined above to a subject in need thereof.

The present invention provides a method of preventing a disease or disorder involving cells expressing CD38 in a subject, which method comprises administration of a peptide as defined above, an immunoconjugate as defined above, a pharmaceutical composition as defined above, or an expression vector as defined above to a subject in need thereof.

In one embodiment the disease or disorder is rheumatoid arthritis.

In one embodiment the disease or disorder is multiple myeloma.

In one embodiment the method comprises administration of one or more further therapeutic agents to the subject.

In one embodiment the one or more further therapeutic agents are selected from a chemotherapeutic agent, an anti-inflammatory agent, or an immunosuppressive and/or immunomodulatory agent.

In one embodiment the one or more further therapeutic agents are selected from a group consisting of cisplatin, gefitinib, cetuximab, rituximab, bevacizumab, erlotinib, bortezomib, thalidomide, pamidronate, zoledronic acid, clodronate, risendronate, ibandronate, etidronate, alendronate, tiludronate, arsenic trioxide, lenalidomide, filgrastim, pegfilgrastim, sargramostim, suberoylanilide hydroxamic acid, and SCIO-469.

The present invention provides an in vitro method for detecting the presence of CD38 antigen, or a cell expressing CD38, in a sample comprising:

a) contacting the sample with a peptide as defined above under conditions that allow for formation of a complex between the peptide and CD38; and b) detecting the formation of a complex.

The present invention provides a kit for detecting the presence of CD38 antigen, or a cell expressing CD38, in a sample comprising a peptide as defined above.

The present invention provides an in vivo method for detecting CD38 antigen, or a cell expressing CD38, in a subject comprising:

a) administering peptide as defined above under conditions that allow for formation of a complex between the peptide and CD38; and b) detecting the formed complex.

The present invention provides an anti-idiotypic antibody binding to an antibody as defined above.

In one embodiment the anti-idiotypic antibody is used for detecting the level of a antibody as defined above in a sample.

In one embodiment the anti anti-idiotypic is used for detecting the level of human monoclonal antibody against CD38 in a sample.

BRIEF DESCRIPTION OF THE FIGURES

FIG. 1A shows the binding of −003, −005 and the isotype control antibody HuMab-KLH to CD38-transfected CHO (CHO-CD38) cells as measured by flow cytometry. The experimental setup is described in Example 4.

FIG. 1B shows the binding of −024 and HuMab-KLH to CD38-transfected CHO (CHO-CD38) cells as measured by flow cytometry. The experimental setup is described in Example 4.

FIG. 2A shows the binding of −003, −005 and HuMab-KLH to Daudi cells as measured by flow cytometry. The experimental setup is described in Example 4.

FIG. 2B shows the binding of −024 and HuMab-KLH to Daudi cells as measured by flow cytometry. The experimental setup is described in Example 4.

FIG. 4A shows the ability of −003 and −005 to induce lysis of Daudi cells by ADCC as compared to rituximab and HuMab-KLH. The experimental setup is described in Example 5.

FIG. 4B shows the ability of −024 to induce lysis of Daudi cells by ADCC as compared to HuMab-KLH. The experimental setup is described in Example 5.

FIG. 5A shows the ability of −003, −005 and −024 to induce lysis of fresh multiple myeloma tumor cells by ADCC as compared to HuMab-KLH. The experimental setup is described in Example 5.

FIG. 5B shows the ability of −003, −005 and −024 to induce lysis of fresh plasma cell leukemia tumor cells by ADCC as compared to HuMab-KLH. The experimental setup is described in Example 5.

FIG. 9A shows the CDC-mediated lysis of CHO-CD38 cells induced by −003 and −005 compared to HuMab-KLH. The experimental setup is described in Example 6.

FIG. 9B shows the CDC-mediated lysis of CHO-CD38 cells induced by −024 compared with HuMab-KLH. The experimental setup is described in Example 6.

FIG. 11 shows that −003 and −005 do not cross-block binding to CD38. The experimental setup is described in Example 7.

FIG. 14A shows immunohistological staining of liver endothelium with CD31. The experimental setup is described in Example 10.

FIG. 14B shows immunohistological staining of liver endothelium with vWF. The experimental setup is described in Example 10.

FIG. 14C shows immunohistological staining of liver endothelium with anti-KLH. The experimental setup is described in Example 10.

FIG. 14D shows immunohistological staining of liver endothelium with −003. The experimental setup is described in Example 10.

FIG. 14E shows immunohistological staining of liver endothelium with −005. The experimental setup is described in Example 10.

FIG. 21 shows CD38 staining of B cells in xenografts before implantation (A), or after treatment with anti-KLH (B), or −005 (C). Methods are described in Example 15.

FIG. 22 shows CD138 staining of B cells in xenografts before implantation (A), or after treatment with anti-KLH (B), or −005 (C). Methods are described in Example 15.

FIG. 23 shows the binding of −003 and −005 to wild type and mutant human CD38 as measured by ELISA. 23A: Binding of −003 and −005 to T237A mutant human CD38. 23B: Binding of −003 and −005 to Q272R mutant human CD38. 23C: Binding of −003 and −005 to S274F mutant human CD38. Methods are described in Example 17.

FIG. 24 shows the effect of −003 and −005 compared to HuMab-KLH on proliferation (A), IL-6 production (B) and IFN-γ production (C) of human PBMCs. Methods are described in Examples 18, 19 and 20, respectively.

FIG. 25 shows the enzymatic production of cGDPribose in the presence of various concentrations of −003 (B), −005 (C), −024 (D) or anti-KLH (A). Methods are described in Example 23.

Figure 3:
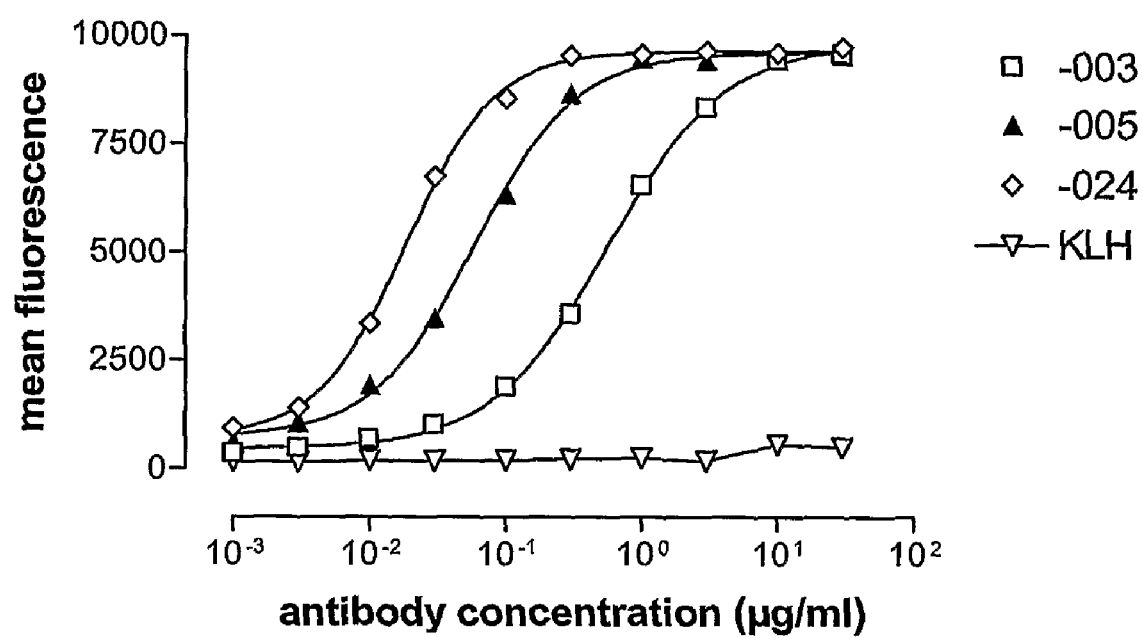
FIG. 3 shows the binding of −003, −005, −024 and HuMab-KLH to multiple myeloma cells. The experimental setup is described in Example 4.

The sequences of the invention are shown in the attached sequence listing.

SEQ ID No:1 is the nucleotide sequence of the $V_L$ region of the antibody −003.

SEQ ID No:2 is the amino acid sequence of the $V_L$ region of the antibody −003.

SEQ ID No:3 is the amino acid sequence of the $V_L$ CDR1 of the antibody −003 comprising aa 24-34 of SEQ ID No:2.

SEQ ID No:4 is the amino acid sequence of the $V_L$ CDR2 of the antibody −003 comprising aa 50-56 of SEQ ID No:2.

SEQ ID No:5 is the amino acid sequence of the $V_L$ CDR3 of the antibody −003 comprising aa 89-97 of SEQ ID No:2.

SEQ ID No:6 is the nucleotide sequence of the $V_H$ region of the antibody −003.

SEQ ID No:7 is the amino acid sequence of the $V_H$ region of the antibody −003.

SEQ ID No:8 is the amino acid sequence of the $V_H$ CDR1 of the antibody −003 comprising aa 31-35 of SEQ ID No:7.

SEQ ID No:9 is the amino acid sequence of the $V_H$ CDR2 of the antibody −003 comprising aa 50-66 of SEQ ID No:7.

SEQ ID No:10 is the amino acid sequence of the $V_H$ CDR3 of the antibody −003 comprising aa 99-109 of SEQ ID No:7.

SEQ ID No:11 is the nucleotide sequence of the $V_L$ region of the antibody −005.

SEQ ID No:12 is the amino acid sequence of the $V_L$ region of the antibody −005.

SEQ ID No:13 is the amino acid sequence of the $V_L$ CDR1 of the antibody −005 comprising aa 24-34 of SEQ ID No:12.

SEQ ID No:14 is the amino acid sequence of the $V_L$ CDR2 of the antibody −005 comprising aa 50-56 of SEQ ID No:12.

SEQ ID No:15 is the amino acid sequence of the $V_L$ CDR3 of the antibody −005 comprising aa 89-97 of SEQ ID No:12.

SEQ ID No:16 is the nucleotide sequence of the $V_H$ region of the antibody −005.

SEQ ID No:17 is the amino acid sequence of the $V_H$ region of the antibody −005.

SEQ ID No:18 is the amino acid sequence of the $V_H$ CDR1 of the antibody −005 comprising aa 31-35 of SEQ ID No:17.

SEQ ID No:19 is the amino acid sequence of the $V_H$ CDR2 of the antibody −005 comprising aa 50-66 of SEQ ID No:17.

SEQ ID No:20 is the amino acid sequence of the $V_H$ CDR3 of the antibody −005 comprising aa 99-111 of SEQ ID No:17.

SEQ ID No:21 is the nucleotide sequence of the $V_L$ region of the antibody −024.

SEQ ID No:22 is the amino acid sequence of the $V_L$ region of the antibody −024.

SEQ ID No:23 is the amino acid sequence of the $V_L$ CDR1 of the antibody −024 comprising aa 24-34 of SEQ ID No:22.

SEQ ID No:24 is the amino acid sequence of the $V_L$ CDR2 of the antibody −024 comprising aa 50-56 of SEQ ID No:22.

SEQ ID No:25 is the amino acid sequence of the $V_L$ CDR3 of the antibody −024 comprising aa 89-97 of SEQ ID No:22.

SEQ ID No:26 is the nucleotide sequence of the $V_H$ region of the antibody −024.

SEQ ID No:27 is the amino acid sequence of the $V_H$ region of the antibody −024.

SEQ ID No:28 is the amino acid sequence of the $V_H$ CDR1 of the antibody −024 comprising aa 31-35 of SEQ ID No:27.

SEQ ID No:29 is the amino acid sequence of the $V_H$ CDR2 of the antibody −024 comprising aa 50-66 of SEQ ID No:27.

SEQ ID No:30 is the amino acid sequence of the $V_H$ CDR3 of the antibody −024 comprising aa 99-111 of SEQ ID No:27.

SEQ ID No:31 is the sequence of human CD38.

SEQ ID No:32 is the sequence of a mutant human CD38, wherein the threonine residue in position 237 has been substituted with an alanine residue.

SEQ ID No:33 is the sequence of a mutant human CD38, wherein the glutamine residue in position 272 has been substituted with an arginine residue.

SEQ ID No:34 is the sequence of a mutant human CD38, wherein the serine residue in position 274 has been substituted with a phenylalanine residue.

DETAILED DESCRIPTION OF THE INVENTION

The present invention provides CD38 binding peptides ("CD38BPs"), which may be useful in the treatment, diagnosis and prevention of a variety of disorders involving cells expressing CD38, such as multiple myeloma.

In one embodiment, a CD38BP of the invention is the antibody −003. −003 is a human monoclonal IgG1 antibody having a $V_L$ region consisting of the sequence of SEQ ID No:2 and a $V_H$ region consisting of the sequence of SEQ ID No:7.

In one embodiment, a CD38BP of the invention is the antibody −005. −005 is a human monoclonal IgG1 antibody having a $V_L$ region consisting of the sequence of SEQ ID No:12 and a $V_H$ region consisting of the sequence of SEQ ID No:17.

In one embodiment, a CD38BP of the invention is the antibody −024. −024 is a human monoclonal IgG1 antibody having a $V_L$ region consisting of the sequence of SEQ ID No:22 and a $V_H$ region consisting of the sequence of SEQ ID No:27.

Antibodies interact with target antigens primarily through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see for instance Riechmann, L. et al., Nature 332, 323-327 (1998), Jones, P. et al., Nature 321, 522-525 (1986) and Queen, C. et al., PNAS USA 86, 10029-10033 (1989)).

Since it is well known in the art that antibody heavy chain CDR3 domains play a particularly important role in the binding specificity/affinity of an antibody for an antigen (Ditzel H J, et al., J. Immunol. 157(2), 739-49 (1996), Barbas S M et al., J. Am. Chem. Soc. 116, 2161-2162 (1994), and Barbas S M et al., Proc Natl Acad Sci USA 92(7), 2529-33 (1995), the CD38BPs of the invention may comprise the heavy chain CDR3s of –003 or –005 or –024. The CD38BPs of the invention may also comprise the heavy and light chain CDR3s of –003 or –005 or –024. The CD38BPs of the invention may further comprise the CDR2s of –003 and –005 and –024, respectively. The CD38BPs of the invention may further comprise the CDR1s of –003 and –005 and –024, respectively.

The present invention provides CD38BPs, which compete with –003 for binding to CD38.

The present invention provides CD38BPs, which compete with –005 for binding to CD38.

The present invention provides CD38BPs, which compete with –024 for binding to CD38.

In one embodiment, the competition is determined by use of an ELISA as described in the Examples section.

In one embodiment, the competition is determined by use of a FACS as described in the Examples section.

The present invention provides a CD38BP that specifically binds to a CD38 epitope, which epitope is also specifically bound by –003 or –005 or –024.

The present invention provides a CD38BP having substantially the same specific binding characteristics for binding human CD38 as –003 or –005 or –024.

The present invention provides a CD38BP comprising a $V_L$ CDR1 consisting essentially of SEQ ID No:3.

The present invention provides a CD38BP comprising a $V_L$ CDR2 consisting essentially of SEQ ID No:4.

The present invention provides a CD38BP comprising a $V_L$ CDR3 consisting essentially of SEQ ID No:5.

The present invention provides a CD38BP comprising a $V_L$ CDR3 consisting essentially of SEQ ID No:5 and a $V_L$ CDR1 consisting essentially of SEQ ID No:3.

The present invention provides a CD38BP comprising a $V_L$ CDR3 consisting essentially of SEQ ID No:5 and a $V_L$ CDR2 consisting essentially of SEQ ID No:4.

The present invention provides a CD38BP comprising a $V_L$ CDR3 consisting essentially of SEQ ID No:5 and a $V_L$ CDR2 consisting essentially of SEQ ID No:4 and a $V_L$ CDR1 consisting essentially of SEQ ID No:3.

The present invention provides a CD38BP comprising a $V_H$ CDR1 consisting essentially of SEQ ID No:8.

The present invention provides a CD38BP comprising a $V_H$ CDR2 consisting essentially of SEQ ID No:9.

The present invention provides a CD38BP comprising a $V_H$ CDR3 consisting essentially of SEQ ID No:10.

The present invention provides a CD38BP comprising a $V_H$ CDR3 consisting essentially of SEQ ID No:10 and a $V_H$ CDR1 consisting essentially of SEQ ID No:8.

The present invention provides a CD38BP comprising a $V_H$ CDR3 consisting essentially of SEQ ID No:10 and a $V_H$ CDR2 consisting essentially of SEQ ID No:9.

The present invention provides a CD38BP comprising a $V_H$ CDR3 consisting essentially of SEQ ID No:10 and a $V_H$ CDR2 consisting essentially of SEQ ID No:9 and a $V_H$ CDR1 consisting essentially of SEQ ID No:8.

The present invention provides a CD38BP comprising a $V_L$ CDR1 consisting essentially of SEQ ID No:13.

The present invention provides a CD38BP comprising a $V_L$ CDR2 consisting essentially of SEQ ID No:14.

The present invention provides a CD38BP comprising a $V_L$ CDR3 consisting essentially of SEQ ID No:15.

The present invention provides a CD38BP comprising a $V_L$ CDR3 consisting essentially of SEQ ID No:15 and a $V_L$ CDR1 consisting essentially of SEQ ID No:13.

The present invention provides a CD38BP comprising a $V_L$ CDR3 consisting essentially of SEQ ID No:15 and a $V_L$ CDR2 consisting essentially of SEQ ID No:14.

The present invention provides a CD38BP comprising a $V_L$ CDR3 consisting essentially of SEQ ID No:15 and a $V_L$ CDR2 consisting essentially of SEQ ID No:14 and a $V_L$ CDR1 consisting essentially of SEQ ID No:13.

The present invention provides a CD38BP comprising a $V_H$ CDR1 consisting essentially of SEQ ID No:18.

The present invention provides a CD38BP comprising a $V_H$ CDR2 consisting essentially of SEQ ID No:19.

The present invention provides a CD38BP comprising a $V_H$ CDR3 consisting essentially of SEQ ID No:20.

The present invention provides a CD38BP comprising a $V_H$ CDR3 consisting essentially of SEQ ID No:20 and a $V_H$ CDR1 consisting essentially of SEQ ID No:18.

The present invention provides a CD38BP comprising a $V_H$ CDR3 consisting essentially of SEQ ID No:20 and a $V_H$ CDR2 consisting essentially of SEQ ID No:19.

The present invention provides a CD38BP comprising a $V_H$ CDR3 consisting essentially of SEQ ID No:20 and a $V_H$ CDR2 consisting essentially of SEQ ID No:19 and a $V_H$ CDR1 consisting essentially of SEQ ID No:18.

The present invention provides a CD38BP comprising a $V_L$ CDR1 consisting essentially of SEQ ID No:23.

The present invention provides a CD38BP comprising a $V_L$ CDR2 consisting essentially of SEQ ID No:24.

The present invention provides a CD38BP comprising a $V_L$ CDR3 consisting essentially of SEQ ID No:25.

The present invention provides a CD38BP comprising a $V_L$ CDR3 consisting essentially of SEQ ID No:25 and a $V_L$ CDR1 consisting essentially of SEQ ID No:23.

The present invention provides a CD38BP comprising a $V_L$ CDR3 consisting essentially of SEQ ID No:25 and a $V_L$ CDR2 consisting essentially of SEQ ID No:24.

The present invention provides a CD38BP comprising a $V_L$ CDR3 consisting essentially of SEQ ID No:25 and a $V_L$ CDR2 consisting essentially of SEQ ID No:24 and a $V_L$ CDR1 consisting essentially of SEQ ID No:23.

The present invention provides a CD38BP comprising a $V_H$ CDR1 consisting essentially of SEQ ID No:28.

The present invention provides a CD38BP comprising a $V_H$ CDR2 consisting essentially of SEQ ID No:29.

The present invention provides a CD38BP comprising a $V_H$ CDR3 consisting essentially of SEQ ID No:30.

The present invention provides a CD38BP comprising a $V_H$ CDR3 consisting essentially of SEQ ID No:30 and a $V_H$ CDR1 consisting essentially of SEQ ID No:28.

The present invention provides a CD38BP comprising a $V_H$ CDR3 consisting essentially of SEQ ID No:30 and a $V_H$ CDR2 consisting essentially of SEQ ID No:29.

The present invention provides a CD38BP comprising a $V_H$ CDR3 consisting essentially of SEQ ID No:30 and a $V_H$ CDR2 consisting essentially of SEQ ID No:29 and a $V_H$ CDR1 consisting essentially of SEQ ID No:28.

The present invention provides a CD38BP comprising (a) a first $V_L$ region comprising three $V_L$ CDRs, which independently of each other consist essentially of SEQ ID No:3, SEQ ID No:4, and SEQ ID No:5; and (b) a first $V_H$ region comprising three $V_H$ CDRs, which independently of each other consist essentially of SEQ ID No:8, SEQ ID No:9, and SEQ ID No:10.

The present invention provides a CD38BP comprising
(a) a first $V_L$ region comprising three $V_L$ CDRs, which independently of each other consist essentially of SEQ ID No:13, SEQ ID No:14, and SEQ ID No:15; and
(b) a first $V_H$ region comprising three $V_H$ CDRs, which independently of each other consist essentially of SEQ ID No:18, SEQ ID No:19, and SEQ ID No:20.

The present invention provides a CD38BP comprising
(a) a first $V_L$ region comprising three $V_L$ CDRs, which independently of each other consist essentially of SEQ ID No:23, SEQ ID No:24, and SEQ ID No:25; and
(b) a first $V_H$ region comprising three $V_H$ CDRs, which independently of each other consist essentially of SEQ ID No:28, SEQ ID No:29, and SEQ ID No:30.

In one embodiment, the $V_L$ region and the $V_H$ region are present on the same chain in the peptide.

In a further embodiment, the $V_L$ region and the $V_H$ region are separated by a flexible linker.

In one embodiment, the $V_L$ region and the $V_H$ region are present on the separate chains in the peptide.

In a further embodiment, the $V_L$ region and the $V_H$ region are present on the separate chains in the peptide in the context of an immunoglobulin fold protein.

In one embodiment, the first $V_L$ region and the first $V_H$ region are oriented such that the three CDRs in the $V_L$ region and the three CDRs in the $V_H$ region cooperatively associate to contribute in selectively and/or specifically bind an antigenic determinant on human CD38.

In a further embodiment, the peptide comprises a second $V_L$ region identical to the first $V_L$ region and a second $V_H$ region identical to the first $V_H$ region, where the second $V_L$ region and the second $V_H$ region cooperatively associate to contribute in selectively and/or specifically bind an antigenic determinant on human CD38.

The present invention provides a CD38BP comprising a $V_L$ region that is a functional variant of the $V_L$ region of –003 or –005 or –024.

In one embodiment, the $V_L$ region of the CD38BP consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:2 or SEQ ID No:12 or SEQ ID No:22, respectively. In one embodiment, the CD38BP has at least about 50%, at least about 60%, at least about 70%, at least about 80%, at least about 90%, or at least about 95% of the epitope binding characteristics of –003 or –005 or –024, respectively.

The present invention provides a CD38BP comprising a $V_H$ region that is a functional variant of the $V_H$ region of –003 or –005 or –024.

In one embodiment, the $V_H$ region of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:7 or SEQ ID No:17 or SEQ ID No:27, respectively. In one embodiment, the CD38BP has at least about 50%, at least about 60%, at least about 70%, at least about 80%, at least about 90%, or at least about 95% of the epitope binding characteristics of –003 or –005 or –024, respectively.

The present invention provides a CD38BP comprising at least one CDR that is a functional variant of a CDR of –003 or –005 or –024.

In one embodiment, at least one of the CDRs of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:3, SEQ ID No:4, SEQ ID No:5, SEQ ID No:8, SEQ ID No:9, or SEQ ID No:10, or according to SEQ ID No:13, SEQ ID No:14, SEQ ID No:15, SEQ ID No:18, SEQ ID No:19, or SEQ ID No:20, or according to SEQ ID No:23, SEQ ID No:24, SEQ ID No:25, SEQ ID No:28, SEQ ID No:29, or SEQ ID No:30, respectively. In one embodiment, the CD38BP has at least about 50%, at least about 60%, at least about 70%, at least about 80%, at least about 90%, or at least about 95% of the epitope binding characteristics of –003 or –005 or –024, respectively.

In one embodiment, the CD38BP has at least about 50%, at least about 60%, at least about 70%, at least about 80%, at least about 90%, or at least about 95% of the affinity, avidity or specificity of –003 or –005 or –024.

In one embodiment, the CD38BP competes with either –003 or –005 or –024 for binding to CD38. In a further embodiment, the competition is determined by use of an ELISA as described in the Examples section. In another further embodiment, the competition is determined by use of a FACS as described in the Examples section.

In one embodiment, the CD38BP specifically binds to a CD38 epitope, which epitope is also specifically bound by –003 or –005 or –024.

In one embodiment, the CD38BP binds to human CD38 with greater affinity than –003 or –005 or –024.

In one embodiment, the CD38BP has substantially the same specific CD38 binding characteristics as –003 or –005 or –024.

In one embodiment, the CD38BP is substantially free of other CD38 binding peptides.

In one embodiment, a CD38BP of the present invention is an antibody. In a further embodiment, the CD38BP is a human antibody. In another further embodiment, the CD38BP is a humanized antibody. In another further embodiment, the CD38BP is a chimeric antibody.

In one embodiment, the antibody of the present invention is a monoclonal antibody.

In one embodiment, the antibody of the present invention is an IgG1, IgG2, IgG3, IgG4, IgD, IgA, IgE, or IgM antibody. In a further embodiment, the antibody is an IgG1 antibody. In a further embodiment, the antibody is a IgG1,κ antibody. In another further embodiment, the antibody is an IgM antibody. In a further embodiment, the antibody is an IgM,κ antibody.

In one embodiment, the antibody of the present invention is an antibody fragment or a single chain antibody.

In one embodiment, the CD38BP is glycosylated in a eukaryotic cell.

In one embodiment, the CD38BP further comprises a chelator linker for attaching a radioisotope.

In one embodiment, the CD38BP is in a substantially isolated form.

The present invention provides an isolated nucleic acid encoding a CD38BP of the present invention.

The present invention provides an expression vector comprising a nucleic acid sequence encoding a CD38BP of the present invention.

In one embodiment, the expression vector comprises a $V_L$ nucleotide sequence of SEQ ID No:1, a $V_H$ nucleotide sequence of SEQ ID No:6, or a $V_L$ nucleotide sequence of SEQ ID No:1 and a $V_H$ nucleotide sequence of SEQ ID No:6.

In one embodiment, the expression vector comprises a $V_L$ nucleotide sequence of SEQ ID No:11, a $V_H$ nucleotide sequence of SEQ ID No:16, or a $V_L$ nucleotide sequence of SEQ ID No:11 and a $V_H$ nucleotide sequence of SEQ ID No:16.

In one embodiment, the expression vector comprises a $V_L$ nucleotide sequence of SEQ ID No:21, a $V_H$ nucleotide sequence of SEQ ID No:26, or a $V_L$ nucleotide sequence of SEQ ID No:21 and a $V_H$ nucleotide sequence of SEQ ID No:26.

In a further embodiment, the expression vector further comprises a nucleotide sequence encoding the constant region of a light chain, a heavy chain or both light and heavy chains of a human antibody.

In a further embodiment, the nucleotide sequence encoding the constant region of a light chain, a heavy chain or both light and heavy chains of a human antibody encodes a IgG1 antibody.

The present invention provides a hybridoma which produces a human monoclonal anti-CD38 antibody encoded by human light chain and human heavy chain nucleic acids comprising nucleotide sequences in the variable light chain region as set forth in SEQ ID No:1, or conservative sequence modifications thereof, and nucleotide sequences in the variable heavy chain region as set forth in SEQ ID No:6, or conservative sequence modifications thereof. In one embodiment, the human light chain nucleic acids comprises a nucleotide sequence as set forth in SEQ ID No:1, and the human heavy chain nucleic acids comprises a nucleotide sequence as set forth in SEQ ID No:6.

The present invention provides a hybridoma which produces a human monoclonal anti-CD38 antibody having human heavy chain and light chain variable regions which comprise the human light chain variable amino acid sequence as set forth in SEQ ID No:2, or conservative sequence modifications thereof, and the human light chain variable amino sequence as set forth in SEQ ID No:7, or conservative sequence modifications thereof. In one embodiment, the human light chain variable region comprises an amino acid sequence as set forth in SEQ ID No:2, and the human heavy chain variable region comprises an amino acid sequence as set forth in SEQ ID No:7.

The present invention provides a transfectoma which produces a human monoclonal anti-CD38 antibody encoded by human light chain variable nucleic acids as set forth in SEQ ID No:1, or conservative sequence modifications thereof, and human heavy chain nucleic acids as set forth SEQ ID No:6, or conservative sequence modifications thereof. In one embodiment, the human monoclonal anti-CD38 antibody is encoded by human light chain variable nucleic acids as set forth in SEQ ID No:1, and human heavy chain nucleic acids as set forth SEQ ID No:6.

The present invention provides a transfectoma which produces a human monoclonal anti-CD38 antibody having human light chain and heavy chain variable regions which comprise the human light chain variable amino acid sequence as set forth in SEQ ID No:2, or conservative sequence modifications thereof, and the human heavy chain variable amino sequence as set forth in SEQ ID No:7, or conservative sequence modifications thereof. In one embodiment, the human light chain comprises the human light chain variable amino acid sequence as set forth in SEQ ID No:2, and the human heavy chain comprises the human heavy chain variable amino sequence as set forth in SEQ ID No:7.

The present invention provides a hybridoma which produces a human monoclonal anti-CD38 antibody encoded by human light chain and human heavy chain nucleic acids comprising nucleotide sequences in the variable light chain region as set forth in SEQ ID No:11, or conservative sequence modifications thereof, and nucleotide sequences in the variable heavy chain region as set forth in SEQ ID No:16, or conservative sequence modifications thereof. In one embodiment, the human light chain nucleic acids comprises a nucleotide sequence as set forth in SEQ ID No:11, and the human heavy chain nucleic acids comprises a nucleotide sequence as set forth in SEQ ID No:16.

The present invention provides a hybridoma which produces a human monoclonal anti-CD38 antibody having human heavy chain and light chain variable regions which comprise the human light chain variable amino acid sequence as set forth in SEQ ID No:12, or conservative sequence modifications thereof, and the human light chain variable amino sequence as set forth in SEQ ID No:17, or conservative sequence modifications thereof. In one embodiment, the human light chain variable region comprises an amino acid sequence as set forth in SEQ ID No:12, and the human heavy chain variable region comprises an amino acid sequence as set forth in SEQ ID No:17.

The present invention provides a transfectoma which produces a human monoclonal anti-CD38 antibody encoded by human light chain variable nucleic acids as set forth in SEQ ID No:11, or conservative sequence modifications thereof, and human heavy chain nucleic acids as set forth SEQ ID No:16, or conservative sequence modifications thereof. In one embodiment, the human monoclonal anti-CD38 antibody is encoded by human light chain variable nucleic acids as set forth in SEQ ID No:11, and human heavy chain nucleic acids as set forth SEQ ID No:16.

The present invention provides a transfectoma which produces a human monoclonal anti-CD38 antibody having human light chain and heavy chain variable regions which comprise the human light chain variable amino acid sequence as set forth in SEQ ID No:12, or conservative sequence modifications thereof, and the human heavy chain variable amino sequence as set forth in SEQ ID No:17, or conservative sequence modifications thereof. In one embodiment, the human light chain comprises the human light chain variable amino acid sequence as set forth in SEQ ID No:12, and the human heavy chain comprises the human heavy chain variable amino sequence as set forth in SEQ ID No:17.

The present invention provides a hybridoma which produces a human monoclonal anti-CD38 antibody encoded by human light chain and human heavy chain nucleic acids comprising nucleotide sequences in the variable light chain region as set forth in SEQ ID No:21, or conservative sequence modifications thereof, and nucleotide sequences in the variable heavy chain region as set forth in SEQ ID No:26, or conservative sequence modifications thereof. In one embodiment, the human light chain nucleic acids comprises a nucleotide sequence as set forth in SEQ ID No:21, and the human heavy chain nucleic acids comprises a nucleotide sequence as set forth in SEQ ID No:26.

The present invention provides a hybridoma which produces a human monoclonal anti-CD38 antibody having human heavy chain and light chain variable regions which comprise the human light chain variable amino acid sequence as set forth in SEQ ID No:22, or conservative sequence modifications thereof, and the human light chain variable amino sequence as set forth in SEQ ID No:27, or conservative sequence modifications thereof. In one embodiment, the human light chain variable region comprises an amino acid sequence as set forth in SEQ ID No:22, and the human heavy chain variable region comprises an amino acid sequence as set forth in SEQ ID No:27.

The present invention provides a transfectoma which produces a human monoclonal anti-CD38 antibody encoded by human light chain variable nucleic acids as set forth in SEQ ID No:21, or conservative sequence modifications thereof, and human heavy chain nucleic acids as set forth SEQ ID No:26, or conservative sequence modifications thereof. In one embodiment, the human monoclonal anti-CD38 antibody is encoded by human light chain variable nucleic acids as set forth in SEQ ID No:21, and human heavy chain nucleic acids as set forth SEQ ID No:26.

The present invention provides a transfectoma which produces a human monoclonal anti-CD38 antibody having human light chain and heavy chain variable regions which comprise the human light chain variable amino acid sequence as set forth in SEQ ID No:22, or conservative sequence modifications thereof, and the human heavy chain variable amino sequence as set forth in SEQ ID No:27, or conservative sequence modifications thereof. In one embodiment, the human light chain comprises the human light chain variable amino acid sequence as set forth in SEQ ID No:22, and the human heavy chain comprises the human heavy chain variable amino sequence as set forth in SEQ ID No:27.

The present invention provides a eukaryotic or prokaryotic host cell which produces a CD38BP of the present invention.

The present invention provides a eukaryotic or prokaryotic host cell containing an expression vector of the present invention.

The present invention provides a transgenic nonhuman animal or plant comprising nucleic acids encoding a human heavy chain and a human light chain, wherein the animal or plant produces a detectable amount of a CD38BP of the present invention.

The present invention provides an immunoconjugate comprising a CD38BP of the present invention linked to a cytotoxic agent, a radioisotope, or a drug. In one embodiment, the peptide is a monomeric IgM antibody linked to a cytotoxic agent, a radioisotope, or a drug.

The present invention provides a bispecific or multispecific molecule comprising a CD38BP of the present invention and a binding specificity for a human effector cell. In one embodiment, the binding specificity for a human effector cell is a binding specificity for CD3, CD4, CD138, IL-15R, membrane bound or receptor bound TNF-α, a human Fc receptor, or membrane bound or receptor bound IL-15.

The present invention provides an anti-idiotypic antibody binding to a CD38BP of the present invention.

The present invention provides the use of an anti-idiotypic antibody of the present invention for detecting the level of human monoclonal antibody against CD38 in a sample.

The following is a list of selected embodiments of the present invention.

Embodiment 1

An antibody binding to human CD38 encoded by human light chain and human heavy chain nucleic acids comprising nucleotide sequences in their variable regions as set forth in SEQ ID No:1 and SEQ ID No:6, respectively, or conservative sequence modifications thereof.

Embodiment 2

An antibody binding to human CD38 encoded by human light chain and human heavy chain nucleic acids comprising nucleotide sequences in their variable regions as set forth in SEQ ID No:1 and SEQ ID No:6, respectively.

Embodiment 3

An antibody binding to human CD38 encoded by human light chain and human heavy chain nucleic acids comprising nucleotide sequences in their variable regions as set forth in SEQ ID No:11 and SEQ ID No:16, respectively, or conservative sequence modifications thereof.

Embodiment 4

An antibody binding to human CD38 encoded by human light chain and human heavy chain nucleic acids comprising nucleotide sequences in their variable regions as set forth in SEQ ID No:11 and SEQ ID No:16, respectively.

Embodiment 5

An antibody binding to human CD38 encoded by human light chain and human heavy chain nucleic acids comprising nucleotide sequences in their variable regions as set forth in SEQ ID No:21 and SEQ ID No:26, respectively, or conservative sequence modifications thereof.

Embodiment 6

An antibody binding to human CD38 encoded by human light chain and human heavy chain nucleic acids comprising nucleotide sequences in their variable regions as set forth in SEQ ID No:21 and SEQ ID No:26, respectively.

Embodiment 7

A peptide which competes with an antibody according to embodiment 2 for binding to CD38.

Embodiment 8

A peptide according to embodiment 7, wherein the competition is determined by use of an ELISA as described in Example 8 or 9 of the specification.

Embodiment 9

A peptide according to embodiment 7, wherein the competition is determined by use of cross-blocking measurements as described in Example 7 of the specification.

Embodiment 10

A peptide that specifically binds to a CD38 epitope, which epitope is also specifically bound by an antibody according to embodiment 2.

Embodiment 11

A peptide having substantially the same specific binding characteristics for binding human CD38 as an antibody according to embodiment 2.

Embodiment 12

A peptide comprising a $V_L$ CDR1 consisting essentially of SEQ ID No:3.

Embodiment 13

A peptide comprising a $V_L$ CDR2 consisting essentially of SEQ ID No:4.

Embodiment 14

A peptide comprising a $V_L$ CDR3 consisting essentially of SEQ ID No:5.

Embodiment 15

A peptide according to embodiment 14, which peptide also comprises a $V_L$ CDR1 consisting essentially of SEQ ID No:3.

Embodiment 16

A peptide according to embodiment 14, which peptide also comprises a $V_L$ CDR2 consisting essentially of SEQ ID No:4.

Embodiment 17

A peptide according to embodiment 16, which peptide also comprises a $V_L$ CDR1 consisting essentially of SEQ ID No:3.

Embodiment 18

A peptide comprising a $V_H$ CDR1 consisting essentially of SEQ ID No:8.

Embodiment 19

A peptide comprising a $V_H$ CDR2 consisting essentially of SEQ ID No:9.

Embodiment 20

A peptide comprising a $V_H$ CDR3 consisting essentially of SEQ ID No:10.

Embodiment 21

A peptide according to embodiment 20, which peptide also comprises a $V_H$ CDR1 consisting essentially of SEQ ID No:8.

Embodiment 22

A peptide according to embodiment 20, which peptide also comprises a $V_H$ CDR2 consisting essentially of SEQ ID No:9.

Embodiment 23

A peptide according to embodiment 22, which peptide also comprises a $V_H$ CDR1 consisting essentially of SEQ ID No:8.

Embodiment 24

A peptide comprising
(a) a first $V_L$ region comprising three $V_L$ CDRs, which independently of each other consist essentially of SEQ ID No:3, SEQ ID No:4, and SEQ ID No:5; and
(b) a first $V_H$ region comprising three $V_H$ CDRs, which independently of each other consist essentially of SEQ ID No:8, SEQ ID No:9, and SEQ ID No:10.

Embodiment 25

A peptide according to embodiment 24, wherein the $V_L$ region and the $V_H$ region are present on the same chain in the peptide.

Embodiment 26

A peptide according to embodiment 25, wherein the $V_L$ region and the $V_H$ region are separated by a flexible linker.

Embodiment 27

A peptide according to embodiment 24, wherein the $V_L$ region and the $V_H$ region are present on the separate chains in the peptide.

Embodiment 28

A peptide according to embodiment 27, wherein the $V_L$ region and the $V_H$ region are present on the separate chains in the peptide in the context of an immunoglobulin fold protein.

Embodiment 29

A peptide according to any of embodiments 24 to 28, wherein the first $V_L$ region and the first $V_H$ region are oriented such that the three CDRs in the $V_L$ region and the three CDRs in the $V_H$ region cooperatively associate to contribute in selectively and/or specifically bind an antigenic determinant on human CD38.

Embodiment 30

A peptide according to embodiment 29, wherein the peptide comprises a second $V_L$ region identical to the first $V_L$ region and a second $V_H$ region identical to the first $V_H$ region, where the second $V_L$ region and the second $V_H$ region cooperatively associate to contribute in selectively and/or specifically bind an antigenic determinant on human CD38.

Embodiment 31

A peptide comprising a $V_L$ region that is a functional variant of the $V_L$ region of an antibody of embodiment 2.

Embodiment 32

A peptide according to embodiment 31, wherein the $V_L$ region of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:2.

Embodiment 33

A peptide comprising a $V_H$ region that is a functional variant of the $V_H$ region of an antibody of embodiment 2.

Embodiment 34

A peptide according to embodiment 33, wherein the $V_H$ region of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:7.

Embodiment 35

A peptide comprising at least one CDR that is a functional variant of a CDR of an antibody of embodiment 2.

Embodiment 36

A peptide according to embodiment 35, wherein at least one of the CDRs of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:3, SEQ ID No:4, SEQ ID No:5, SEQ ID No:8, SEQ ID No:9, or SEQ ID No:10.

Embodiment 37

A peptide according to any of embodiments 31 to 36, wherein the peptide has at least about 50%, at least about 60%, at least about 70%, at least about 80%, at least about 90%, or at least about 95% of the epitope binding characteristics of an antibody of embodiment 2.

Embodiment 38

A peptide according to any of embodiments 31 to 36, wherein the peptide has at least about 50%, at least about 60%, at least about 70%, at least about 80%, at least about 90%, or at least about 95% of the affinity, avidity or specificity of an antibody of embodiment 2.

Embodiment 39

A peptide according to any of embodiments 12 to 38, which peptide specifically binds human CD38.

Embodiment 40

A peptide according to any of embodiments 12 to 39, which peptide competes with an antibody according to embodiment 2 for binding to CD38.

Embodiment 41

A peptide according to embodiment 40, wherein the competition is determined by use of an ELISA as described in Example 8 or 9 of the specification.

Embodiment 42

A peptide according to embodiment 7, wherein the competition is determined by use of cross-blocking measurements as described in Example 7 of the specification.

Embodiment 43

A peptide according to embodiment 39, which peptide specifically binds to a CD38 epitope, which epitope is also specifically bound by an antibody according to embodiment 2.

Embodiment 44

A peptide according to any of embodiments 39 to 43, wherein the peptide binds to human CD38 with greater affinity than an antibody according to embodiment 2.

Embodiment 45

A peptide according to any of embodiments 39 to 43, wherein the peptide has substantially the same specific CD38 binding characteristics as an antibody according to embodiment 2.

Embodiment 46

A peptide according to any of embodiments 39 to 45, wherein the CD38 binding peptide is substantially free of other CD38 binding peptides.

Embodiment 47

A peptide which binds to human CD38 (SEQ ID No:31), and which does not bind to a mutant human CD38, wherein the serine residue in position 274 has been substituted with a phenylalanine residue (SEQ ID No:34) to the same degree that it binds to human CD38 (SEQ ID No:31).

Embodiment 48

A peptide according to embodiment 47, wherein the $EC_{50}$ of the binding of the peptide to a mutant human CD38, wherein the serine residue in position 274 has been substituted with a phenylalanine residue (SEQ ID No:34), is less than 50% of the $EC_{50}$ of the binding of the peptide to human CD38 (SEQ ID No:31).

Embodiment 49

A peptide according to embodiment 48, wherein the $EC_{50}$ of the binding of the peptide to a mutant human CD38, wherein the serine residue in position 274 has been substituted with a phenylalanine residue (SEQ ID No:34), is less than 10% of the $EC_{50}$ of the binding of the peptide to human CD38 (SEQ ID No:31).

Embodiment 50

A peptide according to embodiment 49, wherein the $EC_{50}$ of the binding of the peptide to a mutant human CD38, wherein the serine residue in position 274 has been substituted with a phenylalanine residue (SEQ ID No:34), is less than 5% of the $EC_{50}$ of the binding of the peptide to human CD38 (SEQ ID No:31).

Embodiment 51

A peptide according to embodiment 50, wherein the $EC_{50}$ of the binding of the peptide to a mutant human CD38, wherein the serine residue in position 274 has been substituted with a phenylalanine residue (SEQ ID No:34), is less than 1% of the $EC_{50}$ of the binding of the peptide to human CD38 (SEQ ID No:31).

Embodiment 52

A peptide which binds to human CD38 (SEQ ID No:31), and which does not bind to a mutant human CD38, wherein the glutamine residue in position 272 has been substituted with an arginine residue (SEQ ID No:33) to the same degree that it binds to human CD38 (SEQ ID No:31).

Embodiment 53

A peptide according to embodiment 52, wherein the $EC_{50}$ of the binding of the peptide to a mutant human CD38, wherein the serine residue in position 274 has been substituted with a phenylalanine residue (SEQ ID No:34), is less than 50% of the $EC_{50}$ of the binding of the peptide to human CD38 (SEQ ID No:31).

Embodiment 54

A peptide according to embodiment 53, wherein the $EC_{50}$ of the binding of the peptide to a mutant human CD38, wherein the serine residue in position 274 has been substituted with a phenylalanine residue (SEQ ID No:34), is less than 10% of the $EC_{50}$ of the binding of the peptide to human CD38 (SEQ ID No:31).

Embodiment 55

A peptide any of embodiments 47 to 51 which does not bind to a mutant human CD38, wherein the glutamine residue in position 272 has been substituted with an arginine residue (SEQ ID No:33) to the same degree that it binds to human CD38 (SEQ ID No:31).

Embodiment 56

A peptide according to embodiment 55, wherein the $EC_{50}$ of the binding of the peptide to a mutant human CD38, wherein the serine residue in position 274 has been substituted with a phenylalanine residue (SEQ ID No:34), is less than 50% of the $EC_{50}$ of the binding of the peptide to human CD38 (SEQ ID No:31).

Embodiment 57

A peptide according to embodiment 56, wherein the $EC_{50}$ of the binding of the peptide to a mutant human CD38, wherein the serine residue in position 274 has been substituted with a phenylalanine residue (SEQ ID No:34), is less than 10% of the $EC_{50}$ of the binding of the peptide to human CD38 (SEQ ID No:31).

Embodiment 58

A peptide according to any of embodiments 47 to 57, wherein said peptide binds to a mutant human CD38, wherein the threonine residue in position 237 has been substituted with a alanine residue (SEQ ID No:32) to the same degree that it binds to human CD38 (SEQ ID No:31).

Embodiment 59

A peptide according to embodiment 58, wherein the $EC_{50}$ of the binding of the peptide to a a mutant human CD38, wherein the threonine residue in position 237 has been substituted with a alanine residue (SEQ ID No:32) is more than 75% of the $EC_{50}$ of the binding of the peptide to human CD38 (SEQ ID No:31).

Embodiment 60

A peptide according to embodiment 59 wherein the $EC_{50}$ of the binding of the peptide to a a mutant human CD38, wherein the threonine residue in position 237 has been substituted with a alanine residue (SEQ ID No:32) is more than 85% of the $EC_{50}$ of the binding of the peptide to human CD38 (SEQ ID No:31).

Embodiment 61

A peptide according to embodiment 60, wherein the $EC_{50}$ of the binding of the peptide to a a mutant human CD38, wherein the threonine residue in position 237 has been substituted with a alanine residue (SEQ ID No:32) is more than 90% of the $EC_{50}$ of the binding of the peptide to human CD38 (SEQ ID No:31).

Embodiment 62

A peptide according to embodiment 61, wherein the $EC_{50}$ of the binding of the peptide to a a mutant human CD38, wherein the threonine residue in position 237 has been substituted with a alanine residue (SEQ ID No:32) is more than 95% of the $EC_{50}$ of the binding of the peptide to human CD38 (SEQ ID No:31).

Embodiment 63

A peptide which competes with an antibody according to embodiment 4 for binding to CD38.

Embodiment 64

A peptide according to embodiment 63, wherein the competition is determined by use of an ELISA as described in Example 8 or 9 of the specification.

Embodiment 65

A peptide according to embodiment 63, wherein the competition is determined by use of cross-blocking measurements as described in Example 7 of the specification.

Embodiment 66

A peptide that specifically binds to a CD38 epitope, which epitope is also specifically bound by an antibody according to embodiment 4.

Embodiment 67

A peptide having substantially the same specific binding characteristics for binding human CD38 as an antibody according to embodiment 4.

Embodiment 68

A peptide comprising a $V_L$ CDR1 consisting essentially of SEQ ID No:13.

Embodiment 69

A peptide comprising a $V_L$ CDR2 consisting essentially of SEQ ID No:14.

Embodiment 70

A peptide comprising a $V_L$ CDR3 consisting essentially of SEQ ID No:15.

Embodiment 71

A peptide according to embodiment 70, which peptide also comprises a $V_L$ CDR1 consisting essentially of SEQ ID No:13.

Embodiment 72

A peptide according to embodiment 70, which peptide also comprises a $V_L$ CDR2 consisting essentially of SEQ ID No:14.

Embodiment 73

A peptide according to embodiment 72, which peptide also comprises a $V_L$ CDR1 consisting essentially of SEQ ID No:13.

Embodiment 74

A peptide comprising a $V_H$ CDR1 consisting essentially of SEQ ID No:18.

Embodiment 75

A peptide comprising a $V_H$ CDR2 consisting essentially of SEQ ID No:19.

Embodiment 76

A peptide comprising a $V_H$ CDR3 consisting essentially of SEQ ID No:20.

Embodiment 77

A peptide according to embodiment 76, which peptide also comprises a $V_H$ CDR1 consisting essentially of SEQ ID No:18.

Embodiment 78

A peptide according to embodiment 76, which peptide also comprises a $V_H$ CDR2 consisting essentially of SEQ ID No:19.

Embodiment 79

A peptide according to embodiment 78, which peptide also comprises a $V_H$ CDR1 consisting essentially of SEQ ID No:18.

Embodiment 80

A peptide comprising
(a) a first $V_L$ region comprising three $V_L$ CDRs, which independently of each other consist essentially of SEQ ID No:13, SEQ ID No:14, and SEQ ID No:15; and
(b) a first $V_H$ region comprising three $V_H$ CDRs, which independently of each other consist essentially of SEQ ID No:18, SEQ ID No:19, and SEQ ID No:20.

Embodiment 81

A peptide according to embodiment 80, wherein the $V_L$ region and the $V_H$ region are present on the same chain in the peptide.

Embodiment 82

A peptide according to embodiment 81, wherein the $V_L$ region and the $V_H$ region are separated by a flexible linker.

Embodiment 83

A peptide according to embodiment 80, wherein the $V_L$ region and the $V_H$ region are present on the separate chains in the peptide.

Embodiment 84

A peptide according to embodiment 83, wherein the $V_L$ region and the $V_H$ region are present on the separate chains in the peptide in the context of an immunoglobulin fold protein.

Embodiment 85

A peptide according to any of embodiments 80 to 84, wherein the first $V_L$ region and the first $V_H$ region are oriented such that the three CDRs in the $V_L$ region and the three CDRs in the $V_H$ region cooperatively associate to contribute in selectively and/or specifically bind an antigenic determinant on human CD38.

Embodiment 86

A peptide according to embodiment 85, wherein the peptide comprises a second $V_L$ region identical to the first $V_L$ region and a second $V_H$ region identical to the first $V_H$ region, where the second $V_L$ region and the second $V_H$ region cooperatively associate to contribute in selectively and/or specifically bind an antigenic determinant on human CD38.

Embodiment 87

A peptide comprising a $V_L$ region that is a functional variant of the $V_L$ region of an antibody of embodiment 4.

Embodiment 88

A peptide according to embodiment 87, wherein the $V_L$ region of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:12.

Embodiment 89

A peptide comprising a $V_H$ region that is a functional variant of the $V_H$ region of an antibody of embodiment 4.

Embodiment 90

A peptide according to embodiment 89, wherein the $V_H$ region of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:17.

Embodiment 91

A peptide comprising at least one CDR that is a functional variant of a CDR of an antibody of embodiment 4.

Embodiment 92

A peptide according to embodiment 91, wherein at least one of the CDRs of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:13, SEQ ID No:14, SEQ ID No:15, SEQ ID No:18, SEQ ID No:19, or SEQ ID No:20.

Embodiment 93

A peptide according to any of embodiments 87 to 92, wherein the peptide has at least about 50%, at least about 60%, at least about 70%, at least about 80%, at least about 90%, or at least about 95% of the epitope binding characteristics of an antibody of embodiment 4.

Embodiment 94

A peptide according to any of embodiments 87 to 92, wherein the peptide has at least about 50%, at least about 60%, at least about 70%, at least about 80%, at least about 90%, or at least about 95% of the affinity, avidity or specificity of an antibody of embodiment 4.

Embodiment 95

A peptide according to any of embodiments 68 to 94, which peptide specifically binds human CD38.

Embodiment 96

A peptide according to any of embodiments 68 to 95, which peptide competes with an antibody according to embodiment 4 for binding to CD38.

Embodiment 97

A peptide according to embodiment 96, wherein the competition is determined by use of an ELISA as described in Example 8 or 9 of the specification.

Embodiment 98

A peptide according to embodiment 96, wherein the competition is determined by use of cross-blocking measurements as described in Example 7 of the specification.

Embodiment 99

A peptide according to embodiment 95, which peptide specifically binds to a CD38 epitope, which epitope is also specifically bound by an antibody according to embodiment 4.

Embodiment 100

A peptide according to any of embodiments 95 to 99, wherein the peptide binds to human CD38 with greater affinity than an antibody according to embodiment 4.

Embodiment 101

A peptide according to any of embodiments 95 to 99, wherein the peptide has substantially the same specific CD38 binding characteristics as an antibody according to embodiment 4.

Embodiment 102

A peptide according to any of embodiments 95 to 101, wherein the CD38 binding peptide is substantially free of other CD38 binding peptides.

Embodiment 103

A peptide according to any of embodiments 63 to 102, which binds to human CD38 (SEQ ID No:31), and which does not bind to a mutant human CD38, wherein the serine residue in position 274 has been substituted with a phenylalanine residue (SEQ ID No:34) to the same degree that it binds to human CD38 (SEQ ID No:31).

Embodiment 104

A peptide according to embodiment 103, wherein the $EC_{50}$ of the binding of the peptide to a mutant human CD38, wherein the serine residue in position 274 has been substituted with a phenylalanine residue (SEQ ID No:34), is less than 50% of the $EC_{50}$ of the binding of the peptide to human CD38 (SEQ ID No:31).

Embodiment 105

A peptide according to embodiment 104, wherein the $EC_{50}$ of the binding of the peptide to a mutant human CD38, wherein the serine residue in position 274 has been substituted with a phenylalanine residue (SEQ ID No:34), is less than 10% of the $EC_{50}$ of the binding of the peptide to human CD38 (SEQ ID No:31).

Embodiment 106

A peptide according to embodiment 105, wherein the $EC_{50}$ of the binding of the peptide to a mutant human CD38, wherein the serine residue in position 274 has been substituted with a phenylalanine residue (SEQ ID No:34), is less than 5% of the $EC_{50}$ of the binding of the peptide to human CD38 (SEQ ID No:31).

Embodiment 107

A peptide according to embodiment 106, wherein the $EC_{50}$ of the binding of the peptide to a mutant human CD38, wherein the serine residue in position 274 has been substituted with a phenylalanine residue (SEQ ID No:34), is less than 1% of the $EC_{60}$ of the binding of the peptide to human CD38 (SEQ ID No:31).

Embodiment 108

A peptide which binds to human CD38 (SEQ ID No:31), and which does not bind to a mutant human CD38, wherein the glutamine residue in position 272 has been substituted with an arginine residue (SEQ ID No:33) to the same degree that it binds to human CD38 (SEQ ID No:31).

Embodiment 109

A peptide according to embodiment 108, wherein the $EC_{50}$ of the binding of the peptide to a mutant human CD38, wherein the serine residue in position 274 has been substituted with a phenylalanine residue (SEQ ID No:34), is less than 50% of the $EC_{50}$ of the binding of the peptide to human CD38 (SEQ ID No:31).

Embodiment 110

A peptide according to embodiment 109, wherein the $EC_{50}$ (of the binding of the peptide to a mutant human CD38, wherein the serine residue in position 274 has been substituted with a phenylalanine residue (SEQ ID No:34), is less than 10% of the $EC_{50}$ of the binding of the peptide to human CD38 (SEQ ID No:31).

Embodiment 111

A peptide any of embodiments 103 to 107 which does not bind to a mutant human CD38, wherein the glutamine residue in position 272 has been substituted with an arginine residue (SEQ ID No:33) to the same degree that it binds to human CD38 (SEQ ID No:31).

Embodiment 112

A peptide according to embodiment 111, wherein the $EC_{50}$ of the binding of the peptide to a mutant human CD38, wherein the serine residue in position 274 has been substituted with a phenylalanine residue (SEQ ID No:34), is less than 50% of the $EC_{50}$ of the binding of the peptide to human CD38 (SEQ ID No:31).

Embodiment 113

A peptide according to embodiment 112, wherein the $EC_{50}$ of the binding of the peptide to a mutant human CD38, wherein the serine residue in position 274 has been substituted with a phenylalanine residue (SEQ ID No:34), is less than 10% of the $EC_{50}$ of the binding of the peptide to human CD38 (SEQ ID No:31).

Embodiment 114

A peptide according to any of embodiments 103 to 113, wherein said peptide binds to a mutant human CD38, wherein the threonine residue in position 237 has been substituted with a alanine residue (SEQ ID No:32) to the same degree that it binds to human CD38 (SEQ ID No:31).

Embodiment 115

A peptide according to embodiment 114, wherein the $EC_{50}$ of the binding of the peptide to a a mutant human CD38, wherein the threonine residue in position 237 has been substituted with a alanine residue (SEQ ID No:32) is more than 75% of the $EC_{50}$ of the binding of the peptide to human CD38 (SEQ ID No:31).

Embodiment 116

A peptide according to embodiment 115 wherein the $EC_{50}$ of the binding of the peptide to a a mutant human CD38, wherein the threonine residue in position 237 has been substituted with a alanine residue (SEQ ID No:32) is more than 85% of the $EC_{50}$ of the binding of the peptide to human CD38 (SEQ ID No:31).

Embodiment 117

A peptide according to embodiment 116, wherein the $EC_{50}$ of the binding of the peptide to a a mutant human CD38, wherein the threonine residue in position 237 has been substituted with a alanine residue (SEQ ID No:32) is more than 90% of the $EC_{50}$ of the binding of the peptide to human CD38 (SEQ ID No:31).

Embodiment 118

A peptide according to embodiment 117, wherein the $EC_{50}$ of the binding of the peptide to a a mutant human CD38, wherein the threonine residue in position 237 has been substituted with a alanine residue (SEQ ID No:32) is more than 95% of the $EC_{60}$ of the binding of the peptide to human CD38 (SEQ ID No:31).

Embodiment 119

A peptide which competes with an antibody according to embodiment 6 for binding to CD38.

Embodiment 120

A peptide according to embodiment 119, wherein the competition is determined by use of an ELISA as described in Example 8 or 9 of the specification.

Embodiment 121

A peptide according to embodiment 119, wherein the competition is determined by use of cross-blocking measurements as described in Example 7 of the specification.

Embodiment 122

A peptide that specifically binds to a CD38 epitope, which epitope is also specifically bound by an antibody according to embodiment 6.

Embodiment 123

A peptide having substantially the same specific binding characteristics for binding human CD38 as an antibody according to embodiment 6.

Embodiment 124

A peptide comprising a $V_L$ CDR1 consisting essentially of SEQ ID No:23.

Embodiment 125

A peptide comprising a $V_L$ CDR2 consisting essentially of SEQ ID No:24.

Embodiment 126

A peptide comprising a $V_L$ CDR3 consisting essentially of SEQ ID No:25.

Embodiment 127

A peptide according to embodiment 126, which peptide also comprises a $V_L$ CDR1 consisting essentially of SEQ ID No:23.

Embodiment 128

A peptide according to embodiment 126, which peptide also comprises a $V_L$ CDR2 consisting essentially of SEQ ID No:24.

Embodiment 129

A peptide according to embodiment 128, which peptide also comprises a $V_L$ CDR1 consisting essentially of SEQ ID No:23.

Embodiment 130

A peptide comprising a $V_H$ CDR1 consisting essentially of SEQ ID No:28.

Embodiment 131

A peptide comprising a $V_H$ CDR2 consisting essentially of SEQ ID No:29.

Embodiment 132

A peptide comprising a $V_H$ CDR3 consisting essentially of SEQ ID No:30.

Embodiment 133

A peptide according to embodiment 132, which peptide also comprises a $V_H$ CDR1 consisting essentially of SEQ ID No:28.

Embodiment 134

A peptide according to embodiment 132, which peptide also comprises a $V_H$ CDR2 consisting essentially of SEQ ID No:29.

Embodiment 135

A peptide according to embodiment 134, which peptide also comprises a $V_H$ CDR1 consisting essentially of SEQ ID No:28.

Embodiment 136

A peptide comprising
(a) a first $V_L$ region comprising three $V_L$ CDRs, which independently of each other consist essentially of SEQ ID No:23, SEQ ID No:24, and SEQ ID No:25; and
(b) a first $V_H$ region comprising three $V_H$ CDRs, which independently of each other consist essentially of SEQ ID No:28, SEQ ID No:29, and SEQ ID No:30.

Embodiment 137

A peptide according to embodiment 136, wherein the $V_L$ region and the $V_H$ region are present on the same chain in the peptide.

Embodiment 138

A peptide according to embodiment 137, wherein the $V_L$ region and the $V_H$ region are separated by a flexible linker.

Embodiment 139

A peptide according to embodiment 136, wherein the $V_L$ region and the $V_H$ region are present on the separate chains in the peptide.

Embodiment 140

A peptide according to embodiment 139, wherein the $V_L$ region and the $V_H$ region are present on the separate chains in the peptide in the context of an immunoglobulin fold protein.

Embodiment 141

A peptide according to any of embodiments 136 to 140, wherein the first $V_L$ region and the first $V_H$ region are oriented such that the three CDRs in the $V_L$ region and the three CDRs in the $V_H$ region cooperatively associate to contribute in selectively and/or specifically bind an antigenic determinant on human CD38.

Embodiment 142

A peptide according to embodiment 141, wherein the peptide comprises a second $V_L$ region identical to the first $V_L$ region and a second $V_H$ region identical to the first $V_H$ region, where the second $V_L$ region and the second $V_H$ region cooperatively associate to contribute in selectively and/or specifically bind an antigenic determinant on human CD38.

Embodiment 143

A peptide comprising a $V_L$ region that is a functional variant of the $V_L$ region of an antibody of embodiment 6.

Embodiment 144

A peptide according to embodiment 143, wherein the $V_L$ region of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:22.

Embodiment 145

A peptide comprising a $V_H$ region that is a functional variant of the $V_H$ region of an antibody of embodiment 6.

Embodiment 146

A peptide according to embodiment 145, wherein the $V_H$ region of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:27.

Embodiment 147

A peptide comprising at least one CDR that is a functional variant of a CDR of an antibody of embodiment 6.

Embodiment 148

A peptide according to embodiment 147, wherein at least one of the CDRs of the peptide consists essentially of a sequence having at least about 50%, at least 60%, at least about 70%, at least about 75%, at least about 80%, at least about 85%, at least about 90%, or at least about 95% amino acid sequence identity to a sequence according to SEQ ID No:23, SEQ ID No:24, SEQ ID No:25, SEQ ID No:28, SEQ ID No:29, or SEQ ID No:30.

Embodiment 149

A peptide according to any of embodiments 143 to 148, wherein the peptide has at least about 50%, at least about 60%, at least about 70%, at least about 80%, at least about 90%, or at least about 95% of the epitope binding characteristics of an antibody of embodiment 6.

Embodiment 150

A peptide according to any of embodiments 143 to 148, wherein the peptide has at least about 50%, at least about 60%, at least about 70%, at least about 80%, at least about 90%, or at least about 95% of the affinity, avidity or specificity of an antibody of embodiment 6.

Embodiment 151

A peptide according to any of embodiments 124 to 150, which peptide specifically binds human CD38.

Embodiment 152

A peptide according to any of embodiments 124 to 151, which peptide competes with an antibody according to embodiment 6 for binding to CD38.

Embodiment 153

A peptide according to embodiment 152, wherein the competition is determined by use of an ELISA as described in Example 8 or 9 of the specification.

Embodiment 154

A peptide according to embodiment 152, wherein the competition is determined by use of cross-blocking measurements as described in Example 7 of the specification.

Embodiment 155

A peptide according to embodiment 151, which peptide specifically binds to a CD38 epitope, which epitope is also specifically bound by an antibody according to embodiment 6.

Embodiment 156

A peptide according to any of embodiments 151 to 155, wherein the peptide binds to human CD38 with greater affinity than an antibody according to embodiment 6.

Embodiment 157

A peptide according to any of embodiments 151 to 155, wherein the peptide has substantially the same specific CD38 binding characteristics as an antibody according to embodiment 6.

Embodiment 158

A peptide according to any of embodiments 151 to 157, wherein the CD38 binding peptide is substantially free of other CD38 binding peptides.

Embodiment 159

A peptide according to any of embodiments 1 to 158, wherein the peptide is not an agonist of CD38.

Embodiment 160

A peptide according to any of embodiments 1 to 159, wherein the peptide does not induce significant proliferation of peripheral blood mononuclear cells.

Embodiment 161

A peptide according to any of embodiments 1 to 160, wherein the peptide does not induce release of significant IL-6 by human monocytes or peripheral blood mononuclear cells.

Embodiment 162

A peptide according to any of embodiments 1 to 161, wherein the peptide does not induce release of detectable IFN-γ by human T cells or peripheral blood mononuclear cells.

Embodiment 163

A peptide according to any of embodiments 7 to 162, wherein the peptide is an antibody.

Embodiment 164

An antibody according to any of embodiments 1 to 6, or 163, which antibody is a human antibody.

Embodiment 165

An antibody according to any of embodiments 1 to 6, or 163, which antibody is a humanized antibody.

Embodiment 166

An antibody according to any of embodiments 1 to 6, or 163, which antibody is a chimeric antibody.

Embodiment 167

An antibody according to any of embodiments 1 to 6, or 163 to 166, which antibody is a monoclonal antibody.

Embodiment 168

An antibody according to any of embodiments 1 to 6, or 163 to 167, characterized in that it is an IgG1, IgG2, IgG3, IgG4, IgD, IgA, IgE, or IgM antibody.

Embodiment 169

An antibody according to embodiment 168, characterized in that it is an IgG1 antibody.

Embodiment 170

An antibody according to embodiment 169, wherein the antibody is a IgG1,κ antibody.

Embodiment 171

An antibody according to embodiment 168, characterized in that it is an IgM antibody.

Embodiment 172

An antibody according to embodiment 171, wherein the antibody is a IgM,κ antibody.

Embodiment 173

A peptide according to any of embodiments 2 to 172, wherein the peptide is glycosylated in a eukaryotic cell.

Embodiment 174

An antibody according to any of embodiments 1 to 6, or 163 to 173, which is an antibody fragment or a single chain antibody.

Embodiment 175

A peptide or antibody according to any of embodiments 1 to 174, further comprising a chelator linker for attaching a radioisotope.

Embodiment 176

A peptide according to any of embodiments 1 to 175, which is in a substantially isolated form.

Embodiment 177

An isolated nucleic acid encoding a peptide according to any of embodiments 1 to 175.

Embodiment 178

An expression vector comprising a nucleic acid sequence encoding a peptide according to any of embodiments 1 to 175.

Embodiment 179

An expression vector comprising a $V_L$ nucleotide sequence of SEQ ID No:1, a $V_H$ nucleotide sequence of SEQ ID No:6, or a $V_L$ nucleotide sequence of SEQ ID No:1 and a $V_H$ nucleotide sequence of SEQ ID No:6.

Embodiment 180

An expression vector comprising a $V_L$ nucleotide sequence of SEQ ID No:11, a $V_H$ nucleotide sequence of SEQ ID No:16, or a $V_L$ nucleotide sequence of SEQ ID No:11 and a $V_H$ nucleotide sequence of SEQ ID No:16.

Embodiment 181

An expression vector according to embodiment 179 or embodiment 180, further comprising a nucleotide sequence encoding the constant region of a light chain, a heavy chain or both light and heavy chains of a human antibody.

Embodiment 182

An expression vector according to embodiment 181, wherein the nucleotide sequence encoding the constant region of a light chain, a heavy chain or both light and heavy chains of a human antibody encodes a IgG1 antibody.

Embodiment 183

A hybridoma which produces a human monoclonal anti-CD38 antibody encoded by human light chain and human heavy chain nucleic acids comprising nucleotide sequences in the variable light chain region as set forth in SEQ ID No:1, or conservative sequence modifications thereof, and nucleotide sequences in the variable heavy chain region as set forth in SEQ ID No:6, or conservative sequence modifications thereof.

Embodiment 184

A hybridoma according to embodiment 183, wherein the human light chain nucleic acids comprises a nucleotide sequence as set forth in SEQ ID No:1, and the human heavy chain nucleic acids comprises a nucleotide sequence as set forth in SEQ ID No:6.

Embodiment 185

A hybridoma which produces a human monoclonal anti-CD38 antibody having human heavy chain and light chain variable regions which comprise the human light chain variable amino acid sequence as set forth in SEQ ID No:2 or conservative sequence modifications thereof, and the human light chain variable amino sequence as set forth in SEQ ID No:7, or conservative sequence modifications thereof.

Embodiment 186

A hybridoma according to embodiment 185, wherein the human light chain variable region comprises an amino acid sequence as set forth in SEQ ID No:2, and the human heavy chain variable region comprises an amino acid sequence as set forth in SEQ ID No:7.

Embodiment 187

A transfectoma which produces a human monoclonal anti-CD38 antibody encoded by human light chain variable nucleic acids as set forth in SEQ ID No:1, or conservative sequence modifications thereof, and human heavy chain nucleic acids as set forth SEQ ID No:6, or conservative sequence modifications thereof.

Embodiment 188

A transfectoma according to embodiment 187, wherein the human monoclonal anti-CD38 antibody is encoded by human light chain variable nucleic acids as set forth in SEQ ID No:1, and human heavy chain nucleic acids as set forth SEQ ID No:6.

Embodiment 189

A transfectoma which produces a human monoclonal anti-CD38 antibody having human light chain and heavy chain variable regions which comprise the human light chain variable amino acid sequence as set forth in SEQ ID No:2, or conservative sequence modifications thereof, and the human heavy chain variable amino sequence as set forth in SEQ ID No:7, or conservative sequence modifications thereof.

Embodiment 190

A transfectoma according to embodiment 189, wherein the human light chain comprises the human light chain variable amino acid sequence as set forth in SEQ ID No:2, and the human heavy chain comprises the human heavy chain variable amino sequence as set forth in SEQ ID No:7.

Embodiment 191

A hybridoma which produces a human monoclonal anti-CD38 antibody encoded by human light chain and human heavy chain nucleic acids comprising nucleotide sequences in the variable light chain region as set forth in SEQ ID No:11, or conservative sequence modifications thereof, and nucleotide sequences in the variable heavy chain region as set forth in SEQ ID No:16, or conservative sequence modifications thereof.

Embodiment 192

A hybridoma according to embodiment 191, wherein the human light chain nucleic acids comprises a nucleotide sequence as set forth in SEQ ID No:11, and the human heavy chain nucleic acids comprises a nucleotide sequence as set forth in SEQ ID No:16.

Embodiment 193

A hybridoma which produces a human monoclonal anti-CD38 antibody having human heavy chain and light chain variable regions which comprise the human light chain variable amino acid sequence as set forth in SEQ ID No:12, or conservative sequence modifications thereof, and the human heavy chain variable amino sequence as set forth in SEQ ID No:17, or conservative sequence modifications thereof.

Embodiment 194

A hybridoma according to embodiment 193, wherein the human light chain variable region comprises an amino acid sequence as set forth in SEQ ID No:12, and the human heavy chain variable region comprises an amino acid sequence as set forth in SEQ ID No:17.

Embodiment 195

A transfectoma which produces a human monoclonal anti-CD38 antibody encoded by human light chain variable nucleic acids as set forth in SEQ ID No:11, or conservative sequence modifications thereof, and human heavy chain nucleic acids as set forth SEQ ID No:16, or conservative sequence modifications thereof.

Embodiment 196

A transfectoma according to embodiment 195, wherein the human monoclonal anti-CD38 antibody is encoded by human light chain variable nucleic acids as set forth in SEQ ID No:11, and human heavy chain nucleic acids as set forth SEQ ID No:16.

Embodiment 197

A transfectoma which produces a human monoclonal anti-CD38 antibody having human light chain and heavy chain variable regions which comprise the human light chain variable amino acid sequence as set forth in SEQ ID No:12, or conservative sequence modifications thereof, and the human heavy chain variable amino sequence as set forth in SEQ ID No:17, or conservative sequence modifications thereof.

Embodiment 198

A transfectoma according to embodiment 197, wherein the human light chain comprises the human light chain variable amino acid sequence as set forth in SEQ ID No:12, and the human heavy chain comprises the human heavy chain variable amino acid sequence as set forth in SEQ ID No:17.

Embodiment 199

A eukaryotic or prokaryotic host cell which produces a peptide according to any of embodiments 1 to 175.

Embodiment 200

A eukaryotic or prokaryotic host cell containing an expression vector according to embodiment 178.

Embodiment 201

A transgenic nonhuman animal or plant comprising nucleic acids encoding a human heavy chain and a human light chain, wherein the animal or plant produces a detectable amount of a peptide according to any of embodiments 1 to 175.

Embodiment 202

An immunoconjugate comprising a peptide according to any of embodiments 1 to 174 linked to a cytotoxic agent, a radioisotope, or a drug.

Embodiment 203

An immunoconjugate comprising a peptide according to any of embodiments 1 to 168 or embodiments 171 to 174, wherein the peptide is a monomeric IgM antibody linked to a cytotoxic agent, a radioisotope, or a drug.

Embodiment 204

A bispecific or multispecific molecule comprising a peptide according to any of embodiments 1 to 175 and a binding specificity for a human effector cell.

Embodiment 205

A bispecific or multispecific molecule comprising a peptide according to any of embodiments 1 to 175 and a binding specificity for CD3, CD4, IL-15R, membrane bound or receptor bound TNF-α, a human Fc receptor, or membrane bound or receptor bound IL-15.

Embodiment 206

A pharmaceutical composition comprising a peptide according to any of embodiments 1 to 176 or an immunoconjugate according to any of embodiments 202 to 205 and a pharmaceutically acceptable carrier.

Embodiment 207

A pharmaceutical composition according to embodiment 206 comprising one or more further therapeutic agents.

Embodiment 208

A method of inhibiting growth and/or proliferation of a cell expressing CD38, comprising administration of a peptide according to any of embodiments 1 to 176, an immunoconjugate according to any of embodiments 202 to 205, a pharmaceutical composition according to embodiment 206 or 207, or an expression vector according to any of embodiments 178 to 182, such that the growth and/or proliferation of the cell is inhibited.

Embodiment 209

A method of treating a disease or disorder involving cells expressing CD38 in a subject, which method comprises administration of a therapeutically effective amount of a peptide according to any of embodiments 1 to 176, an immunoconjugate according to any of embodiments 202 to 205, a pharmaceutical composition according to embodiment 206 or 207, or an expression vector according to any of embodiments 178 to 182 to a subject in need thereof.

Embodiment 210

A method of preventing a disease or disorder involving cells expressing CD38 in a subject, which method comprises administration of a therapeutically effective amount of a peptide according to any of embodiments 1 to 176, an immunoconjugate according to any of embodiments 202 to 205, a pharmaceutical composition according to embodiment 206 or 207, or an expression vector according to any of embodiments 178 to 182 to a subject in need thereof.

Embodiment 211

A method according to embodiment 209 or embodiment 210, wherein the disease or disorder is rheumatoid arthritis.

Embodiment 212

A method according to embodiment 209 or embodiment 210, wherein the disease or disorder is multiple myeloma.

Embodiment 213

A method according to any of embodiments 209 to 212, wherein the method comprises administration of one or more further therapeutic agents to the subject.

Embodiment 214

A method according to embodiment 213, wherein the one or more further therapeutic agents are selected from a chemotherapeutic agent, an anti-inflammatory agent, or an immunosuppressive and/or immunomodulatory agent.

Embodiment 215

A method according to embodiment 213, wherein the one or more further therapeutic agents are selected from a group consisting of cisplatin, gefitinib, cetuximab, rituximab, bevacizumab, erlotinib, bortezomib, thalidomide, pamidronate, zoledronic acid, clodronate, risendronate, ibandronate, etidronate, alendronate, tiludronate, arsenic trioxide, lenalidomide, filgrastim, pegfilgrastim, sargramostim, suberoylanilide hydroxamic acid, and SCIO-469.

Embodiment 216

An in vitro method for detecting the presence of CD38 antigen, or a cell expressing CD38, in a sample comprising:
a) contacting the sample with a peptide according to any of embodiments 1 to 176 under conditions that allow for formation of a complex between the antibody and CD38; and
b) detecting the formation of a complex.

Embodiment 217

An in vitro method according to embodiment 216, wherein said peptide is an antibody.

Embodiment 218

A kit for detecting the presence of CD38 antigen, or a cell expressing CD38, in a sample comprising a peptide according to any of embodiments 1 to 176.

Embodiment 219

An in vivo method for detecting CD38 antigen, or a cell expressing CD38, in a subject comprising:
a) administering peptide according to any of embodiments 1 to 176 under conditions that allow for formation of a complex between the antibody and CD38; and
b) detecting the formed complex.

Embodiment 220

An in vitro method according to embodiment 219, wherein said peptide is an antibody.

Embodiment 221

An anti-idiotypic antibody binding to a peptide according to any of embodiments 2, 4, or 163 to 174.

Embodiment 222

Use of an anti-idiotypic antibody according to embodiment 221 for detecting the level of a peptide according to any of embodiments 2, 4, or 163 to 174 in a sample.

Embodiment 223

Use of an anti-idiotypic antibody according to embodiment 221 for detecting the level of human monoclonal antibody against CD38 in a sample.

The terms "CD38" and "CD38 antigen" are used interchangeably herein, and include any variants, isoforms and species homologs of human CD38, which are naturally expressed by cells or are expressed on cells transfected with the CD38 gene. Synonyms of CD38, as recognized in the art, include ADP ribosyl cyclase 1, cADPr hydrolase 1, Cd38-rs1, Cyclic ADP-ribose hydrolase 1, 1-19, NIM-R5 antigen.

The term peptide with respect to both CD38-binding peptides and non-CD38 peptides described herein includes any suitable peptide and can be used synonymously with the terms polypeptide and protein, unless otherwise stated or contradicted by context; provided that the reader recognize that each type of respective amino acid polymer-containing molecule can be associated with significant differences and thereby form individual embodiments of the present invention (for example, a peptide such as an antibody, which is composed of multiple polypeptide chains, is significantly different from, for example, a single chain antibody, a peptide immunoadhesin, or single chain immunogenic peptide). Therefore, the term peptide herein should generally be understood as referring to any suitable peptide of any suitable size and composition (with respect to the number of amino acids and number of associated chains in a protein molecule). Moreover, peptides in the context of the inventive methods and compositions described herein may comprise non-naturally occurring and/or non-L amino acid residues, unless otherwise stated or contradicted by context.

As will be discussed further herein, unless otherwise stated or contradicted by context, the term peptide (and if discussed as individual embodiments of the term(s) polypeptide and/or protein) also encompasses derivatized peptide molecules. Briefly, in the context of the present invention, a derivative is a peptide in which one or more of the amino acid residues of the peptide have been chemically modified (for instance by alkylation, acylation, ester formation, or amide formation) or associated with one or more non-amino acid organic and/or inorganic atomic or molecular substituents (for instance a polyethylene glycol (PEG) group, a lipophilic substituent (which optionally may be linked to the amino acid sequence of the peptide by a spacer residue or group such as β-alanine, γ-aminobutyric acid (GABA), L/D-glutamic acid, succinic acid, and the like), a fluorophore, biotin, a radionuclide, etc.) and may also or alternatively comprise non-essential, non-naturally occurring, and/or non-L amino acid residues, unless otherwise stated or contradicted by context (however, it should again be recognized that such derivatives may, in and of themselves, be considered independent features of the present invention and inclusion of such molecules within the meaning of peptide is done for the sake of convenience in describing the present invention rather than to imply any sort of equivalence between naked peptides and such derivatives). Non-limiting examples of such amino acid residues include for instance 2-aminoadipic acid, 3-amino-adipic acid, β-alanine, β-aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allohydroxylysine, 3-hydroxyproline, 4-hydroxyproline, isodesmosine, alloisoleucine, N-methylglycine, N-methylisoleucine, 6-N-methyllysine, N-methylvaline, norvaline, nor-leucine, ornithine, and statine halogenated amino acids.

Antigen binding peptides refers to any peptide that specifically binds to a portion of a given antigen under cellular and/or physiological conditions for an amount of time sufficient to induce, promote, enhance, and/or otherwise modulate a physiological effect associated with the antigen; to allow detection by ELISA, Western blot, or other similarly suitable protein binding technique described herein and/or known in the art and/or to otherwise be detectably bound thereto after a relevant period of time (for instance at least about 15 minutes, at least about 30 minutes, at least about 45 minutes, at least about 1 hour, at least about 2 hours, at least about 4 hours, at least about 6 hours, at least about 12 hours, about 1-24 hours, about 1-36 hours, about 1-48 hours, about 1-72 hours, about one week, or longer).

A CD38 binding peptide, or CD38BP, is an antigen binding peptide that specifically binds to the antigen CD38. In one embodiment, the binding of the CD38BP to CD38 is measured by use of the method described in Example 4.

The term immunoglobulin refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$) and a heavy chain constant region. The heavy chain constant region typically is comprised of three domains, $C_H1$, $C_H2$, and $C_H3$. Each light chain typically is comprised of a light chain variable region (abbreviated herein as $V_L$) and a light chain constant region. The light chain constant region typically is comprised of one domain, $C_L$. The $V_H$ and $V_L$ regions can be further subdivided into regions of hypervariability (or hypervariable regions which can be hypervariable in sequence and/or form of structurally defined loops), also termed complementarity determining regions (CDRs), interspersed with regions that are more conserved, termed framework regions (FRs).

Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term antibody (Ab) in the context of the present invention refers to an immunoglobulin molecule, a fragment of an immunoglobulin molecule, or a derivative of either thereof, which has the ability to specifically bind to an antigen under typical physiological conditions for significant periods of time such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen).

The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and the first component (Clq) of the classical complement system.

An anti-CD38 antibody may be a bispecific antibody, diabody, or similar molecule (see for instance PNAS USA 90(14), 6444-8 (1993) for a description of diabodies). Indeed, bispecific antibodies, diabodies, and the like, provided by the present invention may bind any suitable target in addition to a portion of CD38.

As indicated above, the term antibody herein, unless otherwise stated or clearly contradicted by context, includes fragments of an antibody that retain the ability to specifically bind to an antigen. It has been shown that the antigen-binding function of an antibody can be performed by fragments of a full-length antibody. Examples of binding fragments encompassed within the term "antibody" include (i) a Fab fragment, a monovalent fragment consisting of the $V_L$, $V_H$, $C_L$ and $C_H1$ domains; (ii) F(ab)$_2$ and F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain; (vi) an isolated complementarity determining region (CDR), and (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Other forms of single chain antibodies, such as diabodies are included within the term antibody. Although such fragments are generally included within the meaning of antibody, they collectively and each independently are unique features of the present invention, exhibiting different biological properties and utility. These and other useful antibody fragments in the context of the present invention are discussed further herein.

It also should be understood that the term antibody also generally includes polyclonal antibodies, monoclonal antibodies (mAbs), antibody-like polypeptides, such as chimeric antibodies and humanized antibodies, anti-idiotypic (anti-Id) antibodies to antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

An anti-CD38 antibody is an antibody as described above, which binds specifically to the antigen CD38.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

The term "bispecific molecule" is intended to include any agent, such as a protein, peptide, or protein or peptide complex, which has two different binding specificities. For example, the molecule may bind to, or interact with, (a) a cell surface antigen and (b) an Fc receptor on the surface of an effector cell. The term "multispecific molecule" is intended to include any agent, for instance a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the present invention includes, but is not limited to, bispecific, trispecific, tetraspecific, and other multispecific molecules which are directed to CD38, and to other cell surface antigens or targets, such as Fc receptors on effector cells.

The term "bispecific antibodies" is intended to include any anti-CD38 antibody, which is a bispecific molecule. The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see for instance Holliger, P. et al., PNAS USA 90, 6444-6448 (1993), Poljak, R. J. et al., Structure 2, 1121-1123 (1994)).

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, neutronphils, polymorphonuclear cells, granulocytes, mast cells, and basophils. Some effector cells express specific Fc receptors and carry out specific immune functions. In some embodiments, an effector cell is capable of inducing antibody-dependent cellular cytotoxicity (ADCC), such as a neutrophil capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen, target cell, or microorganism. The expression of a particular FcR on an effector cell can be regulated by humoral factors such as cytokines. For example, expression of FcγRI has been found to be up-regulated by interferon γ (IFN-γ) and/or G-CSF. This enhanced expression increases the cytotoxic activity of FcγRI-bearing cells against targets. An effector cell can phagocytose or lyse a target antigen or a target cell.

The term "human antibody", as used herein, is intended to include antibodies having variable and constant regions derived from human germline immunoglobulin sequences. The human antibodies of the present invention may include amino acid residues not encoded by human germline immunoglobulin sequences (for instance mutations introduced by random or site-specific mutagenesis in vitro or by somatic mutation in viva). However, the term "human antibody", as used herein, is not intended to include antibodies in which CDR sequences derived from the germline of another mammalian species, such as a mouse, have been grafted onto human framework sequences.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline VH or VL variable region gene segment. Typically, a human antibody derived from a particular human germline VH or VL variable region gene segment sequence will display no more than 10 amino acid differences, such as no more than 5, for instance no more than 4, 3, 2, or 1 amino acid difference from the amino acid sequence encoded by the germline immunoglobulin gene.

A chimeric antibody is an antibody that contains one or more regions from one antibody and one or more regions from one or more other antibodies derived from another species. A monovalent chimeric antibody is a dimer (HL)) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody may also be produced, for example, by employing a CH region that oligomerizes (for instance from an IgM H chain, or μ chain). Typically, a chimeric antibody refers to an antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see for instance U.S. Pat. No. 4,816,567 and Morrison et al., PNAS USA 81, 6851-6855 (1984)). Chimeric antibodies are produced by recombinant processes well known in the art (see for instance Cabilly et al., PNAS USA 81, 3273-3277 (1984), Morrison et al., PNAS USA 81, 6851-6855 (1984), Boulianne et al., Nature 312, 643-646 (1984), EP125023, Neuberger et al., Nature 314, 268-270 (1985), EP171496, EP173494, WO86/01533, EP184187, Sahagan et al., J. Immunol. 137, 1066-1074 (1986), WO87/02671, Liu et al., PNAS USA 84, 3439-3443 (1987), Sun et al., PNAS USA 84, 214-218 (1987), Better et al., Science 240, 1041-1043 (1988) and Harlow et al., Antibodies: A Laboratory Manual, Cold Spring Harbor Laboratory Press, Cold Spring Harbor, N.Y., (1988)).

A humanized antibody is an antibody that is derived from a non-human species, in which certain amino acids in the framework and constant domains of the heavy and light chains have been mutated so as to avoid or abrogate an immune response in humans. Humanized forms of non-human (for instance murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired antigen-binding characteristics such as specificity, and affinity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further optimize antibody performance. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody optionally also will comprise at least a portion of an immunoglobulin constant region (Fc), typically that of a human immunoglobulin. For further details, see Jones et al., Nature 321, 522-525 (1986), Riechmann et al., Nature 332, 323-329 (1988) and Presta, Curr. Op. Struct. Biol. 2, 593-596 (1992).

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell. A monoclonal antibody may be abbreviated as mAb.

The term "recombinant human antibody", as used herein, includes all human antibodies that are prepared, expressed, created or isolated by recombinant means, such as (a) antibodies isolated from an animal (such as a mouse) that is transgenic or transchromosomal for human immunoglobulin genes or a hybridoma prepared therefrom (described further elsewhere herein), (b) antibodies isolated from a host cell transformed to express the antibody, such as from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies may be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, a "heterologous antibody" is defined in relation to the transgenic non-human organism producing such an antibody. This term refers to an antibody having an amino acid sequence corresponding to that found in an organism not consisting of the non-human animal, and generally from a species other than that of the transgenic non-human animal.

An "isolated antibody," as used herein, is intended to refer to an antibody which is substantially free of other antibodies having different antigenic specificities (for instance an isolated antibody that specifically binds to CD38 is substantially free of antibodies that specifically bind antigens other than CD38). An isolated antibody that specifically binds to an epitope, isoform or variant of human CD38 may, however, have cross-reactivity to other related antigens, for instance from other species (such as CD38 species homologs). Moreover, an isolated antibody may be substantially free of other cellular material and/or chemicals. In one embodiment of the present invention, a combination of "isolated" monoclonal antibodies having different specificities are combined in a well defined composition.

As used herein, "specific binding" refers to an antigen binding peptide, such as an antibody, binding to a predetermined antigen. Typically, the antigen binding peptide, such as an antibody, binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by surface plasmon resonance (SPR) technology in a BIAcore 3000 instrument using recombinant CD38 as the ligand and the antibody as the analyte. The antigen binding peptide may bind to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antigen binding peptide, so that when the $K_D$ of the antigen binding peptide is very low (that is, the antigen binding peptide is highly specific), then the amount with which the affinity for the antigen is lower than the affinity for a non-specific antigen may be at least 10,000 fold. The phrases "an antigen binding peptide recognizing an antigen" and "an antigen binding peptide specific for an antigen" are used interchangeably herein with the term "an antigen binding peptide which binds specifically to an antigen". Likewise, the phrases "an antibody recognizing an antigen" and "an antibody specific for an antigen" are used interchangeably herein with the term "an antibody which binds specifically to an antigen".

The term "$k_d$" (sec$^{-1}$), as used herein, is intended to refer to the dissociation equilibrium rate constant of a particular antibody-antigen interaction. Said value is also referred to as the $k_{off}$ value.

The term "$k_a$" (M$^{-1}$ × sec$^{-1}$), as used herein, is intended to refer to the association equilibrium rate constant of a particular antibody-antigen interaction.

The term "$K_D$" (M), as used herein, is intended to refer to the dissociation equilibrium constant of a particular antibody-antigen interaction.

The term "$K_A$" (M$^{-1}$), as used herein, is intended to refer to the association equilibrium constant of a particular antibody-antigen interaction and is obtained by dividing the $k_a$ by the $k_d$.

As used herein, "isotype" refers to the antibody class (for instance IgG1, IgG2, IgG3, IgG4, IgD, IgA, IgE, or IgM) that is encoded by heavy chain constant region genes.

As used herein, "isotype switching" refers to the phenomenon by which the class, or isotype, of an antibody changes from one immunoglobulin class to one of the other immunoglobulin classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human σμ and human Σμ (δ-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (for instance γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin (antibody) protein. A glycosylation pattern of a heterologous antibody may be characterized as being substantially similar to glycosylation patterns which occur naturally on antibodies produced by the species of the non-human transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but is preferably double-stranded DNA. The nucleic acids may be present in whole cells, in a cell lysate, or in a partially purified or substantially pure form. A nucleic acid is "isolated" or "rendered substantially pure" when purified away from other cellular components or other contaminants, such as other cellular nucleic acids or proteins, by standard techniques, including alkaline/SDS treatment, CsCl banding, column chromatography, agarose gel electrophoresis and others well known in the art. See, F. Ausubel et al., ed. Current Protocols in Molecular Biology, Greene Publishing and Wiley InterScience New York (1987).

A nucleic acid is "operably linked" when it is placed into a functional relationship with another nucleic acid sequence. For instance, a promoter or enhancer is operably linked to a coding sequence if it affects the transcription of the sequence. With respect to transcription of regulatory sequences, operably linked means that the DNA sequences being linked are contiguous and, where necessary to join two protein coding regions, contiguous and in reading frame. For switch sequences, operably linked indicates that the sequences are capable of effecting switch recombination.

As used herein, the term "inhibits growth" (for instance when referring to cells) is intended to include any measurable decrease in the cell growth when contacted with a CD38BP, such as an anti-CD38 antibody, as compared to the growth of the same cells not in contact with a CD38BP, such as an anti-CD38 antibody, for instance an inhibition of growth of a cell culture by at least about 10%, 20%, 30%, 40%, 50%, 60%, 70%, 80%, 90%, 99%, or 100%.

As used herein, the terms "inhibits binding" and "blocks binding" (for instance when referring to inhibition/blocking of binding of a CD38 binding partner to CD38) are used interchangeably and encompass both partial and complete inhibition/blocking. The inhibition/blocking of binding of a CD38 binding partner to CD38 may reduce or alter the normal level or type of cell signaling that occurs when a CD38 binding partner binds to CD38 without inhibition or blocking. Inhibition and blocking are also intended to include any measurable decrease in the binding affinity of a CD38 binding partner to CD38 when in contact with a CD38BP, such as an anti-CD38 antibody, as compared to the ligand not in contact with a CD38BP, such as an anti-CD38 antibody, for instance a blocking of binding of a CD38 binding partner to CD38 by at least about 10%, 20%, 30%, 40%, 50%, 60%, 70%, 80%, 90%, 99%, or 100%.

"Target cell" shall mean any undesirable cell in a subject (for instance a human or animal) that can be targeted by a composition (comprising for instance a CD38BP, such as a human monoclonal anti-CD38 antibody, and/or a bispecific or a multispecific molecule directed against CD38) of the present invention. In some embodiments, the target cell is a cell expressing or overexpressing CD38. Cells expressing CD38 typically include hemopoietic cells, such as medullary thymocytes, activated T and B cells, 80% of resting NK cells and monocytes, lymph node germinal center lymphoblasts, plasma B cells and some intrafollicular cells, dendritic cells, normal bone marrow cells, particular precursor cells, 50-80% of umbilical cord blood cells, erythrocytes and platelets. CD38 can also be expressed by non-hemopoietic cells, such as intra-epithelial cells and lamina propria lymphocytes in the gut, by Purkinje cells and neurofibrillary tangles in the brain, by epithelial cells in the prostate, β-cells in the pancreas, osteoclasts in the bone, retinal cells in the eye, and sarcolemma of smooth and striated muscle. On malignant cells, CD38 is expressed in a variety of malignant hematological diseases, including but not restricted to multiple myeloma, primary or secondary plasma cell leukemia, B-cell chronic lymphocytic leukemia, B-cell acute lymphocytic leukemia, Waldenström macroglobulinemia, primary systemic amyloidosis, mantle-cell lymphoma, pro-lymphocytic/myelocytic leukemia, acute myeloid leukemia, chronic myeloid leukemia, follicular lymphoma, and NK-cell leukemia.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, NS/0 cells, and lymphocytic cells.

The term "regulatory sequence" is intended to include promoters, enhancers and other expression control elements (for instance polyadenylation signals) that control the transcription or translation of the antibody chain genes. Such regulatory sequences are described, for example, in Goeddel, Gene Expression Technology. Methods in Enzymology 185, Academic Press, San Diego, Calif. (1990). It will be appreciated by those skilled in the art that the design of the expression vector; including the selection of regulatory sequences may depend on such factors as the choice of the host cell to be transformed, the level of expression of protein desired, etc. Examples of regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter As used herein, the term "subject" includes any human or non-human animal. The term "non-human animal" includes all vertebrates, for instance mammals and non-mammals, such as non-human primates, sheep, dog, cow, chickens, amphibians, reptiles, etc.

The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, lipofectin transfection and the like.

The term "transfectoma", as used herein, includes recombinant eukaryotic host cells expressing the antibody, such as CHO cells, NS/0 cells, HEK293 cells, plant cells, or fungi, including yeast cells.

The term "non-human animal" includes all vertebrates, for instance, mammals and non-mammals, such as non-human primates, sheep, dog, cow, chickens, amphibians, reptiles, etc. The term "non-human animal" includes all vertebrates, for instance, mammals and non-mammals, such as non-human primates, sheep, dog, cow, chickens, amphibians, reptiles, etc. The term "non-human animal" includes all vertebrates, for instance, mammals and non-mammals, such as non-human primates, sheep, dog, cow, chickens, amphibians, reptiles, etc.

The terms "transgenic, non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD38 antibodies when immunized with CD38 antigen and/or cells expressing CD38. The human heavy chain transgene can be integrated into the chromosomal DNA of the mouse, as is the case for transgenic mice, for instance HuMAb mice, such as HCo7 or HCo12 mice, or the human heavy chain transgene can be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

The term specificity herein refers to the ability of a CD38 binding peptide, such as an anti-CD38 antibody, to recognize an epitope within CD38, while only having little or no detectable reactivity with other portions of CD38 (including other epitopes that are bound by other CD38BPs, such as anti-CD38 antibodies). Specificity can be relatively determined by competition assays as described herein. Specificity can more particularly be determined by any of the epitope identification/characterization techniques described herein or their equivalents known in the art.

An antibody specific for a particular antigenic determinant may nonetheless cross-react with other biomolecules that may be present in some biological context with CD38. More typically, a CD38BP, such as an anti-CD38 antibody, may cross-react with CD38 homologues from other species. In either or both contexts, typically such cross-reactive antibodies are selective for human CD38 with respect to relevant structure and/or environmental factors.

The term selectivity herein refers to the preferential binding of a CD38BP, such as an anti-CD38 antibody, for a particular region, target, or peptide; typically a region or epitope in CD38, as opposed to one or more other biological molecules, structures, cells, tissues, etc. In one embodiment, a CD38BP, such as an anti-CD38 antibody, of the present invention is selective for a portion of CD38 in the context of colon cancer cells (i.e., the anti-CD38 antibody will selectively bind to the portion of CD38 over other components of a colon cancer cell).

The CD38BPs of the present invention are typically used in and provided in an at least substantially isolated form. A substantially isolated molecule is a molecule that is the predominant species in the composition wherein it is found with respect to the class of molecules to which it belongs (i.e., it makes up at least about 50% of the type of molecule in the composition and typically will make up at least about 70%, at least about 80%, at least about 85%, at least about 90%, at least about 95%, or more of the species of molecule, e.g., peptide, in the composition (e.g., the composition will exhibit at least about 98%, 98%, or 99% homogeneity for the CD38BP in the context of all present peptide species)).

An isolated molecule refers to a molecule that is not associated with significant levels (such as more than about 1%, more than about 2%, more than about 3%, or more than about 5%) of any extraneous and undesirable physiological factors, such as non-CD38 binding biomolecules (or CD38 binding molecules that may interfere with the binding and/or activity of a CD38BP of the present invention) contained within a cell or animal in which the CD38BP is produced. An isolated molecule also refers to any molecule that has passed through such a stage of purity due to human intervention (whether automatic, manual, or both). In many of the various compositions provided by the present invention, such as in a composition comprising one or more pharmaceutically acceptable carriers, a CD38BP may be present in relatively small amounts in terms of numbers of total molecular species in the composition (for instance in the case of a composition comprising a large amount of a pharmaceutically acceptable carrier, stabilizer, and/or preservative). In some cases additional peptides, such as BSA, may be included in such a composition with a previously purified CD38BP. However, provided that such additional constituents of the composition are acceptable for the intended application of the CD38BP, such a composition can still be described as comprising an isolated CD38BP.

The CD38BPs of the present invention are typically substantially free of other CD38BPs, such as CD38BPs having different antigenic specificities. However, the present invention does also provide a composition comprising a number of CD38BPs with different specificities and characteristics (for instance the present invention provides a "cocktail" of CD38BPs having different specificity and/or selectivity characteristics).

"Treatment" means the administration of an effective amount of a therapeutically active compound of the present invention with the purpose of easing, ameliorating, or eradicating (curing) symptoms or disease states.

In one embodiment, the present invention provides a CD38BP comprising a $V_L$ region consisting essentially of the sequence of SEQ ID No:2.

In one embodiment, the present invention provides a CD38BP comprising a $V_H$ region consisting essentially of the sequence of SEQ ID No:6.

In one embodiment, the present invention provides a CD38BP comprising a $V_L$ region consisting essentially of the sequence of SEQ ID No:2 and a $V_H$ region consisting essentially of the sequence of SEQ ID No:6.

In one embodiment, the present invention provides a CD38BP comprising a $V_L$ CDR1 consisting essentially of the sequence of SEQ ID No:3.

In one embodiment, the present invention provides a CD38BP comprising a $V_L$ CDR2 consisting essentially of the sequence of SEQ ID No:4.

In one embodiment, the present invention provides a CD38BP comprising a $V_L$ CDR3 consisting essentially of the sequence of SEQ ID No:5.

In one embodiment, the present invention provides a CD38BP comprising a $V_H$ CDR1 consisting essentially of the sequence of SEQ ID No:8.

In one embodiment, the present invention provides a CD38BP comprising a $V_H$ CDR2 consisting essentially of the sequence of SEQ ID No:9.

In one embodiment, the present invention provides a CD38BP comprising a $V_H$ CDR3 consisting essentially of the sequence of SEQ ID No:10.

In one embodiment, the present invention provides a CD38BP comprising $V_L$ CDRs ($V_L$ CDR1, CDR2, and CDR3) consisting essentially of SEQ ID No: 3, SEQ ID No:4 and SEQ ID No:5, respectively.

In one embodiment, the present invention provides a CD38BP that comprises $V_H$ CDRs ($V_H$ CDR1, CDR2, and CDR3) consisting essentially of SEQ ID No:8, SEQ ID No:9 and SEQ ID No:10, respectively.

In one embodiment, the present invention provides a CD38BP that comprises
 (a) three $V_L$ CDRs, which independently consist essentially of SEQ ID No:3, SEQ ID No:4 and SEQ ID No:5 in close proximity to one another (e.g., near the spacing of $V_L$ CDRs in a wild-type anti-CD38 antibody) in the CD38BP and
 (b) three $V_H$ CDRs which independently consist essentially of SEQ ID No:8, SEQ ID No:9 and SEQ ID No:10 in close proximity to one another (e.g., near the spacing of $V_H$ CDRs in a wild-type anti-CD38 antibody) in the CD38BP.

In a further embodiment, the present invention provides a CD38BP that comprises a flexible linker positioned between the $V_L$ region and $V_H$ region of the CD38BP. In another further embodiment, the present invention provides a CD38BP, wherein the $V_L$ and $V_H$ regions are presented on separate chains in the context of an immunoglobulin fold protein and oriented such that the $V_L$ CDR1, CDR2, CDR3 and $V_H$ CDR1, CDR2, and CDR3 cooperatively associate to contribute in selectively and/or specifically bind an antigenic determinant on CD38. In another further embodiment, the present invention provides a CD38BP that comprises two sets of variable domains (sets of associated $V_L$ and $V_H$ domains on associated separate chains), such that the CD38BP comprises two identical antigenic determinant binding sites.

Any of such CD38BPs described in this paragraph are expected to, at least in part, have similar epitope specificity, selectivity, and other characteristics as an antibody having $V_L$ region comprising the sequence of SEQ ID No:2 and a $V_H$ region comprising the sequence of SEQ ID No:7, and, accordingly, may be useful in the treatment of multiple myeloma.

In one embodiment, the present invention provides a CD38BP comprising a $V_L$ region consisting essentially of the sequence of SEQ ID No:12.

In one embodiment, the present invention provides a CD38BP comprising a $V_H$ region consisting essentially of the sequence of SEQ ID No:17.

In one embodiment, the present invention provides a CD38BP comprising a $V_L$ region consisting essentially of the sequence of SEQ ID No:12 and a $V_H$ region consisting essentially of the sequence of SEQ ID No:17.

In one embodiment, the present invention provides a CD38BP comprising a $V_L$ CDR1 consisting essentially of the sequence of SEQ ID No:13.

In one embodiment, the present invention provides a CD38BP comprising a $V_L$ CDR2 consisting essentially of the sequence of SEQ ID No:14.

In one embodiment, the present invention provides a CD38BP comprising a $V_L$ CDR3 consisting essentially of the sequence of SEQ ID No:15.

In one embodiment, the present invention provides a CD38BP comprising a $V_H$ CDR1 consisting essentially of the sequence of SEQ ID No:18.

In one embodiment, the present invention provides a CD38BP comprising a $V_H$ CDR2 consisting essentially of the sequence of SEQ ID No:19.

In one embodiment, the present invention provides a CD38BP comprising a $V_H$ CDR3 consisting essentially of the sequence of SEQ ID No:20.

In one embodiment, the present invention provides a CD38BP comprising $V_L$ CDRs ($V_L$ CDR1, CDR2, and CDR3) consisting essentially of SEQ ID No:13, SEQ ID No:14 and SEQ ID No:15, respectively.

In one embodiment, the present invention provides a CD38BP that comprises $V_H$ CDRs ($V_H$ CDR1, CDR2, and CDR3) consisting essentially of SEQ ID No:18, SEQ ID No:19 and SEQ ID No:20, respectively.

In one embodiment, the present invention provides a CD38BP that comprises
(a) three $V_L$ CDRs, which independently consist essentially of SEQ ID No:13, SEQ ID No:14 and SEQ ID No:15 in close proximity to one another (e.g., near the spacing of $V_L$ CDRs in a wild-type anti-CD38 antibody) in the CD38BP and
(b) three $V_H$ CDRs which independently consist essentially of SEQ ID No:18, SEQ ID No:19 and SEQ ID No:20 in close proximity to one another (e.g., near the spacing of $V_H$ CDRs in a wild-type anti-CD38 antibody) in the CD38BP.

In a further embodiment, the present invention provides a CD38BP that comprises a flexible linker positioned between the $V_L$ region and $V_H$ region of the CD38BP. In another further embodiment, the present invention provides a CD38BP, wherein the $V_L$ and $V_H$ regions are presented on separate chains in the context of an immunoglobulin fold protein and oriented such that the $V_L$ CDR1, CDR2, CDR3 and $V_H$ CDR1, CDR2, and CDR3 cooperatively associate to contribute in selectively and/or specifically bind an antigenic determinant on CD38. In another further embodiment, the present invention provides a CD38BP that comprises two sets of variable domains (sets of associated $V_L$ and $V_H$ domains on associated separate chains), such that the CD38BP comprises two identical antigenic determinant binding sites.

Any of such CD38BPs described in this paragraph are expected to, at least in part, have similar epitope specificity, selectivity, and other characteristics as an antibody having $V_L$ region comprising the sequence of SEQ ID No:12 and a $V_H$ region comprising the sequence of SEQ ID No:17, and, accordingly, may be useful in the treatment of multiple myeloma.

In one embodiment, the present invention provides a CD38BP comprising a $V_L$ region consisting essentially of the sequence of SEQ ID No:22.

In one embodiment, the present invention provides a CD38BP comprising a $V_H$ region consisting essentially of the sequence of SEQ ID No:27.

In one embodiment, the present invention provides a CD38BP comprising a $V_L$ region consisting essentially of the sequence of SEQ ID No:22 and a $V_H$ region consisting essentially of the sequence of SEQ ID No:27.

In one embodiment, the present invention provides a CD38BP comprising a $V_L$ CDR1 consisting essentially of the sequence of SEQ ID No:23.

In one embodiment, the present invention provides a CD38BP comprising a $V_L$ CDR2 consisting essentially of the sequence of SEQ ID No:24.

In one embodiment, the present invention provides a CD38BP comprising a $V_L$ CDR3 consisting essentially of the sequence of SEQ ID No:25.

In one embodiment, the present invention provides a CD38BP comprising a $V_H$ CDR1 consisting essentially of the sequence of SEQ ID No:28.

In one embodiment, the present invention provides a CD38BP comprising a $V_H$ CDR2 consisting essentially of the sequence of SEQ ID No:29.

In one embodiment, the present invention provides a CD38BP comprising a $V_H$ CDR3 consisting essentially of the sequence of SEQ ID No:30.

In one embodiment, the present invention provides a CD38BP comprising $V_L$ CDRs ($V_L$ CDR1, CDR2, and CDR3) consisting essentially of SEQ ID No:23, SEQ ID No:24 and SEQ ID No:25, respectively.

In one embodiment, the present invention provides a CD38BP that comprises $V_H$ CDRs ($V_H$ CDR1, CDR2, and CDR3) consisting essentially of SEQ ID No:28, SEQ ID No:29 and SEQ ID No:30, respectively.

In one embodiment, the present invention provides a CD38BP that comprises
(a) three $V_L$ CDRs, which independently consist essentially of SEQ ID No:23, SEQ ID No:24 and SEQ ID No:25 in close proximity to one another (e.g., near the spacing of V, CDRs in a wild-type anti-CD38 antibody) in the CD38BP and
(b) three $V_H$ CDRs which independently consist essentially of SEQ ID No:28, SEQ ID No:29 and SEQ ID No:30 in close proximity to one another (e.g., near the spacing of $V_H$ CDRs in a wild-type anti-CD38 antibody) in the CD38BP.

In a further embodiment, the present invention provides a CD38BP that comprises a flexible linker positioned between the $V_L$ region and $V_H$ region of the CD38BP. In another further embodiment, the present invention provides a CD38BP, wherein the $V_L$ and $V_H$ regions are presented on separate chains in the context of an immunoglobulin fold protein and oriented such that the $V_L$ CDR1, CDR2, CDR3 and $V_H$ CDR1, CDR2, and CDR3 cooperatively associate to contribute in selectively and/or specifically bind an antigenic determinant on CD38. In another further embodiment, the present invention provides a CD38BP that comprises two sets of variable domains (sets of associated $V_L$ and $V_H$ domains on associated separate chains), such that the CD38BP comprises two identical antigenic determinant binding sites.

Any of such CD38BPs described in this paragraph are expected to, at least in part, have similar epitope specificity, selectivity, and other characteristics as an antibody having $V_L$ region comprising the sequence of SEQ ID No:22 and a $V_H$ region comprising the sequence of SEQ ID No:27, and, accordingly, may be useful in the treatment of multiple myeloma.

In one embodiment, the present invention provides a CD38BP comprising a $V_L$ CDR1 consisting essentially of a sequence according to SEQ ID No:3 or SEQ ID No:13 or SEQ ID No:23, wherein the N-terminal residue and/or one, two, or three of the C-terminal amino acid residues are missing.

In one embodiment, the present invention provides a CD38BP comprising a $V_L$ CDR2 consisting essentially of a sequence according to SEQ ID No:4 or SEQ ID No:14 or SEQ ID No:24, wherein one or two of the N-terminal residues and/or one, two, or three of the C-terminal residues are missing.

In one embodiment, the present invention provides a CD38BP comprising a $V_L$ CDR3 consisting essentially of a sequence according to SEQ ID No:5 or SEQ ID No:15 or SEQ ID No:25, wherein the N-terminal residue and/or one, two, three, or four of the C-terminal residues are missing.

In one embodiment, the present invention provides a CD38BP comprising a $V_H$ CDR1 consisting essentially of a sequence according to SEQ ID No:8 or SEQ ID No:18 or SEQ ID No:28, wherein one, two, three, or four of the N-terminal residues and/or one, two, three, or four C-terminal residues are missing.

In one embodiment, the present invention provides a CD38BP comprising a $V_H$ CDR2 consisting essentially of a sequence according to SEQ ID No:9 or SEQ ID No:19 or SEQ ID No:29, wherein one, two, three, four, or five of the N-terminal amino acids thereof and/or one, two, three, four, five, or six of the C-terminal amino acids thereof are missing.

In one embodiment, the present invention provides a CD38BP comprising a $V_H$ CDR3 consisting essentially of a sequence according to SEQ ID No:10 or SEQ ID No:20 or SEQ ID No:30, wherein the N-terminal one, two, or three amino acid residues and/or the C-terminal one, two, three, or four amino acid residues are missing.

The present invention also provides CD38BPs wherein these "truncated" CDR sequences are combined with each other and/or other CDR sequences described herein.

In one embodiment, the present invention provides a CD38BP that comprises
(a) three $V_L$ CDRs, which independently consist essentially of SEQ ID No: 3, SEQ ID No:4 and SEQ ID No:5 in close proximity to one another in the CD38BP (e.g., near the spacing of $V_L$ CDRs in a wild-type anti-CD38 antibody) and
(b) three $V_H$ CDRs which independently consist essentially of SEQ ID No:8, SEQ ID No:9 and SEQ ID No:10 in close proximity to one another (e.g., near the spacing of $V_H$ CDRs in a wild-type anti-CD38 antibody) in the CD38BP.

In a further embodiment, the present invention provides a CD38BP that comprises a flexible linker positioned between the $V_L$ region and $V_H$ region of the CD38BP.

In a further embodiment, the present invention provides a CD38BP wherein the $V_L$ and $V_H$ regions are presented on separate chains in the context of an immunoglobulin fold protein and oriented such that the $V_L$ CDR1, CDR2, CDR3 and $V_H$ CDR1, CDR2, and CDR3 cooperatively associate to contribute in selectively and/or specifically bind an antigenic determinant on CD38. In a further embodiment, the present invention provides a CD38BP that comprises two sets of variable domains (sets of associated $V_L$ and $V_H$ domains on associated separate chains), such that the CD38BP comprises two identical antigenic determinant binding sites. Any of such CD38BPs described in this paragraph are expected to, at least in part, have similar epitope specificity, selectivity, and other characteristics with an antibody having a $V_L$ sequence of SEQ ID No:2 and a $V_H$ sequence of SEQ ID No:7.

In one embodiment, the present invention provides a CD38BP that comprises
(a) three $V_L$ CDRs, which independently consist essentially of SEQ ID No:13, SEQ ID No:14 and SEQ ID No:15 in close proximity to one another in the CD38BP (e.g., near the spacing of $V_L$ CDRs in a wild-type anti-CD38 antibody) and
(b) three $V_H$ CDRs which independently consist essentially of SEQ ID No:18, SEQ ID No:19 and SEQ ID No:20 in close proximity to one another (e.g., near the spacing of $V_H$ CDRs in a wild-type anti-CD38 antibody) in the CD38BP.

In a further embodiment, the present invention provides a CD38BP that comprises a flexible linker positioned between the $V_L$ region and $V_H$ region of the CD38BP.

In a further embodiment, the present invention provides a CD38BP wherein the $V_L$ and $V_H$ regions are presented on separate chains in the context of an immunoglobulin fold protein and oriented such that the $V_L$ CDR1, CDR2, CDR3 and $V_H$ CDR1, CDR2, and CDR3 cooperatively associate to contribute in selectively and/or specifically bind an antigenic determinant on CD38. In a further embodiment, the present invention provides a CD38BP that comprises two sets of variable domains (sets of associated $V_L$ and $V_H$ domains on associated separate chains), such that the CD38BP comprises two identical antigenic determinant binding sites. Any of such CD38BPs described in this paragraph are expected to, at least in part, have similar epitope specificity, selectivity, and other characteristics with an antibody having a $V_L$ sequence of SEQ ID No:12 and a $V_H$ sequence of SEQ ID No:17.

In one embodiment, the present invention provides a CD38BP that comprises
(a) three V, CDRs, which independently consist essentially of SEQ ID No:23, SEQ ID No:24 and SEQ ID No:25 in close proximity to one another in the CD38BP (e.g., near the spacing of $V_L$ CDRs in a wild-type anti-CD38 antibody) and
(b) three $V_H$ CDRs which independently consist essentially of SEQ ID No:28, SEQ ID No:29 and SEQ ID No:30 in close proximity to one another (e.g., near the spacing of $V_H$ CDRs in a wild-type anti-CD38 antibody) in the CD38BP.

In a further embodiment, the present invention provides a CD38BP that comprises a flexible linker positioned between the $V_L$ region and $V_H$ region of the CD38BP.

In a further embodiment, the present invention provides a CD38BP wherein the $V_L$ and $V_H$ regions are presented on separate chains in the context of an immunoglobulin fold protein and oriented such that the $V_L$ CDR1, CDR2, CDR3 and $V_H$ CDR1, CDR2, and CDR3 cooperatively associate to contribute in selectively and/or specifically bind an antigenic determinant on CD38. In a further embodiment, the present invention provides a CD38BP that comprises two sets of variable domains (sets of associated $V_L$ and $V_H$ domains on associated separate chains), such that the CD38BP comprises two identical antigenic determinant binding sites. Any of such CD38BPs described in this paragraph are expected to, at least in part, have similar epitope specificity, selectivity, and other characteristics with an antibody having a $V_L$ sequence of SEQ ID No:22 and a $V_H$ sequence of SEQ ID No:27.

The present invention also provides CD38BPs comprising functional variants of the $V_L$ region, $V_H$ region, or one or more CDRs of the antibodies of the examples. A functional variant of a $V_L$, $V_H$, or CDR used in the context of a CD38BP still allows the CD38BP to retain at least a substantial proportion (at least about 50%, 60%, 70%, 80%, 90%, 95% or more) of the affinity/avidity and/or specificity/selectivity of the parent antibody and in some cases such a CD38BP may be associated with greater affinity, selectivity, and/or specificity than the parent antibody.

In one embodiment, the present invention provides a CD38BP comprising a variant $V_L$ consisting essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to SEQ ID No:2 or SEQ ID No:12 or SEQ ID No:22, wherein the CD38BP has at least a substantial proportion (at least about 50%, 60%, 70%, 80%, 90%, 95% or more) of the epitope binding characteristics of an antibody having a variant $V_L$ sequence of SEQ ID No:2 or SEQ ID No:12 or SEQ ID No:22, respectively, such as an antibody having a $V_L$ sequence of SEQ ID No:2 and a $V_H$ sequence of SEQ ID No:7, and an antibody having a $V_L$ sequence of SEQ ID No:12 and a $V_H$ sequence of SEQ ID No:17, and an antibody having a $V_L$ sequence of SEQ ID No:22 and a $V_H$ sequence of SEQ ID No:27, respectively.

In one embodiment, the present invention provides a CD38BP comprising a variant $V_L$ CDR1 consisting essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID No:3 or SEQ ID No:13 or SEQ ID No:23, wherein the CD38BP has at least a substantial proportion (at least about 50%, 60%, 70%, 80%, 90%, 95% or more) of the epitope binding characteristics of an antibody having a variant $V_L$ CDR1 sequence of SEQ ID No:3 or SEQ ID No:13 or SEQ ID No:23, respectively, such as an antibody having a $V_L$ sequence of SEQ ID No:2 or SEQ ID No:12 or SEQ ID No:22, respectively, such as an antibody having a $V_L$ sequence of SEQ ID No:2 and a $V_H$ sequence of SEQ ID No:7, or an antibody having a $V_L$ sequence of SEQ ID No:12 and a $V_H$ sequence of SEQ ID No:17, or an antibody having a $V_L$ sequence of SEQ ID No:22 and a $V_H$ sequence of SEQ ID No:27, respectively.

In one embodiment, the present invention provides a CD38BP comprising a variant $V_L$ CDR2 consisting essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID Nos:4 or 14, wherein the CD38BP has at least a substantial proportion (at least about 50%, 60%, 70%, 80%, 90%, 95% or more) of the epitope binding characteristics of an antibody having a variant $V_L$ CDR2 sequence of SEQ ID No:4 or SEQ ID No:14 or SEQ ID No:24, respectively, such as an antibody having a $V_L$ sequence of SEQ ID No:2 or SEQ ID No:12 or SEQ ID No:22, respectively, such as an antibody having a $V_L$ sequence of SEQ ID No:2 and a $V_H$ sequence of SEQ ID No:7, or an antibody having a $V_L$ sequence of SEQ ID No:12 and a $V_H$ sequence of SEQ ID No:17, or an antibody having a $V_L$ sequence of SEQ ID No:22 and a $V_H$ sequence of SEQ ID No:27, respectively.

In one embodiment, the present invention provides a CD38BP comprising a variant $V_L$ CDR3 consisting essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID No:5 or SEQ ID No:15 or SEQ ID No:25, wherein the CD38BP has at least a substantial proportion (at least about 50%, 60%, 70%, 80%, 90%, 95% or more) of the epitope binding characteristics of an antibody having a variant $V_L$ CDR3 sequence of SEQ ID No:5 or SEQ ID No:15 or SEQ ID No:25, respectively, such as an antibody having a $V_L$ sequence of SEQ ID No:2 or SEQ ID No:12 or SEQ ID No:22, respectively, such as an antibody having a $V_L$ sequence of SEQ ID No:2 and a $V_H$ sequence of SEQ ID No:7, or an antibody having a $V_L$ sequence of SEQ ID No:12 and a $V_H$ sequence of SEQ ID No:17, or an antibody having a $V_L$ sequence of SEQ ID No:22 and a $V_H$ sequence of SEQ ID No:27, respectively.

In one embodiment, the present invention provides a CD38BP comprising a variant $V_H$ consisting essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID No:7 or SEQ ID No:17 or SEQ ID No:27, wherein the CD38BP has at least a substantial proportion (at least about 50%, 60%, 70%, 80%, 90%, 95% or more) of the epitope binding characteristics of an antibody having a variant $V_H$ sequence of SEQ ID No:7 or SEQ ID No:17 or SEQ ID No:27, respectively, such as an antibody having a $V_H$ sequence of SEQ ID No:7 and a $V_L$ sequence of SEQ ID No:2, or an antibody having a $V_H$ sequence of SEQ ID No:17 and a $V_L$ sequence of SEQ ID No:12, or an antibody having a $V_H$ sequence of SEQ ID No:27 and a $V_L$ sequence of SEQ ID No:22, respectively.

In one embodiment, the present invention provides a CD38BP comprising a variant $V_H$ CDR1 consisting essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID No:8 or SEQ ID No:18 or SEQ ID No:28, wherein the CD38BP has at least a substantial proportion (at least about 50%, 60%, 70%, 80%, 90%, 95% or more) of the epitope binding characteristics of an antibody having a variant $V_H$ CDR1 sequence of SEQ ID No:8 or SEQ ID No:18 or SEQ ID No:28, respectively, such as an antibody having a $V_H$ sequence of SEQ ID No:7 or SEQ ID No:17 or SEQ ID No:27, respectively, such as an antibody having a $V_H$ sequence of SEQ ID No:7 and a $V_L$ sequence of SEQ ID No:2, or an antibody having a $V_H$ sequence of SEQ ID No:17 and a $V_L$ sequence of SEQ ID No:12, or an antibody having a $V_H$ sequence of SEQ ID No:27 and a $V_L$ sequence of SEQ ID No:22, respectively.

In one embodiment, the present invention provides a CD38BP comprising a variant $V_H$ CDR2 consisting essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID No:9 or SEQ ID No:19 or SEQ ID No:29, wherein the CD38BP has at least a substantial proportion (at least about 50%, 60%, 70%, 80%, 90%, 95% or more) of the epitope binding characteristics of an antibody having a variant $V_H$ CDR2 sequence of SEQ ID No:9 or SEQ ID No:19 or SEQ ID No:29, respectively, such as an antibody having a $V_H$ sequence of SEQ ID No:7 or SEQ ID No:17 or SEQ ID No:27, respectively, such as an antibody having a $V_H$ sequence of SEQ ID No:7 and a $V_L$ sequence of SEQ ID No:2, or an antibody having a $V_H$ sequence of SEQ ID No:17 and a $V_L$ sequence of SEQ ID No:12, or an antibody having a $V_H$ sequence of SEQ ID No:27 and a $V_L$ sequence of SEQ ID No:22, respectively.

In one embodiment, the present invention provides a CD38BP comprising a variant $V_H$ CDR3 consisting essentially of a sequence having at least about 50%, such as at least 60%, for instance at least about 70%, such as at least about 75%, for instance at least about 80%, such as at least about 85%, for instance at least about 90%, such as at least about 95% amino acid sequence identity to a sequence according to any one of SEQ ID No:10 or SEQ ID No:20 or SEQ ID No:30, wherein the CD38BP has at least a substantial proportion (at least about 50%, 60%, 70%, 80%, 90%, 95% or more) of the epitope binding characteristics of an antibody having a variant $V_H$ CDR3 sequence of SEQ ID No:10 or SEQ ID No:20 or SEQ ID No:30, respectively, such as an antibody having a $V_H$ sequence of SEQ ID No:7 or SEQ ID No:17 or SEQ ID No:27, respectively, such as an antibody having a $V_H$ sequence of SEQ ID No:7 and a $V_L$ sequence of SEQ ID No:2, or an antibody having a $V_H$ sequence of SEQ ID No:17 and a $V_L$ sequence of SEQ ID No:12, or an antibody having a $V_H$ sequence of SEQ ID No:27 and a $V_L$ sequence of SEQ ID No:22, respectively.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The percent identity between two nucleotide sequences may be determined using the GAP program in the GCG software package (available at the website of Genetics Computer Group at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences may also be determined using the algorithm of E. Meyers and W. Miller, Comput. Appl. Biosci, 11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol., 444-453 (1970)) algorithm which has been incorporated into the GAP program in the GCG software package (available at the website of Genetics Computer Group at gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention may further be used as a "query sequence" to perform a search against public databases to, for example, identify related sequences. Such searches may be performed using the NBLAST and XBLAST programs (version 2.0) of Altschul et al., J. Mol. Bio. 215, 403-10 (1990). BLAST nucleotide searches may be performed with the NBLAST program, score=100, wordlength=12 to obtain nucleotide sequences homologous to the nucleic acid molecules of the present invention. BLAST protein searches may be performed with the XBLAST program, score=50, wordlength=3 to obtain amino acid sequences homologous to the protein molecules of the present invention. To obtain gapped alignments for comparison purposes, Gapped BLAST may be utilized as described in Altschul et al., Nucleic Acids Res. 25(17), 3389-3402 (1997). When utilizing BLAST and Gapped BLAST programs, the default parameters of the respective programs (e.g., XBLAST and NBLAST) may be used. See the website of the National Center for Biotechnology Information at ncbi.nlm nih gov.

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, about 95% or more (e.g., about 65-99%) of the substitutions in the variant are conservative amino acid residue replacements. In the context of the present invention, conservative substitutions may be defined by substitutions within the classes of amino acids reflected in one or more of the following three tables:

| Amino acid residue classes for conservative substitutions | |
|---|---|
| Acidic Residues | Asp and Glu |
| Basic Residues | Lys, Arg, and His |
| Hydrophilic Uncharged Residues | Ser, Thr, Asn, and Gln |
| Aliphatic Uncharged Residues | Gly, Ala, Val, Leu, and Ile |
| Non-polar Uncharged Residues | Cys, Met, and Pro |
| Aromatic Residues | Phe, Tyr, and Trp |

| Alternative conservative amino acid residue substitution classes | | | |
|---|---|---|---|
| 1 | Ala (A) | Ser (S) | Thr (T) |
| 2 | Asp (D) | Glu (E) | |
| 3 | Asp (N) | Gln (Q) | |
| 4 | Arg (R) | Lys (K) | |
| 5 | Ile (I) | Leu (L) | Met (M) |
| 6 | Phe (F) | Tyr (Y) | Trp (W) |

| Alternative Physical and Functional Classifications of Amino Acid Residues | |
|---|---|
| Alcohol group-containing residues | S and T |
| Aliphatic residues | I, L, V, and M |
| Cycloalkenyl-associated residues | F, H, W, and Y |

-continued

| Alternative Physical and Functional Classifications of Amino Acid Residues | |
|---|---|
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

More conservative substitutions groupings include: valine-leucine-isoleucine, phenylalanine-tyrosine, lysine-arginine, alanine-valine, and asparagine-glutamine. Additional groups of amino acids may also be formulated using the principles described in, e.g., Creighton (1984) Proteins: Structure and Molecular Properties (2d Ed. 1993), W.H. Freeman and Company.

In one embodiment of the present invention, conservation in terms of hydropathic/hydrophilic properties and residue weight/size also is substantially retained in a variant CDR as compared to a CDR of an antibody of the examples (e.g., the weight class, hydropathic score, or both of the sequences are at least about 50%, at least about 60%, at least about 70%, at least about 75%, at least about 80%, at least about 85%, at least about 90%, at least about 95%, or more (e.g., about 65-99%) retained). For example, conservative residue substitutions may also or alternatively be based on the replacement of strong or weak based weight based conservation groups, which are known in the art.

The retention of similar residues may also or alternatively be measured by a similarity score, as determined by use of a BLAST program (e.g., BLAST 2.2.8 available through the NCBI). Suitable variants typically exhibit at least about 45%, such as at least about 55%, at least about 65%, at least about 75%, at least about 85%, at least about 90%, at least about 95%, or more (e.g., about 70-99%) similarity to the parent peptide.

Substantial changes in function may be made by selecting substitutions that are less conservative than those shown in the defined groups, above. For example, non-conservative substitutions may be made which more significantly affect the structure of the peptide in the area of the alteration, for example, the alpha-helical, or beta-sheet structure; the charge or hydrophobicity of the molecule at the target site; or the bulk of the side chain. The substitutions which generally are expected to produce the greatest changes in the peptide's properties are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine. Accordingly, these and other nonconservative substitutions may be introduced into peptide variants where significant changes in function/structure is desired and such changes avoided where conservation of structure/function is desired.

A convenient way for generating substitution variants is affinity maturation using phage using methods known in the art. In order to identify candidate hypervariable region sites for modification, alanine scanning mutagenesis may also be performed to identify hypervariable region residues contributing significantly to antigen binding. Alternatively or additionally, it may be beneficial to analyze a crystal structure of the antigen-antibody complex to identify contact points between the antibody and antigen. Such contact residues and neighboring residues are likely suitable candidates for substitution.

Where hypervariable region insertions are made to generate a variant antibody, the typical range of lengths of the hypervariable region in question in known antibodies should be taken into consideration. For example, for the first hypervariable region of a light chain variable domain, insertions may be introduced into the $V_L$ CDR1 sequence of a parent antibody while retaining a substantially similar and thereby expected appropriate size, which according to Kabat et al., supra, e.g., typically has an overall of about 9-20 (e.g., about 10-17) residues. Similarly, $V_L$ CDR2 typically has an overall length from about 5-10 residues; $V_L$ CDR3 typically has a length of about 7-20 residues; $V_H$ CDR1 typically has a length of about 10-15 residues; $V_H$ CDR2 typically has a length of about 15-20 residues; and $V_H$ CDR3 typically has a length of about 6-30 residues (e.g., 3-25 residues). Insertions in the $V_H$ region typically are made in $V_H$ CDR3 and typically near the C-terminal of the domain, such as about residues 97-102 of the parent $V_H$ CDR3 (for instance adjacent to, or C-terminal in sequence to, residue number 100 of the parent $V_H$ CDR3 sequence) using the alignment and numbering as described in Kabat. Antibody variants with inserted amino acid residue(s) in a hypervariable region thereof may be prepared randomly, especially where the starting binding affinity of the parent antibody for the target antigen is such that randomly produced antibody variants may be readily screened. For example, phage display provides a convenient method of screening such random variants.

In the design, construction, and/or evaluation of CDR variants attention may be paid to the fact that CDR regions may be altered to enable a better binding to the epitope. Antibody CDRs typically operate by providing a complementary surface, possibly including fingers which can protrude into the protein surface of the antigen, or other paratope structure, onto which the epitope fits. If the epitope is not fitting tightly, the antibody may not offer the best affinity. However, as with epitopes, there often are a few key residues in a paratope structure that account for most of this binding. Thus, CDR sequences may vary in length and composition significantly between antibodies for the same peptide. The skilled artisan will recognize that certain residues, such as tyrosine residues (e.g., in the context of $V_H$ CDR3 sequences), that are often significant contributors to such epitope binding, are typically retained in a CDR variant.

Variants of the CDR region may also increase the amino acid contacts between the antigen and an antibody variant, as compared to the amino acid contacts between the antigen and the parent antibody, by introducing one or more amino acid residues (either by substitution or insertions) which increase the contacts or energetically favorable interactions between one or more amino acid residues present in an antigen and one or more amino acid residues present in the antibody. The amino acid interactions of interest may be selected from hydrogen bonding interactions, van der Waals interactions, and ionic interactions.

Those skilled in the art will be aware of additional principles useful in the design and selection of CD38BP comprising CDR variants of the antibodies of the present invention.

In the context of CDR variants, which are variants of the CDRs of the antibodies of the examples, particularly in the context of variant CDR in anti-CD38 antibodies or fragments thereof, residues required to support and/or orientate the CDR structural loop structure(s) may typically be retained; residues which fall within about 10 angstroms of a CDR structural loop (but optionally only residues in this area that also possess a water solvent accessible surface of about 5 angstroms$^2$ or greater) may typically be unmodified or modified only by conservative amino acid residue substitutions; and/or the amino acid sequence may typically be subject to only a limited number of insertions and/or deletions (if any), such that CDR structural loop-like structures are retained in the variant (a description of related techniques and relevant principles is provided in for instance Schiweck et al., J Mol. Biol. 268(5), 934-51 (1997), Morea, Biophys Chem. 68(1-3), 9-16 (1997), Shirai et al., FEBS Lett. 399(1-2), 1-8 (1996), Shirai et al., FEBS Lett. 455(1-2), 188-97 (1999), Reckzo et al., Protein Eng. 8(4), 389-95 (1995) and Eigenbrot et al., J Mol. Biol. 229(4), 969-95 (1993). See also WO 03/048185, WO 03/070747 and WO 03/027246.

Additional techniques that may be used to generate variant antibodies include the directed evolution and other variant generation techniques described in for instance US 20040009498, Marks et al., Methods Mol. Biol. 248, 327-43 (2004), Azriel-Rosenfeld et al., J Mol. Biol. 335(1), 177-92 (2004), Park et al., Biochem Biophys Res Commun. 275(2), 553-7 (2000), Kang et al., Proc Natl Acad Sci USA. 88(24), 11120-3 (1991), Zahnd et al., J Biol. Chem. 279(18), 18870-7 (2004), Xu et al., Chem. Biol. 9(8), 933-42 (2002), Border et al., Proc Natl Acad Sci USA. 97(20), 10701-5 (2000), Crameri et al., Nat. Med. 2(1), 100-2 (1996) and as more generally described in for instance WO 03/048185.

Generated antibody variants may be subjected to any suitable screening technique and antibodies with suitable and desirably superior properties in one or more relevant assays may be selected for further development.

CD38BPs comprising CDR sequences as described above may comprise any suitable number and combination of such $V_L$ and $V_H$ CDRs while retaining at least a substantial proportion (at least about 50%, 60%, 70%, 80%, 90%, 95% or more) of the affinity/avidity and/or specificity/selectivity of an antibody having a $V_L$ sequence of SEQ ID No:2 and a $V_H$ sequence of SEQ ID No:7, and/or an antibody having a $V_L$ sequence of SEQ ID No:12 and a $V_H$ sequence of SEQ ID No:17 and/or an antibody having a $V_L$ sequence of SEQ ID No:22 and a $V_H$ sequence of SEQ ID No:27, but optionally differing in other characteristics, such as immunogenicity in a human patient, affinity for the epitope, increased half-life, etc. In some cases such a CD38BP may be associated with greater affinity, selectivity, and/or specificity than the parent antibody. In one embodiment, less than a full set of $V_L$ CDRs and/or $V_H$ CDRs is present in a CD38BP of the present invention. In one embodiment all of the $V_L$ CDRs and $V_H$ CDRs are present.

Examples of other functional properties of antibodies, which may be altered or retained in variant CD38BPs of the present invention as compared to –003 and –005 and –024, are:
  (1) high affinity binding to CD38;
  (2) low dissociation rate from CD38
  (3) inhibition or blocking of CD38-binding to CD38 target;
  (4) elimination of T cells or B cells expressing CD38;
  (5) induction of a high level of CDC of either CD55/59 negative or CD55/59 positive cells;
  (6) translocation into lipid rafts upon binding to CD38;
  (7) tolerization of T cells;
  (8) inhibition of proliferation of T or B cells expressing CD38;
  (9) internalization of CD38;
  (10) inhibition or induction of CD38 enzymatic activity;
  (11) inhibition or induction of CD38-induced signal transduction;
  (12) induction or inhibition of cytokine production;
  (13) induction or blocking of T cell or B cell differentiation;
  (14) induction of or rescue from apoptosis;
  (15) attenuation or augmentation of lysis induction by NK cells;
  (16) induction or inhibition of insulin production by P cells in pancreas;
  (17) prolonged survival of a subject having tumor cells which express CD38; and/or
  (18) induction of ADCC of CD38 targets when mixed with appropriate effector cells. The present invention also provides CD38BPs which are characterized with respect to their ability to compete (competitively inhibit) or cross-compete (i.e., relatively partially inhibit epitope binding) with an antibody having a $V_L$ sequence of SEQ ID No:2 and a $V_H$ sequence of SEQ ID No:7 (such as antibody –003), or an antibody having a $V_L$ sequence of SEQ ID No:12 and a $V_H$ sequence of SEQ ID No:17 (such as antibody –005) or an antibody having a $V_L$ sequence of SEQ ID No:22 and a $V_H$ sequence of SEQ ID No:27, (such as antibody –024), for binding to CD38.

Such a CD38BP may be, for instance, a Fab fragment, derived from an antibody that binds to an epitope identical to or overlapping with an epitope bound by an antibody having a $V_L$ sequence of SEQ ID No:2 and a $V_H$ sequence of SEQ ID No:7, or an antibody having a $V_L$ sequence of SEQ ID No:12 and a $V_H$ sequence of SEQ ID No:17 or an antibody having a $V_L$ sequence of SEQ ID No:22 and a $V_H$ sequence of SEQ ID No:27. Such a Fab fragment, due to its relatively small size compared to the mAb molecules, may not significantly compete with said antibodies for binding to CD38 although the antibody from which it derived does. Nonetheless, such a CD38BP may be useful in similarly targeting nearby regions of CD38 (e.g., in the context of targeting a cytotoxin, radionuclide, or the like in the context of an immunoconjugate CD38BP). Therefore, such CD38BPs may be useful in the context of the methods of the present invention and, accordingly, are also provided by the present invention.

Competition for binding to CD38 or a portion of CD38 by two or more CD38BPs may be determined by any suitable technique. In one embodiment, competition is determined for example as described in Example 7, 8 and 9.

Competition in the context of the present invention refers to any detectably significant reduction in the propensity for a particular molecule to bind a particular binding partner in the presence of another molecule that binds the binding partner. Typically, competition means an at least about 10% reduction, such as an at least about 15%, or an at least about 20% reduction in binding between a CD38BP and
  (a) a form of CD38 (e.g. "processed", "mature", "unprocessed", "not processed" or "immature" CD38);
  (b) a form of free CD38 (e.g., a CD38 fragment produced by in vivo processing);
  (c) a heterodimeric peptide composed of another peptide associated with CD38, such as a CD31, and CD38;
  (d) a complex of CD38 and one or more substrates, such as cAMP, NAD+ and/or cADPR;
  (e) a dimerized, associated and/or processed dimer of CD38 with a soluble ligand, such as CD31; or
  (f) a portion of CD38, caused by the presence of another CD38BP as determined by, e.g., ELISA analysis or FACS analysis (as described in the examples section) using sufficient amounts of the two or more competing CD38BPs and CD38 molecule. It may also be the case that competition may exist between CD38BPs with respect to more than one of CD38, and/or a portion of CD38, e.g. in a context where the antibody-binding properties of a particular region of CD38 are retained in fragments thereof, such as in the case of a well-presented linear epitope located in various tested fragments or a conformational epitope that is presented in sufficiently large CD38 fragments as well as in CD38.

Assessing competition typically involves an evaluation of relative inhibitory binding using a first amount of a first molecule; a second amount of a second molecule; and a third amount of a third molecule (or a standard determined by binding studies that may be reasonably compared to new binding data with respect to the first and second molecules as a surrogate for actual contemporaneous data), wherein the first, second, and third amounts all are sufficient to make a comparison that imparts information about the selectivity and/or specificity of the molecules at issue with respect to the other present molecules. The first, second, and third amounts may vary with the nature of the CD38BP and potential targets therefore at issue. For instance, for ELISA assessments, similar to those described in the Examples section, about 5-50 µg (e.g., about 10-50 µg, about 20-50 µg, about 5-20 µg, about 10-20 µg, etc.) of CD38BP and/or CD38 targets are required to assess whether competition exists. Conditions also should be suitable for binding. Typically, physiological or near-physiological conditions (e.g., temperatures of about 20-40° C., pH of about 7-8, etc.) are suitable for CD38BP:CD38 binding.

Often competition is marked by a significantly greater relative inhibition than about 5% as determined by ELISA and/or FACS analysis. It may be desirable to set a higher threshold of relative inhibition as a criteria/determinant of what is a suitable level of competition in a particular context (e.g., where the competition analysis is used to select or screen for new antibodies designed with the intended function of blocking the binding of another peptide or molecule binding to CD38 (e.g., the natural binding partners of CD38 such as CD31, also called CD31 antigen, EndoCAM, GPIIA', PECAM-1, platelet/endothelial cell adhesion molecule or naturally occurring anti-CD38 antibody)). Thus, for example, it is possible to set a criteria for competitiveness wherein at least about 10% relative inhibition is detected; at least about 15% relative inhibition is detected; or at least about 20% relative inhibition is detected before an antibody is considered sufficiently competitive. In cases where epitopes belonging to competing antibodies are closely located in an antigen, competition may be marked by greater than about 40% relative inhibition of CD38 binding (e.g., at least about 45% inhibition, such as at least about 50% Inhibition, for instance at least about 55% inhibition, such as at least about 60% inhibition, for instance at least about 65% inhibition, such as at least about 70% inhibition, for instance at least about 75% inhibition, such as at least about 80% inhibition, for instance at least about 85% inhibition, such as at least about 90% inhibition, for instance at least about 95% inhibition, or higher level of relative inhibition).

Competition may be considered the inverse of cross-reactivity between a molecule and two potential binding partners. In certain embodiments, a CD38BP of the present invention specifically binds to one or more residues or regions in CD38 but also does not cross-react with other peptides, peptide regions, or molecules, e.g., the present invention provides an anti-CD38 antibody that does not cross-react with proteins with homology to CD38, such as BST-1 (bone marrow stromal cell antigen-1) and Mo5, also called CD157; or anti-CD38 antibodies that do not cross-react with CD38 in the context of normal tissue, such as tissues not involved in multiple myeloma. Typically, a lack of cross-reactivity means less than about 5% relative competitive inhibition between the molecules when assessed by ELISA and/or FACS analysis using sufficient amounts of the molecules under suitable assay conditions.

In one embodiment, the present invention provides a CD38BP that competes with an antibody having a $V_L$ sequence of SEQ ID No:2 and a $V_H$ sequence of SEQ ID No:7, such as the antibody –003, for binding to CD38 or a portion thereof.

In one embodiment, the present invention provides a CD38BP that competes with an antibody having a $V_L$ sequence of SEQ ID No:12 and a $V_H$ sequence of SEQ ID No:17, such as the antibody –005, for binding to CD38 or a portion thereof.

In one embodiment, the present invention provides a CD38BP that competes with an antibody having a $V_L$ sequence of SEQ ID No:22 and a $V_H$ sequence of SEQ ID No:27, such as the antibody –024, for binding to CD38 or a portion thereof.

As discussed elsewhere herein, unless otherwise stated or clearly contradicted by context, references to binding of a CD38BP to CD38 are intended to refer to binding in any suitable context, such as in a conformational context where the structure of CD38 is present; or in a linear epitope context. Of course, binding in a limited subset of such context(s) may be an important characteristic with respect to any CD38BP provided by the present invention.

Additional methods for determining CD38BP specificity by competitive inhibition may be found in for instance Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley InterScience N.Y., (1992, 1993), and Muller, Meth. Enzymol. 92, 589-601 (1983)).

Human CD38 comprises a number of different epitopes, which may include (1) peptide antigenic determinants that are comprised within single peptide chains within human CD38; (2) conformational antigenic determinants which consist one or more noncontiguous amino acids on a particular chain and/or amino acids present on spatially contiguous but separate peptide chains (typically where the respective amino acid sequences of the chains are located disjointedly along the human CD38 polypeptide sequence); (3) post-translational antigenic determinants which consist, either in whole or part, of molecular structures covalently attached to human CD38, such as carbohydrate groups; or (4) combinations of (1)-(3).

An epitope in the context of the present invention includes any peptide or peptide-derivative determinant capable of specific binding to an immunoglobulin. An epitope may comprise any suitable number of amino acids, in any suitable position (with respect to the linear sequence of CD38) orientation (with respect to folded CD38, or a fragment thereof, amino acid composition (and consequently, at least in part, charge). Thus, for example, an epitope may be composed of about 3-10 amino acids, typically 3-8 amino acids, in one or more contiguous or noncontiguous locations with respect to the primary sequence of CD38 (for instance an epitope may consist essentially of 2, 3, 4, 5, 6, 7, or 8 amino acid residues distributed in 1, 2, 3, 4, or 5 noncontiguous locations in CD38). Alternatively, for example, an epitope may be considered to be defined by a region of about 5-40 contiguous amino acid residues (e.g., about 7-30 amino acid residues, about 5-20 amino acid residues, or about 3-15 amino acid residues) in CD38 (solely or in combination with a portion of an adjacent CD38 domain). In some epitopes it may be the case that just one amino acid residue or only a few amino acid residues are critical to CDR or CDR(s) recognition (and thereby most important to CD38BP:CD38 antigen affinity and avidity). As such, an epitope may be characterized on the basis of one or more of such critical residues, with the recognition that other residues may also make some lesser contribution to the epitope. In the case of an epitope defined by a region of amino acids, it may be that one or more amino acids in the region make only a minor contribution or even negligible contribution to antibody binding, such that the residue may be subject to substitution with an appropriate different residue without resulting in "a loss" of the epitope to at least some CD38BPs specific for it.

In one embodiment, the present invention provides a CD38BP, such as an anti-CD38 antibody, that specifically binds to a CD38 epitope that also is specifically bound by an antibody having a $V_L$ sequence of SEQ ID No:2 and a $V_H$ sequence of SEQ ID No:7 (such as antibody –003), or an antibody having a $V_L$ sequence of SEQ ID No:12 and a $V_H$ sequence of SEQ ID No:17 (such as antibody –005) or an antibody having a $V_L$ sequence of SEQ ID No:22 and a $V_H$ sequence of SEQ ID No:27 (such as antibody –024). It is possible that CD38BPs having one or more CDRs that differ from the CDRs of an antibody having a $V_L$ sequence of SEQ ID No:2 and a $V_H$ sequence of SEQ ID No:7, or the CDRs of an antibody having a $V_L$ sequence of SEQ ID No:12 and a $V_H$ sequence of SEQ ID No:17, or the CDRs of an antibody having a $V_L$ sequence of SEQ ID No:22 and a $V_H$ sequence of SEQ ID No:27, may still be specific for the same epitope as an antibody having a $V_L$ sequence of SEQ ID No:2 and a $V_H$ sequence of SEQ ID No:7, and an antibody having a $V_L$ sequence of SEQ ID No:12 and a $V_H$ sequence of SEQ ID No:17 and an antibody having a $V_L$ sequence of SEQ ID No:22 and a $V_H$ sequence of SEQ ID No:27, respectively. In some such cases, the CD38BP in question may recognize or be more specific/selective for particular structures or regions of the epitope than the antibody having a $V_L$ sequence of SEQ ID No:2 and a $V_H$ sequence of SEQ ID No:7, and the antibody having a $V_L$ sequence of SEQ ID No:12 and a $V_H$ sequence of SEQ ID No:17, and the antibody having a $V_L$ sequence of SEQ ID No:22 and a $V_H$ sequence of SEQ ID No:27 respectively.

A CD38 epitope bound by an antibody having a $V_L$ sequence of SEQ ID No:2 and a $V_H$ sequence of SEQ ID No:7 (such as the antibody –003), or an antibody having a $V_L$ sequence of SEQ ID No:12 and a $V_H$ sequence of SEQ ID No:17 (such as the antibody –005) or an antibody having a $V_L$ sequence of SEQ ID No:22 and a $V_H$ sequence of SEQ ID No:27 (such as antibody –024), may be identified via standard mapping and characterization techniques, further refinement of which may be identified by any suitable technique, numerous examples of which are available to the skilled artisan. These techniques may also be used to identify and/or characterize epitopes for CD38BPs generally. As one example of such mapping/characterization methods, an epitope for an anti-CD38 antibody may be determined by epitope "foot-printing" using chemical modification of the exposed amines/carboxyls in the CD38 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions may be identified at this point by peptic proteolysis, fast microbore high-performance liquid chromatography separation, and/or electrospray ionization mass spectrometry. See, e.g., Ehring H, Analytical Biochemistry, 267(2) 252-259 (1999) and/or Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectres of the free antigen and the antigen complexed with the antigen binding peptide, such as an antibody, are compared. The antigen typically is selectively isotopically labeled with $^{15}N$ so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding may be identified that way. See for instance Ernst Schering Res Found Workshop. (44), 149-67 (2004), Huang et al., Journal of Molecular Biology 281(1), 61-67 (1998) and Saito and Patterson, Methods. 9(3), 516-24 (1996).

Epitope mapping/characterization may also be performed using mass spectrometry methods. See for instance Downward, J Mass Spectrom. 35(4), 493-503 (2000) and Kiselar and Downard, Anal Chem. 71(9), 1792-801 (1999).

Protease digestion techniques may also be useful in the context of epitope mapping and identification. Antigenic determinant-relevant regions/sequences may be determined by protease digestion, e.g. by using trypsin in a ratio of about 1:50 to CD38 overnight (O/N) digestion at 37° C. and pH 7-8, followed by mass spectrometry (MS) analysis for peptide identification. The peptides protected from trypsin cleavage by the CD38BP may subsequently be identified by comparison of samples subjected to trypsin digestion and samples incubated with CD38BP and then subjected to digestion by e.g. trypsin (thereby revealing a foot print for the binder). Other enzymes like chymotrypsin, pepsin, etc. may also or alternatively be used in a similar epitope characterization method. A CD38BP which gives the significantly same result as an antibody having a $V_L$ sequence of SEQ ID No:2 and a $V_H$ sequence of SEQ ID No:7 (such as the antibody –003), or an antibody having a $V_L$ sequence of SEQ ID No:12 and a $V_H$ sequence of SEQ ID No:17 (such as the antibody –005) or an antibody having a $V_L$ sequence of SEQ ID No:22 and a $V_H$ sequence of SEQ ID No:27 (such as antibody –024) in these measurements are deemed to be an antibody that bind the same epitope as an antibody having a $V_L$ sequence of SEQ ID No:2 and a $V_H$ sequence of SEQ ID No:7 (such as the antibody –003), or an antibody having a $V_L$ sequence of SEQ ID No:12 and a $V_H$ sequence of SEQ ID No:17 (such as the antibody –005) or an antibody having a $V_L$ sequence of SEQ ID No:22 and a $V_H$ sequence of SEQ ID No:27 (such as antibody –024), respectively. See for instance Manca, Ann 1st Super Sanita. 27(1), 15-9 (1991) for a discussion of similar techniques.

Epitope mapping by competitive binding to CD38 with two antibodies where one is biotinylated is another method for identifying relevant antigenic determinant regions.

The binding of antibodies to linear and looped peptides of CD38 by a PEPSCAN-based enzyme-linked immuno assay is another method for identifying relevant antigenic determinant regions, see for instance Slootstra-J W et al. Mol-Divers. 1, 87-96 (1996).

Site directed mutagenesis is another method for identifying relevant antigenic determinant regions, see for instance Polyak and Deans, Blood 99, 3956-3962 (2002).

Various phage display techniques may also be used to identify epitopes. See for instance Wang and Yu, Curr Drug Targets. 5(1), 1-15 (2004), Burton, Immunotechnology. 1(2), 87-94 (1995 August), Cortese et al., Immunotechnology. 1(2), 87-94 (1995) and Irving et al., Curr Opin Chem Biol. 5(3), 314-24 (2001). Consensus epitopes may also be identified through modified phage display-related techniques (see, the website at Montana State University at cs.montana.edu/~mumey/papers/jcbo3.pdf) for discussion.

Other methods potentially helpful in mapping epitopes include crystallography techniques, X-ray diffraction techniques (such as the X-ray diffraction/sequence study techniques developed by Polijak and others in the 1970s-1980s), and the application of Multipin Peptide Synthesis Technology. Computer-based methods such as sequence analysis and three dimensional structure analysis and docking may also be used to identify antigenic determinants. For example, an epitope may also be determined by molecular modeling using a structure of CD38 with docking of the structure of the Fab fragment of the individual monoclonal antibody. These and other mapping methods are discussed in Epitope Mapping A Practical Approach (Westwood and Hay Eds.) 2001 Oxford University Press.

In one embodiment, the present invention provides a CD38BP having substantially the same specific CD38-binding characteristics of one or more mAbs selected from an antibody having a $V_L$ sequence of SEQ ID No:2 and a $V_H$ sequence of SEQ ID No:7 (such as the antibody −003), an antibody having a $V_L$ sequence of SEQ ID No:12 and a $V_H$ sequence of SEQ ID No:17 (such as antibody −005), and an antibody having a $V_L$ sequence of SEQ ID No:22 and a $V_H$ sequence of SEQ ID No:27 (such as antibody −024).

Mapping studies have indicated that several monoclonal antibodies raised against human CD38 bind to epitopes in the C-terminal region of CD38 (220-296) (Hoshino et al. and Ferrero et al.). Within this region three amino acid differences have been found between the human and the cynomolgus CD38 sequence: T237, Q272 and S274 in humans correspond to A238, R273 and F275 in cynomolgus. −005 does not bind to cynomolgus tissue (shown in examples 10 and 11). A limited number of amino acid differences exist between the human and the monkey CD38 sequence, for instance in the carboxyterminal part to the protein, for instance the following three amino acid differences between the human and the cynomolgus CD38 sequence: T237, Q272 and S274 in human CD38s correspond to A238, R273 and F275 in cynomolgus monkey CD38 (compare SEQ ID No.21 and SEQ ID No.22). −005 does not bind to a mutant huCD38 protein, wherein the glutamine residue at position 272 of SEQ ID No:31 has been substituted with an arginine residue (Q272R), or to a mutant huCD38 protein, wherein the serine residue of position 274 of SEQ ID No:31 has been substituted with a phenylalanine residue (S274F) (shown in Example 17) to the same degree that it binds to wild type human CD38. Binding of −005 is particularly abrogated by the amino acid substation at position S274F.

Consequently, the present invention provides peptides, which binds to human CD38 (SEQ ID No:31), and which does not bind to a mutant human CD38, wherein the glutamine residue in position 272 has been substituted with an arginine residue (SEQ ID No:33) to the same degree that it binds to human CD38 (SEQ ID No:31).

The present invention also provides peptides, which binds to human CD38 (SEQ ID No:31), and which does not bind to a mutant human CD38, wherein the serine residue in position 274 has been substituted with a phenylalanine residue (SEQ ID No:34) to the same degree that it binds to human CD38 (SEQ ID No:31).

The term "to the same degree" should be interpreted so that the binding of the peptide to the mutant human CD38 is significantly lower than the binding of the peptide to the wild type human CD38. The binding of a peptide to the CD38 molecules (wild type and mutant) may be determined in a number of ways and it is within the common general knowledge of a person skilled in the art to determine whether the binding to the mutant is "significantly lower" than the binding to the wildtype. A large number of different techniques for determining the binding of a peptide to another peptide are available to the person skilled in the art, for example ELISA, radioimmunoassay, BIAcore or flow cytometry.

One method of determining the binding is by determining the $EC_{50}$ of the binding of the peptide to the mutant protein and to the wild type protein and then comparing the values obtained. Another method of determining the binding is by examining the magnitude of binding at saturating concentration (for instance the plateau of binding signal), or by determining kinetic rate constants $k_{on}$ and $k_{off}$ for example by BIAcore.

In one embodiment, the binding of the peptide in question to the CD38 proteins (mutant or wild type) is by use of an ELISA as described in Example 17.

In one embodiment, the $EC_{50}$ of the binding of the peptide to a mutant human CD38, wherein the serine residue in position 274 has been substituted with a phenylalanine residue (SEQ ID No:34), is less than 50% of the $EC_{50}$ of the binding of the peptide to human CD38 (SEQ ID No:31). In one embodiment, the $EC_{50}$ of the binding of the peptide to a mutant human CD38, wherein the serine residue in position 274 has been substituted with a phenylalanine residue (SEQ ID No:34), is less than 10% of the $EC_{50}$ of the binding of the peptide to human CD38 (SEQ ID No:31). In one embodiment, the $EC_{50}$ of the binding of the peptide to a mutant human CD38, wherein the serine residue in position 274 has been substituted with a phenylalanine residue (SEQ ID No:34), is less than 5% of the $EC_{50}$ of the binding of the peptide to human CD38 (SEQ ID No:31). In one embodiment, the $EC_{50}$ of the binding of the peptide to a mutant human CD38, wherein the serine residue in position 274 has been substituted with a phenylalanine residue (SEQ ID No:34), is less than 1% of the $EC_{50}$ of the binding of the peptide to human CD38 (SEQ ID No:31).

In one embodiment, the $EC_{50}$ of the binding of the peptide to a mutant human CD38, wherein the glutamine residue in position 272 has been substituted with an arginine residue (SEQ ID No:33), is less than 50% of the $EC_{50}$ of the binding of the peptide to human CD38 (SEQ ID No:31). In one embodiment, the $EC_{50}$ of the binding of the peptide to a mutant human CD38, wherein the glutamine residue in position 272 has been substituted with an arginine residue (SEQ ID No:33), is less than 10% of the $EC_{50}$ of the binding of the peptide to human CD38 (SEQ ID No:31).

In one embodiment, a peptide according to the invention binds to a mutant human CD38, wherein the threonine residue in position 237 has been substituted with a alanine residue (SEQ ID No:32) to the same degree that it binds to human CD38 (SEQ ID No:31). In one embodiment, the $EC_{60}$ of the binding of the peptide to a a mutant human CD38, wherein the threonine residue in position 237 has been substituted with a alanine residue (SEQ ID No:32) is more than 75% of the $EC_{50}$ of the binding of the peptide to human CD38 (SEQ ID No:31). In one embodiment, the $EC_{50}$ of the binding of the peptide to a a mutant human CD38, wherein the threonine residue in position 237 has been substituted with a alanine residue (SEQ ID No:32) is more than 85% of the $EC_{50}$ of the binding of the peptide to human CD38 (SEQ ID No:31). In one embodiment, the $EC_{50}$ of the binding of the peptide to a a mutant human CD38, wherein the threonine residue in position 237 has been substituted with a alanine residue (SEQ ID No:32) is more than 90% of the $EC_{60}$ of the binding of the peptide to human CD38 (SEQ ID No:31). In one embodiment, the $EC_{50}$ of the binding of the peptide to a a mutant human CD38, wherein the threonine residue in position 237 has been substituted with a alanine residue (SEQ ID No:32) is more than 95% of the $EC_{50}$ of the binding of the peptide to human CD38 (SEQ ID No:31).

To identify more specific likely antigenic determinant regions in CD38, various predictive analytical methods may be applied. In a first analytical approach, CD38 may be analyzed for (1) highly hydropathic regions (using the Kyte-Doolittle method); (2) antigenicity as measured by the Protrusion Index method; (3) antigenicity as determined by the Parker method; (4) antigenicity as determined by the Hopp/Woods method; and (5) hydrophilicity as measured by the methods of Goldman, Engleman, and Steitz. Sequences ranging from 10-40 amino acids in length may be selected based on exhibiting one or more of these properties. The rationale for this approach is the general consensus that many ideal B cell epitopes are hydrophilic, surface-oriented, and flexible sequences of about 8-10 amino acids in length.

The present invention provides CD38BPs specific for CD38-regions of CD38 identified in such a manner. Moreover, the termini of these sequences may be compared to predicted antigenic determinant regions located through the other analyses described herein to provide additional specific likely antigenic-determinant containing regions. Other similar comparisons may readily be made to provide additional likely antigenic determinant regions, where CD38BPs binding to these antigenic determinant regions may be considered another feature of the present invention.

In one embodiment, the CD38BP of the present invention is an antibody. Non-limiting examples of CD38 binding immunoglobulin molecules provided by the present invention include (a) a complete functional, immunoglobulin molecule comprising: (i) two identical chimeric heavy chains comprising a variable region with a human B cell surface antigen specificity and human constant region and (ii) two identical all (i.e. non-chimeric) human light chains; (b) a complete, functional, immunoglobulin molecule comprising: (i) two identical chimeric heavy chains comprising a variable region as indicated, and a human constant region, and (ii) two identical all (i.e. non-chimeric) non-human light chains; (c) a monovalent antibody, i.e., a complete, functional immunoglobulin molecule comprising: (i) two identical chimeric heavy chains comprising a variable region as indicated, and a human constant region, and (ii) two different light chains, only one of which has the same specificity as the variable region of the heavy chains. The resulting antibody molecule binds only to one end thereof and is therefore incapable of divalent binding. As another illustration, immunoglobulin-related peptides provided by the present invention may be said to include the following: (a) a whole immunoglobulin molecule; (b) an scFv; (c) a monoclonal antibody; (d) a human antibody; (e) a chimeric antibody; (f) a humanized antibody; (g) a Fab fragment; (h) an Fab' fragment; (i) an $F(ab')_2$ fragment; (j) an Fv molecule; and (k) a disulfide-linked Fv molecule.

In one embodiment, the CD38BP of the present invention is a polyclonal antibody. In one embodiment, the CD38BP of the present invention is an monoclonal antibody. In a further embodiment, the CD38BP of the present invention is a human monoclonal antibody. In another further embodiment, the CD38BP of the present invention is a humanized antibody. In another further embodiment, the CD38BP of the present invention is a chimeric antibody. In another further embodiment, the CD38BP of the present invention is a monoclonal antibody originating entirely from a mammalian species different from humans. In a further embodiment, the CD38BP of the present invention is a fully murine monoclonal antibody.

A monoclonal antibody refers to a composition comprising a homogeneous antibody population having a uniform structure and specificity. Typically a monoclonal antibody is an antibody obtained from a population of substantially homogeneous antibodies, i.e., the individual antibodies comprising the population are identical except for possible naturally occurring mutations that may be present in minor amounts. Monoclonal antibodies are highly specific and each monoclonal antibody is typically directed against a single epitope, which is in contrast to polyclonal antibody preparations which typically include different antibodies directed against different epitopes. That an antibody is monoclonal is not to be construed as requiring production of the antibody by any particular method. For example, the monoclonal antibodies of the present invention may be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991).

Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

Alternatively, the cloned antibody genes can be expressed in other expression systems, including prokaryotic cells, such as microorganisms, such as *E. coli*, for the production of single chain Fv antibodies, algi, as well as insect cells. Furthermore, the antibodies can be produced in transgenic non-human animals, such as in milk from sheep and rabbits or in eggs from hens, or in transgenic plants. See for instance Verma, R., et al., J. Immunol. Meth. 216, 165-181 (1998); Pollock, et al., J. Immunol. Meth. 231, 147-157 (1999); and Fischer, R., et al., Biol. Chem. 380, 825-839 (1999).

In one embodiment, human monoclonal antibodies directed against CD38 may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice". A human monoclonal antibody generated in such mice may be abbreviated as HuMab.

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci. 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424). In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

The KM mouse contains a human heavy chain transchromosome and a human kappa light chain transgene. The endogenous mouse heavy and light chain genes also have been disrupted in the KM mice such that immunization of the mice leads to production of human immunoglobulins rather than mouse immunoglobulins. Construction of KM mice and their use to raise human immunoglobulins is described in detail in WO 02/43478.

Splenocytes from these transgenic mice may be used to generate hybridomas that secrete human monoclonal antibodies according to well known techniques. Such transgenic mammals, mammals comprising an operable nucleic acid sequence coding for expression of a CD38BP, mammals stably transfected with one or more CD38-encoding nucleic acid sequences, and the like, are additional features of the present invention.

Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. No. 5,827,690, U.S. Pat. No. 5,756,687, U.S. Pat. No. 5,750,172 and U.S. Pat. No. 5,741,957.

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hoogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized, for instance as described elsewhere herein.

Humanized monoclonal antibodies of the present invention may be generated by fusing the constant domains from a human antibody to the variable domains of a non-human species. Examples of how to make humanized antibodies may be found in for instance U.S. Pat. No. 6,054,297, U.S. Pat. No. 5,886,152 and U.S. Pat. No. 5,877,293. A humanized antibody is designed to have greater homology to a human immunoglobulin than animal-derived monoclonal antibodies. Non-human amino acid residues from an "import" (animal) variable domain typically are transfected into a human "backbone". Humanization may essentially be performed following the method of Winter and co-workers (Jones et al., Nature 321, 522-525 (1986), Riechmann et al., Nature 332, 323-327 (1988), Verhoeyen et al., Science 239, 1534-1536 (1988)), by substituting rodent complementarity determining regions ("CDRs") or CDR sequences for the corresponding sequences of a human antibody. Accordingly, in such "humanized" antibodies, the CDR portions of the human variable domain have been substituted by the corresponding sequence from a non-human species. Thus, humanized antibodies are typically human antibodies in which some CDR residues and possibly some framework residues are substituted by residues from analogous sites in rodent antibodies. The choice of human variable domains, both light and heavy, to be used in making the humanized antibodies is important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol. 151, 2296 (1993), Chothia et al., J. Mol. Biol. 196, 901 (1987)). Another method uses a particular framework derived from the consensus sequence of all human antibodies of a particular subgroup of light or heavy chains. The same framework may be used for several different humanized antibodies (Carter et al., PNAS USA 89, 4285 (1992), Presta et al., J. Immunol. 151, 2623 (1993)).

It is typically also important that humanized antibodies retain high affinity for the antigen and other favorable biological properties. To achieve this goal, humanized antibodies may be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of certain residues in the functioning of the candidate immunoglobulin sequence, i.e., the analysis of residues that influence the ability of the candidate immunoglobulin to bind its antigen. In this way, FR residues may be selected and combined from the recipient and import sequences so that the desired antibody characteristic, such as increased affinity for the target antigen(s), is maximized, although it is the CDR residues that directly and most substantially influence antigen binding.

Murine antibodies or antibodies from other species may be humanized or primatized using any suitable techniques, a number of suitable techniques being already well known in the art (see for instance Winter and Harris Immunol Today 14, 43-46 (1993) and Wright et al., Crit. Reviews in Immunol. 125-168 (1992)). The antibody of interest may be engineered by recombinant DNA techniques to substitute the $C_H1$, $C_H2$, $C_H3$, hinge domains, and/or the framework domain with the corresponding human sequence (see WO 92/02190 and U.S. Pat. No. 5,530,101, U.S. Pat. No. 5,585,089, U.S. Pat. No. 5,693,761, U.S. Pat. No. 5,693,792, U.S. Pat. No. 5,714,350, and U.S. Pat. No. 5,777,085).

Humanization of antibodies may also be performed following the method of Winter and co-workers (Jones et al., Nature 321, 522-525 (1986), Riechmann et al., Nature 332, 323-327 (1988), Verhoeyen et al., Science 239, 1534-1536 (1988)), by substituting rodent CDRs or CDR sequences for the corresponding sequences of a human antibody. Accordingly, such "humanized" antibodies are, in a sense, chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Also, the use of Ig cDNA for constructions of chimeric immunoglobulin genes is known in the art (see for instance Liu et al., PNAS USA 84, 3439 (1987) and J. Immunol. 139, 3521 (1987)). mRNA is isolated from a hybridoma or other cell producing the antibody and used to produce cDNA: The cDNA of interest may be amplified by the polymerase chain reaction using specific primers (U.S. Pat. No. 4,683,195 and U.S. Pat. No. 4,683,202). Alternatively, a library is made and screened to isolate the sequence of interest. The DNA sequence encoding the variable region of the antibody is then fused to human constant region sequences. Sequences of human constant regions (as well as variable regions) may be found in Kabat et al., (1991) Sequences of Proteins of Immunological Interest, N.I.H. publication no. 91-3242 and more recent and related data can be accessed at the website of the UCL Research Department of Structural and Molecular Biology at biochem.ucl. ac.uk/~martin/abs/Generalinfo.html. The choice of isotype typically will be guided by the desired effector functions, such as complement fixation, or activity in antibody-dependent cellular cytotoxicity. Exemplary isotypes are IgG1, lgG2, IgG3, and IgG4. Either of the human light chain constant regions, kappa or lambda, may be used. The chimeric, humanized antibody may then be expressed by conventional methods.

CD38BPs of the present invention may be in any suitable form with respect to multimerization. Anti-CD38 antibodies and antibody fragments may be at least in heterotrimeric form if not in higher multimeric forms such as those associated with IgM antibodies. In other embodiments, a CD38BP may be presented as a dimer or monomer. Monomeric CD38BPs of the present invention may be, for example, modified by any suitable technique so as to form multimeric peptide compositions.

If desired, the class of a anti-CD38 antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses.

In one embodiment an antibody of the present invention is an IgG1 antibody, for instance an IgG1,κ or IgG1,λ isotype. In another embodiment an antibody of the present invention is an IgG3 antibody, for instance an IgG3,κ or IgG3,λ isotype. In another embodiment an antibody of the present invention is an IgG4 antibody, for instance an IgG4,κ or IgG4,λ isotype. In another embodiment an antibody of the present invention is an IgA1 or IgA2 antibody. In another embodiment an antibody of the present invention is an IgM antibody.

Anti-CD38 antibodies may be recovered from recombinant combinatorial antibody libraries, such as a scFv phage display library, which may be made with human $V_L$ and $V_H$ cDNAs prepared from mRNA derived from human lymphocytes. Methods for preparing and screening such libraries are known in the art. There are a number of commercially available kits for generating phage display libraries. There are also other methods and reagents that may be used in generating and screening antibody display libraries (see for instance U.S. Pat. No. 5,223,409, WO 92/18619, WO 91/17271, WO 92/20791, WO 92/15679, WO 93/01288, WO 92/01047, WO 92/09690, Fuchs et al., Bio/Technology 9, 1370-1372 (1991), Hay et al., Hum. Antibod. Hybridomas 3, 81-85 (1992), Huse et al., Science 246, 1275-1281 (1989), McCafferty et al., Nature 348, 552-554 (1990), Griffiths et al., EMBO J. 12, 725-734 (1993), Hawkins et al., J. Mol. Biol. 226, 889-896 (1992), Clackson et al., Nature 352, 624-628 (1991), Gram et al., PNAS USA 89, 3576-3580 (1992), Garrad et al., Bio/Technology 9, 1373-1377 (1991), Hoogenboom et al., Nuc Acid Res 19, 4133-4137 (1991) and Barbas et al., PNAS USA 88, 7978-7982 (1991)). Suitable $V_L$ and $V_H$ nucleic acid sequences may be selected using any appropriate method. For example, $V_L$ and $V_H$ nucleic acids may be selected by employing the epitope imprinting methods described in WO 93/06213. Antibody libraries, such as scFv libraries may be prepared and screened using known and suitable methods (with human CD38-containing peptides as antigen(s)), such as those described in for instance WO92/01047, McCafferty et al., Nature 348, 552-554 (1990) and Griffiths et al., EMBO J. 12, 725-734 (1993). Such antibody libraries and other combinations of CD38BPs (libraries, pools, etc.) are features of the present invention that may be used therapeutically to provide a more comprehensive immune response; as tools in screening methods for immunogenic peptides, small molecules, other anti-CD38 antibodies (e.g., by way of competition assays), and the like; and/or in diagnostic methods and compositions (e.g., an immunoassay chip comprising a panel of such antibodies optionally in association with other antibodies may be prepared by standard techniques). Once initial human $V_L$ and $V_H$ segments are selected, "mix and match" experiments, in which different pairs of the initially selected $V_L$ and $V_H$ segments are screened for CD38-containing peptide binding, may be performed to select desirable $V_L/V_H$ pair combinations. For example, reactivity of the peptides may be determined by ELISA or other suitable epitope analysis methods (see for instance Scott, J. K. and Smith, G. P. Science 249, 386-390 (1990), Cwirla et al., PNAS USA 87, 6378-6382 (1990), Felici et al., J. Mol. Biol. 222, 301-310 (1991) and Kuwabara et al., Nature Biotechnology 15, 74-78 (1997) for discussion of such techniques and principles). Antibodies may be selected by their affinity for antigen and/or by their kinetics of dissociation (off-rate) from antigen (see for instance Hawkins et al., J. Mol. Biol. 226, 889-896 (1992)).

To further improve the quality and/or diversity of anti-CD38 antibodies, the $V_L$ and $V_H$ segments of $V_L/V_H$ pair(s) may be randomly mutated, for instance within the CDR3 region of $V_H$ and/or $V_L$, in a process analogous to the in vivo somatic mutation process responsible for affinity maturation of antibodies during a natural immune response. This in vitro affinity maturation may be accomplished by amplifying $V_H$ and $V_L$ regions using PCR primers complimentary to the $V_H$ CDR3 or $V_L$ CDR3, respectively, which primers typically are "spiked" with a random mixture of the four nucleotide bases at certain positions, such that the resultant PCR products encode $V_H$ and $V_L$ segments into which random mutations have been introduced into the $V_H$ and/or $V_L$ CDR3 regions. These randomly mutated $V_H$ and $V_L$ segments may be re-screened for binding to CD38-containing peptides.

Following screening, nucleic acid encoding a selected antibody may be recovered from the display package (e.g., from the phage genome) and subcloned into an appropriate vector by standard recombinant DNA techniques. If desired, such an antibody-encoding nucleic acid may be further manipulated to create other antibody forms or CD38BPs. To express a recombinant antibody isolated by screening of a combinatorial library, typically a nucleic acid comprising a sequence encoding the antibody is cloned into a recombinant expression vector and introduced into appropriate host cells (mammalian cells, yeast cells, etc.) under conditions suitable for expression of the nucleic acid and production of the antibody.

High-affinity antibody peptides, such as human single-chain Fv (scFv) and Fab antibody fragments, may also be isolated from such libraries using a panning technique in which the antigen of interest is immobilized on a solid surface, such as microtiter plates or beads (see for instance Barbas and Burton, Trends. Biotechnol. 14, 230-234 (1996) and Aujame et al., Hum. Antibodies 8, 155-68 (1997). Phage display of large naïve libraries also makes it possible to isolate human antibodies directly without immunization (see for instance de Haard et al., J. Biol. Chem. 274(26), 18218-18230 (1999)).

In one embodiment, the present invention provides variant anti-CD38 antibodies. A "variant" anti-CD38 antibody is an antibody that differs from a parent antibody (typically generated by immunization) by one or more suitable amino acid residue alterations, that is substitutions, deletions, insertions, or terminal sequence additions, in the CDRs or other $V_H$ and/or $V_L$ sequences (provided that at least a substantial amount of the epitope binding characteristics of the parent antibody are retained, if not improved upon, by such changes).

Variations in an antibody variant may be made in each of the framework regions, the constant domain, and/or the variable regions (or any one or more CDRs thereof in a single variant antibody. Alternatively, variations may be made in only one of the framework regions, the variable regions (or single CDR thereof), or the constant domain in an antibody. Alanine scanning mutagenesis techniques, such as described by Cunningham and Wells, Science 244, 1081-1085 (1989), may be used to identify suitable residues for substitution or deletion in generating CD38BPs comprising variant $V_L$, $V_H$, or particular CDR sequences, although other suitable mutagenesis techniques also may be applied. Multiple amino acid substitutions may also be made and tested using known methods of mutagenesis and screening, such as those disclosed by Reidhaar-Olson and Sauer, Science 241, 53-57 (1988) or Bowie and Sauer, PNAS USA 86, 2152-2156 (1989).

Thus, for example, in an antibody variant one or more amino acid residues may be introduced or inserted in or adjacent to one or more of the hypervariable regions of a parent antibody, such as in one or more CDRs. An anti-CD38 antibody variant may comprise any number of inserted amino acid residues, provided again that at least a substantial amount of the epitope binding characteristics of the parent antibody are retained. An anti-CD38 antibody variant of the present invention may for example comprise from about 1-30 inserted amino acid residues, for instance from about 1-10, such as for instance from about 2-10, for instance from 2-5 or such as from about 1-5 inserted amino acid residues. Likewise, an anti-CD38 antibody variant of the present invention may for example comprise from about 1-30 deleted amino acid residues, for instance from about 1-10, such as for instance from about 2-10, for instance from 2-5 or such as from about 1-5 deleted amino acid residues. Likewise, an anti-CD38 antibody variant of the present invention may for example comprise from about 1-30 substituted amino acid residues, for instance from about 1-10, such as for instance from about 2-10, for instance from 2-5 or such as from about 1-5 substituted amino acid residues. Likewise, an anti-CD38 antibody variant of the present invention may for example comprise from about 1-30 terminal sequence amino acid residue additions, for instance from about 1-10, such as for instance from about 2-10, for instance from 2-5 or such as from about 1-5 terminal sequence amino acid residue additions. A antibody variant of the present invention may also comprises a combination of two or more of such insertions, deleting, substitutions and terminal sequence amino acid residue additions, provided that the variant possesses at least a substantial proportion of the parent antibodies affinity, specificity, and/or selectivity with respect to one or more CD38 epitopes.

Considerations in the selection of antibody variants (e.g., conservation of amino acid residue functional characteristics, conservation of amino acid residues based on hydropathic characteristics, and/or conservation of amino acid residues on the basis of weight/size), are described elsewhere herein. Typically, amino acid sequence alterations, such as conservative substitution variations, desirably do not substantially change the structural characteristics of the parent sequence (e.g., a replacement amino acid should not tend to disrupt secondary structure that characterizes the function of the parent sequence). Examples of art-recognized polypeptide secondary and tertiary structures are described in, e.g., Proteins, Structures and Molecular Principles (Creighton, Ed., W.H. Freeman and Company, New York (1984)), Introduction to Protein Structure (C. Branden and J. Tooze, eds., Garland Publishing, New York, N.Y. (1991)) and Thornton et al., Nature 354, 105 (1991). Additional principles relevant to the design and construction of peptide variants is discussed in for instance Collinet et al., J Biol Chem 275(23), 17428-33 (2000).

Amino acid sequence variants of an antibody may be obtained by introducing appropriate nucleotide changes into the antibody-encoding nucleic acid (e.g., by site directed mutagenesis) or by chemical peptide synthesis. Such variants include, for example, deletions from, and/or insertions into and/or substitutions of and/or terminal sequence additions of residues within the amino acid sequences of the antibodies of the examples herein. Any combination of deletions, insertions, and substitutions may be made to arrive at a desired variant, provided that the variant possesses at least a substantial proportion of epitope binding characteristics of the parent antibody. Amino acid sequence changes, with respect to a parent antibody, also may alter post-translational processes of the variant antibody with respect to a parent antibody, such as by changing the number or position of glycosylation sites.

Variant antibodies of the present invention may comprise alterations in the hypervariable region, such as in the CDRs. Examples of CD38BPs comprising such CDR variants are described elsewhere herein, and, as described above, such CD38BPs may be antibodies.

Variant antibodies of the present invention may comprise framework (FR) alterations, that is outside the hypervariable region, for Instance in the Fc region, which alterations may be associated with advantageous properties, such as changing the functional or pharmacokinetic properties of the antibodies. For example, a substitution or other modification (insertion, deletion, terminal sequence additions or combination of any thereof) in a framework region or constant domain may be associated with an increase in the half-life of the variant antibody with respect to the parent antibody, or may be made to alter the immunogenicity of the variant antibody with respect to the parent antibody, to provide a site for covalent or non-covalent binding to another molecule, or to alter such properties as complement fixation, for instance resulting in a decrease or increase of C1q binding and CDC or of FcγR binding and antibody-dependent cellular cytotoxicity (ADCC). Substitutions may for example be made in one or more of the amino acid residues 234, 235, 236, 237, 297, 318, 320, and 322 of the heavy chain constant region, thereby causing an alteration in an effector function while retaining binding to antigen as compared with the unmodified antibody, cf. U.S. Pat. No. 5,624,821 and U.S. Pat. No. 5,648,260. Further reference may be had to WO 00/42072 disclosing antibodies with altered Fc regions that increase ADCC, and WO 94/29351 disclosing antibodies having mutations in the N-terminal region of the $C_H2$ domain that alter the ability of the antibodies to bind to FcRI and thereby decreases the ability of the antibodies to bind to C1q which in turn decreases the ability of the antibodies to fix complement. Furthermore, Shields et al., J. Biol. Chem. 276, 6591-6604 (2001) teaches combination variants, that improve FcγRIII binding, for instance T256A/S298A, S298A/E333A, and S298A/E333A/K334A.

The in vivo half-life of the antibodies may also be improved by modifying the salvage receptor epitope of the Ig constant domain or an Ig-like constant domain such that the molecule does not comprise an intact $C_H2$ domain or an intact Ig Fc region, cf. U.S. Pat. No. 6,121,022 and U.S. Pat. No. 6,194,551. The in vivo half-life may furthermore be increased by making mutations in the Fc region, e.g. by substituting threonine for leucine at position 252, threonine for serine at position 254, or threonine for phenylalanine at position 256, cf. U.S. Pat. No. 6,277,375.

In one embodiment, the present invention provides variant anti-CD38 antibodies wherein potential T cell epitopes in the antibody have been reduced or eliminated through rationale design. Thus, for example, in one embodiment the present invention provides a "deimmunized" anti-CD38 antibody in which the potential T cell epitopes have been eliminated. The design and construction of deimmunized anti-CD38 antibodies may be accomplished by any suitable known technique (see for instance WO9852976 with respect to methods for preparing deimmunized antibodies). Immunogenicity in humans is expected to be eliminated or substantially reduced when such CD38BPs (e.g., anti-CD38 variant antibodies) are administered according to the present invention.

Other framework mutations may include sequence changes which may reduce susceptibility to proteolysis, reduce susceptibility to oxidation, and/or confer or modify other physicochemical or functional properties on the associated variant antibody.

Amino acid sequence variations in the framework may also result in an altered glycosylation pattern in the variant antibody with respect to a parent antibody. By altering is meant deleting one or more carbohydrate moieties found in the parent antibody, and/or adding one or more glycosylation sites that are not present in the parent antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are common recognition sequences for enzymatic attachment of the carbohydrate moiety to the asparagine side chain. Thus, the presence of either of these tripeptide sequences in a polypeptide may create a potential glycosylation site. O-linked glycosylation refers to the attachment of sugars such as N-aceylgalactosamine, galactose, or xylose to a hydroxyamino acid, most commonly serine or threonine, although 5-hydroxyproline or 5-hydroxylysine may also be used. Addition of glycosylation sites to the antibody may be conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibodies may also be expressed in a transfectoma which does not add the fucose unit normally attached to the carbohydrate attached to Asn at position 297 of Fc in order to enhance the affinity of Fc for FcγRIII which in turn will result in an increased ADCC of the antibodies in the presence of NK cells, cf. Shield et al., J. Biol. Chem. 277, 26733 (2002). Other methods of modifying the glycosylation with focus on the fucosylation is described in WO 00/61739 to Kyowa. Furthermore, modification of galactosylation may be made in order to modify CDC. Further reference may be had to WO 99/54342 and Umana et al., Nat. Biotechnol. 17, 176 (1999) disclosing a CHO cell line engineered to express GntIII resulting in the expression of monoclonal antibodies with altered glycoforms and improved ADCC activity.

Other potentially suitable techniques for preparing novel anti-CD38 antibodies include CDR walking mutagenesis, antibody chain shuffling, "parsimonious mutagenesis" (Balint and Larrick, Gene 137, 109-118 (1993)), and other affinity maturation techniques (see for instance Wu et al., PNAS USA 95, 6037-42 (1998)). Repertoire cloning procedures may also be useful in the production of variant antibodies (see for instance WO 96/33279).

There are a number of techniques known for generating CDR variants, any suitable technique or combination of which may be used in the context of the present invention for generating CDR variants of the CDRs of the antibodies of the examples. Examples of such techniques include the removal of nonessential residues as described in Studnicka et al., Protein Engineering Z, 805-814 (1994) (see also Soderlind et al., Immunotechnology. 4(3-4), 279-85 (1999), CDR walking mutagenesis and other artificial affinity maturation techniques (see for instance Yang et al., Journal of Molecular Biology 254(3), 392-403 (1995), CDR shuffling techniques wherein typically CDRs are amplified from a diverse set of gene templates optionally comprising synthetic oligonucleotides, the constant regions of the $V_L$, $V_H$, and/or CDRs are amplified, and the various fragments mixed (in single-stranded or double-stranded format) and assembled by polymerase chain reaction (PCR) to produce a set of antibody-fragment encoding gene products carrying shuffled CDR introduced into the master framework, which is amplified using external primers annealing to sites beyond inserted restriction sites to ensure production of full-length products, which are inserted into a vector of choice and used to expressed variant CDR-containing proteins. Appropriate structure may be determined by superimposition of the variantmimetic structures and those of the parent sequences, e.g., by comparison of NMR solution structures. Useful methods for rational design of CDR sequence variants are described in for instance WO 91/09967 and WO 93/16184. Additional examples of such methods are provided elsewhere herein.

The present invention also provides fragments of antibodies (including variant antibodies) of the present invention, which fragments has the ability to bind to CD38 (CD38 binding fragments). CD38BPs thus include antibody-like molecules that comprise less than the full tetrameric structure associated with naturally-occurring antibodies. An antibody fragment may be any peptide that comprises a portion of a full length antibody, generally the antigen binding or variable region thereof (this includes, for example, fragments of humanized antibodies comprising CDRs from an antibody of the present invention, variants thereof, or other CDRs that allow the antigen fragment to compete with an antibody of the present invention for CD38 binding). In one embodiment, an antibody fragment refers to a peptide that consists essentially or consists only of a portion of an antibody molecule. In one embodiment, the present invention provides an antibody fragment comprising at least a portion of a heavy chain variable domain containing one or more $V_H$ CDRs of an antibody of the present invention and optionally also a light chain-variable domain comprising one or more $V_L$ CDRs of an antibody of the present invention, wherein the heavy chain variable domain, and optionally the light chain variable domain, optionally is (are) fused to an additional moiety, such as an immunoglobulin constant domain. Constant domain sequences may be added to the heavy chain and/or light chain sequence(s) to form species with partial length heavy and/or light chain(s). Constant regions, or portions thereof, of any antibody isotype may be used for this purpose, including IgG, IgM, IgA, IgD, and IgE constant regions.

Examples of CD38-binding antibody fragments include Fab, Fab', F(ab')$_2$, and Fv fragments. An antibody fragment in the context of the present invention may also include a a peptide comprising a CDR, and the like. In one embodiment, the present invention provides an antibody fragment comprising a first polypeptide chain that comprises any of the heavy chain CDRs described herein and a second polypeptide chain that comprises any of the light chain CDRs described herein, wherein the two polypeptide chains are covalently linked by one or more interchain disulfide bonds. In one embodiment, the present invention provides a two-chain antibody fragment having such features wherein the antibody fragment is selected from Fab, Fab', Fab'-SH, Fv, and/or F(ab')$_2$ fragments.

Antibodies may be fragmented using conventional techniques, and the fragments screened for utility in the same manner as described above for whole antibodies. For example, F(ab')$_2$ fragments may be generated by treating antibody with pepsin. The resulting F(ab')$_2$ fragment may be treated to reduce disulfide bridges to produce Fab' fragments. Fab fragments may be obtained by treating an IgG antibody with papain; Fab' fragments may be obtained with pepsin digestion of IgG antibody. A Fab' fragment may also be produced by binding Fab' described below via a thioether bond or a disulfide bond. A Fab' fragment is an antibody fragment obtained by cutting a disulfide bond of the hinge region of the F(ab')$_2$. A Fab' fragment may be obtained by treating a F(ab')$_2$ fragment with a reducing agent, such as dithiothreitol. Antibody fragment peptides may also be generated by expression of nucleic acids encoding such peptides in recombinant cells (see for instance Evans et al., J. Immunol. Meth. 184, 123-38 (1995)). For example, a chimeric gene encoding a portion of a F(ab')$_2$ fragment could include DNA sequences encoding the $C_H1$ domain and hinge region of the H chain, followed by a translational stop codon to yield such a truncated antibody fragment molecule.

CD38BPs also include univalent antibodies and single chain antibodies. Single chain antibodies are peptides in which the heavy and light chain Fv regions are connected. In one embodiment, the present invention provides a single-chain Fv (scFv) wherein the heavy and light chains in the Fv of an anti-CD38 antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used.

In one embodiment of the present invention, a CD38BP may be derivatized or linked to another functional molecule, for instance another peptide or protein (such as a Fab' fragment) to generate a bispecific or multispecific molecule which binds to multiple binding sites or target epitopes. For example, an antibody of the present invention may be functionally linked (for instance by chemical coupling, genetic fusion, noncovalent association or otherwise) to one or more other binding molecules, such as another antibody, peptide or binding mimetic. In one embodiment, the CD38BP is an antibody of the present invention.

Accordingly, the present invention includes bispecific and multispecific molecules comprising at least one first binding specificity for CD38 and a second binding specificity for a second target epitope. In one embodiment of the present invention, the second target epitope is an Fc receptor, e.g., human FcγRI (CD64) or a human Fcα receptor (CD89), or a T cell receptor, e.g., CD3. In one embodiment, the present invention provides bispecific and multispecific molecules capable of binding both to FcγR, FcαR or FcεR expressing effector cells (e.g., monocytes, macrophages or polymorphonuclear cells (PMNs)), and to target cells expressing CD38. These bispecific and multispecific molecules target CD38 expressing cells to effector cell and trigger Fc receptor-mediated effector cell activities, such as phagocytosis of CD38 expressing cells, antibody dependent cellular cytotoxicity (ADCC), cytokine release, or generation of superoxide anion.

Bispecific and multispecific molecules of the present invention may further include a third binding specificity, in addition to an anti-Fc binding specificity and an anti-CD38 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" may be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" may bind an Fc receptor or a target cell antigen. Alternatively, the anti-enhancement factor portion may bind to an entity that is different from the entity to which the first and second binding specificities bind. For example, the anti-enhancement factor portion may bind a cytotoxic T cell (e.g., via CD2, CD3, CD8, CD28, CD4, CD40, ICAM-1 or other immune cell that results in an increased immune response against the target cell).

In one embodiment, the bispecific and multispecific molecules of the present invention comprise as a binding specificity at least one further antibody, including, e.g., an Fab, Fab', F(ab')2, Fv, or a scFv. The further antibody may also be a light chain or heavy chain dimer, or any minimal fragment thereof such as a Fv or a single chain construct as described in Ladner et al., in U.S. Pat. No. 4,946,778. The antibody may also be a binding-domain immunoglobulin fusion protein as disclosed in US 2003/0118592 and US 2003/0133939.

In one embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fc* receptor classes: FcγRI (CD64), FcγRII (CD32), and FcγRIII (CD16). In one embodiment, the Fcγ receptor is a human high affinity FcγRI. The production and characterization of these monoclonal antibodies are described by Fanger et al., in WO 88/00052 and in U.S. Pat. No. 4,954,617. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in the present invention are mAb 22, mAb 32, mAb 44, mAb 62 and mAb 197. In other embodiments, the anti-Fcγ receptor antibody is a humanized form of mAb 22 (H22). The production and characterization of the H22 antibody is described in Graziano, R. F. et al., J. Immunol. 155(10), 4996-5002 (1995) and WO 94/10332. The H22 antibody producing cell line was deposited at the American Type Culture Collection on Nov. 4, 1992 under the designation HA022CL1 and has the accession No. CRL 11177.

In one embodiment, the binding specificity for an Fc receptor is provided by an antibody that binds to a human IgA receptor, e.g., an Fcα receptor (FcαI (CD89)), the binding of which in one embodiment is not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/ macrophages, eosinophilic and neutrophilic granulocytes, but not on non-effector cell populations. FcαRI has medium affinity for both IgA1 and IgA2, which is increased upon exposure to cytokines such as G-CSF or GM-CSF (Morton, H. C. et al., Critical Reviews in Immunology 16, 423-440 (1996)). Four FcαRI-specific monoclonal antibodies, identified as A3, A59, A62 and A77, which bind FcαRI outside the IgA ligand binding domain, have been described (Monteiro, R. C. et al., J. Immunol. 148, 1764 (1992)).

FcαRI, FcγRI, FcγRII and FcγRIII, especially FcγRII and FcγRIII, are examples of trigger receptors for use in the present invention because they (1) are expressed primarily on immune effector cells, e.g., monocytes, PMNs, macrophages and dendritic cells; (2) are expressed at high levels (for instance 5,000-100,000 per cell); (3) are mediators of cytotoxic activities (for instance ADCC, phagocytosis); and (4) mediate enhanced antigen presentation of antigens, including self-antigens, targeted to them.

In one embodiment, a CD38BP of the present invention is a multispecific anti-CD38 antibody or antibody-like molecule, a particular example of which is a bispecific antibody comprising at least one pair of $V_H$ sequence and $V_L$ sequence chains specific for an epitope comprised at least in part in CD38 and a second at least one pair of $V_H$ and $V_L$ sequence chains specific for a second epitope. The $V_H$ and $V_L$ sequences in a bispecific antibody may comprise complete $V_H$ and $V_L$ sequences corresponding to anti-CD38 $V_H$ and $V_L$ regions, variant $V_H$ and/or $V_L$ sequences, or suitable portions of $V_H$ and/or V, regions, such as a suitable combination of CDR sequences and other sequences sufficient to provide binding to the epitopes of interest.

Exemplary bispecific antibody molecules comprise (i) two antibodies one with a specificity to CD38 and another to a second target that are conjugated together, (ii) a single antibody that has one chain specific to CD38 and a second chain specific to a second molecule, and (iii) a single chain antibody that has specificity to CD38 and a second molecule. Typically, the second target/second molecule is a molecule other than CD38. In one embodiment, the second molecule is a cancer antigen/tumor-associated antigen such as carcinoembryonic antigen (CEA), prostate specific antigen (PSA), RAGE (renal antigen), α-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, C-myc, Mart1, MelanA, MUM-1, MUM-2, MUM-3, HLA-B7, and Ep-CAM. In one embodiment, the second molecule is a cancer-associated integrin, such as α5β3 integrin. In one embodiment, the second molecule is an angiogenic factor or other cancer-associated growth factor, such as a vascular endothelial growth factor (VEGF), a fibroblast growth factor (FGF), epidermal growth factor (EGF), epidermal growth factor receptor (EGFR), angiogenin, and receptors thereof, particularly receptors associated with cancer progression (for instance one of the HER1-HER4 receptors). Other cancer progression-associated proteins discussed herein may also be suitable second molecules. In one embodiment, the second molecule is a molecule expressed on the surface of multiple myeloma cells such as CD138.

In one embodiment, a bispecific antibody of the present invention is a diabody.

Bispecific antibodies also include cross-linked or "heteroconjugate" antibodies. For example, one of the antibodies in a heteroconjugate may be coupled to avidin and the other to biotin. Such antibodies have, for example, been proposed to target immune system cells to unwanted cells (see for instance U.S. Pat. No. 4,676,980). Heteroconjugate antibodies may be made using any convenient cross-linking methods. Suitable peptide cross-linking agents and techniques are well known in the art, and examples of such agents and techniques are disclosed in for instance U.S. Pat. No. 4,676,980.

Thus, although the discussion herein may focus on antibodies, it should be understood that the embodiments and features of the antibodies may equally be applied to antibody fragments, such as Fab fragments, Fab' fragments, and scFv peptides, antibody-like peptides (peptides comprising a CDR), bi- and multi-specific antibodies and other CD38BPs, as appropriate, provided that the CD38BP of the present invention retains at least a substantial proportion of the antigen-binding properties of the corresponding complete antibody. In some instances, antibody fragments may be associated with lower antigen-binding affinity, but may offer other advantageous features that may offset for any such loss in affinity.

CD38BPs of the present invention, and particularly anti-CD38 antibodies may be selected based on their ability to provide the ability of complement fixation, or not. There are a number of isotypes of antibodies that are capable of complement fixation and CDC, including, without limitation, the following: murine IgM, murine IgG2a, murine IgG2b, murine IgG3, human IgM, human IgG1, and human IgG3. Those isotypes that do not include, without limitation, human IgG2 and human IgG4. Isotype determination and other methods for modifying the complement fixation and CDC functional characteristics of antibodies are known in the art.

CD38BPs of the present invention also include immunoadhesins, which are molecules wherein one or more CDRs of an anti-CD38 antibody are covalently or noncovalently associated with the molecule. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a CD38.

The present invention also provides CD38BP fusion proteins. CD38BP fusion proteins may comprise any suitable amino acid sequence or combination of sequences that are specific and/or selective for at least one domain that is at least partially comprised within CD38 (e.g., an anti-CD38 antibody $V_H$ domain, $V_L$ domain, or particular CDRs thereof) and at least one nonhomologous and typically substantially non-similar amino acid sequence (e.g., less than about 40%, less than about 35%, less than about 30%, less than about 25%, or less than about 20% amino acid sequence identity to the CD38-specific/selective sequence) that imparts a detectable biological function and/or characteristic to the fusion protein that cannot solely be attributed to the CD38-specific/selective sequence (e.g., increased in vivo half-life, fluorescence, increased targeting to a particular type of cell, etc.). Functional sequences of such a fusion protein may be separated by flexible linker(s). Secondary sequence(s) may also be derived from cytotoxic or apoptotic peptides. Secondary sequences may also confer diagnostic properties. Examples of such sequences include those derived from easily visualized enzymes such as horseradish peroxidase.

CD38BP fusion proteins may also be characterized by comprising an epitope tag. An epitope tag sequence is an amino acid sequence having enough residues to provide an epitope against which an antibody may be made, in the context of the CD38BP, yet is short enough such that it does not substantially interfere with the activity (selectivity, specificity, affinity, and/or biological activity) of the CD38BP (as compared to a parent CD38BP lacking the epitope tag). An epitope tag desirably is sufficiently unique so that the antiepitope tag antibody does not substantially cross-react with other epitopes. Suitable tag polypeptides generally have at least about 6 amino acid residues and usually between about 8-50 amino acid residues (e.g., about 9-30 residues). Examples of epitope tags include the flu HA tag polypeptide and its antibody 12CA5 (Field et al., Mol. Cell. Biol. 8, 2159-2165 (1988)); the c-myc tag and the 8F9, 3C7, 6E10, G4, B7 and 9E10 antibodies thereto (Evan et al., Mol. Cell. Biol. 5(12), 3610-3616 (1985)) and the Herpes Simplex virus glycoprotein D (gD) tag and its antibody (Paborsky et al., Protein Engineering 3(6), 547-553 (1990)). In certain embodiments, the epitope tag is a "salvage receptor binding epitope". As used herein, the term "salvage receptor binding epitope" refers to an epitope of the Fc region of an IgG molecule (for instance IgG1, IgG2, IgG3, or IgG4) that is responsible for increasing the in vivo serum half-life of the IgG molecule.

CD38BPs of the present invention also include CD38BP derivatives. A derivative is a peptide in which one or more of the amino acid residues of the peptide have been chemically modified (e.g. by alkylation, acylation, ester formation, or amide formation) or covalently associated with one or more heterologous substituents (e.g., a lipophilic substituent, a PEG moiety, a peptide side chain linked by a suitable organic moiety linker, etc.). The peptide may also be conjugated to a therapeutic moiety, such as a cytotoxin, a chemotherapeutic drug, an immunosuppressant, or a radioisotope (a socalled immunoconjugate). In general, CD38BPs described herein may be modified by inclusion of any suitable number of such modified amino acids and/or associations with such conjugated substituents. Suitability in this context general is determined by the ability to at least substantially retain CD38 selectivity and/or specificity associated with the non-derivatized parent CD38BP. The inclusion of one or more modified amino acids may be advantageous in, for example, (a) increasing polypeptide serum half-life, (b) reducing polypeptide antigenicity, or (c) increasing polypeptide storage stability. Amino acid (s) are modified, for example, co-translationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On Cd-Rom, Humana Press, Towata, N.J. The modified amino acid may be selected from a glycosylated amino acid, a PEGylated amino acid, a farnesylated amino acid, an acetylated amino acid, a biotinylated amino acid, an amino acid/ conjugated to a lipid moiety, and an amino acid conjugated to an organic derivatizing agent.

Additionally, antibodies may be chemically modified by covalent conjugation to a polymer to for instance increase their circulating half-life. Exemplary polymers, and methods to attach them to peptides, are illustrated in for instance U.S. Pat. No. 4,766,106, U.S. Pat. No. 4,179,337, U.S. Pat. No. 4,495,285 and U.S. Pat. No. 4,609,546. Additional illustrative polymers include polyoxyethylated polyols and polyethylene glycol (PEG) (e.g., a PEG with a molecular weight of between about 1,000 and about 40,000, such as between about 2000 and about 20,000, e.g., about 3,000-12,000).

In one embodiment, the present invention provides a CD38BP that is conjugated to a second molecule that is selected from a radionuclide, an enzyme, an enzyme substrate, a cofactor, a fluorescent marker, a chemiluminescent marker, a peptide tag, or a magnetic particle. In one embodiment, a CD38BP may be conjugated to one or more antibody fragments, nucleic acids (oligonucleotides), nucleases, hormones, immunomodulators, chelators, boron compounds, photoactive agents, dyes, and the like. These and other suitable agents may be coupled either directly or indirectly to CD38BPs of the present invention. One example of indirect coupling of a second agent is coupling by a spacer moiety. These spacers, in turn, may be either insoluble or soluble (see for instance Diener et al., Science 231, 148 (1986)) and may be selected to enable drug release from the CD38BP at a target site and/or under particular conditions. Additional examples of therapeutic agents that may be coupled to CD38BPs include lectins and fluorescent peptides.

In one embodiment, CD38BP derivatives comprising one or more radiolabeled amino acids are provided. A radiolabeled CD38BP may be used for both diagnostic and therapeutic purposes (conjugation to radiolabeled molecules is another possible feature). Nonlimiting examples of labels for polypeptides include, but are not limited to $^3H$, $^{14}C$, $^{15}N$, $^{35}S$, $^{90}Y$, $^{99}Tc$, $^{125}I$, $^{131}I$, and $^{186}Re$. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. No. 4,681,581, U.S. Pat. No. 4,735,210, U.S. Pat. No. 5,101,827, U.S. Pat. No. 5,102,990 (U.S. RE35,500), U.S. Pat. No. 5,648,471 and U.S. Pat. No. 5,697,902. For example, a radioisotope may be conjugated by a chloramine T method.

Advantageous radionuclides in diagnostic contexts are indium isotopes and in the context of therapeutic applications yttrium isotopes, which are cytotoxic. Photon-emitting radioisotopes, in general, are advantageous in diagnostic (radioimmunoscintigraphy (RIS)) methods. Auger electrons have a very short path length (5-10 nm) and need to be internalized to be cytotoxic (see for instance Adelstein et al., Nucl. Med. Biol. 14, 165-169 (1987)). Accordingly, peptides conjugated to such isotopes may be useful in diagnostic methods, but only peptides that are internalized should be considered for radioisotopes that emit Auger electrons in therapeutic contexts. Alpha particles need to be close to a cell (within 3-4 cell diameters) to be effective as therapeutic agents (Vriesendorp et al., "Radioimmunoglobulin therapy," in High Dose Cancer Therapy Armitage et al., (eds). (Williams & Wilkins, Baltimore, Md. 1992)). Both Auger electrons and alpha emitters may be considered to have high selectivity because their short-range emission typically will not irradiate neighboring normal cells.

The radiometals $^{111}In$ and $^{90}Y$ are, respectively, a pure γ-emitter and a pure β-emitter. Iodine-125, the most commonly used emitter of Auger electrons, has a half-life of about 60 days and frequently is released by immunoconjugates in vivo (due to dehalogenation). The most commonly considered alpha emitters for clinical use, astatine-211 and bismuth-212, have relatively short half-lives (7.2 h and 1.0 h, respectively) and decay into radioactive isotopes that may not be retained by the immunoconjugate after the first alpha emission (Wilbur, Antibiot. Immunoconjug. Radiopharm. 4, 5-97 (1991)). For diagnostic applications, CD38BPs labeled with indium-111 or technetium-99m may be used. Both of these isotopes emit gamma rays within the appropriate energy range for imaging, (100-250 keV). Energies below this range typically are not penetrating enough to reach an external imaging device. Higher energy levels are difficult to collimate and provide diagnostic images with poor resolution. The short-half life of $^{99}Tc$ typically restricts its use to immunoconjugates with rapid tumor uptake.

In one embodiment, first and second CD38BPs conjugated with first and second radioisotopes are provided. In another embodiment, a single CD38BP conjugated with two radioisotopes is provided. An advantage of using two separate radioisotopes, e.g., one for imaging and one for therapy, is that it facilitates outpatient treatment. The low amount of radioactivity used diagnostically does not represent a radiation hazard, while the radiation emitted by a therapeutic isotope, such as a pure β-emitter, typically will largely be absorbed in the vicinity of the targeted cells.

Radioisotopes may be attached directly or indirectly to a CD38BP. The radioisotopes $^{125}I$, $^{131}I$, $^{99}Tc$, $^{188}Re$, and $^{188}Re$ may be, for example, covalently bound to proteins (including antibodies) through amino acid functional groups. For radioactive iodine it is usually through the phenolic group found on tyrosine. There are numerous methods to accomplish this: chloramine-T (see for instance Greenwood et al., Biochem J. 89, 114-123 (1963) and Iodogen (Salacinski et al., Anal. Biochem. 117, 136-146 (1981)). Tc and Re isotopes may be covalently bound through the sulfhydryl group of cysteine (see for instance Griffiths et al., Cancer Res. 51, 4594-4602 (1991)). However, such compositions may be relatively better suited for diagnostic purposes as the body often can break these covalent bonds, releasing the radioisotopes to the circulatory system.

A CD38BP may also be labeled with enzymes that are useful for detection, such as horseradish peroxidase, β-galactosidase, luciferase, alkaline phosphatase, glucose oxidase, and the like. A CD38BP also be labeled with biotin, and accordingly detected through indirect measurement of avidin or streptavidin binding. A CD38BP may also be labeled with a predetermined polypeptide epitopes recognized by a secondary reporter (e.g., leucine zipper pair sequences, binding sites for secondary antibodies, metal binding domains, epitope tags, etc.). Additional examples of enzyme conjugate candidates include malate dehydrogenase, staphylococcal nuclease, delta-V-steroid isomerase, yeast alcohol dehydrogenase, α-glycerophosphate dehydrogenase, triose phosphate isomerase, asparaginase, glucose oxidase, ribonuclease, urease, catalase, glucose-6-phosphate dehydrogenase, glucoamylase, and acetylcholinesterase.

Additional exemplary labeling moieties generally include, but are not limited to spin-labeled molecules and other labeling moieties of diagnostic value.

In one embodiment, the present invention provides crosslinked CD38BP derivatives. For example, such a CD38BP derivative may be produced by crosslinking two or more antibodies, at least one of which is specific/selective for CD38 (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

CD38BPs may also be conjugated with any suitable type of chemical group, such as polyethylene glycol (PEG), a methyl or ethyl group, or a carbohydrate group. These and other suitable conjugated groups may be used to improve the biological characteristics of the CD38BP, e.g., to increase serum half-life, solubility, and/or tissue binding.

CD38BP derivatives may be produced by chemically conjugating a radioisotope, protein, or other agent/moiety/compound to (a) the N-terminal side or C-terminal side of the CD38BP or subunit thereof (e.g., an anti-CD38 antibody H chain, L chain, or anti-CD38 specific/selective fragment thereof) an appropriate substituent group or side chain or (b) a sugar chain in the CD38BP (see, e.g., Antibody Engineering Handbook, edited by Osamu Kanemitsu, published by Chijin Shokan (1994)). Derivatives may also be generated by conjugation at internal residues or sugars, where appropriate.

CD38BPs may also be derivatized with a detection agents, for instance fluorescent compounds, including fluorescein, fluorescein isothiocyanate, rhodamine, 5-dimethylamine-1-napthalenesulfonyl chloride, lanthanide phosphors, and the like. Additional examples of suitable fluorescent labels include a $^{125}$Eu label, an isothiocyanate label, a phycoerythrin label, a phycocyanin label, an allophycocyanin label, an o-phthaldehyde label, a fluorescamine label, etc. Examples of chemiluminescent labels include luminal labels, isoluminal labels, aromatic acridinium ester labels, imidazole labels, acridinium salt labels, oxalate ester labels, a luciferin labels, luciferase labels, aequorin labels, etc.

In one embodiment, a CD38BP derivative comprises a conjugated nucleic acid or nucleic acid-associated molecule. In one such facet of the present invention, the conjugated nucleic acid is a cytotoxic ribonuclease. In one embodiment, the conjugated nucleic acid is an antisense nucleic acid (for instance a S100A10 targeted antisense molecule, which may also be an independent component in a combination composition or combination administration method of the present invention—see for instance Zhang et al., J Biol. Chem. 279 (3), 2053-62 (2004)). In one embodiment, the conjugated nucleic acid is an inhibitory RNA molecule (e.g., a siRNA molecule). In one embodiment, the conjugated nucleic acid is an immunostimulatory nucleic acid (e.g., an immunostimulatory CpG motif-containing DNA molecule). In one embodiment, the conjugated nucleic acid is an expression cassette coding for expression of a tumor suppressor gene, anti-cancer vaccine, anti-cancer cytokine, or apoptotic agent. Such derivatives also may comprise conjugation of a nucleic acid coding for expression of one or more cytotoxic proteins, such as plant and bacterial toxins.

In one embodiment, a CD38BP is conjugated to a functional nucleic acid molecule. Functional nucleic acids include antisense molecules, interfering nucleic acid molecules (e.g., siRNA molecules), aptamers, ribozymes, triplex forming molecules, and external guide sequences. The functional nucleic acid molecules may act as affectors, inhibitors, modulators, and stimulators of a specific activity possessed by a target molecule, or the functional nucleic acid molecules may possess a de novo activity independent of any other molecules. A representative sample of methods and techniques which aid in the design and use of antisense molecules can be found in the following non-limiting list of US patents: U.S. Pat. No. 5,135,917, U.S. Pat. No. 5,294,533, U.S. Pat. No. 5,627,158, U.S. Pat. No. 5,641,754, U.S. Pat. No. 5,691,317, U.S. Pat. No. 5,780,607, U.S. Pat. No. 5,786,138, U.S. Pat. No. 5,849,903, U.S. Pat. No. 5,856,103, U.S. Pat. No. 5,919,772, U.S. Pat. No. 5,955,590, U.S. Pat. No. 5,990,088, U.S. Pat. No. 5,994,320, U.S. Pat. No. 5,998,602, U.S. Pat. No. 6,005,095, U.S. Pat. No. 6,007,995, U.S. Pat. No. 6,013,522, U.S. Pat. No. 6,017,898, U.S. Pat. No. 6,018,042, U.S. Pat. No. 6,025,198, U.S. Pat. No. 6,033,910, U.S. Pat. No. 6,040,296, U.S. Pat. No. 6,046,004, U.S. Pat. No. 6,046,319 and U.S. Pat. No. 6,057,437.

In one embodiment, a CD38BP is conjugated to an aptamer. Aptamers are molecules that interact with a target molecule, for instance in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Representative examples of how to make and use aptamers to bind a variety of different target molecules can be found in the following non-limiting list of US patents: U.S. Pat. No. 5,476,766, U.S. Pat. No. 5,503,978, U.S. Pat. No. 5,631,146, U.S. Pat. No. 5,731,424, U.S. Pat. No. 5,780,228, U.S. Pat. No. 5,792,613, U.S. Pat. No. 5,795,721, U.S. Pat. No. 5,846,713, U.S. Pat. No. 5,858,660, U.S. Pat. No. 5,861,254, U.S. Pat. No. 5,864,026, U.S. Pat. No. 5,869,641, U.S. Pat. No. 5,958,691, U.S. Pat. No. 6,001,988, U.S. Pat. No. 6,011,020, U.S. Pat. No. 6,013,443, U.S. Pat. No. 6,020,130, U.S. Pat. No. 6,028,186, U.S. Pat. No. 6,030,776 and U.S. Pat. No. 6,051,698.

In one embodiment, the present invention provides a CD38BP which is conjugated to a ribozyme. Ribozymes are nucleic acid molecules that are capable of catalyzing a chemical reaction, either intramolecularly or intermolecularly. Ribozymes are thus catalytic nucleic acids. There are a number of different types of ribozymes that catalyze nuclease or nucleic acid polymerase type reactions which are based on ribozymes found in natural systems, such as (a) hammerhead ribozymes, (described in for example U.S. Pat. No. 5,334,711, U.S. Pat. No. 5,436,330, U.S. Pat. No. 5,616,466, U.S. Pat. No. 5,633,133, U.S. Pat. No. 5,646,020, U.S. Pat. No. 5,652,094, U.S. Pat. No. 5,712,384, U.S. Pat. No. 5,770,715, U.S. Pat. No. 5,856,463, U.S. Pat. No. 5,861,288, U.S. Pat. No. 5,891,683, U.S. Pat. No. 5,891,684, U.S. Pat. No. 5,985,621, U.S. Pat. No. 5,989,908, U.S. Pat. No. 5,998,193, U.S. Pat. No. 5,998,203, WO 9858058, WO 9858057 and WO 9718312), (b) hairpin ribozymes (described in for instance U.S. Pat. No. 5,631,115, U.S. Pat. No. 5,646,031, U.S. Pat. No. 5,683,902, U.S. Pat. No. 5,712,384, U.S. Pat. No. 5,856,188, U.S. Pat. No. 5,866,701, U.S. Pat. No. 5,869,339 and U.S. Pat. No. 6,022,962), and (c) tetrahymena ribozymes (described in for instance U.S. Pat. No. 5,595,873 and U.S. Pat. No. 5,652,107). There are also a number of ribozymes that are not found in natural systems, but which have been engineered to catalyze specific reactions de novo (examples of which are described in for instance U.S. Pat. No. 5,580,967, U.S. Pat. No. 5,688,670, U.S. Pat. No. 5,807,718 and U.S. Pat. No. 5,910,408). Ribozymes typically cleave RNA or DNA substrates, and more commonly cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of US patents: U.S. Pat. No. 5,646,042, U.S. Pat. No. 5,693,535, U.S. Pat. No. 5,731,295, U.S. Pat. No. 5,811,300, U.S. Pat. No. 5,837,855, U.S. Pat. No. 5,869,253, U.S. Pat. No. 5,877,021, U.S. Pat. No. 5,877,022, U.S. Pat. No. 5,972,699, U.S. Pat. No. 5,972,704, U.S. Pat. No. 5,989,906 and U.S. Pat. No. 6,017,756.

In one embodiment, the present invention provides a CD38BP that is conjugated to a triplex forming function nucleic acid. Such nucleic acid molecules can interact with either double-stranded or single-stranded nucleic acid. When triplex molecules interact with a target region, a structure called a triplex is formed, in which three strands of DNA form a complex dependant on both Watson-Crick and Hoogsteen base-pairing. Triplex molecules can bind target regions with high affinity and specificity. Representative examples of how to make and use triplex forming molecules to bind a variety of different target molecules can be found in the following non-limiting list of US patents: U.S. Pat. No. 5,176,996, U.S. Pat. No. 5,645,985, U.S. Pat. No. 5,650,316, U.S. Pat. No. 5,683,874, U.S. Pat. No. 5,693,773, U.S. Pat. No. 5,834,185, U.S. Pat. No. 5,869,246, U.S. Pat. No. 5,874,566 and U.S. Pat. No. 5,962,426.

In one embodiment, a CD38BP is conjugated to an external guide sequence. External guide sequences (EGSs) are molecules that bind a target nucleic acid molecule forming a complex that is recognized by RNase P, which cleaves the target molecule. EGSs may be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (see for instance WO 92/03566 and Forster and Altman, Science 238, 407-409 (1990) for discussion). Representative examples of how to make and use EGS molecules to facilitate cleavage of a variety of different target molecules are provided in the following non-limiting list of US patents: U.S. Pat. No. 5,168,053, U.S. Pat. No. 5,624,824, U.S. Pat. No. 5,683,873, U.S. Pat. No. 5,728,521, U.S. Pat. No. 5,869,248 and U.S. Pat. No. 5,877,162.

In one embodiment, a CD38BP is conjugated to an interfering nucleic acid molecule, such as a siRNA or other RNAi molecule (e.g., an inhibitory double stranded (ds) RNA molecule of about 20-25 nucleotides), which is targeted to interfere with the action of a target gene expression product, such as a gene expression product involved in a CD38 mediated disease or condition. Methods for the production and use of interfering nucleic acid molecules are provided in for instance Nishikura, Cell. 107(4), 415-8 (2001), Fjose et al., Biotechnol Annu Rev. 7, 31-57 (2001), Hanon, Nature 418, 244-51 (2002), Brantl, Biochim Biophys Acta. 1575(1-3), 15-25 (2002), Tuschl, Chembiochem. 2(4), 239-45 (2001), Caplen, Expert Opin Biol Ther. 3(4), 575-86 (2003), Lu et al., Curr Opin Mol. Ther. 5(3), 225-34 (2003), Shuey et al., Drug Discov Today. 7(20), 1040-6 (2002), Shi, Trends Genet. 19(1), 9-12 (2003), Kovar et al., Semin Cancer Biol. 13(4), 275-81 (2003), Lavrey et al., Curr Opin Drug Discov Devel. 6(4), 561-9 (2003), Clewey, Commun Dis Public Health. 6(2), 162-3 (2003), Duxbury et al., J Surg Res. 117(2), 339-44 (2004), Caplen et al., Ann N Y Acad. Sci. 1002, 56-62 (2003), WO 01/75164, U.S. Pat. No. 6,506,559, US 20040086884, US 20040077574, US 20040063654, US 20040033602, US 20030167490, US 20030157030, US 20030114409, US 20030108923, US 20040014113 and US 20020132788.

In one embodiment, a CD38BP is conjugated to a tumor targeting domain peptide or molecule. In one embodiment, a CD38BP is conjugated to a tumor targeting factor VII sequence.

Any method known in the art for conjugating the CD38BP to the conjugated molecule(s), such as those described above, may be employed, including those methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Linkage/conjugation may be accomplished in any suitable way. For example, a covalent linkage may take the form of a disulfide bond (if necessary and suitable, a CD38BP could be engineered to contain an extra cysteine codon, which desirably does not interfere with the CD38 binding activity of the molecule. A toxin molecule, derivatized with a sulfhydryl group reactive with the cysteine of the modified CD38BP, may form an immunoconjugate with the CD38BP peptide. Alternatively, a sulfhydryl group may be introduced directly to a CD38BP using solid phase polypeptide techniques. For example, the introduction of sulfhydryl groups into peptides is described by Hiskey, Peptides 3, 137 (1981). The introduction of sulfhydryl groups into proteins is described in Maasen et al., Eur. J. Biochem. 134, 32 (1983). Once the correct sulfhydryl groups are present, the cytotoxin and CD38BP may be purified, both sulfur groups reduced; cytotoxin and ligand mixed (for instance in a ratio of about 1:5 to 1:20); and disulfide bond formation allowed to proceed to completion (generally about 20 to 30 minutes) at room temperature. The mixture may then be dialyzed against phosphate buffered saline or chromatographed in a resin such as Sephadex to remove unreacted ligand and toxin molecules.

Numerous types of cytotoxic compounds may be joined to proteins through the use of a reactive group on the cytotoxic compound or through the use of a cross-linking agent. A common reactive group that will form a stable covalent bond in vivo with an amine is isothiocyanate (Means et al., Chemical modifications of proteins (Holden-Day, San Francisco 1971) pp. 105-110). This group preferentially reacts with the $\epsilon$-amine group of lysine. Maleimide is a commonly used reactive group to form a stable in vivo covalent bond with the sulfhydryl group on cysteine (Ji., Methods Enzymol 91, 580-609 (1983)). Monoclonal antibodies typically are incapable of forming covalent bonds with radiometal ions, but they may be attached to the antibody indirectly through the use of chelating agents that are covalently linked to the antibodies. Chelating agents may be attached through amines (Meares et al., Anal. Biochem. 142, 68-78 (1984)) and sulfhydral groups (Koyama, Chem. Abstr. 120, 217262t (1994)) of amino acid residues and also through carbohydrate groups (Rodwell et al., PNAS USA 83, 2632-2636 (1986), Quadri et al., Nucl. Med. Biol. 20, 559-570 (1993)). Since these chelating agents contain two types of functional groups, one to bind metal ions and the other to joining the chelate to the antibody, they are commonly referred as bifunctional chelating agents (Sundberg et al., Nature 250, 587-588 (1974)).

Crosslinking agents that have two reactive functional groups are classified as being homo or heterobifunctional. Examples of homobifunctional crosslinking agents include bismaleimidohexane (BMH) which is reactive with sulfhydryl groups (Chen et al., J Biol Chem 266, 18237-18243 (1991)) and ethylene glycolbis[succinimidylsucciate] (EGS) which is reactive with amino groups (Browning et al., J. Immunol. 143, 1859-1867 (1989)). An example of a heterobifunctional crosslinker is m-maleimidobenzoyl-N-hydroxysuccinimide ester (MBS) (Myers et al., J. Immunol. Meth. 121, 129-142 (1989)). These methodologies are simple and are commonly employed.

A therapeutic or diagnostic agent may also or alternatively be attached at the hinge region of a reduced antibody component via disulfide bond formation. As an alternative, such peptides may be attached to the antibody component using a heterobifunctional cross-linker, such as N-succinyl 3-(2-pyridyldithio)proprionate (SPDP). Yu et al., Int. J. Cancer 56, 244 (1994). General techniques for such conjugation are well known in the art. See, for example, Wong, Chemistry Of Protein Conjugation And Cross-Linking (CRC Press 1991), Upeslacis et al., "Modification of Antibodies by Chemical Methods," In Monoclonal Antibodies: Principles And Applications, Birch et al., (eds.) (Wiley-Liss, Inc. 1995), Price, "Production and Characterization of Synthetic Peptide-Derived Antibodies," in Monoclonal Antibodies: Production, Engineering And Clinical Application, Ritter et al., (eds.) (Cambridge University Press 1995).

In some embodiments, labels or other conjugated substituents are attached to the CD38BP amino acid sequence by spacer arms of various lengths to reduce potential steric hindrance.

Unlabeled CD38BP(s) may be used in combination with other labeled antibodies (second antibodies) that are reactive with the CD38BP(s), such as antibodies specific for human immunoglobulin constant regions that bind to anti-CD38 mAbs. Alternatively, a CD38BP may be directly labeled. A wide variety of labels may be employed for direct or indirect labeling of CD38BPs, such as labeling with radionuclides, fluors, enzymes, enzyme substrates, enzyme cofactors, enzyme inhibitors, ligands (particularly haptens), etc.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertion variants of the antibody molecule include the fusion to the N- or C-terminus of the antibody of an enzyme or a polypeptide or PEG which increases the serum half-life of the antibody. Such anti-CD38 antibody fusion proteins and similar fusion proteins comprising CD38BP sequences are another feature of the present invention.

In one embodiment, the present invention provides molecules comprising a CD38BP, such as a human anti-CD38 antibody, of the present invention conjugated to a therapeutic moiety, such as a cytotoxin, a chemotherapeutic drug, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. For a description of these classes of drugs which are well known in the art, and their mechanisms of action, see Goodman et al., Goodman and Gilman's The Pharmacological Basis Of Therapeutics, 8th Ed., Macmillan Publishing Co., 1990. Additional techniques relevant to the preparation of antibody immunotoxins are provided in for instance Vitetta, Immunol. Today 14, 252 (1993) and U.S. Pat. No. 5,194,594.

Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, actinomycin D, 1-dehydro-testosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, calicheamicin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, *sapaonaria officinalis* inhibitor, gelonin, mitogellin, restrictocin, phenomycin, and enomycin toxins. Therapeutic agents, which may be administered in combination with a CD38BP of the present invention as described elsewhere herein, may also be candidates for therapeutic moieties useful for conjugation to a CD38BP of the present invention. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors and apotopic inducing protein isolated from mitochondria.

In one embodiment, the cytotoxic agent is calicheamicin, $^{90}Y$, $^{125}I$ and $^{131}I$.

Other examples of therapeutic cytotoxins that may be conjugated to a CD38BP of the present invention include calicheamicins and duocarmycins. As indicated above, the drug moiety need not be construed as limited to classical chemical therapeutic agents. For example, the drug moiety may be a protein or polypeptide possessing a desired biological activity. Such proteins may include, for example, an agent active at the cell surface, such as phospholipase enzymes, e.g. phospholipase C.

The lysing portion of a toxin typically may be readily joined to the Fab fragment of an antibody or antibody fragment of the present invention. Other suitable conjugated molecules include ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Additional toxins suitable for use in the present invention are known to those of skill in the art (see for instance U.S. Pat. No. 6,077,499).

Conjugates of CD38BPs, such as antibodies, and such cytotoxic moieties may be made using a variety of bifunctional protein coupling agents. Examples of such reagents include SPDP, IT, bifunctional derivatives of imidoesters such a dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene and anti-mitotic agents (e.g., vincristine, vinblastine, docetaxel, paclitaxel and vinorelbin).

Techniques for conjugating such therapeutic moieties to CD38BPs, such as antibodies, are well known, see for instance Arnon et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985), Hellstrom et al., "Antibodies For Drug Delivery", in Controlled Drug Delivery (2nd Ed.), Robinson et al., (eds.), pp. 623-53 (Marcel Dekker, Inc. 1987), Thorpe, "Antibody Carriers Of Cytotoxic Agents In Cancer Therapy: A Review", in Monoclonal Antibodies'84: Biological And Clinical Applications, Pinchera et al., (eds.), pp. 475-506 (1985), "Analysis, Results, And Future Prospective Of The Therapeutic Use Of Radiolabeled Antibody In Cancer Therapy", in Monoclonal Antibodies For Cancer Detection And Therapy, Baldwin et al., (eds.), pp. 303-16 (Academic Press 1985) and Thorpe et al., "The Preparation And Cytotoxic Properties Of Antibody-Toxin Conjugates", Immunol. Rev. 62, 119-58 (1982).

In one embodiment, the present invention provides a CD38BP that is conjugated to a mixed toxin. A mixed toxin molecule is a molecule derived from two different (typically polypeptide) toxins. Generally, peptide toxins comprise one or more domains responsible for generalized eukaryotic cell binding, at least one enzymatically active domain, and at least one translocation domain. The binding and translocation domains are required for cell recognition and toxin entry respectively. Naturally-occurring proteins which are known to have a translocation domain include diphtheria toxin, Pseudomonas exotoxin A, and possibly other peptide toxins. The translocation domains of diphtheria toxin and Pseudomonas exotoxin A are well characterized (see for instance Hoch et al., PNAS USA 82, 1692 (1985), Colombatti et al., J. Biol. Chem. 261, 3030 (1986) and Deleers et al., FEBS Lett. 160, 82 (1983)), and the existence and location of such a domain in other molecules may be determined by methods such as those employed by Hwang et al., Cell 48, 129 (1987) and Gray et al., PNAS USA 81 2645 (1984). In view of these techniques, a useful mixed toxin hybrid molecule may be formed, for example, by fusing the enzymatically active A subunit of E. coli Shiga-like toxin (Calderwood et al., PNAS USA 84, 4364 (1987)) to the translocation domain (amino acid residues 202 through 460) of diphtheria toxin, and to a molecule targeting a particular cell type, as described in U.S. Pat. No. 5,906,820. The targeting portion of the three-part hybrid can cause the molecule to attach specifically to the targeted cells, and the diphtheria toxin translocation portion can act to insert the enzymatically active A subunit of the Shiga-like toxin into a targeted cell. The enzymatically active portion of Shiga-like toxin, like diphtheria toxin, acts on the protein synthesis machinery of the cell to prevent protein synthesis, thus killing the targeted cell.

Immunoconjugates according to the present invention may also comprise a radioisotope, e.g., iodine-131, yttrium-90 or indium-111, to generate cytotoxic radiopharmaceuticals for treating a CD38-related disorder, such as multiple myeloma.

In one embodiment, the CD38BPs, such as the human antibodies of the present invention are attached to a linker-chelator, e.g., tiuxetan, which allows for the antibody to be conjugated to a radioisotope.

Additionally useful conjugate substituents include anti-cancer retinoids. Taxane conjugates (see for instance Jaime et al., Anticancer Res. 21(2A), 1119-28 (2001), cisplatin conjugates, thapsigargin conjugates, linoleic acid conjugates, calicheamicin conjugates (see for instance Damle et al., Curr Opin Pharmacol. 3(4), 386-90 (2003), doxorubicin conjugates, geldanamycin conjugates, and the like, also may be useful in promoting the treatment of cancer (see, generally, Trail et al., Cancer Immunol Immunother. 52(5), 328-37 (2003)).

In one embodiment, the present invention provides secondary and anti-idiotypic antibodies raised against anti-CD38 antibodies of the present invention. A secondary antibody refers to an antibody specific for, and typically raised against, an anti-CD38 antibody. An anti-idiotypic (Id) antibody is an antibody which recognizes unique determinants generally associated with the antigen-binding site of an antibody. An Id antibody may be prepared by immunizing an animal of the same species and genetic type as the source of an anti-CD38 mAb with the mAb to which an anti-Id is being prepared. The immunized animal typically can recognize and respond to the idiotypic determinants of the immunizing antibody by producing an antibody to these idiotypic determinants (the anti-Id antibody). Such antibodies are described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein with respect to anti-CD38 antibodies and other CD38BPs of the present invention. For example, anti-Id mAbs may be coupled to a carrier such as keyhole limpet hemocyanin (KLH) and used to immunize BALB/c mice. Sera from these mice typically will contain anti-anti-Id antibodies that have the binding properties similar if not identical to an original/parent CD38 antibody.

In one embodiment, the present invention provides a nucleic acid encoding a CD38BP. A CD38BP-encoding nucleic acid may have any suitable characteristics and comprise any suitable features or combination thereof. Thus, for example, a CD38BP-encoding nucleic acid may be in the form of DNA, RNA, or a hybrid thereof, and may include normaturally-occurring bases, a modified backbone (e.g., a phosphothioate backbone that promotes stability of the nucleic acid), or both. The nucleic acid advantageously comprises features that promote desired expression in target host cell(s), replication, and/or selection. Examples of such features include an origin of replication component, a selection gene component, a promoter component, an enhancer element component, a polyadenylation sequence component, a termination component, and the like.

In one embodiment, the present invention provides a vector comprising a CD38BP-encoding nucleic acid. A vector refers to a delivery vehicle that promotes the expression of a CD38BP-encoding nucleic acid, the production of a CD38BP peptide, the transfection/transformation of target cells, the replication of the CD38BP-encoding nucleic acid, promotes stability of the nucleic acid, promotes detection of the nucleic acid and/or transformed/transfected cells, or otherwise imparts advantageous biological function to the CD38BP-encoding nucleic acid. A vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a CD38BP-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC19/18, or pUC118/119, a "midge" minimally-sized nucleic acid vector (as described in for instance Schakowski et al., Mol Ther 3, 793-800 (2001)), or as a precipitated nucleic acid vector construct, such as a CaPO4-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. No. 5,589,466 and U.S. Pat. No. 5,973,972).

In one embodiment, the vector is suitable for expression of the CD38BP in a bacterial cell. Examples of such vectors include, for example, vectors which direct high level expression of fusion proteins that are readily purified (for instance multifunctional *E. coli* cloning and expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors for use in for instance *Saccharomyces cerevisiae* include, for example, vectors comprising constitutive or inducible promoters such as alpha factor, alcohol oxidase and PGH (reviewed in: F. Ausubel et al., ed. Current Protocols in Molecular Biology, Greene Publishing and Wiley Inter-Science New York (1987), and Grant et al., Methods in Enzymol 153, 516-544 (1987)).

A nucleic acid and/or vector may also comprises a nucleic acid sequence encoding a secretion/localization sequence, which can target a polypeptide, such as a nascent polypeptide chain, to a desired cellular compartment, membrane, or organelle, or which directs polypeptide secretion to periplasmic space or into cell culture media. Such sequences are known in the art, and include secretion leader or signal peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

CD38BP-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In one embodiment, the nucleic acid may be positioned in and/or delivered to the host cell or host animal via a viral vector. Any suitable viral vector may be used in this respect, and several are known in the art. A viral vector may comprise any number of viral polynucleotides, alone or in combination with one or more viral proteins, which facilitate delivery, replication, and/or expression of the nucleic acid of the present invention in a desired host cell. The viral vector may be a polynucleotide comprising all or part of a viral genome, a viral protein/nucleic acid conjugate, a virus-like particle ($V_LP$), a vector similar to those described in U.S. Pat. No. 5,849,586 and WO 97/04748, or an intact virus particle comprising viral nucleic acids and the nucleic acid of the present invention. A viral particle viral vector may comprise a wild-type viral particle or a modified viral particle. The viral vector may be a vector which requires the presence of another vector or wild-type virus for replication and/or expression (i.e., it may be a helper-dependent virus), such as an adenoviral vector amplicon. Typically, such viral vectors consist essentially of a wild-type viral particle, or a viral particle modified in its protein and/or nucleic acid content to increase transgene capacity or aid in transfection and/or expression of the nucleic acid (examples of such vectors include the herpes virus/AAV amplicons). Typically, a viral vector is similar to and/or derived from a virus that normally infects humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors. Examples of such viruses and viral vectors are in for instance Fields et al., eds., Virology Raven Press, Ltd., New York (3rd ed., 1996 and 4th ed., 2001), Encyclopedia of Virology, R. G. Webster et al., eds., Academic Press (2nd ed., 1999), Fundamental Virology, Fields et al., eds., Lippincott-Raven (3rd ed., 1995), Levine, "Viruses," Scientific American Library No. 37 (1992), Medical Virology, D. O. White et al., eds., Acad. Press (2nd ed. 1994), and Introduction to Modern Virology, Dimock, N. J. et al., eds., Blackwell Scientific Publications, Ltd. (1994).

Viral vectors that may be employed with polynucleotides of the present invention and the methods described herein include adenovirus and adeno-associated vectors, as in for instance Carter, Curr Opinion Biotech 3, 533-539 (1992) and Muzcyzka, Curr Top Microbiol Immunol 158, 97-129 (1992). Additional types and aspects of AAV vectors are described in for instance Carter, Contrib. Microbiol. 4, 85-86 (2000), Smith-Arica, Curr. Cardiol. Rep. 3(1), 41-49 (2001), Taj, J. Biomed. Sci. 7(4), 279-91 (2000), Vigna et al., J. Gene Med. 2(5), 308-16 (2000), Klimatcheva et al., Front. Biosci. 4, D481-96 (1999), Lever et al., Biochem. Soc. Trans. 27(6), 841-47 (1999), Snyder, J Gene Med. 1(3), 166-75 (1999), Gerich et al., Knee Surg. Sports Traumatol. Arthrosc. 5(2), 118-23 (1998), and During, Adv. Drug Deliv. Review 27(1), 83-94 (1997) and U.S. Pat. No. 4,797,368, U.S. Pat. No. 5,139,941, U.S. Pat. No. 5,173,414, U.S. Pat. No. 5,614,404, U.S. Pat. No. 5,658,785, U.S. Pat. No. 5,858,775 and U.S. Pat. No. 5,994,136). Adeno-associated viral vectors may be constructed and/or purified using the methods set forth, for example, in U.S. Pat. No. 4,797,368 and Laughlin et al., Gene 23, 65-73 (1983).

Another type of viral vector that may be employed with polynucleotides and methods of the present invention is a papillomaviral vector. Suitable papillomaviral vectors are known in the art and described in, e.g., Hewson, Mol Med Today 5(1), 8 (1999), Stephens, Biochem J. 248(1), 1-11 (1987) and U.S. Pat. No. 5,719,054. Examples of papillomaviral vectors are provided in for instance WO 99/21979. Alphavirus vectors may be gene delivery vectors in other contexts. Alphavirus vectors are known in the art and described in for instance Carter, Curr Opinion Biotech 3, 533-539 (1992), Muzcyzka, Curr Top Microbiol Immunol. 158, 97-129 (1992), Schlesinger, Expert Opin Biol Ther. 1(2), 177-91 (2001), Polo et al., Dev Biol (Basel). 104, 181-5 (2000), Wahlfors et al., Gene Ther. 7(6), 472-80 (2000), Colombage et al., Virology. 250(1), 151-63 (1998) and WO 01/81609, WO 00/39318, WO 01/81553, WO 95/07994 and WO 92/10578.

Another group of viral vectors are herpes viral vectors. Examples of herpes viral vectors are described in for instance Lachmann et al., Curr Opin Mol Ther 1(5), 622-32 (1999), Fraefel et al., Adv Virus Res. 55, 425-51 (2000), Huard et al., Neuromuscul 7(5), 299-313 (1997), Glorioso et al., Annu Rev Microbiol. 49, 675-710 (1995), Latchman, Mol. Biotechnol. 2(2), 179-95 (1994), and Frenkel et al., Gene Ther. 1 (Suppl 1), S40-6 (1994), as well as U.S. Pat. No. 6,261,552 and U.S. Pat. No. 5,599,691.

Retroviral vectors, including lentiviral vectors, also may be advantageous gene delivery vehicles in particular contexts. There are numerous retroviral vectors known in the art. Examples of retroviral vectors are described in for instance Miller, Curr Top Microbiol Immunol 158, 1-24 (1992), Salmons and Gunzburg, Human Gene Therapy 4, 129-141 (1993), Miller et al., Methods in Enzmmolosv 217, 581-599 (1994), Weber et al., Curr Opin Mol. Ther. 3(5), 439-53 (2001), Hu et al., Pharmacol Rev. 52(4), 493-511 (2000), Kim et al., Adv Virus Res. 55, 545-63 (2000), Palu et al., Rev Med. Virol. 10(3), 185-202 (2000) and Takeuchi et al., Adv Exp Med. Biol. 465, 23-35 (2000), as well as U.S. Pat. No. 6,326,195, U.S. Pat. No. 5,888,502, U.S. Pat. No. 5,580,766, and U.S. Pat. No. 5,672,510.

Adenoviral vectors may also be suitable viral vectors for gene transfer. Adenoviral vectors are well known in the art and described in for instance Graham et al, Mol Biotechnol 33(3), 207-220 (1995), Stephenson, Clin Diagn Virol 10(2-3), 187-94 (1998), Jacobs, Clin Sci (Lond). 85(2), 117-22 (1993), U.S. Pat. No. 5,922,576, U.S. Pat. No. 5,965,358 and U.S. Pat. No. 6,168,941 and WO98/22588, WO98/56937, WO99/15686, WO99/54441, and WO00/32754. Adenoviral vectors, herpes viral vectors and Sindbis viral vectors, useful in the practice of the present invention, are described in for instance Jolly Cancer Gene Therapy 1, 51-64 (1994), Latchman Molec Biotechnol 2, 179-195 (1994) and Johanning et al., Nucl Acids Res 23, 1495-1501 (1995).

Other suitable viral vectors include pox viral vectors. Examples of such vectors are discussed in for instance Berencsi et al., J Infect Dis 183(8), 1171-9 (2001), Rosenwirth et al., Vaccine 19(13-14), 1661-70 (2001), Kittlesen et al., J Immunol 164(8), 4204-11 (2000), Brown et al., Gene Ther 7(19), 1680-9 (2000), Kanesa-thasan et al., Vaccine 19(4-5), 483-91 (2000), Sten, Drua 60(2), 249-71 (2000). Vaccinia virus vectors may be pox virus vectors. Examples of such vectors and uses thereof are provided in for instance Venugopal et al., Res Vet Sci 57(2), 188-193 (1994), Moss Dev Biol Stand 82, 55-63 (1994), Weisz et al., Mol Cell Biol 43, 137-159 (1994), Mahr and Payne, Immunobioloev 184(2-3), 126-146 (1992), Hruby, Clin Microbiol Rev 3(2), 153-170 (1990) and WO92/07944, WO98/13500, and WO89/08716.

Other features of the present invention include recombinant cells, such as yeast, bacterial, and mammalian cells (e.g., immortalized mammalian cells) comprising such a nucleic acid, vector, or combinations of either or both thereof. For example, in one embodiment, the present invention provides a cell comprising a nucleic acid stably integrated into the cellular genome that comprises a sequence coding for expression of a CD38BP of the present invention. In one embodiment, the present invention provides a cell comprising a non-integrated nucleic acid, such as a plasmid, cosmid, phagemid, or linear expression element, which comprises a sequence coding for expression of a CD38BP.

The present invention also provides immunogenic peptides comprising any of the above-described antigenic determinant portions of CD38 specific for the CD38BPs of the present invention, such as the antigenic determinant portions of CD38 specific for -003 and -005 and -024. Such immunogens may be used to elicit a direct immune response in a method comprising an active immunotherapy regimen. The present invention further provides a fusion protein comprising such a CD38 immunogen and a fusion partner sequence that improves the half-life of the fusion protein (e.g., by inclusion of an immunoglobulin domain sequence); facilitates detection and/or purification of the fusion protein (by comprising, e.g., a fluorescent peptide sequence, a reporter enzyme sequence, an epitope tag, a hexa-histidine sequence (SEO ID NO: 37), or the like); promotes the targeting of the fusion protein (e.g., by comprising a ligand or portion of a ligand specific for a receptor on a target cell); promotes induction of a distinct immune response (e.g., corresponds to a cancer antigen or an immunogenic fragment thereof); is a cytotoxic agent; or achieves any combination thereof (e.g., a heat shock fusion protein partner can increase an immune response generated against a non-similar, heterologous antigen portion of a fusion protein, while also increasing the in vivo half-life of a fusion protein). Fusion proteins may also comprise one or more cleavage sites, particularly between domains.

Variants of such peptides, and derivatives of such immunogenic peptides or immunogenic peptide variants are additional features of the present invention (e.g., such CD38 immunogenic peptide derivatives may be modified by chemical coupling, genetic fusion, non-covalent association, and the like, to other molecular entities such as antibodies, toxins, radioisotope, cytotoxic agents, or cytostatic agents). Peptide mimitopes, comprising CD38 epitope sequences may also, for example, be useful as vaccine candidates. Such peptides may also be useful in the purification of anti-CD38 antibodies. In addition to the B-cell epitope sequences described herein, such peptides may be engineered or selected to also or alternatively comprise one or more anti-CD38 T cell epitopes. Such epitopes may be identified by any suitable technique known in the art (e.g., by T cell epitope prediction software applications).

In one embodiment, the present invention provides a nucleic acid encoding such an immunogenic peptide. Such a nucleic acid may be delivered to a host in a suitable vector, such as a replication-deficient targeted vector (e.g., a targeted nucleic acid vector or a replication-deficient, targeted adenovirus vector). The present invention also provides compositions of one or more of such immunogenic peptides and/or immunogenic peptide-encoding nucleic acids.

CD38BPs of the present invention include "neutralizing" CD38BPs, such as neutralizing antibodies. The terms "neutralizing" CD38BP" and "neutralizing antibody" refer to a CD38BP or an antibody that is capable of substantially inhibiting or eliminating a biological activity of a CD38-associated peptide. Typically, a neutralizing CD38BP, such as a neutralizing anti-CD38 antibody, may inhibit, directly or indirectly, the function of CD38, such as enzymatic activity, signal transduction, induction of cytokine expression, induction of proliferation or differentiation, or induction of lysis, in a degree that is about equal or greater than the inhibition of such cells due to administration of an approximately equal amount of -003 or -005 or -024.

A CD38BP of the present invention may have any suitable affinity and/or avidity for one or more epitopes contained at least partially in CD38. Affinity refers to the strength of binding of the CD38BP to such an epitope. Typically, affinity is measured by dissociation constant $K_d$, defined as [Ab]×[Ag]/[Ab–Ag] where [Ab–Ag] is the molar concentration of the antibody-antigen complex (or the CD38BP-antigen complex), [Ab] is the molar concentration of the unbound antibody (or CD38BP) and [Ag] is the molar concentration of the unbound antigen. The affinity constant $K_a$ is defined by $1/K_d$. Suitable methods for determining specificity and affinity by competitive inhibition can be found in for instance Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley InterScience N.Y., (1992, 1993) and Muller, Meth. Enzymol. 92, 589-601 (1983).

A CD38BP, and particularly anti-CD38 antibodies of the present invention may have an affinity for at least one epitope at least partially comprised in CD38 in the range of about $10^4$ to about $10^{10}$ M$^{-1}$. The term immunoreact herein typically refers to binding of a CD38BP to a CD38 epitope with a dissociation constant $K_d$ lower than about $10^{-4}$ M.

A CD38BP may have an affinity that is at least as great for CD38 as –003 and –005 and –024, and in some embodiments have an affinity that is at least about as great as –003 and –005 and –024. Affinity may be determined by any of the methods described elsewhere herein or their known equivalents in the art. An example of one method that may be used to determine affinity is provided in Scatchard analysis of Munson & Pollard, Anal. Biochem. 107, 220 (1980). Binding affinity also may be determined by equilibrium methods (for instance enzyme-linked immunoabsorbent assay (ELISA) or radioimmunoassay (RIA)) or kinetics analysis (for instance BIA-CORE™ analysis).

Typically, the disassociation constant for CD38BPs, such as anti-CD38 antibodies, of the present invention is less than about 100 nM, less than about 50 nM, less than about 10 nM, about 5 nM or less, about 1 nM or less, about 0.5 nM or less, about 0.1 nM or less, about 0.01 nM or less, or even about 0.001 nM or less.

CD38BPs, such as anti-CD38 antibodies, of the present invention may exhibit similar functional characteristics as –003 and –005 and –024, such as may be determined by antibody-dependent cellular cytotoxicity (ADCC) and complement-mediated cytotoxicity (CDC) assays (see for instance U.S. Pat. No. 5,500,362).

In one embodiment, a peptide according to the present invention does not act as an agonist of CD38, but as an antagonist of CD38. An agonist of CD38 is a molecule, which activates one or more of the functions ascribed to CD38. Such functions may include receptor mediation in adhesion and signaling events and (ecto-) enzymatic activity. Furthermore, as an ectoenzyme, CD38 uses NAD$^+$ as substrate for the formation of cyclic ADP-ribose (cADPR) and ADPR, but also of nicotinamide and nicotinic acid-adenine dinucleotide phosphate (NMDP). cADPR has been shown to act as second messenger for Ca$^{2+}$ mobilization from the endoplasmatic reticulum. In addition to signaling via Ca$^{2+}$, CD38 signaling occurs via cross-talk with antigen-receptor complexes on T and B cells or other types of receptor complexes, e.g. MHC molecules, and is in this way involved in several cellular responses, but also in switching and secretion of IgG1.

In one embodiment, a peptide according to the present invention does not induce significant proliferation of PBMCs. In one embodiment, a peptide according to the present invention does not induce release of significant IL-6 levels. In one embodiment, a peptide according to the present invention does not induce release of detectable IFN-γ levels. Such assays may be measured as described in Ausiello et al., Tissue antigens 56, 538-547 (2000).

Anti-CD38 antibodies of the present invention, as well as other CD38BPs of the present invention, may be prepared by recombinant expression in any suitable type of cells or animals.

Recombinant CD38BPs, such as recombinant antibodies, such as recombinant human antibodies, include CD38BPs, such as antibodies, such as human antibodies that are prepared, expressed, created or isolated by recombinant means, such as CD38BPs, such as antibodies, such as human antibodies expressed using a recombinant expression vector transfected into a host cell.

Recombinant antibodies, such as recombinant human antibodies also include antibodies isolated from a recombinant, combinatorial human antibody library, antibodies isolated from an animal, such as a transgenic animal, or antibodies prepared, expressed, created or isolated by any other means that involves splicing of human immunoglobulin-encoding nucleic acid sequences to other nucleic acid sequences exogenous to the human immunoglobulin-encoding nucleic acids and human immunoglobulin-encoding genes. Recombinant human antibodies typically have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and, thus, the amino acid sequences of the $V_H$ and $V_L$ regions of the recombinant antibodies may be sequences that, while derived from and related to human germline $V_H$ and $V_L$ sequences, may not naturally exist within the human antibody germline repertoire in vivo. Both types of human antibodies are provided by the present invention.

Suitable methods for recombinant protein production are known in the art, see for instance (Sambrook and Russell (eds.), Molecular cloning, third edition, 2001, Cold Spring Harbor Laboratory Press, Cold Spring Harbor, N.Y., USA.

Likewise, suitable methods for antibody production are known in the art and include those described in for instance Harlow et al., Antibodies: A Laboratory Manual, Cold Spring Harbor Laboratory Press, Cold Spring Harbor, N.Y., (1988), Harlow and Lane: Using Antibodies: A Laboratory Manual (Cold Spring Harbor Laboratory Press (1999)), U.S. Pat. No. 4,376,110 and Ausubel et al., eds., Current Protocols In Molecular Biology, Greene Publishing Assoc. and Wiley InterScience N.Y., (1987, 1992). Monoclonal antibodies may be made using the hybridoma method first described by Kohler et al., Nature 256, 495 (1975), or by other well-known, subsequently-developed methods (see, e.g., Goding, Monoclonal Antibodies: Principles and Practice, pp. 59-103 (Academic Press, 1986)). Hybridomas useful in the production of anti-CD38 antibodies of the present invention are also provided by the present invention. Such hybridomas may be formed by chemical fusion, electrical fusion, or any other suitable technique, with any suitable type of myeloma, heteromyeloma, phoblastoid cell, plasmacytoma or other equivalent thereof and any suitable type of antibody-expressing cell. Transformed immortalized B cells may also be used to efficiently produce antibodies of the present invention and are also provided by the present invention. Such cells may be produced by standard techniques, such as transformation with an Epstein Barr Virus, or a transforming gene. (See, e.g., "Continuously Proliferating Human Cell Lines Synthesizing Antibody of Predetermined Specificity," Zurawaki, V. R. et al., in Monoclonal Antibodies, ed. by Kennett R. H. et al., Plenum Press, N.Y. 1980, pp 19-33.). Thus, stable and continuous and/or immortalized anti-CD38 antibody expressing cells and cell lines are a feature of the present invention. Eukaryotic and prokaryotic cells (e.g., yeast cells, continuous and/or immortalized mammalian cell lines (e.g., lymphoid antibody-producing cell derived cell lines), plant cells, insect cells, and bacterial cells such as E. coli cells, etc.) comprising CD38BP-encoding or CD38BP-fragment-encoding nucleic acids are provided by the present invention. Transgenic animals, such as non-human primates, rodents (e.g., hamsters, guinea pigs, and rats—including modified strains thereof such as severe combined immunodeficient (SCID) mice and other immunocompromised animal strains), dogs, etc., expressing human anti-CD38 antibodies of the present invention also are provided by the present invention.

Recombinant cells comprising exogenous nucleic acids encoding CD38BPs may be prepared by any suitable technique (e.g., transfection/transformation with a naked DNA plasmid vector, viral vector, invasive bacterial cell vector or other whole cell vector, etc., comprising a CD38BP-encoding sequence (or sequences) delivered into the cell by calcium phosphate-precipitation facilitated transfection, receptor-mediated targeting and transfection, biolistic delivery, electroporation, dextran-mediated transfection, liposome-mediated transformation, protoplast fusion, direct microinjection, etc.). Methods of transforming/transfecting cells are well known in the art (see, e.g., Sambrook et al., Molecular Cloning: A Laboratory Manual, Cold Spring Harbor Laboratory Press (2d Edition, 1989 and 3rd Edition, 2001) and F. Ausubel et al., ed. Current Protocols in Molecular Biology, Greene Publishing and Wiley InterScience New York (1987). Such recombinant cells are a feature of the present invention.

Cell lines available as hosts for recombinant protein expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Other cell lines that may be used are insect cell lines, such as Sf9 cells. When nucleic acids (or nucleic acid-containing vectors) encoding proteins, such as CD38BPs (including anti-CD38 antibodies), are introduced into mammalian host cells, proteins, such as CD38BPs, may be produced by culturing the host cells for a period of time sufficient to allow for expression of the protein, such as a CD38BP, in the host cells or by secretion of the protein, such as a CD38BP, into the culture medium in which the host cells are grown. CD38BPs may be recovered from the culture medium using standard protein purification methods. CD38BPs may also be recovered from host cell lysates when directly expressed without a secretory signal.

CD38BPs, such as anti-CD38 antibodies, may also be produced in bacterial cells and eukaryotic unicellular microorganisms, such as yeast. Bacterial cell produced CD38BPs, such as anti-CD38 antibodies, typically lack normal glycosylation and bacterial cell produced anti-CD38 antibodies may thus be more or less deficient in terms of ADCC functions and other aspects of the immune response associated with anti-CD38 antibodies produced in mammalian cells and/or animals (e.g., the recruitment of NK cells). Yeast cell produced CD38BPs, such as anti-CD38 antibodies normally exhibit different types of glycosylation patterns than antibodies produced in mammalian cells. However, methods for producing antibodies with effective glycosylation in yeast are currently being developed by companies such as Glycofi, Inc. (Lebanon, N.H., USA). See also Wildt S et al., Nat Rev Microbiol. 3(2), 119-28 (2005).

When recombinant expression vectors encoding CD38BP genes (including anti-CD38 antibody genes) are introduced into mammalian host cells, the CD38BPs are produced by culturing the host cells for a period of time sufficient to allow for expression of the CD38BP in the host cells or for secretion of the antibody into the culture medium in which the host cells are grown. The purification of antibodies and other CD38BPs from cell cultures, cell lysates, and animals (e.g., from the ascites fluid of a transgenic animal producing anti-CD38 antibodies) may be achieved by application of any number of suitable techniques known in the art including, e.g., immunoaffinity column purification; sulfate precipitation; chromatofocusing; preparative SDS-PAGE, and the like.

Human monoclonal antibodies of the present invention may also be produced by a variety of other techniques, including conventional monoclonal antibody methodology, e.g., the standard somatic cell hybridization technique of Kohler and Milstein, Nature 256, 495 (1975). Other techniques for producing monoclonal antibody may also be employed, e.g. phage display techniques using libraries of human antibody genes. In one embodiment, anti-CD38 antibodies of the present invention produced by use of hybridomas generated in a murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

To generate fully human monoclonal antibodies to CD38, transgenic or transchromosomal mice containing human immunoglobulin genes (e.g., HCo12, HCo7 or KM mice) may be immunized with an enriched preparation of CD38 antigen and/or cells expressing CD38, as described, for example, by Lonberg et al., (1994), supra, Fishwild et al., (1996), supra, and WO 98/24884. Alternatively, mice may be immunized with DNA encoding human CD38. The mice may be 6-16 weeks of age upon the first infusion. For example, an enriched preparation (5-50 µg) of the CD38 antigen may be used to immunize the HuMAb mice intraperitoneally. In the event that immunizations using a purified or enriched preparation of the CD38 antigen do not result in antibodies, mice may also be immunized with cells expressing CD38, e.g., a cell line, to promote immune responses.

Cumulative experience with various antigens has shown that the HuMAb transgenic mice respond best when initially immunized intraperitoneally (i.p.) or subcutaneously (s.c.) with CD38 expressing cells in complete Freund's adjuvant, followed by every other week i.p. immunizations (up to a total of 10) with CD38 expressing cells in PBS. The immune response may be monitored over the course of the immunization protocol with plasma samples being obtained by retroorbital bleeds. The plasma may be screened by FACS analysis, and mice with sufficient titers of anti-CD38 human immunoglobulin may be used for fusions. Mice may be boosted intravenously with CD38 expressing cells for Examples 4 and 3 days before sacrifice and removal of the spleen.

To generate hybridomas producing human monoclonal antibodies to human CD38, splenocytes and lymph node cells from immunized mice may be isolated and fused to an appropriate immortalized cell line, such as a mouse myeloma cell line. The resulting hybridomas may then be screened for the production of antigen-specific antibodies. For example, single cell suspensions of splenic lymphocytes from immunized mice may be fused to SP2/0 nonsecreting mouse myeloma cells (ATCC, CRL 1581) with 50% PEG (w/v). Cells may be plated at approximately 1×105 per well in flat bottom microtiter plate, followed by a two week incubation in selective medium containing besides usual reagents 10% fetal Clone Serum, 5-10% origin hybridoma cloning factor (IGEN) and 1×HAT (Sigma). After approximately two weeks, cells may be cultured in medium in which the HAT is replaced with HT. Individual wells may then be screened by ELISA for human kappa-light chain containing antibodies and by FACS analysis using CD38 expressing cells for CD38 specificity. Once extensive hybridoma growth occurs, medium may be observed usually after 10-14 days. The antibody secreting hybridomas may be replated, screened again, and if still positive for human IgG, anti-CD38 monoclonal antibodies may be subcloned at least twice by limiting dilution. The stable subclones may then be cultured in vitro to generate antibody in tissue culture medium for characterization.

Human antibodies of the present invention may also be produced in a host cell transfectoma using, for example, a combination of recombinant DNA techniques and gene transfection methods as is well known in the art, see for instance Morrison, S., Science 229, 1202 (1985).

For example, to express the antibodies, or antibody fragments thereof, DNAs encoding partial or full-length light and heavy chains, may be obtained by standard molecular biology techniques (for instance PCR amplification, site directed mutagenesis) and may be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene may be inserted into separate vectors or, more typically, both genes are inserted into the same expression vector. The antibody genes may be inserted into the expression vector by standard methods (e.g., ligation of complementary restriction sites on the antibody gene fragment and vector, or blunt end ligation if no restriction sites are present). The light and heavy chain variable regions of the antibodies described herein may be used to create full-length antibody genes of any antibody isotype by inserting them into expression vectors already encoding heavy chain constant and light chain constant regions of the desired isotype such that the $V_H$ segment is operatively linked to the CH segment (s) within the vector and the $V_L$ segment is operatively linked to the CL segment within the vector. Additionally or alternatively, the recombinant expression vector may encode a signal peptide that facilitates secretion of the antibody chain from a host cell. The antibody chain gene may be cloned into the vector such that the signal peptide is linked in-frame to the amino terminus of the antibody chain gene. The signal peptide may be an immunoglobulin signal peptide or a heterologous signal peptide (i.e., a signal peptide from a non-immunoglobulin protein).

In addition to the antibody chain genes, the recombinant expression vectors of the present invention carry regulatory sequences that allows and control the expression of the antibody chain genes in a host cell.

In addition to the antibody chain genes and regulatory sequences, the recombinant expression vectors of the present invention may carry additional sequences, such as sequences that regulate replication of the vector in host cells (e.g., origins of replication) and selectable marker genes. The selectable marker gene facilitates selection of host cells into which the vector has been introduced (see for instance U.S. Pat. No. 4,399,216, U.S. Pat. No. 4,634,665 and U.S. Pat. No. 5,179,017). For example, typically the selectable marker gene confers resistance to drugs, such as G418, hygromycin or methotrexate, on a host cell into which the vector has been introduced. Examples of selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The host cells may be prokaryotic or eukaryotic, such as mammalian, host cells. For instance antigen binding fragments may be expressed in prokaryotic host cells and full-length antibodies may be expressed in eukaryotic host cells.

In one embodiment the antibodies are expressed in eukaryotic cells, such as mammalian host cells. Examples of mammalian host cells for expressing the recombinant antibodies of the present invention include CHO cells (including dhfr-CHO cells, described in Urlaub and Chasin, PNAS USA 77, 4216-4220 (1980), used with a DHFR selectable marker, for instance as described in R. J. Kaufman and P. A. Sharp, Mol. Biol. 159, 601-621 (1982)), NS/0 myeloma cells, COS cells, HEK293 cells and SP2.0 cells. In particular for use with NS/0 myeloma cells, another example of a expression system is the GS (glutamine synthetase) gene expression system disclosed in WO87/04462, WO89/01036 and EP338 841.

The CD38BP genes may be expressed in other expression systems, including prokaryotic cells, such as microorganisms, e.g. *E. coli* for the production of scFv antibodies, algi, as well as insect cells. Furthermore, the CD38BPs may be produced in transgenic non-human animals, such as in milk from sheep and rabbits or eggs from hens, or in transgenic plants. See for instance Verma, R. et al., J. Immunol. Meth. 216, 165-181 (1998), Pollock et al., J. Immunol. Meth. 231, 147-157 (1999) and Fischer, R. et al., Biol. Chem. 380, 825-839 (1999).

Bispecific and multispecific CD38BPs of the present invention may be made using chemical techniques (see for instance D. M. Kranz et al., PNAS USA 78, 5807 (1981)), "polydoma" techniques (See U.S. Pat. No. 4,474,893) or recombinant DNA techniques.

Bispecific antibodies of the present invention may be produced by a variety of known methods including fusion of hybridomas or linking of Fab' fragments (see for instance Songsivilai & Lachmann, Clin. Exp. Immunol. 79, 315-321 (1990) and Kostelny et al., J. Immunol. 148, 1547-1553 (1992)). Traditionally, the recombinant production of bispecific antibodies is based on the co-expression of two immunoglobulin heavy chain-light chain pairs, where the two heavy chains have different specificities (see for instance Milstein and Cuello, Nature 305, 537 (1983)). Because of the random assortment of immunoglobulin heavy and light chains, these hybridomas (quadromas) produce a potential mixture of 10 different antibody molecules, of which only one has the correct bispecific structure. Similar procedures are disclosed in WO 93/08829 and Traunecker et al., EMBO J. 10, 3655 (1991).

According to a different approach, antibody variable domains with the desired binding specificities (antibody-antigen combining sites) are fused to immunoglobulin constant domain sequences by recombinant or synthetic methods. The variable domain sequence is typically fused to an immunoglobulin heavy chain constant domain, comprising at least part of the hinge, $C_H2$, and $C_H3$ regions. Also typically, a first heavy-chain constant region ($C_H1$), containing the site necessary for light chain binding, also is present in at least one of the fusion peptides. In a more specific example of this type of approach, a bispecific antibody is produced comprising a hybrid immunoglobulin heavy chain with a first binding specificity in one arm, and a hybrid immunoglobulin heavy chain-light chain pair (providing a second binding specificity) in the other arm. Such an asymmetric structure can facilitate the separation of the desired bispecific compound from unwanted immunoglobulin chain combinations (such an approach is described in WO 94/04690). For further details of generating bispecific antibodies see, for example, Suresh et al., Methods in Enzymology 121, 210 (1986).

In another approach, the interface between a pair of antibody molecules may be engineered to maximize the percentage of heterodimers that are recovered from recombinant cell culture so as to form a population of bispecific antibody molecules. Typically, such an interface comprises at least a part of the $C_H3$ domain of an antibody constant region. Normally in such a method, one or more amino acid residues with smaller side chains from the interface of the first antibody molecule are replaced with amino acid residues with larger side chains (such as tyrosine or tryptophan). Compensatory "cavities" of identical or similar size to the large side chain amino acid residue(s) are created on the interface of the second antibody molecule by replacing large amino acid side chain residues with smaller ones (such as alanine or threonine). This may provide a mechanism for increasing the yield of the heterodimer over other unwanted end-products such as homodimers.

Bispecific and multispecific molecules of the present invention may be prepared by conjugating the constituent binding specificities, e.g., the anti-FcR and anti-CD38 binding specificities, using methods known in the art. For example, each binding specificity of the bispecific and multispecific molecule may be generated separately and then conjugated to one another. When the binding specificities are proteins or peptides, a variety of coupling or cross-linking agents may be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedi-maleimide (oPDM), N-succinimidyl-3-(2-pyridyldithio)propionate (SPDP) and sulfosuccin-imidyl 4-(N-maleimidomethyl)cyclohexane-1-carboxylate (sulfo-SMCC), see for instance Karpovsky et al., J. Exp. Med. 160, 1686 (1984), Liu, M. A. et al., PNAS USA 82, 8648 (1985). In another example, Brennan et al., Science 229, 81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated may then converted to thionitrobenzoate (TNB) derivatives. One of the Fab'-TNB derivatives may then be reconverted to the Fab'-thiol by reduction with mercaptoethylamine and mixed with an equimolar amount of the other Fab'-TNB derivative to form a bispecific antibody. Shalaby et al., J. Exp. Med. 175, 217-225 (1992) describes the production of a fully humanized bispecific antibody $F(ab')_2$ molecule, according to a related technique. Other methods include those described by Paulus (Behring Ins. Mitt. No. 78, 118-132 (1985)) and Glennie et al., J. Immunol. 139, 2367-2375 (1987). Examples of conjugating agents are SATA and sulfo-SMCC, both available from Pierce Chemical Co. (Rockford, Ill.).

When the binding specificities are antibodies, they may be conjugated via sulfhydryl bonding of the C-terminus hinge regions of the two heavy chains. In one embodiment, the hinge region is modified to contain an odd number of sulfhydryl residues, for instance one, prior to conjugation.

Alternatively, both binding specificities may be encoded in the same vector and expressed and assembled in the same host cell. This method is particularly useful where the bispecific and multispecific molecule is a mAb×mAb, mAb×Fab, Fab×F(ab')$_2$ or ligand×Fab fusion protein. A bispecific and multispecific molecule of the present invention, e.g., a bispecific molecule may be a single chain molecule, such as a single chain bispecific antibody, a single chain bispecific molecule comprising one single chain antibody and a binding determinant, or a single chain bispecific molecule comprising two binding determinants. Bispecific and multispecific molecules may also be single chain molecules or may comprise at least two single chain molecules. Methods for preparing bi- and multispecific molecules are described for example in U.S. Pat. No. 5,260,203, U.S. Pat. No. 5,455,030, U.S. Pat. No. 4,881,175, U.S. Pat. No. 5,132,405, U.S. Pat. No. 5,091,513, U.S. Pat. No. 5,476,786, U.S. Pat. No. 5,013,653, U.S. Pat. No. 5,258,498 and U.S. Pat. No. 5,482,858.

Various techniques for making and isolating bispecific antibody fragments directly from recombinant cell culture have also been described. For example, bispecific antibodies have been produced using leucine zippers (see for instance Kostelny et al., J. Immunol. 148(5), 1547-1553 (1992)). Leucine zipper peptides from the Fos and Jun proteins can be linked to the Fab' portions of two different antibodies by gene fusion and the resulting antibody homodimers reduced at the hinge region to form monomers that can be re-oxidized to form the antibody heterodimers. The "diabody" technology described by Hollinger et al., PNAS USA 90, 6444-6448 (1993) also has provided an alternative mechanism for making bispecific antibody fragments. Another strategy for making bispecific antibody fragments by the use of single-chain Fv (sFv) dimers has also been reported. See for instance Gruber et al., J. Immunol. 152, 5368 (1994).

In addition, bispecific antibodies may be formed as "diabodies" (Holliger et al., PNAS USA, 90, 6444-6448 (1993)) or "Janusins" (Traunecker et al., EMBO J. 10, 3655-3659 (1991) and Traunecker et al., Int J Cancer Suppl 7, 51-52 (1992)). Bispecific antibodies, by definition, do not exist in the form of fragments having a single binding site (e.g., Fab, Fab', and Fv fragments, which also are provided by the present invention).

Binding of the bispecific and multispecific molecules to their specific targets may be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes may be detected using e.g., an enzyme-linked antibody or antibody fragment which recognizes and specifically binds to the antibody-FcR complexes. Alternatively, the complexes may be detected using any of a variety of other immunoassays. For example, the antibody may be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope may be detected by such means as the use of a γ counter or a scintillation counter or by autoradiography.

As stated earlier, antibodies interact with target antigens primarily through amino acid residues that are located in the six heavy and light chain complementarity determining regions (CDRs). The present invention provides antibodies having CDR regions identical to or otherwise derived from the CDR regions of −003 or −005 or −024. Such antibodies may be generated by constructing expression vectors that include CDR sequences from −003 or −005 or −024 grafted onto framework sequences from a different antibody with different properties.

Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. For this reason, it is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences may be combined with synthetic oligonucleotides by ligation or PCR amplification. Alternatively, the entire variable region may be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, J. Biol. Chem. 266, 19867-19870 (1991); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides may be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site of the gamma heavy chain) in the PCR amplification to generate fragments that can easily be cloned into the expression vector constructs.

The reconstructed heavy and light chain variable regions are then combined with cloned promoter, leader, translation initiation, constant region, 3' untranslated, polyadenylation, and transcription termination, sequences to form expression vector constructs. The heavy and light chain expression constructs may be combined into a single vector, co-transfected, serially transfected, or separately transfected into host cells which are then fused to form a host cell expressing both chains.

A similar procedure may be followed to graft novel antigen-specificity into an existing mature antibody. Typically, an acceptor antibody is chosen which originates from the same variable germ-line gene as the CDR-donor antibody, but other acceptor antibodies may also be chosen. One or more CDRs from the donor antibody are then transferred using the techniques described above.

In one embodiment of the present invention, the structural features of –003 and –005 and –024 are used to create structurally related anti-CD38 antibodies, for instance human anti-CD38 antibodies, that retain at least one functional property of –003 and –005 and –024, namely binding to CD38. More specifically, one or more CDR regions of –003 or –005 and –024 may be combined recombinantly with known human framework regions and CDRs to create additional, recombinantly-engineered, human anti-CD38 antibodies of the present invention.

Exemplary plasmids for use in construction of expression vectors for human IgGκ are described below. The plasmids were constructed so that PCR amplified V kappa heavy and V kappa light chain cDNA sequences could be used to reconstruct complete heavy and light chain minigenes. These plasmids may be used to express completely human IgG1,κ or IgG4,κ antibodies. Similar plasmids may be constructed for expression of other heavy chain isotypes, or for expression of antibodies comprising lambda light chains.

CD38BPs of the present invention, such as human anti-CD38 antibodies of the present invention, may be isolated and characterized in a number of different ways. For example, selected hybridomas may be grown in suitable flasks for monoclonal antibody purification. Supernatants may then be filtered and concentrated before affinity chromatography with protein A-sepharose (for IgG1 isotype antibodies) (Pharmacia, Piscataway, N.J.) or anti-human IgG coated sepharose or protein G-sepharose in case of IgG3 isotype antibodies. Eluted IgG may be checked by gel electrophoresis and high performance liquid chromatography to ensure purity. The buffer solution may be exchanged into PBS, and the concentration may be determined by $OD_{280}$ using 1.43 extinction coefficient. The monoclonal antibodies may be aliquoted and stored at –80° C.

To determine if the selected CD38BPs, such as human anti-CD38 monoclonal antibodies, bind to unique epitopes, site-directed or multi-site directed mutagenesis may be used.

To determine the isotype of purified antibodies, isotype ELISAs may be performed. Wells of microtiter plates may be coated with 10 µg/ml of anti-human Ig overnight at 4° C. After blocking with 5% BSA (bovine serum albumin), the plates are reacted with 10 µg/ml of monoclonal antibodies or purified isotype controls, at ambient temperature for two hours. The wells may then be reacted with either human IgG1, IgG2, IgG3 or IgG4, IgE, IgA1, IgA2, or human IgM-specific alkaline phosphatase-conjugated probes. After washing, the plates are developed with pNPP substrate (1 mg/ml) and analyzed by OD at 405 nm.

In order to demonstrate the presence of anti-CD38 antibodies in sera of immunized mice or the binding of CD38BPs (including anti-CD38 antibodies) to live cells expressing the CD38, flow cytometry may be used. Briefly, cell lines expressing CD38 (grown under standard growth conditions) are mixed with various concentrations of CD38BP in PBS containing 0.1% BSA and 0.02% sodium-azide, and incubated at 4° C. for 30 minutes. After washing, the cells are reacted with fluorescein-labeled anti-human IgG antibody under the same conditions as the primary antibody staining. The samples may be analyzed by flow cytometry with a flow cytometer (e.g., Becton Dickinson FACS instrument) using light and side scatter properties to gate on single, living cells. An alternative assay using fluorescence microscopy may be used (in addition to or instead of the flow cytometry assay. Cells may be stained exactly as described above and examined by fluorescence microscopy. This method allows visualization of individual cells, but may have diminished sensitivity depending on the density of the antigen.

CD38BPs, such as anti-CD38 human IgGs, may be further tested for reactivity with CD38 antigen by Western blotting. Briefly, cell extracts from cells expressing CD38 may be prepared and subjected to sodium dodecyl sulfate (SDS) polyacrylamide gel electrophoresis. After electrophoresis, the separated antigens will be transferred to nitrocellulose membranes, blocked with 20% non-fat milk, and probed with the CD38BPs to be tested. Human IgG binding may be detected using anti-human IgG alkaline phosphatase and developed with BCIP/NBT substrate tablets (Sigma Chem. Co., St. Louis, Mo.), but detecting agents directed at other specific portions of the CD38BP may also be used.

In addition to binding specifically to CD38, CD38BPs (including human anti-CD38 antibodies) may be tested for their ability to inhibit various activities of cells expressing CD38, such as but not restricted to insulin production, $Ca^{2+}$ release, cytokine production, lysis induction, differentiation, and proliferation.

In one embodiment, the present invention provides transgenic and transchromosomal nonhuman animals, such as transgenic or transchromosomal mice, which are capable of expressing human antibodies that specifically bind to CD38. In a particular embodiment, the present invention provides a transgenic or transchromosomal mouse having a genome comprising a human heavy chain transgene, such that the mouse produces human anti-CD38 antibodies when immunized with cells expressing CD38. The human heavy chain transgene may be integrated into the chromosomal DNA of the mouse, as is the case for transgenic, e.g., HuMAb mice, as described in detail herein. Alternatively, the human heavy chain transgene may be maintained extrachromosomally, as is the case for transchromosomal (e.g., KM) mice as described in WO 02/43478. Such transgenic and transchromosomal animals are capable of producing multiple isotypes of human monoclonal antibodies to CD38 (e.g., IgG, IgA and/or IgE) by undergoing V-D-J/V-J recombination and isotype switching. The design of a transgenic or transchromosomal nonhuman animal that responds to foreign antigen stimulation with a heterologous antibody repertoire, requires that the heterologous immunoglobulin transgenes contained within the transgenic animal function correctly throughout the pathway of B cell development. This includes, for example, isotype switching of the heterologous heavy chain transgene. Accordingly, transgenes are constructed so that isotype switching may be induced and one or more of the following characteristics of antibody genes: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology,* 2nd edition (1989), Paul William E., ed. Raven Press, N.Y.

In certain embodiments, the transgenic or transchromosomal nonhuman animals used to generate the human monoclonal antibodies of the present invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al., Nucl. Acids Res. 15, 7305-7316 (1991) Sideras et al., Intl. Immunol. 1, 631-642 (1989)). For each of the foregoing transgenic animals, functionally rearranged heterologous heavy and light chain immunoglobulin transgenes are found in a significant fraction of the B cells of the transgenic animal (at least 10%).

The transgenes used to generate the transgenic nonhuman animals of the present invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic animal in that they are derived from, or correspond to, DNA encoding immunoglobulin heavy and light chain gene segments from a species not consisting of the transgenic nonhuman animal. In one embodiment of the present invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and may support incorporation of all or a portion of a D region gene segment in the resultant rearranged immunoglobulin heavy chain within the transgenic animal when exposed to CD38 antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the nonhuman animal used in the present invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

Examples of transgenic and transchromosomal nonhuman animals, such as mice, will exhibit immunoglobulin production with a significant repertoire, ideally substantially similar to that of a human after adjusting for volume.

The repertoire will ideally approximate that shown in a human when adjusted for volume, usually with a diversity at least about 10% as great, such as 25 to 50% or more. Generally, at least about a thousand different immunoglobulins (ideally IgG), such as $10^4$ to $10^6$ or more, will be produced, depending on the number of different V, J and D regions introduced into the mouse genome and driven by the additional diversity generated by V(-D-)J gene segment rearrangements and random nucleotide additions at the joining regions. Typically, the Immunoglobulins will exhibit an affinity ($K_D$) for preselected antigens of below $10^{-8}$ M, such as of below $10^{-9}$ M, $10^{-10}$ M or $10^{-11}$ M or even lower. Transgenic and transchromosomal nonhuman animals, e.g., mice, as described above, may be immunized with, for example, cells expressing CD38. Alternatively, the transgenic animals may be immunized with DNA encoding human CD38. The animals will then produce B cells which undergo class-switching via switch recombination (cis-switching) and express immunoglobulins reactive with CD38. The immunoglobulins will be human antibodies (also referred to as "human sequence antibodies"), wherein the heavy and light chain polypeptides are encoded by human transgene sequences, which may include sequences derived by somatic mutation and V region recombinatorial joints, as well as germline-encoded sequences; these human antibodies may be referred to as being substantially identical to a polypeptide sequence encoded by a human $V_L$ and $J_L$ or $V_H$, $D_H$ and $J_H$ gene segments, even though other non-germline sequences may be present as a result of somatic mutation and differential V-J and V-D-J recombination joints. The variable regions of each antibody chain are typically at least 80 percent similar to human germine V, and J gene segments, and, in the case of heavy chains, human germline V, D, and J gene segments; frequently at least 85 percent similar to human germline sequences present on the transgene; often 90 or 95 percent or more similar to human germline sequences present on the transgene. However, since non-germline sequences are introduced by somatic mutation and VJ and VDJ joining, the human sequence antibodies will frequently have some variable region sequences which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

The present invention also provides B cells derived from transgenic or transchromosomal nonhuman animals as described herein. The B cells may be used to generate hybridomas expressing human monoclonal antibodies which bind with high affinity (for instance with a dissociation equilibrium constant ($K_D$) of lower than $10^{-8}$ M) to human CD38. Thus, in one embodiment, the present invention provides a hybridoma which produces a human antibody having an affinity ($K_D$) of below $10^{-8}$ M, such as of below $10^{-9}$ M, $10^{-10}$ M or $10^{-11}$ M or even lower when determined by scatchard analysis of CD38 expressing cells using a radio-actively labeled monoclonal antibody or by determination of the half-maximal binding concentration using FACS analysis, or by analysis using surface plasmon resonance as measured on a BIAcore instrument.

The present invention provides an anti-CD38 antibody comprising a human sequence light chain composed of (1) a light chain variable region having a polypeptide sequence which is substantially identical to a polypeptide sequence encoded by a human $V_L$ gene segment and a human $J_L$ segment, and (2) a light chain constant region encoded by a human $C_L$ gene segment; and a human sequence heavy chain composed of a (1) a heavy chain variable region having a polypeptide sequence which is substantially identical to a polypeptide sequence encoded by a human $V_H$ gene segment, a D region, and a human $J_H$ segment, and (2) a constant region encoded by a human $C_H$ gene segment. It should be noted that human D genes may be substantially altered by recombination and somatic mutation events such that the original human germ-line sequence may not be readily recognized.

The development of high affinity human monoclonal antibodies against CD38 can be facilitated by a method for expanding the repertoire of human variable region gene segments in a transgenic nonhuman animal having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome (YAC) comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic animal produced by the V repertoire expansion method, wherein the animal expresses an immunoglobulin chain comprising a variable region sequence encoded by a V region gene segment present on the V region transgene and a C region encoded on the human Ig transgene. By means of the V repertoire expansion method, transgenic animals having at least 5 distinct V genes can be generated; as can animals containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a nonhuman animal germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast is no longer necessary (i.e., prior to introduction into a mouse ES cell or mouse prozygote). Methods of propagating the trait of human sequence immunoglobulin expression, include breeding a transgenic animal having the human Ig transgene(s), and optionally also having a functional YAC having an expanded V segment repertoire. Both $V_H$ and $V_L$ gene segments may be present on the YAC. The transgenic animal may be bred into any background desired by the practitioner, including backgrounds harboring other human transgenes, including human Ig transgenes and/or transgenes encoding other human lymphocyte proteins. The present invention also provides a high affinity human sequence immunoglobulin produced by a transgenic mouse having an expanded V region repertoire YAC transgene. Although the foregoing describes a specific embodiment of the transgenic animal of the present invention, other embodiments are contemplated which have been classified in three categories:

I. Transgenic animals containing an unrearranged heavy and rearranged light chain immunoglobulin transgene;
II. Transgenic animals containing an unrearranged heavy and unrearranged light chain immunoglobulin transgene; and
III. Transgenic animal containing rearranged heavy and an unrearranged light chain immunoglobulin transgene.

In one embodiment, the present invention provides a pharmaceutical composition comprising a therapeutically effective amount of a CD38BP of the present invention. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) on antigen binding.

A pharmaceutical composition of the present inventions may also include diluents, fillers, salts, buffers, detergents (e.g., a nonionic detergent, such as Tween-80), stabilizers, stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and can be selected by those of ordinary skill in the art.

The compounds of the present invention may be administered via any suitable route, such as an oral, nasal, inhalable, topical (including buccal, transdermal and sublingual), rectal, vaginal and/or parenteral route In one embodiment, a pharmaceutical composition of the present invention is administered orally, for example, with an inert diluent or an assimilable edible carrier. The active ingredient may be enclosed in a hard or soft shell gelatin capsule, compressed into tablets, or incorporated directly into the subject's diet. Pharmaceutical compositions of the present invention which are suitable for oral administration include ingestible tablets, buccal tablets, troches, capsules, elixirs, suspensions, syrups, wafers, and the like containing such carriers as are known in the art to be appropriate. To administer a compound of the present invention oral administration, it may be necessary to coat the compound with, or co-administer the compound with, a material to prevent its inactivation.

In one embodiment, a pharmaceutical composition of the present invention is administered nasally. Pharmaceutical compositions of the present invention which are suitable for nasal administration are known in the art and typically include sprays, nose drops and inhalants.

In one embodiment, a pharmaceutical composition of the present invention is administered topically. Pharmaceutical compositions of the present invention which are suitable for topical or transdermal administration include powders, sprays, ointments, pastes, creams, lotions, gels, solutions, patches and inhalants containing such carriers as are known in the art to be appropriate.

In one embodiment, a pharmaceutical composition of the present invention is administered rectally. Pharmaceutical compositions of the present invention which are suitable for rectal administration are known in the art and include gels, pastes, spray formulations, suppositories.

In one embodiment, a pharmaceutical composition of the present invention is administered vaginally. Pharmaceutical compositions of the present invention which are suitable for vaginal administration include pessaries, tampons, creams, gels, pastes, foams or spray formulations containing such carriers as are known in the art to be appropriate.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

In one embodiment the compounds of the present invention are administered in crystalline form by subcutaneous injection, cf. Yang et al., PNAS USA 100(12), 6934-6939 (2003).

The pharmaceutical compositions may be administered with medical devices known in the art. For example, in one embodiment, a pharmaceutical composition of the present invention may be administered with a needleless hypodermic injection device, such as the devices disclosed in U.S. Pat. No. 5,399,163, U.S. Pat. No. 5,383,851, U.S. Pat. No. 5,312,335, U.S. Pat. No. 5,064,413, U.S. Pat. No. 4,941,880, U.S. Pat. No. 4,790,824, or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

Pharmaceutical compositions of the present invention may be formulated for particular routes of administration, such as oral, nasal, topical (including buccal, transdermal and sublingual), rectal, vaginal and/or parenteral administration. The pharmaceutical compositions may conveniently be presented in unit dosage form and may be prepared by any methods known in the art of pharmacy. The amount of active ingredient which may be combined with a carrier material to produce a single dosage form will vary depending upon the subject being treated, and the particular mode of administration. The amount of active ingredient which may be combined with a carrier material to produce a single dosage form will generally be that amount of the composition which produces a therapeutic effect. Generally, out of one hundred percent, this amount will range from about 0.01% to about 99% of active ingredient, such as from about 0.1% to about 70%, for instance from about 1% to about 30%.

Regardless of the route of administration selected, the compounds of the present invention, which may be used in the form of a pharmaceutically acceptable salt or in a suitable hydrated form, and/or the pharmaceutical compositions of the present invention, are formulated into pharmaceutically acceptable dosage forms by conventional methods known to those of skill in the art. A "pharmaceutically acceptable salt" refers to a salt that retains the desired biological activity of the parent compound and does not impart any undesired toxicological effects (see for instance Berge, S. M. et al., J. Pharm. Sci. 66, 1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous acids and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols such as mannitol, sorbitol, glycerol or sodium chloride in the compositions Pharmaceutically acceptable diluents include saline and aqueous buffer solutions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. Compounds of the present invention may for instance be admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. Other examples of adjuvants are QS21, GM-CSF, SRL-172, histamine dihydrochloride, thymocartin, Tio-TEPA, monophosphoryl-lipid A/micobacteria compositions, alum, incomplete Freund's adjuvant, montanide ISA, ribi adjuvant system, TiterMax adjuvant, syntex adjuvant formulations, immune-stimulating complexes (ISCOMs), gerbu adjuvant, CpG oligodeoxynucleotides, lipopolysaccharide, and polyinosinic:polycytidylic acid.

Prevention of presence of microorganisms may be ensured both by sterilization procedures and by the inclusion of various antibacterial and antifungal agents, for example, paraben, chlorobutanol, phenol, sorbic acid, and the like. In addition, prolonged absorption of the injectable pharmaceutical form may be brought about by the inclusion of agents which delay absorption such as aluminum monostearate and gelatin.

Pharmaceutical compositions of the present invention comprising a compound of the present invention may also include a suitable salt therefor. Any suitable salt, such as an alkaline earth metal salt in any suitable form (e.g., a buffer salt), may be used in the stabilization of the compound of the present invention. Suitable salts typically include sodium chloride, sodium succinate, sodium sulfate, potassium chloride, magnesium chloride, magnesium sulfate, and calcium chloride. In one embodiment, an aluminum salt is used to stabilize a compound of the present invention in a pharmaceutical composition of the present invention, which aluminum salt also may serve as an adjuvant when such a composition is administered to a patient.

Pharmaceutical compositions according to the present invention may be in a variety of suitable forms. Such forms include, for example, liquid, semi-solid and solid dosage forms, such as liquid solutions (e.g., injectable and infusible solutions), dispersions or suspensions, emulsions, microemulsions, gels, creams, granules, powders, tablets, pills, powders, liposomes, dendrimers and other nanoparticles (see for instance Baek et al., Methods Enzymol. 362, 240-9 (2003), Nigavekar et al., Pharm Res. 21(3), 476-83 (2004), microparticles, and suppositories.

The optima form depends on the chosen mode of administration, the nature of the composition, and the therapeutic application. Formulations may include, for instance, powders, pastes, ointments, jellies, waxes, oils, lipids, lipid (cationic or anionic) containing vesicles, DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing may be appropriate in treatments and therapies in accordance with the present invention, provided that the active ingredient in the pharmaceutical composition is not inactivated by the formulation and the formulation is physiologically compatible and tolerable with the route of administration. See also for instance Powell et al., "Compendium of excipients for parenteral formulations" PDA J Pharm Sci Technol. 52, 238-311 (1998) and the citations therein for additional information related to excipients and carriers well known to pharmaceutical chemists.

The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl disteatrate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

To administer compositions of the present invention by certain routes of administration, it may be necessary to coat the compound with, or co-administer the compound with, a material to prevent its inactivation. For example, the compound of the present invention may be administered to a subject in an appropriate carrier, for example, liposomes, or a diluent. Liposomes include water-in-oil-in-water CGF emulsions as well as conventional liposomes (Strejan et al., J. Neuroimmunol. 7, 27 (1984)).

Depending on the route of administration, the active compound may be coated in a material to protect the compound from the action of acids and other natural conditions that may inactivate the compound. For example, the compound may be administered to a subject in an appropriate carrier, for example, liposomes. Liposomes include water-in-oil-in-water CGF emulsions as well as conventional liposomes (Strejan et al., J. Neuroimmunol. 7, 27 (1984)).

In one embodiment, the compounds of the present invention may be formulated to ensure proper distribution in vivo. For example, the blood-brain barrier (BBB) excludes many highly hydrophilic compounds. To ensure that the therapeutic compounds of the present invention cross the BBB (if desired), they may be formulated, for example, in liposomes. For methods of manufacturing liposomes, see for instance U.S. Pat. No. 4,522,811, U.S. Pat. No. 5,374,548 and U.S. Pat. No. 5,399,331. The liposomes may comprise one or more moieties which are selectively transported into specific cells or organs, thus enhance targeted drug delivery (see for instance V.V. Ranade J. Clin. Pharmacol. 29, 685 (1989)). Exemplary targeting moieties include folate or biotin (see for instance U.S. Pat. No. 5,416,016), mannosides (Umezawa et al., Biochem. Biophys. Res. Commun. 153, 1038 (1988)), antibodies (P. G. Bloeman et al., FEBS Lett. 357, 140 (1995), M. Owais et al., Antimicrob. Agents Chemother. 39, 180 (1995)), surfactant protein A receptor (Briscoe et al., Am. J. Physiol. 1233, 134 (1995)), different species of which may comprise the pharmaceutical compositions of the present inventions, as well as components of the invented molecules, p120 (Schreier et al., J. Biol. Chem. 269, 9090 (1994)), see also K. Keinanen, M. L. Laukkanen, FEBS Lett. 346, 123 (1994) and J. J. Killion, I. J. Fidler, Immunomethods 4, 273 (1994).

In one embodiment of the present invention, the compounds of the present invention are formulated in liposomes. In a further embodiment, the liposomes include a targeting moiety. In a further embodiment, the compounds in the liposomes are delivered by bolus injection to a site proximal to the desired area, e.g., the site of inflammation or infection, or the site of a tumor. The composition must be fluid to the extent that easy syringability exists. It must be stable under the conditions of manufacture and storage and must be preserved against the contaminating action of microorganisms such as bacteria and fungi.

In one embodiment, the compounds of the present invention may be formulated to prevent or reduce their transport across the placenta. This may be done by methods known in the art, e.g., by PEGylation of the compounds or by use of F(ab')$_2$ fragments. Further references can be made to Cunningham-Rundles C et al., J Immunol Methods. 152, 177-190 (1992) and to Landor M., Ann Allergy Asthma Immunol 74, 279-283 (1995).

Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The pharmaceutical composition of the present invention may contain one compound of the present invention or a combination of compounds of the present invention. Thus, in one embodiment, a pharmaceutical composition of the present invention includes a combination of multiple (e.g., two or more) compounds of the present invention which act by different mechanisms, e.g., one compound which predominately acts by inducing CDC in combination with another compound which predominately acts by inducing apoptosis.

The CD38BPs (including anti-CD38 antibodies, immunoconjugates, bispecific/multispecific molecules, compositions and other derivatives described herein) of the present invention have numerous in vitro and in vivo diagnostic and therapeutic utilities involving the diagnosis and treatment of disorders involving cells expressing CD38. For example, the antibodies may be administered to cells in culture, e.g., in vitro or ex vivo, or to human subjects, e.g., in vivo, to treat, prevent and to diagnose a variety of disorders. As used herein, the term "subject" is intended to include human and non-human animals which respond to the CD38BP. Subjects may for instance include human patients having disorders that may be corrected or ameliorated by inhibiting CD38 function, such as enzymatic activity, signal transduction, induction of cytokine expression, induction of proliferation or differentiation, and/or induction of lysis and/or eliminating/reducing the number of CD38 expressing cells.

For example, the CD38BPs may be used to elicit in vivo or in vitro one or more of the following biological activities: inhibition CD38 function (such as enzymatic activity, signal transduction, induction of cytokine expression, induction of proliferation or differentiation, and/or induction of lysis), killing a cell expressing CD38, mediating phagocytosis or ADCC of a cell expressing CD38 in the presence of human effector cells, and by mediating CDC of a cell expressing CD38 in the presence of complement or by killing CD38 expressing cells by apoptosis.

Any composition comprising CD38BPs of the present invention having complement binding sites, such as portions from IgG1, -2, or -3 or IgM which bind complement, may also be used in the presence of complement. In one embodiment, ex vivo treatment of a population of cells comprising target cells with a CD38BP of the present invention and appropriate effector cells may be supplemented by the addition of complement or serum containing complement. Phagocytosis or lysis of target cells coated with a CD38BP of the present invention may be improved by binding of complement proteins. In one embodiment target cells coated with the CD38BPs of the present invention may also be lysed by complement. In one embodiment, the CD38BPs of the present invention do not activate complement.

The CD38BPs of the present invention may also be administered together with complement. Accordingly, within the scope of the present invention are compositions comprising CD38BPs with serum or complement. In these compositions the complement is located in close proximity to the CD38BPs, for instance by conjugation or may be suited for simultaneous administration. Alternatively, the CD38BPs and the complement or serum may be administered separately.

The CD38BPs of the present invention may also be used to target cells expressing FcγR or CD38, for example for labeling such cells. For such use, the CD38BP may be linked to a molecule that can be detected. Thus, the present invention provides methods for localizing ex vivo or in vitro cells expressing Fc receptors, such as FcγR, or CD38. The detectable label may be, e.g., a radioisotope, a fluorescent compound, an enzyme, or an enzyme co-factor.

Target-specific effector cells, e.g., effector cells linked to a CD38BP of the present invention may also be used as therapeutic agents. Effector cells for targeting may be human leukocytes such as macrophages, neutrophils or monocytes. Other cells include eosinophils, natural killer cells and other IgG- or IgA-receptor bearing cells. If desired, effector cells may be obtained from the subject to be treated. The target-specific effector cells, may be administered as a suspension of cells in a physiologically acceptable solution. The number of cells administered may be in the order of $10^8$ to $10^9$ but will vary depending on the therapeutic purpose. In general, the amount will be sufficient to obtain localization at the target cell, e.g., a tumor cell expressing CD38, and to effectively kill the cell by, e.g., phagocytosis or lysis.

Therapy with target-specific effector cells may be performed in conjunction with other techniques for removal of targeted cells. For example, anti-tumor therapy using the CD38BPs of the present invention and/or effector cells armed with these compositions may be used in conjunction with chemotherapy. Additionally, combination immunotherapy may be used to direct two distinct cytotoxic effector populations toward tumor cell rejection. For example, CD38BP linked to anti-FcγRI or anti-CD3 may be used in conjunction with IgG- or IgA-receptor specific binding agents. Bispecific and multispecific molecules of the present invention may also be used to modulate FcαR or FcγR levels on effector cells, such as by capping and elimination of receptors on the cell surface. Mixtures of anti-Fc receptors may also be used for this purpose.

In one embodiment, the present invention provides methods for detecting the presence of CD38 antigen in a sample, or measuring the amount of CD38 antigen, comprising contacting the sample, and a control sample, with a CD38BP which specifically binds to CD38, under conditions that allow for formation of a complex between the CD38BP or portion thereof and CD38. The formation of a complex is then detected, wherein a difference complex formation between the sample compared to the control sample is indicative the presence of CD38 antigen in the sample. Examples of methods for detecting immunoassays include, without limitation, an ELISA, an RIA, FACS assays, plasmon resonance assays, chromatographic assays, tissue immunohistochemistry, Western blot, and/or immunoprecipitation.

In one embodiment, CD38BPs of the present invention may be used to detect levels of circulating CD38 or levels of cells which contain CD38 on their membrane surface, which levels can then be linked to certain disease symptoms. Alternatively, the CD38BPs may be used to deplete or interact with the function of CD38 expressing cells, thereby implicating these cells as important mediators of the disease. This may be achieved by contacting a sample and a control sample with the anti-CD38 antibody under conditions that allow for the formation of a complex between the antibody and CD38. Any complexes formed between the antibody and CD38 are detected and compared in the sample and the control.

CD38BPs of the present invention may be initially tested for binding activity associated with therapeutic or diagnostic use in vitro. For example, the CD38BPs may be tested using flow cytometric assays. Moreover, activity of the CD38BPs in triggering at least one effector-mediated effector cell activity may be assayed. For example, the ability of anti-CD38 antibodies of the present invention to trigger CDC and/or apoptosis may be assayed. Protocols for assaying for CDC, homotypic adhesion, molecular clustering or apoptosis are well known in the art.

In one embodiment, the present invention provides a method for detecting the presence or quantifying the amount of CD38-expressing cells in vivo or in vitro. The method comprises (i) administering to a subject a CD38BP of the present invention conjugated to a detectable marker; (ii) exposing the subject to a means for detecting said detectable marker to identify areas containing CD38-expressing cells.

In one embodiment, immunoconjugates of the present invention may be used to target compounds (e.g., therapeutic agents, labels, cytotoxins, immunosuppressants, etc.) to cells which have CD38 bound to their surface by using such target compounds as the therapeutic moieties in immunoconjugates of the present invention.

In one embodiment, the present invention also provides methods for localizing ex vivo or in vitro cells expressing CD38 (e.g., with a detectable label, such as a radioisotope, a fluorescent compound, an enzyme, or an enzyme co-factor).

In one embodiment, the present invention provides methods for killing cells which have CD38 bound to their surface by administering immunotoxins of the present invention.

The present invention provides methods for treating or preventing a disorder involving cells expressing CD38 in a subject, which method comprises administration of a therapeutically effective amount of a CD38BP of the present invention to a subject in need thereof. Such CD38BPs are used to inhibit CD38 induced activities associated with certain disorders or to eliminate or reduce the number of cells expressing CD38.

Such a method involves administering to a subject a CD38BP composition of the present invention in an amount effective to treat or prevent the disorder. The CD38BP composition may be administered alone or along with another therapeutic agent, such as is described elsewhere herein which acts in conjunction with or synergistically with the CD38BP composition to treat or prevent the diseases involving CD38 expressing cells. Alternatively, immunoconjugates may be used to kill cells which have CD38 expressed on their surface by targeting cytotoxins or radiotoxins to CD38.

In one embodiment of the present invention, the disorder involving cells expressing CD38 may be a tumorigenic disorder, such as a disorder characterized by the presence of tumor cells expressing CD38 including, for example, B cell lymphoma, plasma cell malignancies, T/NK cell lymphoma and myeloid malignancies.

Examples of such tumorigenic diseases include B cell lymphoma/leukemias including precursor B cell lymphoblastic leukemia/lymphoma and B cell non-Hodgkin's lymphomas; acute promyelocytic leukemia acute lymphoblastic leukemia and mature B cell neoplasms, such as B cell chronic lymhocytic leukemia(CLL)/small lymphocytic lymphoma (SLL), B cell acute lymphocytic leukemia, B cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B cell lymphoma (MALT type, nodal and splenic type), hairy cell leukemia, diffuse large B cell lymphoma, Burkitt's lymphoma, plasmacytoma, plasma cell myeloma, plasma cell leukemia, post-transplant lymphoproliferative disorder, Waldenström's macroglobulinemia, plasma cell leukemias and anaplastic large-cell lymphoma (ALCL).

In one embodiment, the disorder involving cells expressing CD38 is multiple myeloma.

Examples of B cell non-Hodgkin's lymphomas are lymphomatoid granulomatosis, primary effusion lymphoma, intravascular large B cell lymphoma, mediastinal large B cell lymphoma, heavy chain diseases (including γ, μ, and α disease), lymphomas induced by therapy with immunosuppressive agents, such as cyclosporine-induced lymphoma, and methotrexate-induced lymphoma.

In one embodiment of the present invention, the disorder involving cells expressing CD38 may be Hodgkin's lymphoma.

Examples of a disorder involving cells expressing CD38 may be a malignancy derived from T and NK cells including: mature T cell and NK cell neoplasms including T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, subcutaneous panniculitis-like T cell lymphoma, blastic NK cell lymphoma, Mycosis Fungoides/Sezary Syndrome, primary cutaneous CD30 positive T cell lymphoproliferative disorders (primary cutaneous anaplastic large cell lymphoma C-ALCL, lymphomatoid papulosis, borderline lesions), angioimmunoblastic T cell lymphoma, peripheral T cell lymphoma unspecified, and anaplastic large cell lymphoma.

Examples of malignancies derived from myeloid cells include acute myeloid leukemia, including acute promyelocytic leukemia, and chronic myeloproliferative diseases, including chronic myeloid leukemia.

In one embodiment of the present invention, the disorder involving cells expressing CD38 may be immune disorders in which CD38 expressing B cells, plasma cells, monocytes and T cells are involved Examples of immune disorders in which CD38 expressing B cells, plasma cells, monocytes and T cells are involved include autoimmune disorders, such as psoriasis, psoriatic arthritis, dermatitis, systemic scleroderma and sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, multiple sclerosis, Raynaud's syndrome, Sjögren's syndrome, juvenile onset diabetes, Reiter's disease, Behçet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, systemic lupus erythematosus, rheumatoid arthritis (RA), atopic dermatitis, pemphigus, Graves' disease, Hashimoto's thyroiditis, Wegener's granulomatosis, Omenn's syndrome, chronic renal failure, acute infectious mononucleosis, multiple sclerosis, HIV, and herpes virus associated diseases. Further examples are severe acute respiratory distress syndrome and choreoretinitis. Furthermore, other diseases and disorders are included such as those caused by or mediated by infection of B-cells with virus, such as Epstein-Barr virus (EBV).

In one embodiment, the disorder involving cells expressing CD38 is rheumatoid arthritis.

Further examples of inflammatory, immune and/or autoimmune disorders in which autoantibodies and/or excessive B and T lymphocyte activity are prominent and which may be treated according to the present invention include the following:

vasculitides and other vessel disorders, such as microscopic polyangiitis, Churg-Strauss syndrome, and other ANCA-associated vasculitides, polyarteritis nodosa, essential cryoglobulinaemic vasculitis, cutaneous leukocytoclastic angiitis, Kawasaki disease, Takayasu arteritis, giant cell arthritis, Henoch-Schönlein purpura, primary or isolated cerebral angiitis, erythema nodosum, thrombangiitis obliterans, thrombotic thrombocytopenic purpura (including hemolytic uremic syndrome), and secondary vasculitides, including cutaneous leukocytoclastic vasculitis (e.g., secondary to hepatitis B, hepatitis C, Waldenström's macroglobulinemia, B-cell neoplasias, rheumatoid arthritis, Sjögren's syndrome, or systemic lupus erythematosus); further examples are erythema nodosum, allergic vasculitis, panniculitis, Weber-Christian disease, purpura hyperglobulinaemica, and Buerger's disease;

skin disorders, such as contact dermatitis, linear IgA dermatosis, vitiligo, pyoderma gangrenosum, epidermolysis bullosa acquisita, pemphigus vulgaris (including cicatricial pemphigoid and bullous pemphigoid), alopecia greata (including alopecia universalis and alopecia totalis), dermatitis herpetiformis, erythema multiforme, and chronic autoimmune urticaria (including angioneurotic edema and urticarial vasculitis);

immune-mediated cytopenias, such as autoimmune neutropenia, and pure red cell aplasia;

connective tissue disorders, such as CNS lupus, discoid lupus erythematosus, CREST syndrome, mixed connective tissue disease, polymyositis/dermatomyositis, inclusion body myositis, secondary amyloidosis, cryoglobulinemia type I and type II, fibromyalgia, phospholipid antibody syndrome, secondary hemophilia, relapsing polychondritis, sarcoidosis, stiff man syndrome, and rheumatic fever; a further example is eosinophil fasciitis;

arthritides, such as ankylosing spondylitis, juvenile chronic arthritis, adult Still's disease, and SAPHO syndrome; further examples are sacroileitis, reactive arthritis, Still's disease, and gout;

hematologic disorders, such as aplastic anemia, primary hemolytic anemia (including cold agglutinin syndrome), hemolytic anemia secondary to CLL or systemic lupus erythematosus; POEMS syndrome, pernicious anemia, and Waldemström's purpura hyperglobulinaemica; further examples are agranulocytosis, autoimmune neutropenia, Franklin's disease, Seligmann's disease, gamma heavy chain disease, paraneoplastic syndrome secondary to thymoma and lymphomas, an, paraneoplastic syndrome secondary to thymoma and lymphomas, and factor VIII inhibitor formation;

endocrinopathies, such as polyendocrinopathy, and Addison's disease; further examples are autoimmune hypoglycemia, autoimmune hypothyroidism, autoimmune insulin syndrome, de Quervain's thyroiditis, and insulin receptor antibody-mediated insulin resistance;

hepato-gastrointestinal disorders, such as celiac disease, Whipple's disease, primary biliary cirrhosis, chronic active hepatitis, and primary sclerosing cholangitis; a further example is autoimmune gastritis;

nephropathies, such as rapid progressive glomerulonephritis, post-streptococcal nephritis, Goodpasture's syndrome, membranous glomerulonephritis, and cryoglobulinemic nephritis; a further example is minimal change disease;

neurological disorders, such as autoimmune neuropathies, mononeuritis multiplex, Lambert-Eaton's myasthenic syndrome, Sydenham's chorea, tabes dorsalis, and Guillain-Barré's syndrome; further examples are myelopathy/tropical spastic paraparesis, myasthenia gravis, acute inflammatory demyelinating polyneuropathy, and chronic inflammatory demyelinating polyneuropathy; multiple sclerosis;

cardiac and pulmonary disorders, such as COPD, fibrosing alveolitis, bronchiolitis obliterans, allergic aspergillosis, cystic fibrosis, Löffler's syndrome, myocarditis, and pericarditis; further examples are hypersensitivity pneumonitis, and paraneoplastic syndrome secondary to lung cancer;

allergic disorders, such as bronchial asthma and hyper-IgE syndrome; a further example is amaurosis fugax;

opthalmologic disorders, such as idiopathic chorioretinitis;

infectious diseases, such as parvovirus B infection (including hands-and-socks syndrome);

gynecological-obstretical disorders, such as recurrent abortion, recurrent fetal loss, and intrauterine growth retardation; a further example is paraneoplastic syndrome secondary to gynecological neoplasms;

male reproductive disorders, such as paraneoplastic syndrome secondary to testicular neoplasms; and transplantation-derived disorders, such as allograft and xenograft rejection, and graft-versus-host disease.

The antibody may also be administered prophylactically in order to reduce the risk of developing cancer, such as a tumorigenic disorder as described above, delay the onset of the occurrence of an event in such cancer progression, and/or reduce the risk of recurrence when such a cancer is in remission. This may be especially useful in patients wherein it is difficult to locate a tumor that is known to be present due to other biological factors.

Compositions of the present invention may include a "therapeutically effective amount" or a "prophylactically effective amount" of a CD38BP. A "therapeutically effective amount" refers to an amount effective, at dosages and for periods of time necessary, to achieve a desired therapeutic result. A therapeutically effective amount of a CD38BP may vary according to factors such as the disease state, age, sex, and weight of the individual, and the ability of the CD38BP to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result (e.g., a reduction in the likelihood of developing a disorder, a reduction in the intensity or spread of a disorder, an increase in the likelihood of survival during an imminent disorder, a delay in the onset of a disease condition, etc.). Typically, because a prophylactic dose is used in subjects prior to or at an earlier stage of disease, the prophylactically effective amount will be less than the therapeutically effective amount.

A "therapeutically effective amount" for tumor therapy may also be measured by its ability to stabilize the progression of disease. The ability of a compound to inhibit cancer may be evaluated in an animal model system predictive of efficacy in human tumors. Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

A "therapeutically effective amount" for rheumatoid arthritis may result in an at least $ACR_{20}$ Preliminary Definition of Improvement in the patients, such as in at least an $ACR_{50}$ Preliminary Definition of Improvement, for instance at least an $ARC_{70}$ Preliminary Definition of Improvement.

$ACR_{20}$ Preliminary Definition of Improvement is defined as:
$\geq$20% improvement in: Tender Joint Count (TJC) and Swollen Joint Count (SJC) and $\geq$20% improvement in 3 of following 5 assessments: Patient Pain Assessment (VAS), Patient Global assessment (VAS), Physician Global Assessment (VAS), Patent Self-Assessed Disability (HAQ), Acute Phase Reactant (CRP or ESR).

$ACR_{50}$ and $ACR_{70}$ are defined in the same way with $\geq$50% and $\geq$70% improvements, respectively. For further details see Felson et al., in American College of Rheumatology Preliminary Definition of Improvement in Rheumatoid Arthritis; Arthritis Rheumatism 38, 727-735 (1995).

Alternatively, a therapeutically effective amount for rheumatoid arthritis can be measured by DAS (disease activity score), including DAS28 and/or DAS56, as defined by EULAR.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the CD38BPs of the present invention depend on the disease or condition to be treated and may be determined by the persons skilled in the art. An exemplary, non-limiting range for a therapeutically effective amount of a compound of the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg.

A physician or veterinarian having ordinary skill in the art may readily determine and prescribe the effective amount of the pharmaceutical composition required. For example, the physician or veterinarian could start doses of the CD38BPs of the present invention employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

In one embodiment, the CD38BPs of the present invention may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours.

In one embodiment, the CD38BPs of the present invention may be administered by slow continuous infusion over a long period, such as more than 24 hours, in order to reduce toxic side effects.

In one embodiment the CD38BPs of the present invention may be administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the CD38BPs of the present invention.

In one embodiment, the CD38BPs of the present invention may be administered by maintenance therapy, such as, e.g., once a week for a period of 6 months or more.

In one embodiment, the CD38BPs of the present invention may be administered by a regimen including one infusion of a CD38BP of the present invention followed by an infusion of a CD38BP of the present invention conjugated to a radioisotope. The regimen may be repeated, e.g., 7 to 9 days later.

As non-limiting examples, treatment according to the present invention may be provided as a daily dosage of a compound of the present invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

The pharmaceutical compositions of the present invention may also be administered in combination therapy, i.e., combined with other therapeutic agents relevant for the disease or condition to be treated. Such administration may be simultaneous, separate or sequential. For simultaneous administration the agents may be administered as one compositions or as separate compositions, as appropriate.

Accordingly, the present invention provides methods for treating a disorder involving cells expressing CD38 as described above, which methods comprise administration of a CD38BP of the present invention combined with one or more additional therapeutic agents as described below.

The present invention also provides the use of a CD38BP of the present invention for the preparation of a pharmaceutical composition to be administered with at least one chemotherapeutic agent for a disorder involving cells expressing CD38 as described above.

In one embodiment, the combination therapy may include administration of a composition of the present invention together with at least one chemotherapeutic agent, at least one anti-inflammatory agent, or at least one immunosuppressive and/or immunomodulatory agent.

In one embodiment, the present invention provides a method for treating a disorder involving cells expressing CD38 in a subject, which method comprises administration of a therapeutically effective amount of a CD38BP of the present invention and at least one chemotherapeutic agent to a subject in need thereof.

In one embodiment, the present invention provides a method for treating multiple myeloma, which method comprises administration of a therapeutically effective amount of a CD38BP of the present invention and at least one chemotherapeutic agent to a subject in need thereof.

In one embodiment, the present invention provides the use of a CD38BP of the present invention for the preparation of a pharmaceutical composition to be administered with at least one chemotherapeutic agent for treating multiple myeloma.

In one embodiment, such a chemotherapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine, cladribine and similar agents.

In one embodiment, such a chemotherapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin, and similar agents.

In one embodiment, such a chemotherapeutic agent may be selected from an antibiotic, such as dactinomycin (formerly actinomycin), bleomycin, daunorubicin (formerly daunomycin), doxorubicin, idarubicin, mithramycin, mitomycin, mitoxantrone, plicamycin, anthramycin (AMC) and similar agents.

In one embodiment, such a chemotherapeutic agent may be selected from an anti-mitotic agent, such as taxanes, for instance docetaxel, and paclitaxel, and vinca alkaloids, for instance vindesine, vincristine, vinblastine, and vinorelbine.

In one embodiment, such a chemotherapeutic agent may be selected from a topoisomerase inhibitor, such as topotecan.

In one embodiment, such a chemotherapeutic agent may be selected from a growth factor inhibitor, such as an inhibitor of ErbB1 (EGFR) (such as gefitinib (Iressa®), cetuximab (Erbitux®), erlotinib (Tarceva®), HuMax-EGFr (2F8 disclosed in WO 2002/100348) and similar agents), an inhibitor of ErbB2 (Her2/neu) (such as trastuzumab (Herceptin®) and similar agents) and similar agents. In one embodiment, such a growth factor inhibitor may be a farnesyl transferase Inhibitor, such as SCH-66336 and R115777. In one embodiment, such a growth factor inhibitor may be a vascular endothelial growth factor (VEGF) inhibitor, such as bevacizumab (Avastin®).

In one embodiment, such a chemotherapeutic agent may be a tyrosine kinase inhibitor, such as imatinib (Glivec, Gleevec ST1571), lapatinib, PTK787/ZK222584 and similar agents.

In one embodiment, such a chemotherapeutic agent may be a histone deacetylase inhibitor. Examples of such histone deacetylase inhibitors include hydroxamic acid-based hybrid polar compounds, such as SAHA (suberoylanilide hydroxamic acid).

In one embodiment, such a chemotherapeutic agent may be a P38a MAP kinase inhibitor, such as SCIO-469.

In one embodiment, the present invention provides a method for treating a disorder involving cells expressing CD38 in a subject, which method comprises administration of a therapeutically effective amount of a CD38BP of the present invention and at least one inhibitor of angiogenesis, neovascularization, and/or other vascularization to a subject in need thereof.

In one embodiment, the present invention provides a method for treating multiple myeloma, which method comprises administration of a therapeutically effective amount of a CD38BP of the present invention and at least one inhibitor of angiogenesis, neovascularization, and/or other vascularization to a subject in need thereof.

In one embodiment, the present invention provides the use of a CD38BP of the present invention for the preparation of a pharmaceutical composition to be administered with at least one inhibitor of angiogenesis, neovascularization, and/or other vascularization for treating multiple myeloma.

Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF, bFGF, and angiopoietin-1), thalidomide (Thalomid®), thalidomide analogs (such as CC-5013 (lenalidomide, Revlimid™) and CC4047 (Actimid™), Sugen 5416, SU5402, antiangiogenic ribozyme (such as angiozyme), interferon α (such as interferon α2α), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2) and similar agents.

Other examples of such inhibitors of angiogenesis, neovascularization, and/or other vascularization are anti-angiogenic heparin derivatives and related molecules (e.g., heperinase III), temozolomide, NK4, macrophage migration inhibitory factor (MIF), cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other relevant targets (such as anti-alpha-v/beta-3 integrin and anti-kininostatin mAbs) and similar agents.

In one embodiment, the present invention provides the use of a CD38BP of the present invention for the preparation of a pharmaceutical composition to be administered with thalidomide (Thalomid®), thalidomide analogs (such as CC-5013 (lenalidomide, Revlimid™) and/or CC4047 (Actimid™). In a further embodiment, the present invention provides the use of a CD38BP of the present invention for the preparation of a pharmaceutical composition to be administered with thalidomide.

In one embodiment, the present invention provides the use of a CD38BP of the present invention for the preparation of a pharmaceutical composition to be administered with an anti-CD20 antibody, such as rituximab (Rituxan®, Mabthera®), a human monoclona lanti-CD20 antibody as disclosed in WO 2004/035607, such as 11B8, 2F2 or 7D8.

In one embodiment, a therapeutic agent for use in combination with the CD38BPs of the present invention for treating the disorders as described above may be a proteasome inhibitor, such as bortezomib (Velcade®).

In one embodiment, a therapeutic agent for use in combination with the CD38BPs of the present invention for treating the disorders as described above may be a corticosteroid, such as prednisone, prednisolone, dexamethasone, etc.

In one embodiment, a therapeutic agent for use in combination with the CD38BPs of the present invention for treating the disorders as described above may be a corticosteroid, such as prednisone, prednisolone, dexamethasone, etc.

In one embodiment, a therapeutic agent for use in combination with the CD38BPs of the present invention for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines), tumor-derived heat shock proteins, and similar agents. A number of other suitable cancer antigens/tumor-associated antigens described elsewhere herein and similar molecules known in the art may also or alternatively be used in such embodiment. Anti-cancer immunogenic peptides also include anti-idiotypic "vaccines" such as BEC2 anti-idiotypic antibodies, Mitumomab, CeaVac and related anti-idiotypic antibodies, anti-idiotypic antibody to MG7 antibody, and other anti-cancer anti-idiotypic antibodies (see for instance Birebent et al., Vaccine. 21(15), 1601-12 (2003), Li et al., Chin Med J (Engl). 114(9), 962-6 (2001), Schmitt et al., Hybridoma. 13(5), 389-96 (1994), Maloney et al., Hybridoma. 4(3), 191-209 (1985), Raychardhuri et al., J. Immunol. 137(5), 1743-9 (1986), Pohl et al., Int J. Cancer. 50(6), 958-67 (1992), Bohlen et al., Cytokines Mol. Ther. 2(4), 231-8 (1996) and Maruyama, J Immunol Methods. 264(1-2), 121-33 (2002)). Such anti-idiotypic Abs may optionally be conjugated to a carrier, which may be a synthetic (typically inert) molecule carrier, a protein (for instance keyhole limpet hemocyanin (KLH) (see for instance Ochi et al., Eur J. Immunol. 17(11), 1645-8 (1987)), or a cell (for instance a red blood cell—see for instance Wi et al., J Immunol Methods. 122(2), 227-34 (1989)).

In one embodiment, a therapeutic agent for use in combination with the CD38BPs of the present invention for treating the disorders as described above may be a bisphosphonate. Examples of potentially suitable biphosphonates are pamidronate (Aredia®), zoledronic acid (Zometa®), clodronate (Bonefos®), risendronate (Actonel®), ibandronate (Boniva®), etidronate (Didronel®), alendronate (Fosamax®), tiludronate (Skelid®), incadronate (Yamanouchi Pharmaceutical) and minodronate (YM529, Yamanouchi).

In one embodiment, a therapeutic agent for use in combination with the CD38BPs of the present invention for treating the disorders as described above may be a colony stimulating factor. Examples of suitable colony stimulating factors are granulocyte-colony stimulating factors (G-CSF), such as filgrastim (Neupogen®) and pegfilgrastim (Neulasta®), and granulocyte macrophage-colony stimulating factors (GM-CSF) such as sargramostim (Leukine®).

In one embodiment, a therapeutic agent for use in combination with the CD38BPs of the present invention for treating the disorders as described above may be a erythropoietic agent. Examples of suitable erythropoietic agents are erythropoietin (EPO), such as epoetin alfa (for instance Procrit®, Epogen®, and Eprex®) and epoetin beta (for instance Neo-Recormon®) and erythropoiesis-stimulating proteins (for instance Aranesp®).

In one embodiment, a therapeutic agent for use in combination with the CD38BPs of the present invention for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1α from the human CXC and C—C chemokine families. Suitable cytokines include cytokine derivatives, cytokine variants, cytokine fragments, and cytokine fusion proteins.

These and other methods or uses involving naturally occurring peptide-encoding nucleic acids herein may alternatively or additionally be performed by "gene activation" and homologous recombination gene upregulation techniques, such as are described in U.S. Pat. No. 5,968,502, U.S. Pat. No. 6,063,630 and U.S. Pat. No. 6,187,305 and EP 0505500.

In one embodiment, a therapeutic agent for use in combination with the CD38BPs of the present invention for treating the disorders as described above may be an agent that modulates, e.g., enhances or inhibits, the expression or activity of Fcα or Fcγ receptors. Examples of agents suitable for this use include interleukin-1 (IL-1), interleukin-2 (IL-2), interleukin-6 (IL-6), granulocyte colony-stimulating factor (G-CSF), such as filgrastim (Neupogen®) and pegfilgrastim (Neulasta®), and granulocyte macrophage-colony stimulating factors (GM-CSF) such as sargramostim (Leukine®), interferon-γ (IFN-γ), and tumor necrosis factor (TNF).

In one embodiment, a therapeutic agent for use in combination with the CD38BPs of the present invention for treating the disorders as described above may be a cell cycle control/apoptosis regulator (or "regulating agent"). A cell cycle control/apoptosis regulator may include molecules (i) that target and modulate cell cycle control/apoptosis regulators such as cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. No. 6,440,735 and U.S. Pat. No. 6,713,055). Non-limiting examples of molecules that interfere with apoptotic pathways include TNF-related apoptosis-inducing ligand (TRAIL)/apoptosis-2 ligand (Apo-2L), agents inducing NF-κB blockade leading to inhibition of IL-6 production, antibodies that activate TRAIL receptors, IFNs, anti-sense Bcl-2, and $As_2O_3$ (arsenic trioxide, Trisenox®).

In one embodiment, a therapeutic agent for use in combination with the CD38BPs of the present invention for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxy-progesterone caproate, medroxyprogesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane), a hormone inhibitor (such as octreotide/sandostatin) and similar agents.

In one embodiment, a therapeutic agent for use in combination with the CD38BPs of the present invention for treating the disorders as described above may be an anti-anergic agents (for instance small molecule compounds, proteins, glycoproteins, or antibodies that break tolerance to tumor and cancer antigens). Examples of such compounds are molecules that block the activity of CTLA-4, such as MDX-010 (Phan et al., PNAS USA 100, 8372 (2003)).

In one embodiment, a therapeutic agent for use in combination with the CD38BPs of the present invention for treating the disorders as described above may be a tumor suppressor gene-containing nucleic acid or vector such as a replication-deficient adenovirus encoding human recombinant wild-type p53/SCH58500, etc.; antisense nucleic acids targeted to oncogenes, mutated, or deregulated genes; or siRNA targeted to mutated or deregulated genes. Examples of tumor suppressor targets include, for example, BRCA1, RB1, BRCA2, DPC4 (Smad4), MSH2, MLH1, and DCC.

In one embodiment, a therapeutic agent for use in combination with the CD38BPs of the present invention for treating the disorders as described above may be an anti-cancer nucleic acid, such as genasense (augmerosen/G3139), LY900003 (ISIS 3521), ISIS 2503, OGX-011 (ISIS 112989), LE-AON/LEraf-AON (liposome encapsulated c-raf anti-sense oligonucleotide/ISIS-5132), MG98, and other anti-sense nucleic acids that target PKCα, clusterin, IGFBPs, protein kinase A, cyclin D1, or Bcl-2h.

In one embodiment, a therapeutic agent for use in combination with the CD38BPs of the present invention for treating the disorders as described above may be an anti-cancer inhibitory RNA molecule (see for instance Lin et al., Curr Cancer Drug Targets. 1(3), 241-7 (2001), Erratum in: Curr Cancer Drug Targets. 3(3), 237 (2003), Lima et al., Cancer Gene Ther. 11(5), 309-16 (2004), Grzmil et al., Int J. Oncol. 4(1), 97-105 (2004), Collis et al., Int J Radiat Oncol Biol Phys. 57(2 Suppl), S144 (2003), Yang et al., Oncogene. 22(36), 5694-701 (2003) and Zhang et al., Biochem Biophys Res Commun. 303(4), 1169-78 (2003)).

Compositions and combination administration methods of the present invention also include the administration of nucleic acid vaccines, such as naked DNA vaccines encoding such cancer antigens/tumor-associated antigens (see for instance U.S. Pat. No. 5,589,466, U.S. Pat. No. 5,593,972, U.S. Pat. No. 5,703,057, U.S. Pat. No. 5,879,687, U.S. Pat. No. 6,235,523, and U.S. Pat. No. 6,387,888). In one embodiment, the combination administration method and/or combination composition comprises an autologous vaccine composition. In one embodiment, the combination composition and/or combination administration method comprises a whole cell vaccine or cytokine-expressing cell (for instance a recombinant IL-2 expressing fibroblast, recombinant cytokine-expressing dendritic cell, and the like) (see for instance Kowalczyk et al., Acta Biochim Pol. 50(3), 613-24 (2003), Reilly et al., Methods Mol. Med. 69, 233-57 (2002) and Tirapu et al., Curr Gene Ther. 2(1), 79-89 (2002). Another example of such an autologous cell approach that may be useful in combination methods of the present invention is the MyVax® Personalized Immunotherapy method (previously referred to as GTOP-99) (Genitope Corporation—Redwood City, Calif., USA).

In one embodiment, the present invention provides combination compositions and combination administration methods wherein a CD38BP is combined or co-administered with a virus, viral proteins, and the like. Replication-deficient viruses, that generally are capable of one or only a few rounds of replication in vivo, and that are targeted to tumor cells, may for instance be useful components of such compositions and methods. Such viral agents may comprise or be associated with nucleic acids encoding immunostimulants, such as GM-CSF and/or IL-2. Both naturally oncolytic and such recombinant oncolytic viruses (for instance HSV-1 viruses, reoviruses, replication-deficient and replication-sensitive adenovirus, etc.) may be useful components of such methods and compositions. Accordingly, in one embodiment, the present invention provides combination compositions and combination administration methods wherein a CD38BP is combined or co-administered with an oncolytic virus. Examples of such viruses include oncolytic adenoviruses and herpes viruses, which may or may not be modified viruses (see for instance Shah et al., J. Neurooncol. 65(3), 203-26 (2003), Stiles et al., Surgery. 134(2), 357-64 (2003), Sunarmura et al., Pancreas. 28(3), 326-9 (2004), Teshigahara et al., J Surg Oncol. 85(1), 42-7 (2004), Varghese et al., Cancer Gene Ther. 9(12), 967-78 (2002), Wildner et al., Cancer Res. 59(2), 410-3 (1999), Yamanaka, Int J. Oncol. 24(4), 919-23 (2004) and Zwiebel et al., Semin Oncol. 28(4), 336-43 (2001).

Combination compositions and combination administration methods of the present invention may also involve "whole cell and "adoptive" immunotherapy methods. For instance, such methods may comprise infusion or re-infusion of immune system cells (for instance tumor-infiltrating lymphocytes (TILs), such as $CD4^+$ and/or $CD8^+$ T cells (for instance T cells expanded with tumor-specific antigens and/or genetic enhancements), antibody-expressing B cells or other antibody producing/presenting cells, dendritic cells (e.g., anti-cytokine expressing recombinant dendritic cells, dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions.

In one embodiment, a CD38BP of the present invention may be delivered to a patient in combination with the application of an internal vaccination method. Internal vaccination refers to induced tumor or cancer cell death, such as drug-induced or radiation-induced cell death of tumor cells, in a patient, that typically leads to elicitation of an immune response directed towards (i) the tumor cells as a whole or (ii) parts of the tumor cells including (a) secreted proteins, glycoproteins or other products, (b) membrane-associated proteins or glycoproteins or other components associated with or inserted in membranes, and/or (c) intracellular proteins or other intracellular components. An internal vaccination-induced immune response may be humoral (i.e. antibody—complement-mediated) or cell-mediated (e.g., the development and/or increase of endogenous cytotoxic T lymphocytes that recognize the internally killed tumor cells or parts thereof). In addition to radiotherapy, non-limiting examples of drugs and agents that may be used to induce said tumor cell-death and internal vaccination are conventional chemotherapeutic agents, cell-cycle inhibitors, anti-angiogenesis drugs, monoclonal antibodies, apoptosis-inducing agents, and signal transduction inhibitors.

Examples of other anti-cancer agents, which may be relevant as therapeutic agents for use in combination with the CD38BPs of the present invention for treating the disorders as described above are differentiation inducing agents, retinoic acid and retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFR-beta, Flk2, Flt4, FGFR1, FGFR2, FGFR3, FGFR4, TRKA, TRKC, c-met, Ron, Sea, Tie, Tie2, Eph, Ret, Ros, Alk, LTK, PTK7 and similar agents.

Examples of other anti-cancer agents, which may be relevant as therapeutic agents for use in combination with the CD38BPs of the present invention for treating the disorders as described above are cathepsin B, modulators of cathepsin D dehydrogenase activity, glutathione-S-transferase (such as glutamylcysteine synthetase and lactate dehydrogenase), and similar agents.

Examples of other anti-cancer agents, which may be relevant as therapeutic agents for use in combination with the CD38BPs of the present invention for treating the disorders as described above are estramustine and epirubicin.

Examples of other anti-cancer agents, which may be relevant as therapeutic agents for use in combination with the CD38BPs of the present invention for treating the disorders as described above are a HSP90 inhibitor like 17-allyl amino geld-anamycin, antibodies directed against a tumor antigen such as PSA, CA125, KSA, etc., integrins like integrin β1, inhibitors of VCAM and similar agents Examples of other anti-cancer agents, which may be relevant as therapeutic agents for use in combination with the CD38BPs of the present invention for treating the disorders as described above are calcineurin-inhibitors (such as valspodar, PSC 833 and other MDR-1 or p-glycoprotein inhibitors), TOR-inhibitors (such as sirolimus, everolimus and rapamycin), and inhibitors of "lymphocyte homing" mechanisms (such as FTY720), and agents with effects on cell signaling such as adhesion molecule inhibitors (for instance anti-LFA, etc.).

In one embodiment, the present invention provides a method for treating a disorder involving cells expressing CD38 in a subject, which method comprises administration of a therapeutically effective amount of a CD38BP of the present invention and radiotherapy to a subject in need thereof.

In one embodiment, the present invention provides a method for treating multiple myeloma, which method comprises administration of a therapeutically effective amount of a CD38BP of the present invention and radiotherapy to a subject in need thereof.

In one embodiment, the present invention provides the use of a CD38BP of the present invention for the preparation of a pharmaceutical composition to be administered with radiotherapy for treating multiple myeloma.

Radiotherapy may comprise radiation or associated administration of radiopharmaceuticals to a patient is provided. The source of radiation may be either external or internal to the patient being treated (radiation treatment may, for example, be in the form of external beam radiation therapy (EBRT), brachytherapy (BT) or skeletal targeted radiotherapy). Radioactive elements that may be used in practicing such methods include, e.g., radium, cesium-137, iridium-192, americium-241, gold-198, cobalt-57, copper-67, technetium-99, iodide-123, iodide-131, and indium-111.

In one embodiment, the present invention provides a method for treating a disorder involving cells expressing CD38 in a subject, which method comprises administration of a therapeutically effective amount of a CD38BP of the present invention to a subject in need thereof combined with autologous peripheral stem cell or bone marrow transplantation.

In one embodiment, the present invention provides a method for treating multiple myeloma, which method comprises administration of a therapeutically effective amount of a CD38BP of the present invention to a subject in need thereof combined with autologous peripheral stem cell or bone marrow transplantation.

In one embodiment, the present invention provides the use of a CD38BP of the present invention for the preparation of a pharmaceutical composition to be administered with autologous peripheral stem cell or bone marrow transplantation for treating multiple myeloma.

In one embodiment, the present invention provides a method for treating a disorder involving cells expressing CD38 in a subject, which method comprises administration of a therapeutically effective amount of a CD38BP of the present invention to a subject in need thereof combined with orthopedic intervention.

In one embodiment, the present invention provides the use of a CD38BP of the present invention for the preparation of a pharmaceutical composition to be administered with autologous peripheral stem cell or bone marrow transplantation for treating multiple myeloma.

Orthopedic interventions may be used in the treatment of a disorder involving cells expressing CD38, such as multiple myeloma, to help control pain or retain function or mobility. Such interventions may include physical therapy, splinting of bones to prevent or treat fractures, or surgical procedures (minor or major) to repair fractures.

In one embodiment, a CD38BP of the present invention may be administered in connection with the delivery of one or more agents that promote access of the CD38BP or combination composition to the interior of a tumor. Such methods may for example be performed in association with the delivery of a relaxin, which is capable of relaxing a tumor (see for instance U.S. Pat. No. 6,719,977). In one embodiment, a CD38BP of the present invention may be bonded to a cell penetrating peptide (CPP). Cell penetrating peptides and related peptides (such as engineered cell penetrating antibodies) are described in for instance Zhao et al., J Immunol Methods. 254(1-2), 137-45 (2001), Hong et al., Cancer Res. 60(23), 6551-6 (2000). Lindgren et al., Biochem J. 377(Pt 1), 69-76 (2004), Buerger et al., J Cancer Res Clin Oncol. 129 (12), 669-75 (2003), Pooga et al., FASEB J. 12(1), 67-77 (1998) and Tseng et al., Mol. Pharmacol. 62(4), 864-72 (2002).

In one embodiment, the present invention provides a method for treating a disorder involving cells expressing CD38 in a subject, which method comprises administration of a therapeutically effective amount of a CD38BP of the present invention and at least one anti-inflammatory agent to a subject in need thereof.

In one embodiment, the present invention provides a method for treating multiple myeloma, which method comprises administration of a therapeutically effective amount of a CD38BP of the present invention and at least one anti-inflammatory agent to a subject in need thereof.

In one embodiment, the present invention provides the use of a CD38BP of the present invention for the preparation of a pharmaceutical composition to be administered with at least one anti-inflammatory agent for treating multiple myeloma.

In one embodiment such an anti-inflammatory agent may be selected from a steroidal drug and a NSAID (nonsteroidal anti-inflammatory drug).

In one embodiment such an anti-inflammatory agent may be selected from aspirin and other salicylates, Cox-2 inhibitors (such as rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies, anti-IL15 antibodies, anti-IL15R antibodies, anti-CD4 antibodies, anti-CD11a antibodies (e.g., efalizumab), anti-alpha4/beta-1 integrin ($V_L A4$) antibodies (e.g natalizumab), CTLA4-1 g for the treatment of inflammatory diseases, prednisolone, prednisone, disease modifying antirheumatic drugs (DMARDs) such as methotrexate, hydroxychloroquine, sulfasalazine, pyrimidine synthesis inhibitors (such as leflunomide), IL-1 receptor blocking agents (such as anakinra), TNF-α blocking agents (such as etanercept, infliximab, and adalimumab) and similar agents.

In one embodiment, the present invention provides a method for treating a disorder involving cells expressing CD38 in a subject, which method comprises administration of a therapeutically effective amount of a CD38BP of the present invention and at least one immunosuppressive and/or immunomodulatory agent to a subject in need thereof.

In one embodiment, the present invention provides a method for treating multiple myeloma, which method comprises administration of a therapeutically effective amount of a CD38BP of the present invention and at least one immunosuppressive and/or immunomodulatory agent to a subject in need thereof.

In one embodiment, the present invention provides the use of a CD38BP of the present invention for the preparation of a pharmaceutical composition to be administered with at least one immunosuppressive and/or immunomodulatory agent for treating multiple myeloma.

In one embodiment, such an immunosuppressive and/or immunomodulatory agent may be selected from cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents.

In one embodiment, such an immunosuppressive and/or immunomodulatory agent may be selected from immunosuppressive antibodies, such as antibodies binding to p75 of the IL-2 receptor, or antibodies binding to for instance MHC, CD2, CD3, CD4, CD7, CD28, B7, CD40, CD45, IFNγ, TNF-α, IL-4, IL-5, IL-6R, IL-6; IGF, IGFR1, IL-7, IL-8, IL-10, CD11a, or CD58, or antibodies binding to their ligands.

In one embodiment, such an immunosuppressive and/or immunomodulatory agent may be selected from soluble IL-15R, IL-10, B7 molecules (B7-1, B7-2, variants thereof, and fragments thereof, ICOS, and OX40, an inhibitor of a negative T cell regulator (such as an antibody against CTLA4) and similar agents.

In one embodiment, the CD38BPs of the present invention may be administered in combination with two or more immunosuppressive and/or immunomodulatory agents, such as in combination with prednisone and cyclosporine; prednisone, cyclosporine and azathioprine; or prednisone, cyclosporine and mycophenolate mofetil.

In one embodiment, the present invention provides a method for treating a disorder involving cells expressing CD38 in a subject, which method comprises administration of a therapeutically effective amount of a CD38BP of the present invention and an anti-C3b(i) antibody to a subject in need thereof.

In one embodiment, the present invention provides a method for treating multiple myeloma, which method comprises administration of a therapeutically effective amount of a CD38BP of the present invention and an anti-C3b(i) antibody to a subject in need thereof.

In one embodiment, the present invention provides the use of a CD38BP of the present invention for the preparation of a pharmaceutical composition to be administered with an anti-C3b(i) antibody for treating multiple myeloma.

In one embodiment, a therapeutic agent for use in combination with the CD38BPs of the present invention for treating the disorders as described above may be selected from histone deacetylase inhibitors (for instance phenylbutyrate) and/or DNA repair agents (for instance DNA repair enzymes and related compositions such as dimericine).

Methods of the present invention for treating a disorder as described above comprising administration of a therapeutically effective amount of a CD38BP of the present invention may also comprise anti-cancer directed photodynamic therapy (for instance anti-cancer laser therapy—which optionally may be practiced with the use of photosensitizing agent, see, for instance Zhang et al., J Control Release. 93(2), 141-50 (2003)), anti-cancer sound-wave and shock-wave therapies (see for instance Kambe et al., Hum Cell. 10(1), 87-94 (1997)), and/or anti-cancer nutraceutical therapy (see for instance Roudebush et al., Vet Clin North Am Small Anim Pract. 34(1), 249-69, viii (2004) and Rafi, Nutrition. 20(1), 78-82 (2004). Likewise, a CD38BP of the present invention may be used for the preparation of a pharmaceutical composition for treating a disorder as described above to be administered with anti-cancer directed photodynamic therapy (for instance anti-cancer laser therapy—which optionally may be practiced with the use of photosensitizing agent, anti-cancer sound-wave and shock-wave therapies, and/or anti-cancer nutraceutical therapy.

As described above, a pharmaceutical composition of the present invention may be administered in combination therapy, i.e., combined with one or more agents relevant for the disease or condition to be treated either as separate pharmaceutical compositions or with a compound of the present invention coformulated with one or more additional therapeutic agents as described above. Such combination therapies may require lower dosages of the compound of the present invention and/or the co-administered agents, thus avoiding possible toxicities or complications associated with the various monotherapies.

In one embodiment, the present invention provides a CD38BP that is conjugated to an immunomodulator, such as an immunomodulating cytokine, stem cell growth factor, lymphotoxin (such as a TNF such as TNFα), or a hematopoietic factor. Examples of such molecules that may be useful as conjugates include IL-1, IL-2, IL-3, IL-6, IL-10, IL-12, IL-18, and IL-21, colony stimulating factors (such as granulocyte-colony stimulating factor (G-CSF) and granulocyte macrophage-colony stimulating factor (GM-CSF)), interferons (such as IFNα, IFNβ, and IFNγ) the stem cell growth factor designated "S1 factor," erythropoietin, and thrombopoietin, active fragments thereof, derivatives thereof, variants thereof, or a combination of any thereof.

In one embodiment, the CD38BPs of the present invention may be used in vivo or in vitro for diagnosing diseases wherein activated cells expressing CD38 play an active role in the pathogenesis by detecting levels of CD38, or levels of cells which contain CD38 on their membrane surface. This may be achieved, for example, by contacting a sample to be tested, optionally along with a control sample, with the CD38BP under conditions that allow for formation of a complex between the antibody and CD38. Complex formation is then detected (e.g., using an ELISA). When using a control sample along with the test sample, complex is detected in both samples and any statistically significant difference in the formation of complexes between the samples is indicative of the presence of CD38 in the test sample.

More specifically, the present invention provides methods for the identification of, and diagnosis of invasive cells and tissues, and other cells targeted by CD38BPs of the present invention, and for the monitoring of the progress of therapeutic treatments, status after treatment, risk of developing cancer, cancer progression, and the like.

In one example of such a diagnostic assay, the present invention provides a method of diagnosing the level of invasive cells in a tissue comprising forming an immunocomplex between a CD38BP and potential CD38 containing tissues, and detecting formation of the immunocomplex, wherein the formation of the immunocomplex correlates with the presence of invasive cells in the tissue. The contacting may be performed in vivo, using labeled isolated antibodies and standard imaging techniques, or may be performed in vitro on tissue samples.

CD38BPs may be used to detect CD38-containing peptides and peptide fragments in any suitable biological sample by any suitable technique. Examples of conventional immunoassays provided by the present invention include, without limitation, an ELISA, an RIA, FACS assays, plasmon resonance assays, chromatographic assays, tissue immunohistochemistry, Western blot, and/or immunoprecipitation using a CD38BP. Anti-CD38 antibodies of the present invention may be used to detect CD38 and CD38-fragments from humans. Suitable labels for the CD38BP and/or secondary antibodies used in such techniques include, without limitation, various enzymes, prosthetic groups, fluorescent materials, luminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$, and $^3H$.

CD38BPs may also be assayed in a biological sample by a competition immunoassay utilizing CD38 peptide standards labeled with a detectable substance and an unlabeled CD38BP, such as an unlabelled anti-CD38 antibody, for example. In such an assay, the biological sample, the labeled CD38 peptide standard(s) and the CD38BP are combined and the amount of labeled CD38 standard bound to the unlabeled CD38BP is determined. The amount of CD38 peptide in the biological sample is inversely proportional to the amount of labeled CD38 standard bound to the CD38BP.

The CD38BPs are particularly useful in the in vivo imaging of tumors. In vivo imaging of tumors associated with CD38 may be performed by any suitable technique. For example, $^{99}Tc$-labeling or labeling with another gamma-ray emitting isotope may be used to label anti-CD38 antibodies in tumors or secondary labeled (e.g., FITC labeled) CD38BP:CD38 complexes from tumors and imaged with a gamma scintillation camera (e.g., an Elscint Apex 409ECT device), typically using low-energy, high resolution collimator or a low-energy all-purpose collimator. Stained tissues may then be assessed for radioactivity counting as an indicator of the amount of CD38-associated peptides in the tumor. The images obtained by the use of such techniques may be used to assess biodistribution of CD38 in a patient, mammal, or tissue, for example in the context of using CD38 or CD38-fragments as a biomarker for the presence of invasive cancer cells. Variations on this technique may include the use of magnetic resonance imaging (MRI) to improve imaging over gamma camera techniques. Similar immunoscintigraphy methods and principles are described in, e.g., Srivastava (ed.), Radiolabeled Monoclonal Antibodies For Imaging And Therapy (Plenum Press 1988), Chase, "Medical Applications of Radioisotopes," in Remington's Pharmaceutical Sciences, 18th Edition, Gennaro et al., (eds.), pp. 624-652 (Mack Publishing Co., 1990), and Brown, "Clinical Use of Monoclonal Antibodies," in Biotechnology And Pharmacy 227-49, Pezzuto et al., (eds.) (Chapman & Hall 1993). Such images may also be used for targeted delivery of other anti-cancer agents, examples of which are described herein (e.g., apoptotic agents, toxins, or CHOP chemotherapy compositions). Moreover, such images may also or alternatively serve as the basis for surgical techniques to remove tumors. Furthermore, such in vivo imaging techniques may allow for the identification and localization of a tumor in a situation where a patient is identified as having a tumor (due to the presence of other biomarkers, metastases, etc.), but the tumor cannot be identified by traditional analytical techniques. All of these methods are features of the present invention.

The in vivo imaging and other diagnostic methods provided by the present invention are particularly useful in the detection of micrometastases in a human patient (e.g., a patient not previously diagnosed with cancer or a patient in a period of recovery/remission from a cancer). Carcinoma cancer cells, which may make up to 90% of all cancer cells, for example, have been demonstrated to stain very well with anti-CD38 antibody conjugate compositions. Detection with monoclonal anti-CD38 antibodies and other CD38BPs described herein may be indicative of the presence of carcinomas that are aggressive/invasive and also or alternatively provide an indication of the feasibility of using related monoclonal anti-CD38 antibody, CD38BP, or related composition treatments against such micrometastases. Moreover, monoclonal anti-CD38 antibodies that are associated with cancer cells are advantageously able to distinguish such cancer-associated tissues and cells from normal cells that other forms of CD38 may be associated with.

In one embodiment, the present invention provides an in vivo imaging method wherein an CD38BP, such as an anti-CD38 antibody, of the present invention is conjugated to a detection-promoting radio-opaque agent, the conjugated antibody is administered to a host, such as by injection into the bloodstream, and the presence and location of the labeled antibody in the host is assayed. Through this technique and any other diagnostic method provided herein, the present invention provides a method for screening for the presence of disease-related cells in a human patient or a biological sample taken from a human patient.

For diagnostic imaging, radioisotopes may be bound to a CD38BP either directly, or indirectly by using an intermediary functional group. Useful intermediary functional groups include chelators, such as ethylenediaminetetraacetic acid and diethylenetriaminepentaacetic acid (see for instance U.S. Pat. No. 5,057,313). In such diagnostic assays involving radioisotope-conjugated CD38BPs, the dosage of conjugated peptide delivered to the patient typically is maintained at as low a level as possible through the choice of isotope for the best combination of minimum half-life, minimum retention in the body, and minimum quantity of isotope, which will permit detection and accurate measurement.

In addition to radioisotopes and radio-opaque agents, diagnostic methods may be performed using CD38BPs that are conjugated to dyes (such as with the biotin-streptavidin complex), contrast agents, fluorescent compounds or molecules and enhancing agents (e.g. paramagnetic ions) for magnetic resonance imaging (MRI) (see, e.g., U.S. Pat. No. 6,331,175, which describes MRI techniques and the preparation of antibodies conjugated to a MRI enhancing agent). Such diagnostic/detection agents may be selected from agents for use in magnetic resonance imaging, and fluorescent compounds. In order to load a CD38BP, such as an antibody, component with radioactive metals or paramagnetic ions, it may be necessary to react it with a reagent having a long tail to which are attached a multiplicity of chelating groups for binding the ions. Such a tail may be a polymer such as a polylysine, polysaccharide, or other derivatized or derivatizable chain having pendant groups to which can be bound chelating groups such as, e.g., porphyrins, polyamines, crown ethers, bisthiosemicarbazones, polyoximes, and like groups known to be useful for this purpose. Chelates may be coupled to CD38BPs using standard chemistries. A chelate is normally linked to a CD38BP, such as an anti-CD38 mAB, by a group, which enables formation of a bond to the molecule with minimal loss of immunoreactivity and minimal aggregation and/or internal cross-linking. Other, more unusual, methods and reagents for conjugating chelates to antibodies are disclosed in for instance U.S. Pat. No. 4,824,659. Examples of potentially useful metal-chelate combinations include 2-benzyl-DTPA and its monomethyl and cyclohexyl analogs, used with diagnostic isotopes in the general energy range of 60 to 4,000 keV, such as $^{125}$I, $^{123}$I, $^{124}$I, $^{62}$Cu, $^{64}$Cu, $^{18}$F, $^{111}$In, $^{67}$Ga, $^{67}$Ga, $^{99}$Tc, $^{94}$Tc, $^{11}$C, $^{13}$N, $^{15}$O, and $^{76}$BR, for radio-imaging. These and similar chelates, when complexed with non-radioactive metals, such as manganese, iron, and gadolinium may be useful for MRI diagnostic methods in connection with CD38BPs. Macrocyclic chelates such as NOTA, DOTA, and TETA are of use with a variety of metals and radiometals, most particularly with radionuclides of gallium, yttrium, and copper, respectively. Such metal-chelate complexes may be made very stable by tailoring the ring size to the metal of interest. Other ring-type chelates such as macrocyclic polyethers, which are of interest for stably binding nuclides, such as $^{223}$Ra for RAIT may also be suitable in diagnostic methods.

Thus, the present invention provides diagnostic CD38BP conjugates, wherein the CD38BP is conjugated to a contrast agent (such as for magnetic resonance imaging, computed tomography, or ultrasound contrast-enhancing agent) or a radionuclide that may be, for example, a gamma-, beta-, alpha-, Auger electron-, or positron-emitting isotope. Additional useful conjugated CD38BPs are described elsewhere herein, which may also be useful in diagnostic methods and compositions (e.g., diagnostic kits) provided by the present invention.

In one embodiment, the present invention provides a kit for diagnosis of cancer comprising a container comprising a CD38BP, such as an anti-CD38 antibody, and one or more reagents for detecting binding of the CD38BP to a CD38 peptide. Reagents may include, for example, fluorescent tags, enzymatic tags, or other detectable tags. The reagents may also include secondary or tertiary antibodies or reagents for enzymatic reactions, wherein the enzymatic reactions produce a product that can be visualized. In one embodiment, the present invention provides a diagnostic kit comprising one or more CD38BPs, such as anti-CD38 antibodies, of the present invention in labeled or unlabeled form in suitable container(s), reagents for the incubations for an indirect assay, and substrates or derivatizing agents for detection in such an assay, depending on the nature of the label. Control reagent(s) and instructions for use also may be included.

Diagnostic kits may also be supplied for use with a CD38BP, such as a conjugated/labeled anti-CD38 antibody, for the detection of a cellular activity or for detecting the presence of CD38 peptides in a tissue sample or host. In such diagnostic kits, as well as in kits for therapeutic uses described elsewhere herein, a CD38BP typically may be provided in a lyophilized form in a container, either alone or in conjunction with additional antibodies specific for a target cell or peptide. Typically, a pharmaceutical acceptable carrier (e.g., an inert diluent) and/or components thereof, such as a Tris, phosphate, or carbonate buffer, stabilizers, preservatives, biocides, biocides, inert proteins, e.g., serum albumin, or the like, also are included (typically in a separate container for mixing) and additional reagents (also typically in separate container(s)). In certain kits, a secondary antibody capable of binding to the anti-CD38 antibody or other CD38BP, which typically is present in a separate container, is also included. The second antibody is typically conjugated to a label and formulated in manner similar to the anti-CD38 antibody or other CD38BP of the present invention.

Using the methods described above and elsewhere herein CD38BPs may be used to define subsets of cancer/tumor cells and characterize such cells and related tissues/growths.

In one example, a CD38BP or anti-CD38 antibody, may be added to nitrocellulose, or other solid support which is capable of immobilizing cells, cell particles, or soluble proteins. The support may then be washed with suitable buffers followed by treatment with the detectably labeled CD38 peptide or antibody. The solid phase support may then be washed with the buffer a second time to remove unbound peptide or antibody. The amount of bound label on the solid support may then be detected by known method steps.

Linked enzymes that react with an exposed substrate may be used to generate a chemical moiety which can be detected, for example, by spectrophotometric, fluorometric or by visual means, in the context of a CD38BP conjugate and/or fusion protein. Enzymes which may be used to detectably label CD38BPs and anti-CD38 antibodies include malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholinesterase. It is also possible to label a CD38BP with a fluorescent compound. When the fluorescent labeled antibody is exposed to light of the proper wave length, its presence may be detected due to fluorescence. Among the most commonly used fluorescent labeling compounds are fluorescein isothiocyanate, rhodamine, phycoerythrin, phycocyanin, allophycocyanin, o-phthaldehyde, and fluorescamine.

The CD38BPS, such as anti-CD38 antibodies, may also be detectably labeled using fluorescence-emitting metals such as $^{152}$Eu, or others of the lanthanide series. These metals may be attached to an anti-CD38 antibody, for example, using such metal chelating groups as diethylenetriaminepentaacetic acid (DTPA) or ethylenediaminetetra-acetic acid (EDTA).

CD38BPs and anti-CD38 antibodies may also be detectably labeled by coupling to a chemiluminescent compound. The presence of the chemiluminescently labeled CD38-BP is then determined by detecting the presence of luminescence that arises during the course of a chemical reaction. Examples of particularly useful chemiluminescent labeling compounds are luminol, isoluminol, theromatic acridinium ester, imidazole, acridinium salt, and oxalate ester.

Likewise, a bioluminescent compound may be used to label a CD38BP. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase, and aequorin.

Detection of a labeled peptide or antibody, antibody fragment or derivative may be accomplished by a scintillation counter, for example, if the detectable label is a radioactive gamma emitter, or by a fluorometer, for example, if the label is a fluorescent material. In the case of an enzyme label, the detection may be accomplished by calorimetric methods which employ a substrate for the enzyme. Detection may also be accomplished by visual comparison of the extent of enzymatic reaction of a substrate in comparison with similarly prepared standards.

These and other diagnostic techniques may be used to screen any suitable material for CD38 peptides or CD38-fragments. Examples of materials that may be screened include, for example, blood, serum, lymph, urine, inflammatory exudate, cerebrospinal fluid, amniotic fluid, a tissue extract or homogenate, and the like. However, the present invention is not limited to assays using only these samples, it being possible for one of ordinary skill in the art to determine suitable conditions which allow the use of other samples.

In situ detection may be accomplished by removing a histological specimen from a patient, and providing the combination of labeled CD38BPs, such as anti-CD38 antibodies, of the present invention to such a specimen. The CD38BP, anti-CD38-antibody (or fragment) of the present invention may be provided by applying or by overlaying the labeled CD38BP, such as a labelled anti-CD38 antibody (or fragment), of the present invention to a biological sample. Through the use of such a procedure, it is possible to determine not only the presence of CD38 or CD38-fragment but also the distribution of such peptides in the examined tissue (e.g., in the context of assessing the spread of cancer cells). Using the present invention, those of ordinary skill will readily perceive that any of a wide variety of histological methods (such as staining procedures) may be modified in order to achieve such in situ detection.

The present invention further provides method of promoting the sale and/or use of a CD38BP of the present invention, comprising distributing information (such as by printed materials that are handed out, mailed, etc., by advertising signage, by television programs and advertisements, by radio programs and advertisements, by internet site postings, by email, by telemarketing, by door-to-door or person-to-person marketing, by funding and/or hosting conferences, panels, forums, etc., by employing and/or contracting for the services of salespeople and/or medical/scientific liaisons, by funding and/or hosting scientific research and publications related to such uses, etc.) related to the use of the compound in the prevention or treatment of any condition or combination of conditions as described elsewhere herein to any persons or entities of potential interest (such as pharmaceutical chains, formulary managers, insurance companies, HMOs, hospitals and hospital chains, other health care companies, pharmacy benefit managers, potential patients, cancer patients, former cancer patients, patients in remission, primary care physicians, nurses, doctors of pharmacy, and/or key opinion leaders).

The present invention also provides kits comprising a pharmaceutical composition of a compound of the present invention and instructions for use. The kit may further contain one or more additional agents, such as an immunosuppressive reagent, a chemotherapeutic reagent, an anti-inflammatory agent or a radiotoxic agent as described above, or one or more additional CD38BPs of the present invention (such as an CD38BP having a complementary activity). A kit of the present invention may also include diagnostic agents and/or other therapeutic agents. In one embodiment, a kit of the present invention includes a CD38BP of the present invention and a diagnostic agent that may be used in a diagnostic method for diagnosing the state or existence of a disorder involving cells expressing CD38 in a subject. In one embodiment, the kit includes a CD38BP of the present invention in a highly stable form (such as in a lyophilized form) in combination with pharmaceutically acceptable carrier(s) that may be mixed with the highly stabile composition to form an injectable composition.

All references, including publications, patent applications, and patents, cited herein are hereby incorporated by reference to the same extent as if each reference were individually and specifically indicated to be incorporated by reference and were set forth in its entirety herein.

All headings and sub-headings are used herein for convenience only and should not be construed as limiting the present invention in any way.

Any combination of the above-described elements in all possible variations thereof is encompassed by the present invention unless otherwise indicated herein or otherwise clearly contradicted by context.

The use of the terms "a" and "an" and "the" and similar referents in the context of describing the present invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the present invention and does not pose a limitation on the scope of the present invention unless otherwise indicated. No language in the specification should be construed as indicating any element is essential to the practice of the present invention unless as much is explicitly stated.

The citation and incorporation of patent documents herein is done for convenience only and does not reflect any view of the validity, patentability, and/or enforceability of such patent documents.

The description herein of any embodiment of the present invention using terms such as "comprising", "having," "including," or "containing" with reference to an element or elements is intended to provide support for a similar embodiment of the present invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The present invention includes all modifications and equivalents of the subject matter recited in the embodiments presented herein to the maximum extent permitted by applicable law.

All patents, pending patent applications and other publications cited herein are hereby incorporated by reference in their entirety.

The present invention is further illustrated by the following examples which should not be construed as further limiting.

EXAMPLES

Example 1

Manufacturing Luciferase-Transfected (Daudi-Luc) Cells

Culture of Daudi cells (originating from Burkitt's lymphoma) was cultured in RPMI 1640 culture medium supplemented with 10% FCS (Optimum C241, Wisent Inc., St. Bruno, QC, Canada), 2 mM L-glutamine, 100 IU/ml penicillin, 100 mg/ml streptomycin, 1 mM sodium pyruvate (all derived from Gibco BRL, Life Technologies, Paisley, Scotland). Medium was refreshed twice a week. Before transfection, cells were split and seeded out at $1-1.5 \times 10^6$ cells/ml to ensure viability and optimal growth.

Luciferase Transfection $8.2 \times 10^6$ CD38+ Daudi cells were taken up in 350 µl RPMI (supplemented with 10% dFCS, Gibco BRL) and transferred to an electroporation cuvet (Biorad, Hemel Hempstead, Herts, UK). Then, 40 µg gWIZ luciferase from GTS (Aldevron, Fargo, N. Dak., USA) and 10 µg pPur vector (BD Biosciences, Alphen a/d Rijn, The Netherlands), which confers puromycin resistance, were added. After resting cells on ice for 10 minutes, cells were electroporated (250 V, 950 µF; Gene Pulser II, Biorad Laboratories GmbH, München, Germany). Cells were again rested on ice, and taken up in 40 ml RPMI (supplemented with 10% FCS). Then, cells were plated out in 96-well tissue culture plates (100 µl per well). After 48 hours, puromycin (final concentration: 1 µg/ml; Sigma-Aldrich Chemie BV, Zwijndrecht, The Netherlands) was added. Puromycin-resistant clones were further grown in 24-well tissue culture plates.

Determination of Luciferase Activity

Luciferase activity of cells was determined using the Luciferase Assay System (#E4030, Promega, Madison, Wis., USA). $1 \times 10^5$ cells were centrifuged (13.500 rpm, 1 min) in an eppendorf centrifuge, and the pellet was washed in 100 µl PBS. After centrifugation (13.500 rpm, 1 min), pellet was lysed with 20 µl Reporter Lysis Buffer (Promega), frozen and thawed. After centrifugation (13,500 rpm, 1 min), 20 µl supernatant was discarded, and 100 µl luciferase assay reagent was added (in special luminometer tubes, Promega). Luminescence was measured (10 sec) in a luminometer (LB9507, Berthold, Vilvoorde, Belgium).

Example 2

Immunization of Mice and Generation Og Hybridomas

Immunization Protocol for −003

HCo12 mice were immunized every fortnight with 20 µg purified HA-CD38. The first immunization was performed i.p. in the presence of 100 µl PBS, mixed with 100 µl Complete Freund's Adjuvant (CFA). After this first immunization, subsequent boosts (13×) with purified HA-CD38 were performed in the presence of 100 µl PBS, mixed with 100 µl Incomplete Freund's Adjuvant (IFA) alternating s.c. and i.p. After titer development, mice were boosted with 20 µg HA-CD38 in PBS, i.v.

Immunization Protocol for −005 and −024

HCo12 mice were immunized every fortnight with 20 µg purified HA-CD38 alternating with NIH-3T3-CD38 transfected cells. The first immunization was performed with $5 \times 10^6$ cells in 100 µl PBS, mixed with 100 µl CFA, i.p., the second and following immunizations with HA-CD38 s.c., in the presence of 100 µl PBS, mixed with 100 µl IFA. The following immunizations with transfected cells were performed in the presence of 200 µl PBS. After titer development, mice were boosted with 20 µg HA-CD38 in PBS, i.v.

Generation of Hybridomas Producing Human Monoclonal Antibodies to CD38

The mouse splenocytes were isolated from HCo12 mice and fused with PEG to a mouse myeloma cell line based upon standard protocols. The resulting hybridomas were then screened for human antibody production by ELISA and for CD38 specificity using human CD38-transfected NS/0 cells by FACS analysis and recombinant HA-CD38 protein binding by ELISA. Three hybridoma cell lines were selected expressing the human monoclonal anti-CD38 antibodies, −003, −005 and −024, respectively.

Example 3

Transfection of NIH Cells with CD38

The vector (pclpuroCD38) for producing NIH-3T3-CD38 cells was obtained from Prof. M. Glennie (Tenovus Research Laboratory, Southampton General Hospital, Southampton, UK). NIH-3T3 cells (DSMZ, ACC 59; 150,000 cells/well; 0.5 ml; 96-well flat-bottom plates, Greiner) were cultured in DMEM (supplemented with glucose [4.5 g/l], 10% FCS, L-glutamine, Na-pyruvate; BioWhittaker) for 24 h. Then, DNA (0.8 μg) and lipofectamine (Invitrogen, Breda, The Netherlands) were diluted in DMEM, and mixed (20 min, RT). Thereafter, the mixture (100 μl) was added to each well and incubated (ON, 37° C.).

Screening for CD38 Expression

NIH-3T3-CD38 cells were washed (in 1 ml PBS) and trypsinized (200 μl, trypsin-EDTA, BioWhittaker). Then, 1 ml of DMEM was added and the mixture pipetted into FACS tubes. After centrifugation (1200 rpm, 5 min), cells were washed in FACS Buffer (FB; PBS, 0.05% BSA, 0.02% $NaN_3$) and resuspended in 1 ml FB. After centrifugation (1200 rpm, 5 min), supernatant was removed and mouse anti-human CD38-PE was added (1/50 dilution, Sanquin, Amsterdam, The Netherlands). After washing the cells twice in FB, cells were resuspended in FB for acquisition by flow cytometry.

Expansion and Selection

After trypsine treatment, cells were transferred to T25 flasks (Greiner) in DMEM (supplemented with glucose 4.5 g/l, 2 mM L-glutamine, and puromycin (2 μg/ml) BioWhittaker). Puromycin-resistant cells were tested for stable CD38 expression by flow cytometry after two weeks on puromycin-containing medium. NIH-3T3-CD38 selected cells were subcloned by limiting dilution. After expanding these cells, all 15 NIH-3T3-CD38 clones were screened for CD38 expression. CD38high NIH-3T3-CD38 cells were frozen in liquid nitrogen (−80° C.) until use.

Culture of NIH-3T3-CD38 Cells

Cells are cultured in DMEM (supplemented with glucose (4.5 g/l), 10% FCS, 2 mM L-glutamine, Na-pyruvate, penicillin, streptomycin). Cells are passaged twice a week by use of trypsin/EDTA and seeded in a concentration of $1 \times 10^6$ cells/T75 flask. CD38high NIH-3T3-CD38 cells were frozen in liquid nitrogen (−80° C.) until use.

Purification of HA-CD38 Antigen

Sepharose 4B (Amersham Bioscience, Uppsala, Sweden) was coupled with anti-CD38 antibody (Serotec, Oxford, UK). Column (column tube HR5/20 was packed to 12 cm bedheight, column volume 2.4 ml; maximum flow rate 0.5 ml/min) was equilibrated with at least 5 column volumes (CV) of PBS. Sample was filtrated and loaded to the column. Column was washed with PBS until signal returned to baseline (approximately 3 CV). Elution was carried out with 0.1 M glycine at pH 2. Eluted fractions were neutralized with 1% (v/v) 2 M Tris-HCl, pH 9.

Purification of Anti-CD38 Antibodies

Human anti-CD38 antibodies were purified from tissue culture supernatants. First, the supernatants were filtered over 0.20 μM dead-end filter. Then, the supernant was loaded on a 5 ml Protein A column (rProtein A FF, Amersham Bioscience) and eluted with 0.1 M citric acid-NaOH, pH 3. The eluate was immediately neutralized with 2 M Tris-HCl, pH 9 and dialyzed O/N to 12.6 mM sodium phosphate, 140 mM NaCl, pH 7.4 (B. Braun, Oss, The Netherlands). After dialysis samples were sterile filtered over 0.20 μM dead-end filter.

Purification of His-CD38 Batches

The protein is present in cell culture supernatant of His-CD38-expressing cells, with a DNA construct containing the sequence for the extracellular domain of CD38. An additional poly-His-tag sequence is included in the constructs and present at the N-terminus of the protein. This tag enables purification with immobilized metal affinity chromatography. In this process, a chelator fixed onto the chromatographic resin is charged with $Co^{2+}$ cations. Particularly, a sequence that includes 6 histidine amino acids strongly binds $Co^{2+}$. Therefore the His-tagged CD38 proteins bind strongly to such a column, while other proteins present in the culture supernatant will flow through the column or will be washed away. The strongly bound His-tagged CD38 proteins are then eluted with a buffer containing imidazole, which competes with the binding of His to $Co^{2+}$. When sufficient His-CD38 is purified, the eluent is removed from the protein by buffer exchange on a desalting column.

Example 4

Binding of −003, −005, and −024 to CD38-Transfected CHO(CHO-CD38) Cells, to Daudi-Luc Cells and to Fresh Multiple Myeloma (MM) Tumor Cells After harvesting and counting, Daudi-luc cells, CHO cells transfected with CD38 and control CHO cells were resuspended in PBS ($1 \times 10^6$ cells/ml). Then, cells were put in 96-well V-bottom plates (100 μl/well) and washed twice in PBS-BSA (PBS supplemented with 0.1% BSA and 0.02% Na-azide). Thereafter, 50 μl antibody solution in PBS-BSA was added to the cells (4° C., 30 min). After washing three times in PBS-BSA, 50 μl (1:400 dilution) of rabbit anti-human IgG-FITC in PBS-BSA was added (4° C. in the dark, 30 min). Cells were washed three times and specific binding of CD38-antibodies to CHO-CD38 and Daudi-luc cells was detected by flow cytometry. HuMab-KLH (a human monoclonal antibody against KLH (keyhole limpet haemocyanin) generated by Genmab B. V., Utrecht, The Netherlands by use of the immunization protocols described elsewhere herein) was used as a control. FIGS. 1 and 2 show that −003, −005, and −024 bind to CHO-CD38 cells and to Daudi-luc cells, albeit with different $EC_{50}$ (Table 1). No binding to control CHO cells is observed (data not shown).

Fresh MM tumor cells were obtained from Dr. Lokhorst (University Medical Center Utrecht, Utrecht, The Netherlands. Tumor cells were isolated from bonemarrow of multiple myeloma patients by Ficoll (Bio Whittaker; lymphocyte separation medium, cat 17-829E) gradient centrifugation. After harvesting and counting, MM cells (100,000 cells/well) were resuspended with 25 μl FITC-labeled CD38-specific antibodies and 25 μl CD138. After incubation (4° C., 30 min), cells were washed in PBS-BSA and PE-labeled goat-anti-mouse IgG (1:200; Jackson ImmunoResearch Europe Ltd. Soham, UK) was added. After incubation (4° C., 30 min) and washing of the cells in PBS-BSA, fluorescence was measured by flow cytometry.

FIG. 3 shows that −003, −005 and −024 bind to MM cells.

TABLE 1

$EC_{50}$ values of binding of anti CD38-antibodies on CHO-CD38 cells, Daudi-luc cells and fresh MM tumor cells.

| CD38-specific antibodies | $EC_{50}$ CHO-CD38 (μg/ml) | $EC_{50}$ Daudi-luc (μg/ml) | $EC_{50}$ MM cells (μg/ml) |
|---|---|---|---|
| −003 | 0.54 | 0.26 | 0.56 |
| −005 | 0.23 | 0.09 | 0.04 |
| −024 | 0.08 | 0.05 | 0.02 |

Example 5

Antibody-Dependent Cell-Mediated Cytotoxicity

Daudi-luc cells, fresh multiple myeloma tumor cells, fresh Plasma Cell Leukemia tumor cells and JK6L and AMO-1 multiple myeloma cells were collected ($5 \times 10^6$ cells) in RPMI$^{++}$ (RPMI 1640 culture medium supplemented with 10% cosmic calf serum (HyClone, Logan, Utah, USA)), to which 100 µCi $^{51}$Cr (Chromium-51; Amersham Biosciences Europe GmbH, Roosendaal, The Netherlands) was added, and the mixture was incubated in a 37° C. water bath for 1 hr. After washing of the cells (twice in PBS, 1500 rpm, 5 min), the cells were resuspended in RPMI$^{++}$ and counted by trypan blue exclusion. Cells were brought at concentration of $1 \times 10^5$ cells/ml.

Preparation of Effector Cells

Fresh peripheral blood mononuclear cells (healthy volunteers, UMC Utrecht, Utrecht, The Netherlands) were isolated from 40 ml of heparin blood by Ficoll (Bio Whittaker; lymphocyte separation medium, cat 17-829E) according to the manufacturer's instructions. After resuspension of cells in RPMI$^{++}$, cells were counted by trypan blue exclusion and brought at concentration of $1 \times 10^7$ cells/ml.

ADCC Set Up

50 µl of $^{51}$Cr-labeled targets cells were pipetted into 96-well plates, and 50 µl of antibody was added, diluted in RPMI$^{++}$ (final concentrations 10, 1, 0.1, 0.01 µg/ml). Cells were incubated (RT, 15 min), and 50 µl effector cells were added, resulting in an effector to target ratio of 100:1 (for determination of maximal lysis, 100 µl 5% Triton-X100 was added instead of effector cells; for determination of spontaneous lysis, 50 µl target cells and 100 µl RPMI$^{++}$ were used). Cells were spun down (500 rpm, 5 min), and incubated (37° C., 5% CO$_2$, 4 hr). After spinning down cells (1500 rpm, 5 min), 100 µl of supernatant was harvested into micronic tubes, and counted in gamma counter. The percentage specific lysis was calculated as follows:

(cpm sample–cpm target cells only)/(cpm maximal lysis–cpm target cells only) wherein cpm is counts per minute.

In Daudi-luc cells (FIG. 4 and Table 2) -003, -005, and -024 induce lysis by ADCC, and -003, and -005 perform slightly better than rituximab (anti-CD20 mAb). Interestingly, also when fresh multiple myeloma tumor cells (obtained from Dr. H. Lokhorst, UMCU, The Netherlands) are used as target cells, ADCC is induced by -003, -005 and -024 (FIG. 5A and Table 2).

TABLE 2

EC$_{50}$ values of CD38-specific antibodies obtained in ADCC

| CD38-specific antibodies | EC$_{50}$ Daudi-luc (ng/ml) | EC$_{50}$ MM cells (ng/ml) |
|---|---|---|
| -003 | 9.0 | 27 |
| -005 | 4.5 | 5.7 |
| -024 | 9.7 | 56 |

Enrichment of Human Peripheral Blood Mononuclear Cells Erlangen

Human blood from human volunteers (university Erlangen, Erlangen, Germany) was diluted twice in RPMI 1640 and blood cells were layered on Ficoll (Lymphocyte Separation Medium 1077 g/ml, 710 g, RT, 20 min; BioWhittaker, Cambrex Bio Science Verviers, Verviers, Belgium, cat. 17-829E, lot no. 0148 32). Peripheral blood mononuclear cells (MNCS) were collected from the interphase, washed and resuspended in RPMI 1640 culture medium supplemented with 10% FCS, 2 mM L-glutamine, 5 U/ml penicillin, 50 µg/ml streptomycin (all derived from BioWhittaker) to which 25 mM HEPES (BioWhittaker) was added.

ADCC Set Up II

Target B-cells (fresh plasma cell leukemia tumor cells, JK6L and AMO-1 B-cell lines, obtained from Dr. T. Valerius, University of Erlangen, Erlangen, Germany) were labeled with 20 µCi $^{51}$Cr (Amersham Biosciences, Uppsala, Sweden) for 2 hours. After extensive washing in RPMI-10, cells were adjusted to $1 \times 10^6$ cells/ml. MNCs (50 µl), sensitizing antibodies (50 µl), and RPMI-10 (50 µl) were added to round-bottom microtiter plates (Greiner Bio-One GmbH, Frickenhausen, Germany). Assays were started by adding fresh plasma cell leukemia tumor cells, JK6L or AMO-1 cells (50 µl) giving a final volume of 200 µl. An effector to target (E:T) ratio of 40:1 was used. After incubation (3 hr, 37° C.), assays were stopped by centrifugation, and $^{51}$Cr release from triplicates was measured in counts per minute (cpm) in a scintillation counter. Percentage of cellular cytotoxicity was calculated using the following formula:

% specific lysis=(experimental cpm–basal cpm)/ (maximal cpm–basal cpm)×100 with maximal $^{51}$Cr release determined by adding perchloric acid (3% final concentration) to target cells, and basal release was measured in the absence of sensitizing antibodies and effector cells.

Figure 6:
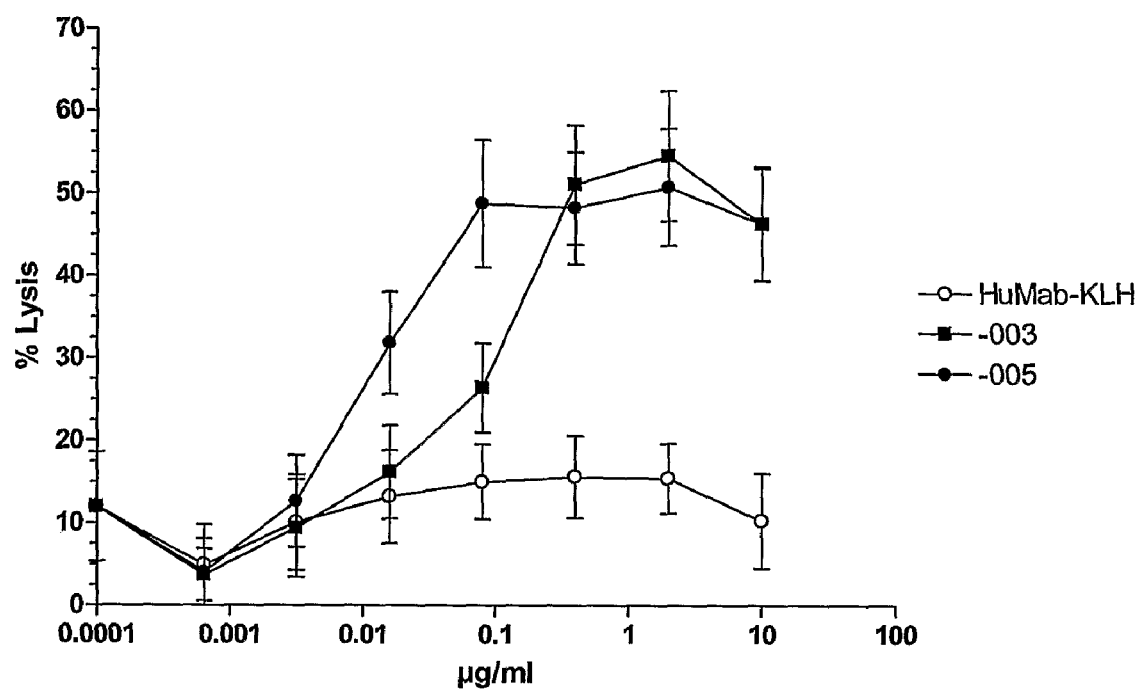
FIG. 6 shows the ability of −003 and −005 to induce lysis of JK6L (a multiple myeloma cell line) by ADCC as compared to HuMab-KLH. The experimental setup is described in Example 5.
Figure 7:
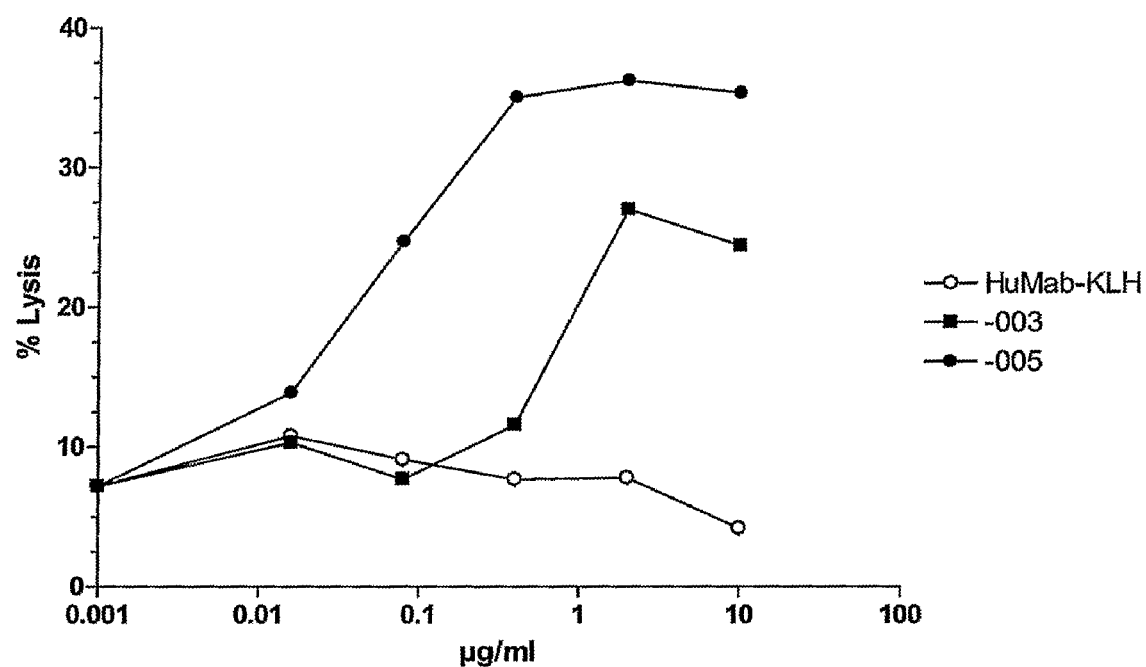
FIG. 7 shows the ability of −003 and −005 to induce lysis of AMO-1 (a multiple myeloma cell line) by ADCC as compared to HuMab-KLH. The experimental setup is described in Example 5.

In both multiple myeloma cell lines (i.e. JK6L and AMO-1), lysis is induced with both -003 and -005 (FIGS. 6 and 7), even when CD38 expression is low (AMO-1 cell line).

-003, -005 and -024 induce ADCC of plasma cell leukemia primary tumor cells (FIG. 5B).

Example 6

Complement-Dependent Cytotoxicity

After harvesting and counting of Daudi-luc cells, the viability of the cells should be ≧90%. After washing (PBS), cells are resuspended at $2.0 \times 10^6$ cells/ml in RPMI-B (RPMI supplemented with 1% BSA). Thereafter, cells are put in 96-well round-bottom plates at $1 \times 10^5$ cells/well (50 µl/well). Then, 50 µl antibodies is added to the wells (final concentration range between 0-100 µg/ml (three-fold dilutions in RPMI-B)). After incubation (RT, 15 min), 11 µl of pooled human serum (pool of 18 healthy donors) was added to each well (37° C., 45 min). Wells were resuspended once and 120 µl was transferred to FACS tubes (Greiner). Then, 10 µl propidium iodide (PI; Sigma-Aldrich Chemie B.V.) was added (10 µg/ml solution) to this suspension. Lysis was detected by flow cytometry (FACScalibur™, Becton Dickinson, San Diego, Calif., USA) by measurement of the percentage of dead cells (corresponds to PI-positive cells).

Figure 8:
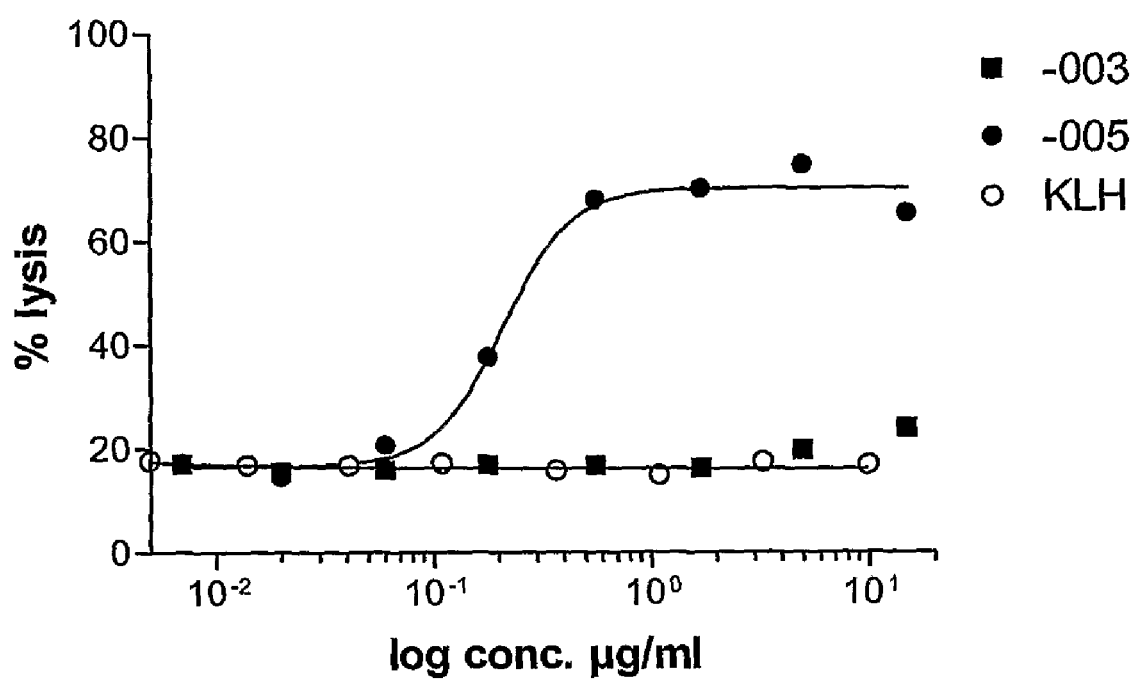
FIG. 8 shows the CDC-mediated lysis of Daudi-luc cells induced by −003 and −005 compared to HuMab-KLH. The experimental setup is described in Example 6.
Figure 10:
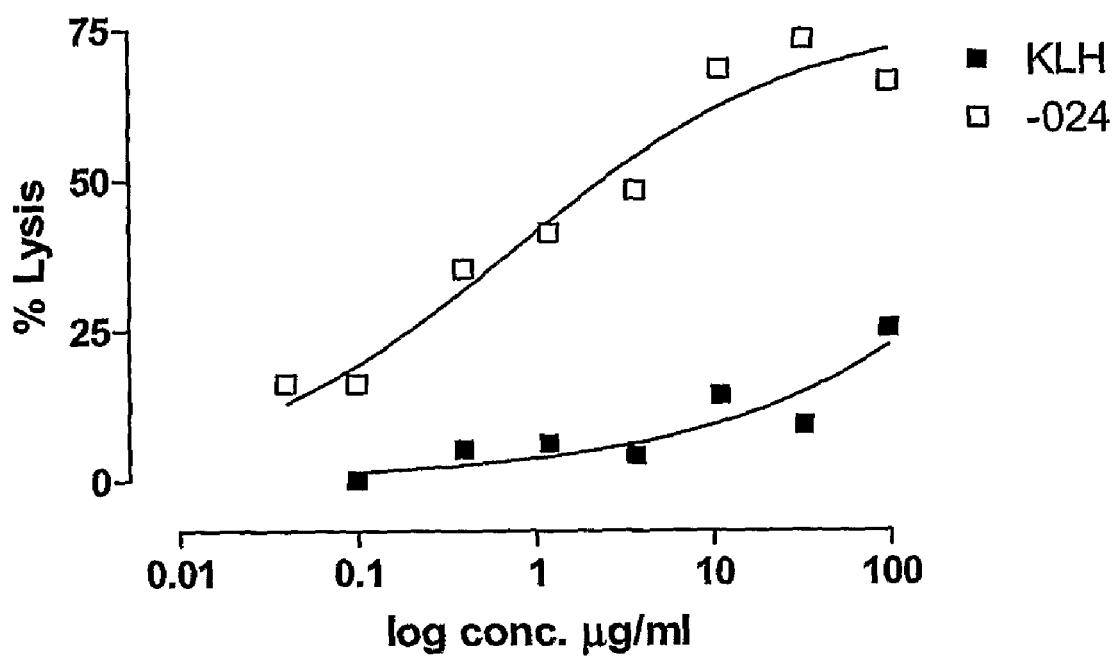
FIG. 10A shows the CDC-mediated lysis of 3% refractory tumor cells in the presence of −003, −005 and HuMab-KLH. The experimental setup is described in Example 6.
FIG. 10B shows the CDC-mediated lysis of 9% refractory tumor cells in the presence of −003, −005 and HuMab-KLH. The experimental setup is described in Example 6.
FIG. 10C shows the CDC-mediated lysis of 3040% tumor cells in the presence of −003, −005 and HuMab-KLH. The experimental setup is described in Example 6.
FIG. 10D shows the CDC-mediated lysis of 70% tumor cells in the presence of −003, −005 and HuMab-KLH. The experimental setup is described in Example 6.
FIG. 10E shows the CDC-mediated lysis of multiple myeloma cells in the presence of −024 and HuMab-KLH. The experimental setup is described in Example 6.

FIG. 8 and Table 2 show that lysis of Daudi-luc cells is induced by -005 (-60% maximum lysis) and that lysis by -003 is only seen at very high antibody concentrations. -024 does not induce CDC in Daudi cells (data not shown). In CHO-CD38 cells, lysis is induced by both -003, -005, and -024 (FIG. 9 and Table 3). Lysis by -003 is induced at higher concentrations. In tumor cells (all obtained from Dr. Lokhorst and Dr. Bloem, University Medical Center Utrecht, The Netherlands), obtained from different MM patients (A: 3% refractory tumor cells, B: 9% refractory tumor cells, C: 30-40% tumor cells, and D: 70% tumor cells), CDC-mediated lysis is observed in the presence of −005, but not in the presence of −003 (FIG. 10). −024 also induced lysis of MM tumor cells (FIG. 10E).

TABLE 3

$EC_{50}$ values of CD38-specific antibodies obtained in CDC

| CD38-specific antibodies | $EC_{50}$ Daudi-luc (µg/ml) | $EC_{50}$ CD38-CHO (µg/ml) |
|---|---|---|
| −003 | >90 | 3.14 |
| −005 | 0.33 | 0.14 |
| −024 | >90 | 0.24 |

Example 7

Cross-Block Studies Using FACS

CHO-CD38 cells were incubated with an excess of unlabelled CD38-specific antibody (4° C., 15 min). Then, cells were incubated with FITC-labeled CD38-specific antibodies (concentration approximates $EC_{90}$, 4° C., 45 min). After twice washing the cells with PBS-BSA, fluorescence was measured by flow cytometry. FIG. 11 shows that unlabelled −003 blocks binding of FITC-labeled −003, whereas binding of FITC-labeled −005 is not blocked. Also unlabelled −005 blocks binding of FITC-labeled −005, whereas binding of FITC-labeled −003 is not blocked. −003 and −005 bind to different epitopes, because they do not compete for binding.

Example 8

Cross-Blocking Studies Using ELISA

Soluble human CD38 is coated on the surface of an ELISA plate. Coated CD38 is incubated with an excess of unlabelled CD38 specific antibodies for about 15 minutes and subsequently biotinylated CD38-specific antibodies are added (concentration approximates $EC_{90}$, RT, 1 hour). After washing three times with PBS/Tween, horseradish peroxidase (HRP)-conjugated streptavidine is added and the mixture is incubated for 1 hour at RT. The complex can be detected by addition of an ABTS-solution and the HRP mediated substrate conversion is measured using an ELISA reader at OD 405 nm.

Example 9

Cross-Blocking Studies Using Sandwich-ELISA

CD38 specific antibodies are coated on the surface of an ELISA plate. Plate-bound antibodies are incubated with biotinylated soluble CD38 in the presence of an excess of CD38 specific antibodies in fluid phase. After washing with PBS/Tween, bound biotinylated CD38 is detected with HRP-conjugated streptavidine for 1 hr at RT. This complex can be detected by addition of an ABTS-solution (after washing with PBS/Tween) and the HRP mediated substrate conversion is measured using an ELISA reader at OD 405 nm.

Example 10

Reactivity with a Panel of Human Tissues and Cross-Reactivity with Cynomolgus Tissue by Immunohistochemistry Sections from frozen human tissue (obtained from Dr. H. Niessen, Free University Medical Center, Amsterdam, The Netherlands) or monkey tissue (Inveresk Research, Glasgow, Scotland) were cut at 6 µm and air-dried overnight. These cryostat sections were fixed in acetone (RT, 10 min) and air-dried (approx. 5 min). Thereafter, sections were incubated with 1× citric acid/phosphate buffer containing 0.1% $H_2O_2$ (pH 5.8; Sigma), to block endogenous peroxidase. After 20 min at RT, sections were washed twice with PBS and 0.05% Tween-20 (PBST, RT, 5 min; Riedel de-Haen, Germany). Then, sections were incubated with avidin (RT, 15 min; DAKO, Glostrup, Denmark), washed twice with PBST, and incubated with biotin (RT, 15 min; DAKO) to block endogenous biotin. After washing the sections twice with PBST, sections were pre-incubated with PBST++ (PBST supplemented with 10% normal human serum (NHS, CLB, Amsterdam, Netherlands) and 10% normal goat serum (NGS; DAKO) (RT, 20 min). After blotting-off of the pre-incubation serum, sections were incubated with FITC-labeled primary antibody diluted in 2% PBST++ at the indicated concentrations (RT, 60 min). Thereafter, sections were incubated with rabbit-anti-FITC (1:1000; DAKO) in 2% PBST++ (RT, 30 min). After washing the sections with PBST, sections were incubated with goat-anti-rabbit-biotin (1:400; DAKO) in 2% PBST++ (RT, 30 min). Then, sections were washed and incubated with SABC-HRP (1:100; DAKO) in 2% PBST++ (RT, 30 min). After washing the sections twice in PBST, they were incubated (RT, 10 min) with amino-ethyl-carbazole (AEC)-development solution (50 mM acetate buffer, pH4.9, 0.01% $H_2O_2$; Riedel-de-Haen). Finally, sections were washed in millipore $H_2O$ (5 min) and counterstained with hematoxylin (DAKO). By use of glycergel (37° C.), sections were fixed with cover slips, and studied by light microscopy (Axiovision-2; Zeiss, Thornwood, N.Y., USA).

Figure 12A:
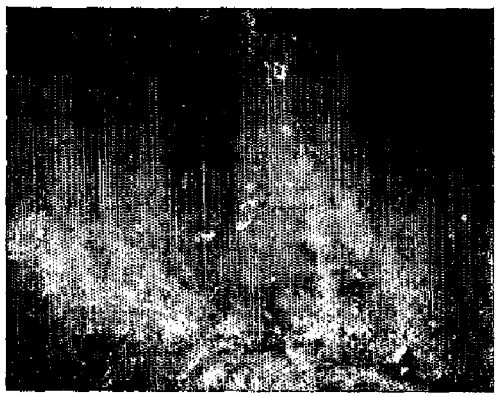
FIG. 12A shows the immunohistological staining of macrophages, lymphocytes and plasma B cells with −003. The experimental setup is described in Example 10.
Figure 12B:
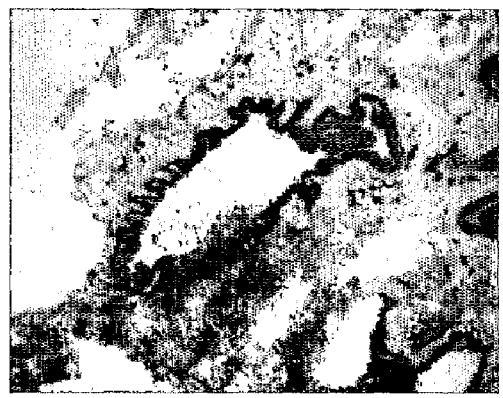
FIG. 12B shows the immunohistological staining of bronchial epithelium with −003. The experimental setup is described in Example 10.
Figure 12C:
FIG. 12C shows the immunohistological staining of myocytes with −003. The experimental setup is described in Example 10.
Figure 12D:
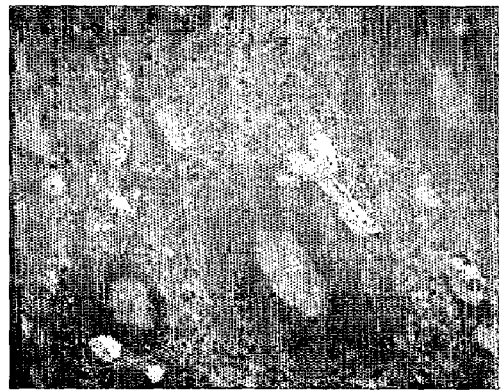
FIG. 12D shows the immunohistological staining of cynomolgus lymphoid tissue with −003. The experimental setup is described in Example 10.
Figure 13A:
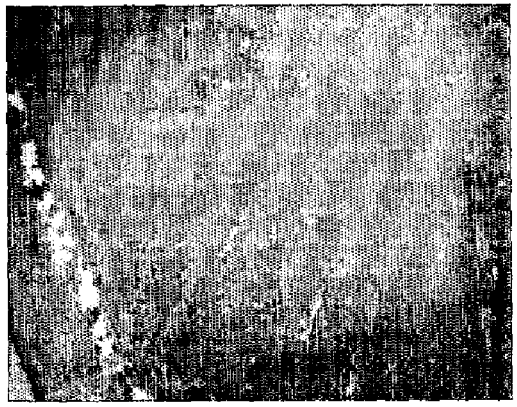
FIG. 13A shows the immunohistological staining of macrophages, lymphocytes and plasma B cells with −005. The experimental setup is described in Example 10.
Figure 13B:
FIG. 13B shows the immunohistological staining of bronchial epithelium with −005. The experimental setup is described in Example 10.
Figure 13C:
FIG. 13C shows the immunohistological staining of myocytes with −005. The experimental setup is described in Example 10.
Figure 13D:
FIG. 13D shows the immunohistological staining of cynomolgus lymphoid tissue with −005. The experimental setup is described in Example 10.

Bronchial epithelium is stained with −003 and −005 (FIGS. 12B and 13B) as well as striated muscle (myocytes, FIGS. 12C and 13C), macrophages, lymphocytes and plasma B cells (FIGS. 12A and 13A). −024 has a similar staining of striated muscle and bronchial epithelium, but staining was less intense. No staining of endothelial cells is observed, neither with −003 (FIG. 14D), −005 (14E) nor −024 (data not shown), whereas clear staining was observed with the positive control antibodies against endothelial cell markers CD31 (FIG. 14A) and vWF (14B). Anti-KLH was used as negative control antibody (FIG. 14C). −003 (FIG. 12D) and −024 (data not shown) but not −005 (FIG. 13D) cross-react with cynomolgus monkey lymphoid tissue.

Example 11

Cross-Reactivity with Cynomolgus or Rhesus Monkey Peripheral Blood Mononuclear Cells (PBMCs) by Flow Cytometry 5 ml of cynomolgus monkey peripheral blood (Inveresk Research) were lysed by adding 4.5 ml shock buffer (1.7 mM NH4CL, 1 mM EDTA), 40 ml $H_2O$ and 450 µl 10% $KHCO_3$. After hemolysis cells were centrifuged (1200 rpm, 10 min)

and washed thrice in PBS. After counting cells with trypan blue, cells were resuspended in PBS-BSA ($1\times10^6$ cell/ml).

17.5 ml of rhesus monkey peripheral blood (BPRC, Rijswijk, The Netherlands) was diluted 1:1 with RPMI 1640 and layered on Ficoll (1.077 g/ml; BioWhittaker, cat. 17-829E, lot no. 0148 32). After centrifugation (710 g, RT, 20 min), the interphase was collected and washed twice in RPMI. After the last wash cells were resuspended in RPMI 1640 at a concentration of $1\times10^5$ cells/50 µl.

Cells were transferred to 96-well plate (100,000 PBMCs/welll), washed in FACS buffer (PBS, 0.05% BSA, 0.02% $NaN_3$) and incubated with the primary antibodies (4° C., 30 min). After washing in PBS-BSA, 50 µl FITC-labeled rb-anti-higG (DAKO, Glostrup, Denmark) was added (4° C., 30 min). Finally, cells were collected in FACS tubes in a total volume of 150 µl. Samples were measured and analyzed by use of FACScalibur™ (Becton Dickinson, San Diego, Calif., USA).

Figure 15A:
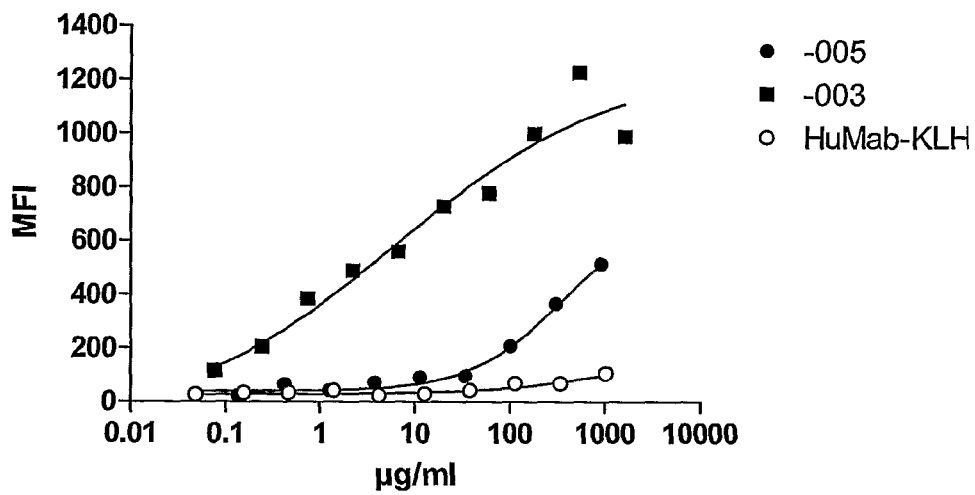
FIG. 15A shows the cross-reactivity of −003 and −005 compared to HuMab-KLH on cynomolgus lymphocytes as measured by flow cytometry. The experimental setup is described in Example 11.
Figure 15B:
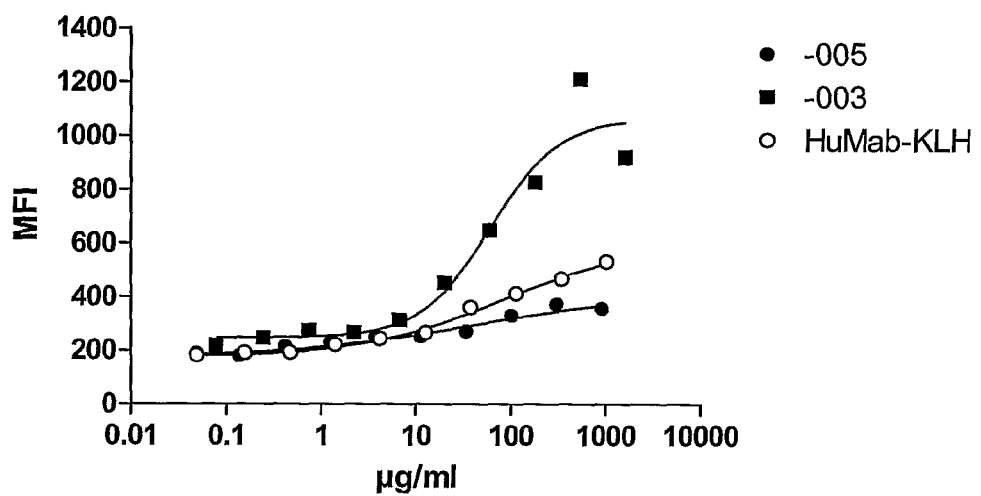
FIG. 15B shows the cross-reactivity of −003 and −005 compared to HuMab-KLH on cynomolgus monocytes as measured by flow cytometry. The experimental setup is described in Example 11.
Figure 15C:
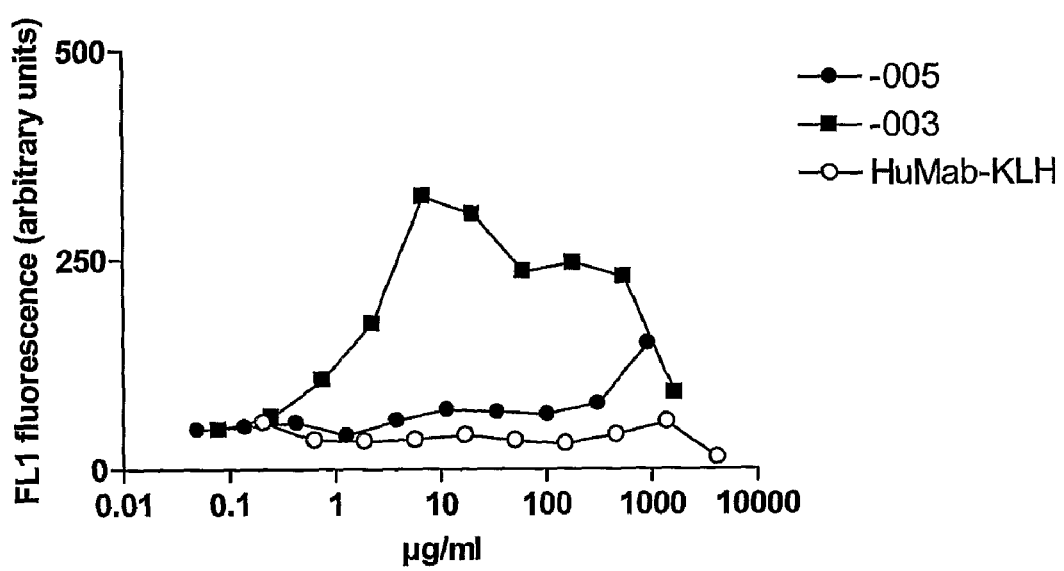
FIG. 15C shows the cross-reactivity of −003 and −005 compared to HuMab-KLH on rhesus monkey PBMCs as measured by flow cytometry. The experimental setup is described in Example 11.

With flow cytometry cross-reactivity of –003 on cynomolgus lymphocytes (FIG. 15A) and monocytes (FIG. 15B) was shown, but not of –005. Also in rhesus monkeys, cross-reactivity of –003 was observed on mononuclear cells, but not of –005 (FIG. 15C).

Example 12

Internalization Experiments

CHO-CD38 cells were stained with a saturating concentration of FITC-labeled CD38-specific antibodies (on ice, 30 min). After washing of cells (in RPMI1640 supplemented with 10% FCS), one cell pool was warmed up to 37° C. to allow internalization, and the other pool was left on ice. At several time intervals (0-120 min) cell aliquots were taken and transferred to ice-cold PBS-BSA to stop internalization. After washing samples twice with PBS-BSA, EtBr (diluted in PBS-BSA, final concentration 2 mg/ml) was added to the samples to quench membrane-bound FITC. Fluorescence was measured by flow cytometry.

Figure 16A:
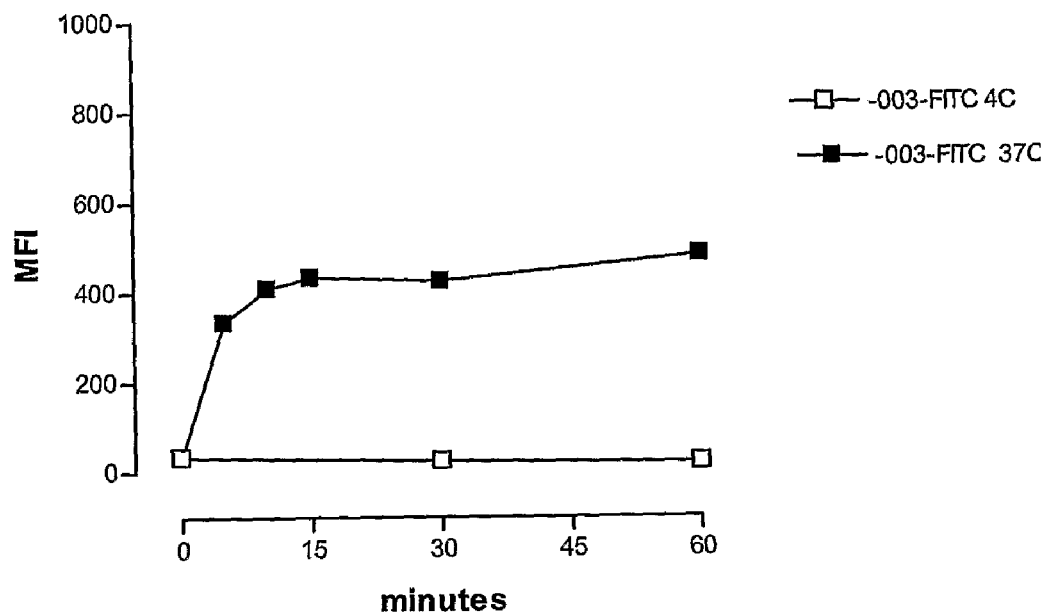
FIG. 16A shows the internalization of −003 as measured by EtBr-quenching. The experimental setup is described in Example 12.
Figure 16B:
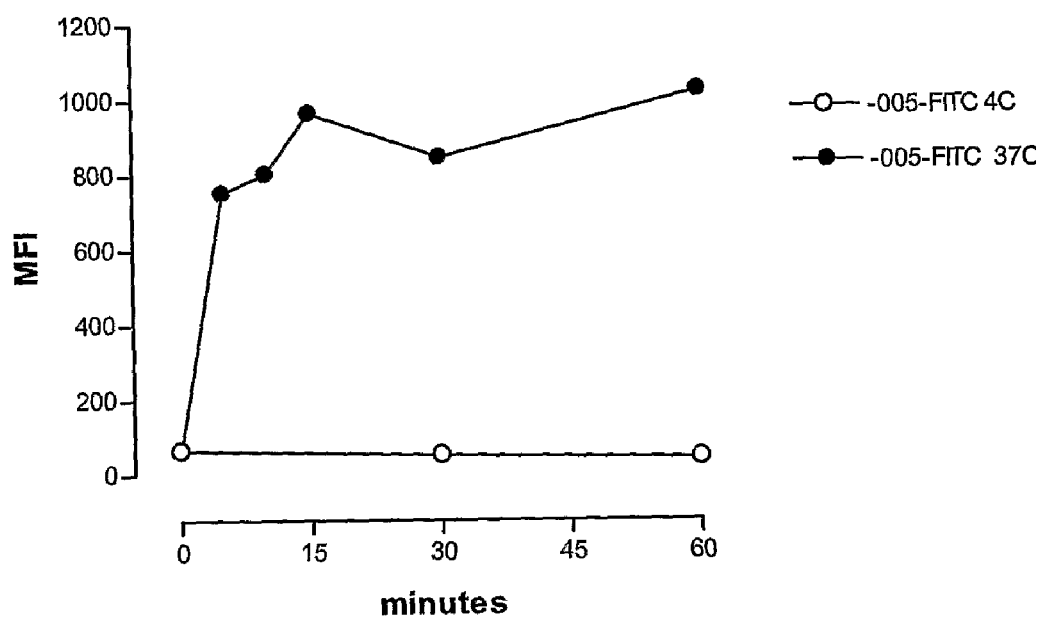
FIG. 16B shows the internalization of −005 as measured by EtBr-quenching. The experimental setup is described in Example 12.

FIGS. 16A and 16B show that –003 and –005 are internalized by CHO-CD38 cells within 5 minutes at 37° C.

Example 13

In Vivo SCID-Luciferase Experiments

In this model tumor cells are transfected with firefly luciferase. Upon administration of luciferin (Molecular Probes, Leiden, The Netherlands) to the mice the labeled cells can be detected in vivo by bioluminescent imaging using a highly sensitive CCD camera, cf. Wetterwald et al., American Journal of Pathology 160(3), 1143-1153 (2002).

Daudi cells were transfected with gWIZ luciferase from Gene Therapy Systems (San Diego, Calif.) and cultured in RPMI with 10% FCS, Pen/Strep, Sodium Pyruvate and 1 µg/ml puromycin (Sigma). Cells were analysed for luciferase expression (expressed in RLU/$1\times105$ cells) in a luminometer and for CD38 expression by FACS. $2.5\times10^6$ luciferase-transfected Daudi cells/mouse were injected i.v. into SCID mice. Mice were treated with –003, –005, isotype control antibody (HuMab-KLH) or rituximab (anti-CD20 antibody). Antibodies were injected intraperitoneally. Four treatment settings were used (see Table 4). In the preventive setting, antibody (100 µg/mouse) and cells were administered simultaneously. In therapeutic setting I, antibody (300 µg/mouse) was administered 7 days after administration of cells. In therapeutic setting II, antibody (10 µg/mouse) was administered 14 days after administration of cells. In therapeutic setting III, antibody (100 µg/mouse) was administered 7 days after administration of cells. For imaging, mice were anesthetized by i.p. injection of a mixture of ketamine/xylazine/atropine. Synthetic D-Luciferin (sodium salt, Molecular Probes) was given i.p. at a dose of 25 mg/ml. Mice were then placed in a light tight box and after 3 min, imaging was started using a VersArray 1300B liquid nitrogen cooled CCD detector (Roper Scientific). Photons emitted from the luciferase were counted over an exposure period of 5 min. Under illumination black and white images were made for reference. MetaVue software (Universal Imaging Corp) was used for data collection and image analysis. Statistical significance of differences between groups was established using one-way analysis of variance with a Newman-Keuls post test using GraphPad PRISM version 3.02 (Graphpad Software Inc).

TABLE 4

Treatment settings for in vivo luciferase experiments

| Experimental setting | Antibody treatment (days after cell inoculation) | Antibody dose (µg/mouse) |
|---|---|---|
| Preventive setting | 0 | 100 |
| Therapeutic setting | 7 | 300 |
| Therapeutic setting II | 14 | 10 |
| Therapeutic setting III | 7 | 100 |

Figure 17A:
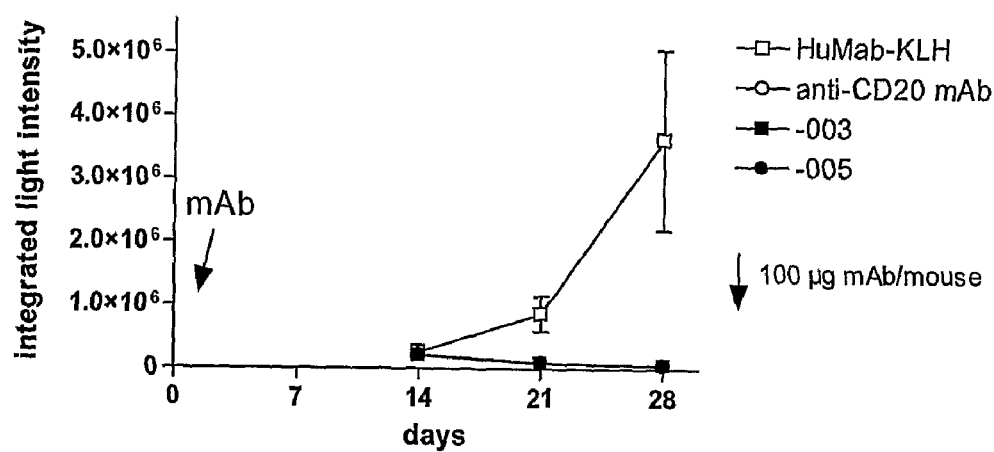
FIG. 17A shows the inhibition caused by −003 and −005 compared to an anti-CD20 monoclonal antibody (rituximab) and HuMab-KLH of the growth of tumor cells in a preventive setting as measured by in vivo SCID luciferase imaging. The experimental setup is described in Example 13.
Figure 17B:
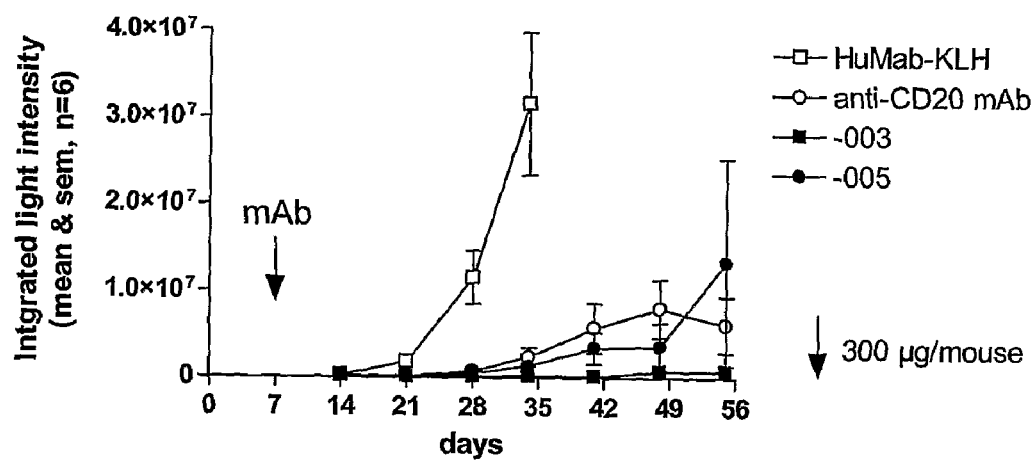
FIG. 17B shows the inhibition caused by −003 and −005 compared to an anti-CD20 monoclonal antibody (rituximab) and HuMab-KLH of the growth of tumor cells in therapeutic setting I as measured by in vivo SCID luciferase imaging. The experimental setup is described in Example 13.
Figure 17C:
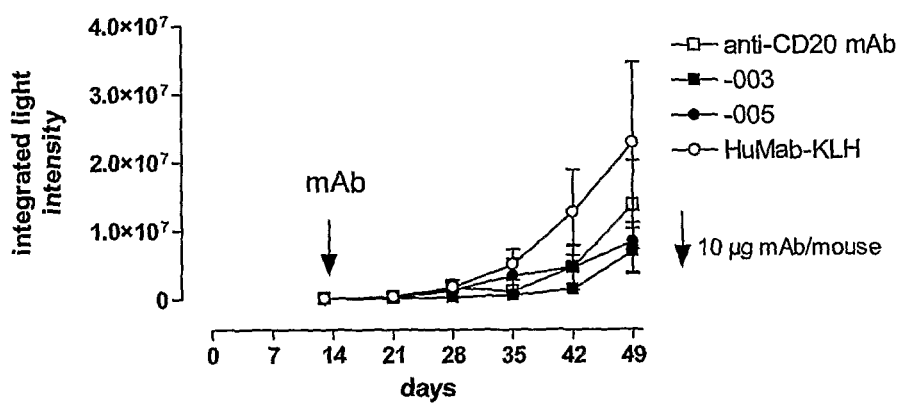
FIG. 17C shows the inhibition caused by −003 and −005 compared to an anti-CD20 monoclonal antibody (rituximab) and HuMab-KLH of the growth of tumor cells in therapeutic setting II as measured by in vivo SCID luciferase imaging. The experimental setup is described in Example 13.
Figure 17D:
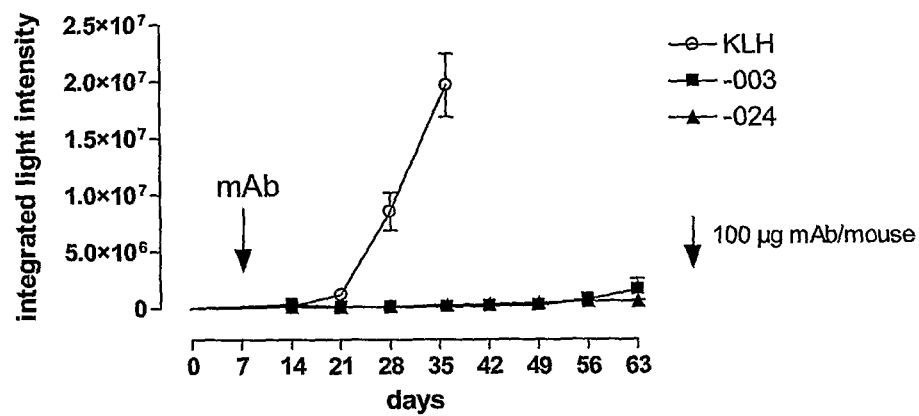
FIG. 17D shows the inhibition of tumor cell growth by −003 and −024 compared to HuMab-KLH in therapeutic setting III as measured by in vivo SCID luciferase imaging. The experimental set up is described in Example 13.

FIGS. 17A and 17B show that –003 and –005 inhibit growth of tumor cells in the preventive setting and in therapeutic setting I, similar to the inhibition observed for the anti-CD20 antibody. Both antibodies perform significantly better than the isotype control antibody. Also in therapeutic setting II CD38-antibodies slow down the growth of Daudi-luc tumor cells (FIG. 17C). In therapeutic setting III, –003 and –024 show a clear inhibition of Daudi-luc tumor cell growth (FIG. 17D).

Example 14

Apoptosis

Apoptosis assay was carried out according to the manufacturer's instructions (Annexin-V Apoptosis kit, BD Biosciences, Alphen a.d. Rijn, Netherlands). In short, CD38 mAbs were added to $2.5\times10^5$ cells (luciferase-transfected Daudi cells, in 0.5 ml RPMI+$^4$ in a 24-wells plate), in a concentration of 5 µg/ml –003 or –005 or an anti-CD20 antibodies alone or in the presence of cross-blocking rb-anti-hIgG (50 µg/ml).

After incubation (37° C., 5% $CO_2$, 20 hr), cells were harvested carefully, and washed with Binding Buffer (1200 rpm, 4° C., 5 min, BD Biosciences). Pellet was resuspended in 100 µl Binding Buffer. Then, 5 µl Annexin-V-FITC (BD Biosciences) and 10 µl PI (BD Biosciences) was added to the suspension and incubated for 15 minutes at RT. 400 µl Binding Buffer was added and the samples were measured (PI readout in FL2). For analysis of apoptotic cells, all Annexin-V-positive cells were counted by flow cytometry using a FACScalibur flow cytometer with CellQuest pro software (BD Biosciences). At least 10,000 events were collected for analysis. This population includes both PI-positive as well as PI-negative cells.

Figure 18:
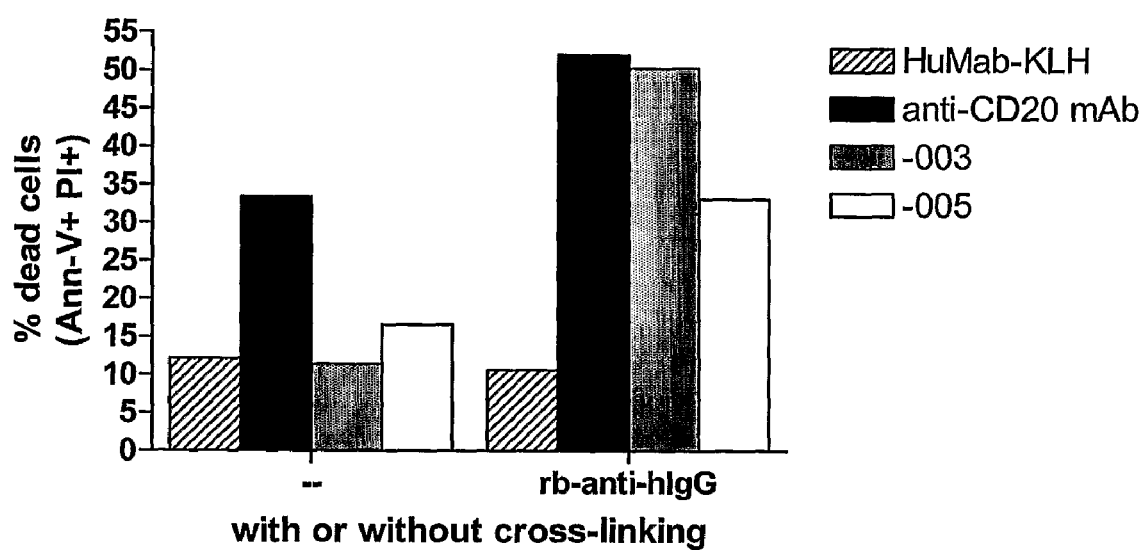
FIG. 18 shows the induction of apoptosis by −003 and −005 compared to an anti-CD20 monoclonal antibody (rituximab) and HuMab-KLH without or with cross-linking. The experimental setup is described in Example 14.

FIG. 18 shows that –003 and –005 do not induce apoptosis. However, after cross-linking, apoptosis of target cells is observed. –003 induced apoptosis after cross-linking that was similar to apoptosis induced by an anti-CD20 antibody (rituximab). -005 was less able to induce apoptosis after cross-linking. Similar results were obtained with RAMOS cells as target cells (data not shown).

Example 15

Effect of -005 on Tissue Graft B Cells in RA-SCID Mouse Model

Implantation of Synovial Tissue

SCID-mice, strain C.B.-17/IcrCrl-SCID-bg, male/female, 4-12 weeks, purchased from Charles River Laboratories Netherland (Maastricht, the Netherlands) were kept in IVC cages under standard conditions of temperature and light, and were fed laboratory chow and water ad libitum. Prior to implantation, mice (three mice in each experimental group, day 0) were anesthetized by intraperitoneal injection of ketamine (NIMATEK, EuroVet) and xylazine (Rompun, Bayer) at ratio 1:1. A small incision of the skin was made using surgical scissors. Inflamed synovial tissue from a patient with rheumatoid arthritis undergoing joint replacement surgery was implanted subcutaneously as a cluster of six small fragments (total 2-3 mm$^3$) on each flank of the mouse. The wound was closed using Permacol cyanoacrylate glue. On day 1 of the experiment, remaining synovial tissue was analyzed in order to check for B cells in the inflamed synovial transplants. -005 (12 mg/kg) or control antibody (anti-KLH, 30 mg/kg) was injected (i.v.), in a volume of 200 µl on day 8 of the experiment. At the end of the experiment (day 14) mice were sacrificed by $CO_2$ inhalation and the synovial grafts were explanted. One of the grafts was snap-frozen in OCT compound (TissueTek, Sacura Finetek Europe) for further immunhistochemical analysis, and another one was frozen by immersion in liquid nitrogen for further RNA analysis.

Immunohistochemistry

5 µM cryosections on SuperFrost (Menzel GmbH, Braunschweig) slides were prepared using LEICA CM1900 cryostate and stored at -80° C. Thawed sections were fixed in acetone for 10 min, dried at room temperature and washed 3×5 min in PBS. All steps were performed at room temperature. Endogenous peroxidase activity was blocked by incubation with PBS supplemented with 0.3% hydrogen peroxide and 0.1% sodium azide for 20 min. Slides were washed 3×5 min in PBS and incubated with 10% normal human serum (NHS)/10% normal rabbit serum (NRbS) in PBS/1% BSA for 30 min. Next, primary antibody (mouse mAb) diluted in PBS supplemented with 1% BSA/10% NHS/10% NRbS was incubated for 60 min. After 3×2 min washes in PBS, HRP-conjugate (goat anti-mouse Ig-HRP; DAKO P0447) diluted 1:50 in PBS (supplemented with 1% BSA/10% NHS/10% NRbS) was added for 30 min. Peroxidase signal was enhanced using TSA™ Biotin system (Perkin Elmer Life Sciences, NEL700). Slides were washed 3×2 min in PBS and incubated with biotinyl tyramide diluted 1:1600 in amplification buffer for 30 min. After 3×2 min washes in PBS, streptavidin-HRP diluted 1:400 in PBS (supplemented with 1% BSA) was added for 30 min. Slides were washed 3×2 min in PBS and incubated with DAB solution (DAKO Cytomation K3465) for 5 min. Color reaction was stopped with distilled water. Finally, slides were counterstained with hematoxylin (MERCK), washed with running water and covered with Kaiser's glycerin and cover slips.

Scoring of Staining Intensity

Scoring of stained synovial tissue xenografts was performed in a blinded fashion by two trained persons. First the strongest section was selected from a series of sections and this reference section was awarded the maximum score 8. The staining intensity in the other sections was then scored on a scale of 0 to 8, relative to the reference section.

Statistical Analysis

Scoring of staining intensity was analyzed by Kruskal-Wallis one-way ANOVA followed by Dunn's multiple comparison test using Graph Pad Prism version 4.01 (Graph Pad software, Inc., San Diego, Calif., USA).

Figure 19:
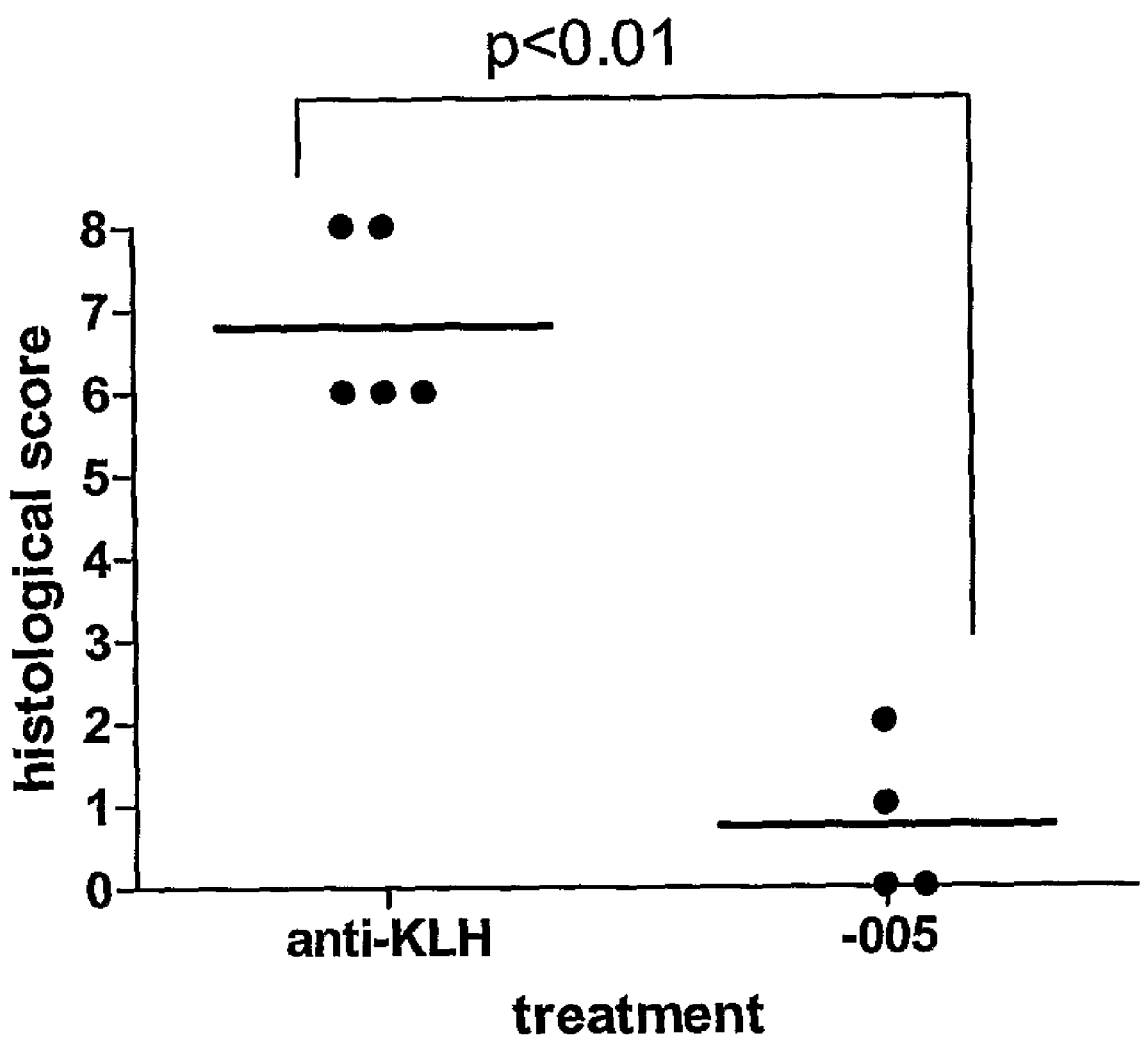
FIG. 19 shows the histological score for CD38-positive cells in implanted RA-SCID mouse xenografts on day 14, after treatment with anti-KLH (HuMab-KLH) or −005. Methods are described in Example 15.
Figure 20:
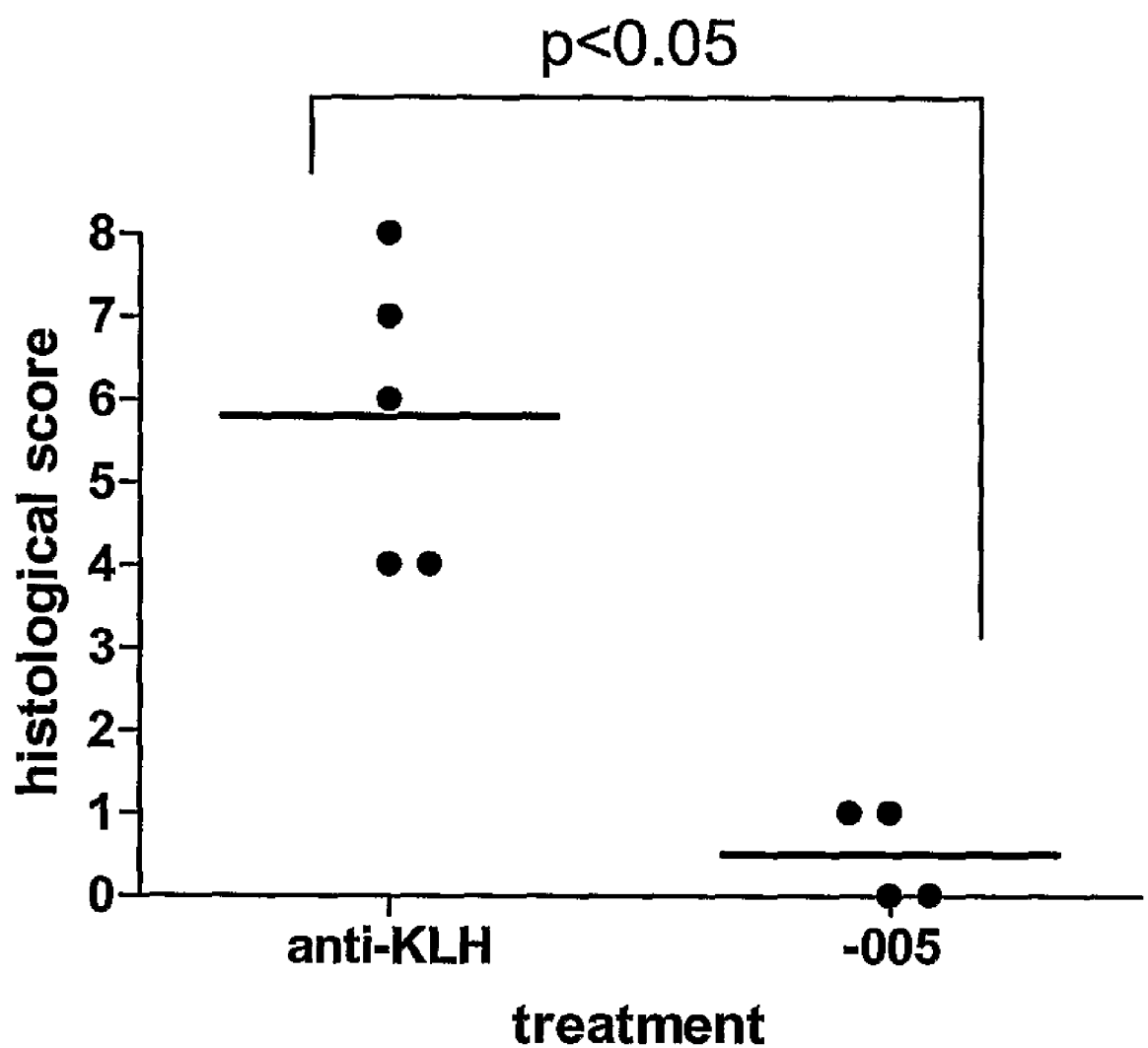
FIG. 20 shows the histological score for CD138-positive cells in implanted RA-SCID mouse xenografts on day 14, after treatment with anti-KLH or −005. Methods are described in Example 15.

FIG. 19 and FIG. 21 show that the numbers of anti-CD38-positive plasma cells are reduced after treatment with -005. Staining of plasma cells with anti-CD138 confirms that -005 results in reduced numbers of plasma cells (FIGS. 20 and 22).

Example 16

Sequencing of the Coding Sequence of Human Antibodies Against CD38

RNA Preparation

Total RNA was prepared from 5×10$^6$ cells of the hybridoma cell lines expressing the monoclonal antibody -003, -005 and -024, respectively, with the RNeasy kit (Qiagen, Westburg, Leusden, Netherlands) according to the manufacturer's protocol.

cDNA Preparation of -003, -005 and -024

5'-RACE-Complementary DNA (cDNA) of RNA was prepared from 100 ng total RNA, using the SMART RACE cDNA Amplification kit (Clontech), following the manufacturer's protocol.

Oligonucleotide primers were synthesized and quantified by Isogen Bioscience (Maarssen, The Netherlands). Primers were dissolved in $H_2O$ to 100 pmol/µl and stored at -20° C. A summary of all PCR and sequencing primers is tabulated (Table 5). For PCR, PfuTurbo® Hotstart DNA polymerase (Stratagene, Amsterdam, The Netherlands; product# 600322) was used according to the manufacturer's instructions. Each reaction mix contained 200 µM mixed dNTPs (Roche Diagnostics, Almere, The Netherlands; product# 1814362), 12 pmol of the reverse primer (RACEG1A1 for $V_H$3003-005, RACEV$_H$ApaI for $V_H$3003-003 and RACEV$_L$BsiWI for $V_L$3003-003 and 005), 7.2 pmol UPM-Mix (UPM-Mix: 2 µM ShortUPMH3 and 0.4 µM LongUPMH3), 0.6 µl of the 5'RACE cDNA template, and 1.5 unit of PfuTurbo® Hotstart DNA polymerase in PCR reaction buffer (supplied with polymerase) in a total volume of 30 µl. PCR reactions were carried out with a TGradient Thermocycler 96 (Whatman Biometra, Goettingen, Germany; product# 050-801) using a 35-cycle program: denaturing at 95° C. for 2 min; 35 cycles of 95° C. for 30 sec, a 55° C. for 30 sec, and 72° C. for 1.5 min; final extension at 72° C. for 10 min. If appropriate, the PCR mixes were stored at 4° C. until further analysis or processing.

TABLE 5

Primers

| Name | Sequence | SEQ ID NO: |
|---|---|---|
| ShortUPMH3 | TGAAAGCTTCTAATACGACTCACTATAGGGC | 38 |
| RACEV$_L$BSiWi | GAAGATGAAGACAGATGGTGCAGCCACCGTACG | 39 |
| RACEV$_H$ApaI | GGAGGGTGCCAGGGGGAAGACCGATGGGCCCTT | 40 |
| RACEG1A1 | GGGAGTAGAGTCCTGAGGACTG | 41 |
| M13reverse | GGATAACAATTTCACACAGG | 42 |
| LongUPMH3 | TGAAAGCTTCTAATACGACTCACTATAGGGCAAG CAGTGGTATCAACGCAGAGT | 43 |
| HCseq5 | GGTCAGGGCGCCTGAGTTCCACG | 44 |
| VH3003-003for | GATAAGCTTGCCGCCACCATGGACTGGACCTGGA GGTTCCTC | 45 |
| VH3003-5for | GATAAGCTTGCCGCCACCATGGAGTTTVGGGCTG AGCTGGCTT | 46 |
| VL3003-5exfor | GATAAGCTTGCCGCCACCATGGAAGCCCCAGCTC AGCTTCTC | 47 |
| VL3003-003for | GATAAGCTTGCCGCCACCATGAGGGTCCTCGCTC AGCTCCTG | 48 |
| VH300324exfor | GATAAGCTTGCCGCCACCATGGGGTCAACCGCCA TCCTCGCC | 49 |
| VL3003-24-5exfor | GATAAGCTTGCCGCCACCATGGAAGCCCCAGCTC AGCTTCTC | 50 |

Cloning of −003-2F5 V$_H$ and V$_L$ and −005 V$_L$ and −024 V$_H$ and V$_L$ in pGEMT-Vector System II The reaction products were separated by electrophoresis on a 1% TAE agarose gel and stained with ethidium bromide. Bands of the correct size were cut from the gels and the DNA was isolated from the agarose using the Qiaexll gel extraction kit (Qiagen, cat no 20021).

Gel isolated PCR fragments were A tailed by a 10 min 72° C. incubation with 200 μM dATP and 2.5 units Amplitaq (Perkin Elmer) and purified using minielute columns (Qiagen). A-tailed PCR fragments were cloned into the pGEMTeasy vector (Promega) using the pGEMT easy vector system II kit and protocol (LJ270, page 3/4). 2 μl of the ligation mixture was transformed into OneShot DH5αT1R competent E. Coli (Invitrogen) and plated on LB/Amp/IPTG/Xgal plates.

Sequencing

The V-regions −003 and −024 and the −005 V$_L$ region were sequenced by AGOWA (Berlin, Germany) after picking respectively 20 (V$_H$−003), 16 (V$_L$−003), 15 (V$_L$−005) and 6 (VH and VL-024) white colonies, isolating plasmid and sequencing with the M13 reverse primer. The −005 V$_H$ region was sequenced directly on the PCR product by using primer HCseq5. Sequences were analyzed using the Vector NTI advanced suite (Invitrogen).

Generation of Expression Vectors for Antibody −003, −005, −024 and Morphosys Antibody 3079

The V$_H$ coding region of −003 was amplified by PCR from a pGemT plasmid clone containing the V$_H$ region of −003, using the primers V$_H$3003-003 for and RACEVHApaI, introducing suitable restriction sites (HindIII and ApaI) for cloning into pConG1f0.4 (Lonza Biologics, Slough, UK) and an ideal Kozak sequence (GCCGCCACC). The pConG1f0.4 vector contains the heavy chain constant region of human IgG1. The V$_H$ PCR fragment was inserted, in frame, into the pConG1f0.4 vector using HindIII and ApaI. The construct was checked by sequence analysis.

The V$_H$ coding region of −005 was amplified by PCR from a pGemT plasmid clone containing the V$_H$ region of −005, using the primers V$_H$3003-5 for and RACEVHApaI, introducing suitable restriction sites (HindIII and ApaI) for cloning into pConG1f0.4 and an ideal Kozak sequence. The V$_H$ PCR fragment was inserted, in frame, into the pConG1f0.4 vector using HindIII and ApaI. The construct was checked by sequence analysis.

The V$_H$ coding region of −024 was amplified by PCR from a pGemT plasmid clone containing the V$_H$ region of −024, using the primers V$_H$300324exfor and RACEVHApaI introducing suitable restriction sites (HindIII and ApaI) for cloning into pConG1f0.4 and an ideal Kozak sequence. The V$_H$ PCR fragment was inserted, in frame, into the pConG1f0.4 vector using HindIII and ApaI. The construct was checked by sequence analysis.

The V$_H$ coding region of Morphosys antibody 3079 was synthesized by GeneArt (Regensburg, Germany), based on the data published in patent WO 2005/103083 A2. The coding region was codon optimized for expression in HEK cells to enhance expression levels and suitable restriction sites (HindIII and ApaI) for cloning into pConG1f0.4 and an ideal Kozak sequence were introduced. The plasmid containing the synthetic V$_H$ region was digested with ApaI and HindIII and the V$_H$ fragment was inserted, in frame, into the pConG1f0.4 vector.

The V$_L$ coding region of −005 was amplified by PCR from a pGemT plasmid clone containing the V$_L$ region of −005, using the primers V$_L$-003-5exfor and RACEVLBsiWI, introducing suitable restriction sites (HindIII and Pfl23II) for cloning into pConKappa0.4 (Lonza Biologics) and an ideal Kozak sequence. The pConKappa0.4 vector contains the kappa light chain constant region. The $V_L$ PCR fragment was inserted, in frame, into the pConKappa0.4 vector using HindIII and Pfl23II. The construct was checked by sequence analysis.

The $V_L$ coding region of −003 was amplified by PCR from a pGemT plasmid clone containing the $V_L$ region of −003, using the primers VL3003-003for and RACEVLBsiWI, introducing suitable restriction sites (HindIII and Pfl23II) for cloning into pConKappa0.4 and an ideal Kozak sequence. The $V_L$ PCR fragment was inserted, in frame, into the pConKappa0.4 vector using HindIII and Pfl23II. The construct was checked by sequence analysis.

The $V_L$ coding region of −024 was amplified by PCR from a pGemT plasmid clone containing the $V_L$ region of −024, using the primers VL3003-24-5exfor and RACEVLBsiWI, introducing suitable restriction sites (HindIII and Pfl23II) for cloning into pConKappa0.4 and an ideal Kozak sequence. The $V_L$ PCR fragment was inserted, in frame, into the pConKappa0.4 vector using HindIII and Pfl23II. The construct was checked by sequence analysis.

The $V_L$ coding region of Morphosys antibody 3079 was synthesized by GeneArt, based on the data published in WO 2005/103083. The coding region was codon optimized for expression in HEK cells; to enhance expression levels and suitable restriction sites (HindIII and Pfl23II) for cloning into pConKappa0.4 and an ideal Kozak sequence were introduced. The plasmid, containing the synthetic $V_L$ region, was digested with Pfl23II and HindIII and the $V_H$ fragment was inserted, in frame, into the pConKappa0.4 vector.

Antibodies were transiently expressed in HEK-293F cells, as described in Example 17, by cotransfecting their heavy chain and light chain vectors.

Generation of Stable Cell Lines in CHO-K1SV Cells

For generation of stable cell lines, the heavy and light chain vectors of −003 or −005 were combined in a single double gene vector by standard cloning techniques.

The double gene vectors of −003 or −005 were linearized and transfected into CHO-K1SV (Lonza Biologics) cells, essentially as described by the manufacturer. Stable cell lines were selected by selection with 25 μM L-Methionine sulphoximine (MSX) as described by Lonza Biologics. Top producing clones were selected and propagated in CD-CHO (Invitrogen) medium and antibodies were purified from cell culture supernatant as described in Example 3.

Example 17

Epitope Mapping Using Site Directed Mutagenesis

Oligonucleotide primers were synthesized and quantified by Isogen Bioscience (Maarssen, The Netherlands). Primers were dissolved in $H_2O$ to 100 μmol/μl and stored at −20° C. A summary of all PCR and sequencing primers is shown in Table 6. For PCR, PfuTurbo® Hotstart DNA polymerase (Stratagene, Amsterdam, The Netherlands) was used according to the manufacturer's instructions. Each reaction mix contained 200 μM mixed dNTPs (Roche Diagnostics, Almere, The Netherlands), 10 μmol of both the forward and reverse primer, 100 ng of genomic DNA or 1 ng of plasmid DNA and 1 unit of PfuTurbo® Hotstart DNA polymerase in PCR reaction buffer (supplied with polymerase) in a total volume of 20 μl. PCR reactions were carried out with a TGradient Thermocycler 96 (Whatman Biometra, Goettingen, Germany) using a 32-cycle program: denaturing at 95° C. for 2 min; 30 cycles of 95° C. for 30 sec, a 60-70° C. gradient (or another specific annealing temperature) for 30 sec, and 72° C. for 3 min; final extension at 72° C. for 10 min. If appropriate, the PCR mixtures were stored at 4° C. until further analysis or processing.

Agarose gel electrophoresis was performed according to Sambrook (Sambrook, Russell et al. 2000) using gels of 50 ml, in 1×Tris Acetate EDTA buffer. DNA was visualized by the inclusion of ethidium bromide in the gel and observation under UV light. Gel images were recorded by a CCD camera and an image analysis system (GeneGnome; Syngene, via Westburg B.V., Leusden, The Netherlands).

Purification of desired PCR fragments was carried out using a MinElute PCR Purification Kit (Qiagen, via Westburg, Leusden, The Netherlands; product# 28006), according to the manufacturer's instructions. Isolated DNA was quantified by UV spectroscopy (see below) and the quality was assessed by agarose gel electrophoresis.

Alternatively, PCR or digestion products were separated by agarose gel electrophoresis (for instance when multiple fragments were present) using a 1% Tris Acetate EDTA agarose gel. The desired fragment was excised from the gel and recovered using the QIAEX II Gel Extraction Kit (Qiagen; product# 20051), according to the manufacturer's instructions.

Optical density of nucleic acids was determined using a NanoDrop ND-1000 Spectrophotometer (Isogen Life Science, Maarssen, The Netherlands) according to the manufacturer's instructions. The DNA concentration was measured by analysis of the optical density (OD) at 260 nm (one $OD_{260nm}$ unit=50 μg/ml). For all samples, the buffer in which the nucleic acids were dissolved was used as a reference.

Restriction enzymes and supplements were obtained from New England Biolabs (Beverly, Mass., USA) or Fermetas (Vilnius, Lithuania) and used according to the manufacturer's instructions. DNA (100 ng) was digested with 5 units of enzyme(s) in the appropriate buffer in a final volume of 10 μl (reaction volumes were scaled up as appropriate). Digestions were incubated at the recommended temperature for a minimum of 60 min. For fragments requiring double digestions with restriction enzymes which involve incompatible buffers or temperature requirements, digestions were performed sequentially. If necessary digestion products were purified by agarose gel electrophoresis and gel extraction.

Ligations of DNA fragments were performed with the Quick Ligation Kit (New England Biolabs) according to the manufacturer's instructions. For each ligation, vector DNA was mixed with approximately three-fold molar excess of insert DNA.

Plasmid DNA (1-5 μl of DNA solution, typically 2 μl of DNA ligation mix) was transformed into One Shot DH5α-T1$^R$ E. coli cells (Invitrogen, Breda, The Netherlands; product# 12297-016) using the heat-shock method, according to the manufacturer's instructions. Next, cells were plated on Luria-Bertani (LB) agar plates containing 50 μg/ml ampicillin. Plates were incubated for 16-18 h at 37° C. until bacterial colonies became evident.

Bacterial colonies were screened for the presence of vectors containing the desired sequences via colony PCR using the ThermoStart PCR Master Mix (Abgene, via Wetsburg, Leusden, The Netherlands; product#AB-938-DC15/b) and primers pConG1seq1 and pEE13.4seqrev2 (Table 6). Selected colonies were lightly touched with a 20 μl pipette tip and touched briefly in 2 ml LB for small scale culture, and then resuspended in the PCR mix. PCR was performed with a TGradient Thermocycler 96 using a 35-cycle program: denaturation at 95° C. for 15 min; 35 cycles of 94° C. for 30 sec, 55° C. for 30 sec and 72° C. for 2 min; followed by a final extension step of 10 min at 72° C. If appropriate, the PCR mixtures were stored at 4° C. until analysis by agarose gel electrophoresis.

Plasmid DNA was isolated from E. coli cultures using the following kits from Qiagen (via Westburg, Leusden, The Netherlands), according to the manufacturer's instructions. For bulk plasmid preparation (50-150 ml culture), either a HiSpeed Plasmid Maxi Kit (product# 12663) or a HiSpeed Plasmid Midi Kit (product# 12643) was used. For small scale plasmid preparation (±2 ml culture) a Qiaprep Spin Miniprep Kit (product# 27106) was used and DNA was eluted in 50 µl elution buffer (supplied with kit).

Construction of HA-CD38 Expression Vector pEE13.4HACD38

The extracellular domain of human CD38 was amplified from plasmid pClpuroCD38 (obtained from Prof. M. Glennie, Tenovus Research Laboratory, Southampton General Hospital, Southampton, UK) using primers cd38forha and cd38exrev. By this PCR reaction an HA-tag was introduced. This PCR product was used as template for a second PCR reaction with primers SPHMM38ex and cd38exrev. By this PCR reaction, signal peptide SPHMM, restriction sites and an ideal Kozak sequence (GCCGCCACC) for optimal expression were introduced. After purification, this PCR fragment was cloned into expression vector pEE13.4 (Lonza Biologics) and the complete coding sequence was confirmed by sequencing with primers pConKseq1, pEE13.4seqrev, cd38seq1for and cd38seq2rev (Table 6). This construct was named pEE13.4HACD38

Site-Directed Mutagenesis

Three single mutant proteins of huCD38 was constructed, in which T was mutated to A at position 237 (T237A, SEQ ID No:32), Q was mutated to R at position 272 (Q272R, SEQ ID No:33), or S was mutated to F at position 274 (S274F, SEQ ID No:34). Site-directed mutagenesis was performed using the QuickChange II XL Site-Directed Mutagenesis Kit (Stratagene, Amsterdam, The Netherlands) according to the manufacturer's instructions. This method included the introduction of a silent extra restriction site or loss of a restriction site to screen for successful mutagenesis (extra Xba1 site for T237A mutant, extra Bcg1 site for Q272R mutant and loss of Ssp1 site for S274F mutant). Briefly, 5 µl 10× reaction buffer, 1 µl oligonucleotide HACD38T237Afor2, HACD38Q272Rfor or HACD38S274Ffor (100 pmol/µl), 1 µl oligonucleotide HACD38T237Arev2, HACD38Q272Rrev or HACD38S274Frev (100 pmol/µl), 1 µl dNTP mix, 3 µl Quicksolution, 1 µl plasmid pEE13.4HACD38 (50 ng/µl) and 1 µl PfuUltra HF DNA polymerase were mixed in a total volume of 50 µl and amplified with a TGradient Thermocycler 96 (Whatman Biometra, Goettingen, Germany; product# 050-801) using an 18-cycle program: denaturing at 95° C. for 1 min; 18 cycles of 95° C. for 50 sec, 60° C. for 50 sec, and 68° C. for 10 min. PCR mixtures were stored at 4° C. until further processing. Next, PCR mixtures were incubated with 1 µl DpnI for 60 min at 37° C. to digest the pEE13.4HACD38 WT vector and stored at 4° C. until further processing. The reaction mixture was precipitated with 5 µl 3 M NaAc and 125 µl ethanol, incubated for 20 minutes at −20° C. and spun down for 20 minutes at 4° C. at 14000×g. The DNA pellet was washed with 70% ethanol, dried and dissolved in 4 µl water. The total 4 µl reaction volume was transformed in One Shot Top 10DH5α T1$^R$ competent E. coli cells (Invitrogen, Breda, The Netherlands) according to the manufacturer's instructions (Invitrogen). Next, cells were plated on Luria-Bertani (LB) agar plates containing 50 µg/ml ampicillin. Plates were incubated for 16-18 h at 37° C. until bacterial colonies became evident. Colonies were screened by colony PCR using primers pConG1seq1 and pEE13.4seqrev2 (Table 5) and digested with the relevant restriction enzymes to screen for incorporation of the mutagenic oligonucleotide. 2 positive clones for each mutant were grown and plasmid DNA was isolated. The complete HACD38 coding sequence was determined using primers cd38seq1for, pConG1seq1 and pEE13.4seqrev2 to confirm the presence of the mutations and the absence of additional undesirable mutations.

DNA Sequencing

Plasmid DNA samples were sent to AGOWA (Berlin, Germany) for sequence analysis. Sequences were analyzed using Vector NTI advanced software (Informax, Oxford, UK).

Transient Expression in HEK-293F Cells

Freestyle™ 293-F (a HEK-293 subclone adapted to suspension growth and chemically defined Freestyle medium, (HEK-293F)) cells were obtained from Invitrogen and transfected with pEE13.4HACD38 and with the three constructs carrying the mutations T237A, Q272R and S274F, according to the manufacturer's protocol using 293fectin (Invitrogen). Culture supernatants of transfected cells were used in ELISA for anti-CD38 binding studies.

Anti-CD38 Antibody Binding

ELISA plates (Greiner, # 655092) were coated O/N at 4° C. with 1 µg anti-HA antibody (Sigma, # H-9658) and subsequently blocked with 2% chicken serum. Culture supernatants of transfected HEK293F cells were diluted, applied to the ELISA plates and incubated for 1 hr at RT. After washing, serial dilutions of HuMabs −003 and −005 were added and incubated for 1 hr at RT. Bound antibodies were detected with HRP-conjugated goat-anti-human IgG antibodies. The assay was developed with ABTS (Roche, # 1112597) and the absorbance was measured at 405 nm using a spectrophotometer.

As can been seen from FIGS. 23A-23C, both −003 and −005 bind to wt human CD38. The binding of −003 was not affected by the introduction of mutations T237A (FIG. 23A), Q272R (FIG. 23B) or S274F (FIG. 23C). −005 was able to bind CD38 harboring mutation T237A (FIG. 23A). Binding of −005 to CD38 with mutation Q272R was severely affected (FIG. 23B), both with respect to $EC_{50}$ and maximum binding capacity. −005 was not able to bind to mutant CD38 wherein serine at position 274 was replaced by phenylalanine (FIG. 23C).

These data shows that −003 and −005 bind to different epitopes. Furthermore these studies revealed that binding of −005 to CD38 is sensitive to mutations at positions 272 and 274. Particularly S274 is essential for −005 binding to CD38.

TABLE 6

Primers

| Name | Sequence | SEQ ID NO: |
|---|---|---|
| cd38forha | CTGCTGTGGCCCATGGTGTGGGCCTACCCTTAC GACGTGCCTGACTACGCCAGGTGGCGCCAGACG TGGAGC | 51 |

TABLE 6-continued

Primers

| Name | Sequence | SEQ ID NO: |
|---|---|---|
| cd38exrev | AGGTCAGGTACCTCAGATCTCAGATGTGCAAG | 52 |
| SPHMM38ex | TATAGCCCGGGGCCGCCACCATGTGGTGGCGCC TGTGGTGGCTGCTGCTGCTGCTGCTGCTGT GGCCCATGGTGTGGGCC | 53 |
| pConG1seq1 | GAAGACTTAAGGCAGCGGCAGAA | 54 |
| pConKseq1 | GTAGTCTGAGCAGTACTCGTTGC | 55 |
| pEE13.4seqrev | TGCATTCATTTTATGTTTCAGGT | 56 |
| pEE13.4seqrev2 | TCGGACATCTCATGACTTTCTTT | 57 |
| cd38seq1for | AGGACACGCTGCTAGGCTACCTT | 58 |
| cd38seq2rev | GTCCTTTCTCCAGTCTGGGCAAG | 59 |
| HACD38T237Arev2 | TCCACCATGTATCACCCAGGCCTCTAGAGCCTG AACCTTCTCTGGTTG | 60 |
| HACD38T237Afor2 | CAACCAGAGAAGGTTCAGGCTCTAGAGGCCTGG GTGATACATGGTGGA | 61 |
| HACD38Q272Rrev | GATATTCTTGCAGGAAAATCGAATATTCCTTTT GCTTAT | 62 |
| HACD38Q272Rfor | ATAAGCAAAAGGAATATTCGATTTTCCTGCAAG AATATC | 63 |
| HACD38S274Frev | TCTGTAGATATTCTTGCAGAAAAATTGAATGTT CCTTTTGCTTATA | 64 |
| HACD38S274Ffor | TATAAGCAAAAGGAACATTCAATTTTTCTGCAAG AATATCTACAGA | 65 |

Example 18

Induction of Proliferation of PBMC

−003, −005 and −024 were tested in an assay essentially as described in Ausiello et al., Tissue antigens 56, 538-547 (2000). Briefly, PBMCs from healthy donors were cultured at $1\times10^5$ cells/well in flat bottom 96-well plates in the presence of antibodies (final concentration: 1.1-3.3-10-30 µg/ml) in 200 µl RPMI$^{++}$. Stimulation of cells with IL-15 (at 333 ng/ml; Amgen Inc., Thousand Oaks, Calif., USA) was used as positive control. After a 4 day incubation at 37° C., 30 µl $^3$H-thymidine (16.7 µCi/ml) was added, and culture was continued O/N. $^3$H-thymidine incorporation was assessed using a Packard Cobra gamma counter (Packard Instruments, Meriden, DT, USA), according to the manufacturer's instructions. Data are shown as the mean cpm (±SEM) of PBMCs obtained from 10 donors. The results show that −003 and −005 do not induce significant proliferation of PBMCs (FIG. 24A). Also −024 did not induce significant proliferation of PBMCs (data not shown).

Example 19

Induction of IL-6

−003, −005 and −024 were tested in an assay as described in Ausiello et al., Tissue antigens 56, 538-547 (2000). Briefly, PBMCs were cultured at $1\times10^6$ cells/well in 48-well plates in the presence of 20 µg/ml of antibodies and 10 ng/ml LPS (Sigma-Aldrich Chemie, Zwijndrecht, The Netherlands) in 500 µl RPMI$^{++}$. After an O/N incubation at 37° C., supernatant was harvested and stored at −20° C. The IL-6 concentration was assessed by ELISA (IL-6 ELISA kit, U-CyTech Biosciences, Utrecht, The Netherlands) according to the manufacturer's instructions. Data are shown mean concentration in pg/ml (±SEM) from 7 donors. The results show that −003 and −005 does not induce release of significant IL-6 levels (FIG. 24B). Also −024 did not induce release of significant IL-6 levels (data not shown).

Example 20

Induction of Release of IFN-γ

−003, −005 and −024 were tested in an assay as described in Ausiello et al., Tissue antigens 56, 538-547 (2000). Briefly, PBMCs were cultured at $1\times10^6$ cells/well in 48-well plates in the presence of 20 µg/ml of antibodies and 1 µg/ml OKT-3 (Sanquin, Amsterdam, The Netherlands) in 500 µl RPMI$^{++}$. After an O/N incubation at 37° C., supernatant was harvested and stored at −20° C. The IFN-γ concentration was assessed by ELISA (IFN-γ ELISA kit, U-CyTech Biosciences, Utrecht, The Netherlands) according to the manufacturer's instructions. Data are shown mean concentration in pg/ml (±SEM) from 9 donors. The results show that −003 and −005 does not induce release of detectable IFN-γ levels (FIG. 24C). Also −024 did not induce release of significant IFN-γ levels (data not shown).

Example 21

Affinity of Binding of −003 and −005 to Recombinant CD38

Binding of −003 and −005 to CD38 was tested using surface plasmon resonance. Briefly, purified antibodies were immobilized on a CM-5 sensor chip (Biacore, Uppsala, Sweden) via anime coupling. HA-tagged CD38 (see Example 3) was flowed over, and the binding of antigen to mAb was detected by a change in refractive index at the surface of the chip using a Biacore 3000 (Biacore). The associated and rate constants for −003 (Table 7) and −005 (Table 8) are summarized below, mean of 3 experiments±SD, and show that both −003 and −005 have a high affinity for CD38.

TABLE 7

Association and rate constants at 25° C. −003

| | |
|---|---|
| $k_a$ (1/Ms) | $2.17 \times 10^5 \pm 2.65 \times 10^4$ |
| $k_d$ (1/s) | $1.9 \times 10^{-4} \pm 4.51 \times 10^{-6}$ |
| $K_A$ (1/M) | $1.14 \times 10^9 \pm 1.58 \times 10^8$ |
| $K_D$ (M) | $8.85 \times 10^{-10} \pm 1.2 \times 10^{-10}$ |

TABLE 8

Association and rate constants at 25° C. −005

| | |
|---|---|
| $k_a$ (1/MS) | $8.88 \times 10^4 \pm 1.95 \times 10^4$ |
| $k_d$ (1/s) | $5.22 \times 10^{-4} \pm 1.16 \times 10^{-5}$ |
| $K_A$ (1/M) | $1.7 \times 10^8 \pm 3.68 \times 10^7$ |
| $K_D$ (M) | $6.06 \times 10^{-9} \pm 1.21 \times 10^{-9}$ |

Example 22

Epitope Mapping

Epitope Mapping Using PEPSCAN Method

According to known procedures (Geysen et al. 1984. Use of peptide synthesis to probe viral antigens for epitopes to a resolution of a single amino acid. *Proc Natl Acad Sci USA* 81:3998; Slootstra et al. 1996. Structural aspects of antibody-antigen interaction revealed through small random peptide libraries. Mol Divers 1:87; Puijk et al. 2001. Segment synthesis. In PCT, The Netherlands, p. 1.), overlapping 20-mer linear and 15-mer looped peptides were synthesized covering 138 amino acids at the C-terminus of human CD38. Furthermore, based on the sequence at the C-terminus single-looped peptides of different size were made covering region KNIYR-PDKFLQCVKNPEDSSCTSEI (SEQ ID NO: 66), region CVHNLQPEKVQTLEAWVIHGG (SEQ ID NO: 67), and region CLESIISKRNIQFSAKNIYRC (SEQ ID NO: 68). In addition, extra sets were designed to reconstruct double-looped regions that were composed of SKRNIQFSCKNIYR (SEQ ID NO: 35) and EKVQTLEAWVIHGG (SEQ ID NO: 36). Native cysteines were replaced by alanines. Peptides were screened in an ELISA-assay using credit-card format mini-PEPSCAN cards.

Synthesis of Peptides

The peptides were synthesized using standard Fmoc-chemistry and deprotected using TFA with scavengers. Subsequently, the deprotected peptides were reacted on the microarray with an 0.5 mM solution of 2,6-bis(bromomethyl) pyridine or 2,4,6-tris(bromomethyl)mesitylene in ammonium bicarbonate (20 mM, pH 7.9), supplemented with acetonitrile (1:1 [volume/volume]). The microarrays were gently shaken in the solution for 30-60 min, while completely covered in the solution. Finally, the microarrays were washed extensively with excess of Millipore $H_2O$ and sonicated in disrupt-buffer containing 1% sodium dodecylsulfate, 0.1% β-mercaptoethanol, in PBS (pH 7.2) at 70° C. for 30 min, followed by sonication in millipore $H_2O$ for another 45 min.

PEPSCAN ELISA-Assay

The 455-well credit card-format polyethylene cards, containing the covalently linked peptides, were incubated with serum (e.g. diluted 1:1000 in blocking solution which contains 5% horse serum [volume/volume]) and 5% ovalbumin [weight/volume]) (4° C., overnight). After washing, the peptides were incubated with rabbit-anti-human Ig peroxidase (dilution 1:1000, 25° C., 1 hour), and after washing the peroxidase substrate (2,2'-azino-di-3-ethylbenzthiazoline sulfonate and 2 μl/ml 3% $H_2O_2$) was added. After one hour, the color development was measured with a CCD-camera and an image processing system. The set up consists of a CCD-camera with a 55 mm lens (Sony CCD Video Camera XC-77RR, Nikon micro-nikkor 55 mm f/2.8 lens), a camera adaptor (Sony Camera adaptor DC-77RR) and the Image Processing Software package Optimas, version 6.5 (Media Cybernetics, Silver Spring, Md. 20910, U.S.A.; Optimas runs on a pentium II computer system).

Method for Epitope Representation

Individual amino acids were identified by dipeptide motifs which represent the smallest unique units in the human CD38 amino acid sequence. All dipeptide motifs present in each of the 1164 peptides tested were awarded the ELISA value obtained for the respective whole peptide. To rank the dipeptide motifs from strong to poor binding, a relative signal was calculated by dividing the ELISA value obtained for each individual motif by the average ELISA value from all 1164 tested linear and looped peptides, and these were sorted for decreasing values. In this manner, amino acid contributions to conformational epitopes were considered. For each of the mAb tested, all dipeptide motifs scoring above 2.5 (i.e. ELISA values of peptides containing these motifs were at least 2.5 times the average ELISA value of those obtained with all 1164 peptides) were selected. The data were de-convoluted into single amino acid contributions represented on the linear CD38 sequence by a scoring system. By walking along the linear CD38 sequence and by using the unique dipeptide units as a reference point, one point was awarded each time a CD38 amino acid was present in this set of high scoring peptides.

−003, 005 and −024 were all found to bind to the regions SKRNIQFSCKNIYR (SEQ ID NO: 35) and EKVQTLE-AWVIHGG (SEQ ID NO: 36) of human CD38. −003 especially recognized the motifs RNIQF (SEQ ID NO: 69) and WVIH (SEQ ID NO: 70), −005 especially recognized the motifs KRN and VQTL (SEQ ID NO: 71).

Example 23

Enzymatic Activity

The enzymatic activity of human CD38 was measured in an assay essentially as described in Graeff et al., J. Biol. Chem. 269, 30260-30267 (1994). Briefly, substrate $NGD^+$ (80 μM) was incubated with CD38 (0.6 μg/ml His-tagged extracellular domain of human CD38, see Example 3 regarding purification of His-CD38) in a buffer containing 20 mM Tris-HCl, pH 7.0. The production of cGDPR can be monitored spectrophotometrically at the emission wavelength of 410 nm (excitation at 300 nm). In this example an excitation filter of 340±60 nm and an emission filter of 430±8 nm was used.

To test the effect of –003, –005 and –024 on the enzymatic activity of CD38, recombinant His-CD38 protein was pre-incubated for 15 min at room temperature with various concentrations (30, 3, 0.3 and 0.03 μg/ml) of the different antibodies before adding the substrate NGD$^+$. The production of cyclic GDP-ribose (cGDPR) was recorded at different time points after addition of antibodies (3, 6, 9, 12, 30, 45, 60, 75 and 90 min).

FIG. 25B shows that –005 has a pronounced inhibitory effect on the production of cGDPR. After 90 minutes, addition of 30 and 3 μg/ml –005 resulted in a 32% and 34% reduced production of cGDPR (Table 9). Similar results were observed in independent experiments using different batches of –005.

No inhibitory effect on cGPDR production was observed after addition of –003 (FIG. 25B, Table 9), –024 (FIG. 25D, Table 9) or anti-KLH (FIG. 25A, Table 9).

Based on these findings –005 is also expected to inhibit the synthesis of Cyclic ADP-ribose (cADPR) from NAD$^+$. Inhibition of the synthesis of cADPR can be determined according to the HPLC method described in Munshi et al., J. Biol. Chem. 275, 21566-21571 (2000).

TABLE 9 cGDPribose production in presence of CD38-specific antibodies or anti-KLH.

| | Production (% of NGD control) | | | |
|---|---|---|---|---|
| | 30 μg/ml | 3 μg/ml | 0.3 μg/ml | 0.03 μg/ml |
| KLH | 110 | 99 | 108 | 111 |
| –003 | 99 | 100 | 107 | 107 |
| –005 | 68 | 66 | 98 | 102 |
| –024 | 99 | 100 | 104 | 105 |

Example 24

Comparison of –003 and –005 with Morphosys Antibody 3079

Figure 26:
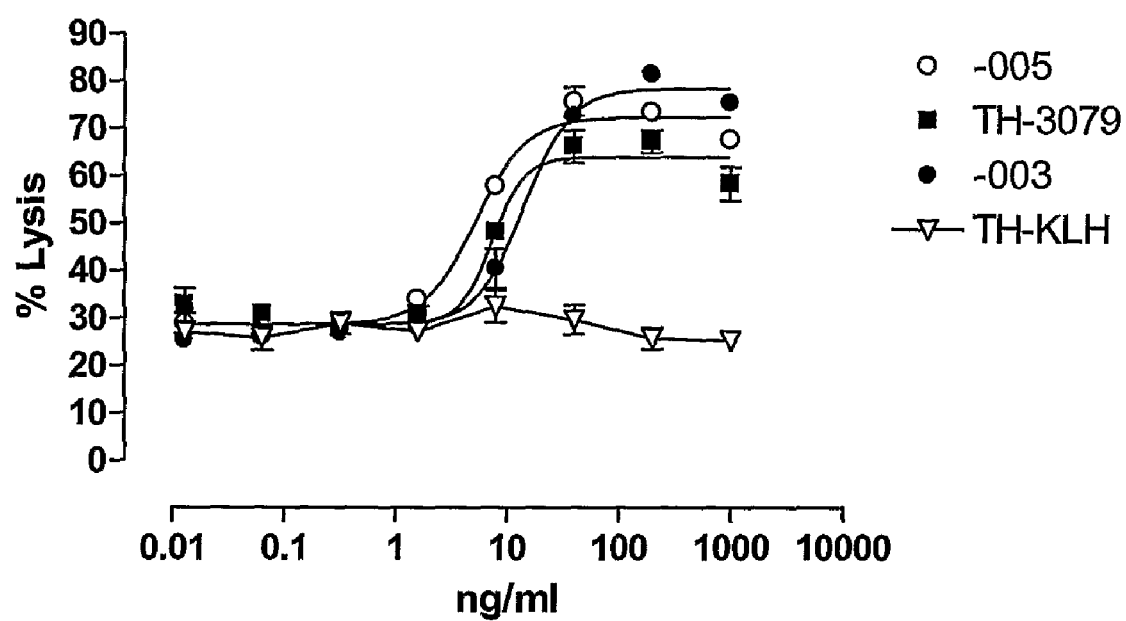
FIG. 26 shows the comparison between −003, −005 and Morphosys antibody TH-3079 in CDC of CHO-CD38 cells (26A), CDC of Daudi cells (26B), and ADCC of Daudi cells (26C).

Antibodies –003 and –005 were functionally compared to Morphosys antibody 3079 (TH-3079). Methods for cloning and expression of Morphosys antibody TH-3079 are described in Example 16. Methods for CDC are described in Example 6. Methods for ADCC are described in Example 5. FIG. 26A shows that –005 and –003 and TH-3079 induce CDC-mediated lysis of CD38-transfected CHO cells, with similar maximal lysis. When EC$_{50}$ values are compared, –005 antibody is better than TH3079 in inducing lysis of CHO-CD38 cells, with 2-times lower EC$_{50}$ (see Table 10).

FIG. 26B shows that –005 is superior to TH-3079 in inducing CDC-mediated lysis of Daudi-luciferase cells, with maximal lysis by –005 being 2-3 times higher than by TH3079. When EC$_{50}$ values are compared, –005 antibody is similar to TH-3079 in inducing lysis of Daudi-luciferase cells (see Table 10). –003 does not induce significant CDC-mediated lysis of Daudi-luciferase cells.

FIG. 26C shows that in this experiment –005, –003 and TH-3079 mediate lysis of Daudi target cells via ADCC. No difference was found in (log) EC$_{50}$ and maximal lysis (Table 11, n=5).

TABLE 10

Maximal lysis and EC50 values of CD38-specific antibodies in CDC.

| | CHO-CD38 cells (n = 2) | | Daudi-luc cells (n = 2) | |
|---|---|---|---|---|
| | EC50 μg/ml | % Max. lysis | EC50 μg/ml | % Max. lysis |
| –005 | 0.15 ± 0.007 | 76.5 ± 3.54 | 0.39 ± 0.00 | 70.5 ± 7.78 |
| TH-3079 | 0.31 ± 0.021 | 81.5 ± 7.78 | 0.34 ± 0.26 | 25.5 ± 12.02 |
| –003 | 4.5 ± 0.933 | 62.0 ± 16.79 | nc | 12 ± 8.49 |

TABLE 11

Maximal lysis and EC$_{50}$ values of CD38 specific antibodies in ADCC.

| | Log EC50 | STD log EC50 | Maximal lysis (%) | STD max. lysis |
|---|---|---|---|---|
| –005 | 0.76 | 0.18 | 49.2 | 12.8 |
| –003 | 1.17 | 0.23 | 64 | 14.2 |
| TH3079 | 0.96 | 0.10 | 43.8 | 12.0 |

The invention claimed is:

1. An isolated full-length antibody which binds to human CD38, wherein the antibody comprises a heavy chain variable region comprising the amino acid sequence set forth in SEQ ID NO:7 or encoded by the nucleotide sequence set forth in SEQ ID NO:6.

2. An isolated full-length antibody which binds to human CD38, wherein the antibody comprises a heavy chain variable region comprising the amino acid sequence set forth in SEQ ID NO:17 or encoded by the nucleotide sequence set forth in SEQ ID NO:16.

3. An isolated full-length antibody which binds to human CD38, wherein the antibody comprises a heavy chain variable region comprising the amino acid sequence set forth in SEQ ID NO:27 or encoded by the nucleotide sequence set forth in SEQ ID NO:26.

4. An isolated full-length antibody which binds to human CD38, wherein the antibody comprises a light chain variable region comprising the amino acid sequence set forth in SEQ ID NO:2 or encoded by the nucleotide sequence set forth in SEQ ID NO: 1.

5. An isolated full-length antibody which binds to human CD38, wherein the antibody comprises a light chain variable region comprising the amino acid sequence set forth in SEQ ID NO: 12 or encoded by the nucleotide sequence set forth in SEQ ID NO: 11.

6. An isolated full-length antibody which binds to human CD38, wherein the antibody comprises a light chain variable region comprising the amino acid sequence set forth in SEQ ID NO:22 or encoded by the nucleotide sequence set forth in SEQ ID NO:21.

7. An isolated full-length antibody which binds to human CD38, wherein the antibody comprises heavy and light chain variable region amino acid sequences as set forth in (a) SEQ ID NOs:7 and 2, respectively; (b) SEQ ID NOs: 17 and 12, respectively; or (c) SEQ ID NOs: 27 and 22, respectively.

8. An isolated full-length antibody which binds to human CD38, wherein the antibody comprises heavy and light chain variable regions encoded by the nucleotide sequence as set forth in (a) SEQ ID NOs:6 and 1, respectively; (b) SEQ ID NOs: 16 and 11, respectively; or (c) SEQ ID NOs: 26 and 21, respectively.

9. An isolated full-length antibody which binds an epitope on human CD38 recognized by the antibody of claim 7.

10. The antibody of claim 9, wherein the antibody binds to the region SKRNIQFSCKNIYR (SEQ ID NO: 35) and the region EKVQTLEAWVIHGG (SEQ ID NO: 36) of human CD38 (SEQ ID No: 31).

11. An isolated full-length antibody which binds to human CD38, wherein the antibody comprises a heavy chain variable region comprising CDR1, CDR2, and CDR3 sequences comprising the amino acid sequences set forth in SEQ ID NOs: 8, 9, and 10, respectively, and a light chain variable region comprising CDR1, CDR2, and CDR3 sequences comprising the amino acid sequences set forth in SEQ ID NOs: 3, 4, and 5, respectively.

12. An isolated full-length antibody which binds to human CD38, wherein the antibody comprises a heavy chain variable region comprising CDR1, CDR2, and CDR3 sequences comprising the amino acid sequences set forth in SEQ ID NOs: 18, 19, and 20, respectively, and a light chain variable region comprising CDR1, CDR2, and CDR3 sequences comprising the amino acid sequences set forth in SEQ ID NOs: 13, 14, and 15, respectively.

13. An isolated full-length antibody which binds to human CD38, wherein the antibody comprises a heavy chain variable region comprising CDR1, CDR2, and CDR3 sequences comprising the amino acid sequences set forth in SEQ ID NOs: 28, 29, and 30, respectively, and a light chain variable region comprising CDR1, CDR2, and CDR3 sequences comprising the amino acid sequences set forth in SEQ ID NOs: 23, 24, and 25, respectively.

14. The antibody of any one of claims 9, 11, 12, or 13, wherein the antibody possesses one or more of the following characteristics:
 (i) acts as an antagonist of CD38;
 (ii) does not induce significant proliferation of peripheral blood mononuclear cells;
 (iii) does not induce release of significant IL-6 by human monocytes or peripheral blood mononuclear cells;
 (iv) does not induce release of detectable IFN-gamma by human T cells or peripheral blood mononuclear cells;
 (v) is internalized by CD38 expressing cells;
 (vi) induces ADCC;
 (vii) induces CDC in the presence of complement; (viii) inhibits the synthesis of cGDPR; (ix) inhibits the synthesis of cADPR;
 (x) binds to human CD38 with an affinity ($K_D$) of below $10^{-8}$ M;
 (xi) binds to a mutant human CD38 with an $EC_{50}$ that is less than 50% compared to the $EC_{50}$ of the binding of the antibody to human CD38 (SEQ ID No: 31), wherein the serine residue in position 274 of the mutant human CD38 has been substituted with a phenylalanine residue (SEQ ID No: 34);
 (xii) binds to a mutant human CD38 with an $EC_{50}$ that is less than 50% compared to the $EC_{50}$ of the binding of the antibody to human CD38 (SEQ ID No: 31), wherein the glutamine residue in position 272 of the mutant human CD38 has been substituted with an arginine residue (SEQ ID No: 33); or
 (xiii) binds to a mutant human CD38 with an $EC_{50}$ that is 75%-125% of the $EC_{50}$ of the binding of the antibody to human CD38 (SEQ ID No: 31), wherein the threonine residue in position 237 of the mutant human CD38 has been substituted with an alanine residue (SEQ ID No: 32).

15. The antibody of any one of claims 9, 11, 12, or 13, which is a human monoclonal antibody.

16. The antibody of any one of claims 9, 11, 12, or 13, wherein the antibody is a full-length IgG1, IgG2, IgG3, IgG4, IgD, IgA, IgE, or IgM antibody.

17. The antibody of any one of claims 9, 11, 12, or 13, wherein the antibody is glycosylated in a eukaryotic cell.

18. The antibody of any one of claims 9, 11, 12, or 13, which is an antibody fragment or a single chain antibody.

19. The antibody of any one of claims 9, 11, 12, or 13, further comprising a chelator linker for attaching a radioisotope.

20. A hybridoma which produces the antibody of claim 7.

21. A hybridoma which produces the antibody of claim 8.

22. An immunoconjugate comprising the antibody of any one of claims 9, 11, 12, or 13.

23. A bispecific or multispecific molecule comprising the antibody of any one of claims 9, 11, 12, or 13.

24. The bispecific or multispecific molecule of claim 23, which comprises a binding specificity for CD3, CD4, CD138, IL-15R, membrane bound TNFα, receptor bound TNFα, a human Fc receptor, membrane bound IL-15, or receptor bound IL-15.

25. A pharmaceutical composition comprising the antibody of any one of claims 9, 11, 12, or 13 and a pharmaceutically acceptable carrier.

26. The pharmaceutical composition according to claim 25 comprising one or more further therapeutic agents.

27. A method of inhibiting growth and/or proliferation of a cell expressing CD38, comprising administration of the antibody of any one of claims 9, 11, 12, or 13, such that the growth and/or proliferation of the cell is inhibited.

28. A kit comprising the antibody of any one of claims 9, 11, 12, or 13 for detecting the presence of CD38 antigen, or a cell expressing CD38 antigen, in a sample.

29. An anti-idiotypic antibody which binds to the antibody of any one of claims 9, 11, 12, or 13.

* * * * *

UNITED STATES PATENT AND TRADEMARK OFFICE
CERTIFICATE OF CORRECTION

| | | |
|---|---|---|
| PATENT NO. | : 7,829,673 B2 | Page 1 of 1 |
| APPLICATION NO. | : 11/886932 | |
| DATED | : November 9, 2010 | |
| INVENTOR(S) | : De Weers et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 156 days.

Signed and Sealed this
Seventh Day of June, 2011

David J. Kappos
*Director of the United States Patent and Trademark Office*

SEQUENCE LISTING

<160> NUMBER OF SEQ ID NOS: 71

<210> SEQ ID NO 1
<211> LENGTH: 321
<212> TYPE: DNA
<213> ORGANISM: Homo sapiens

<400> SEQUENCE: 1

```
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcttccagtt tgcaaagtgg ggtcccatca   180
aggttcagcg gcagtggatc tgggacagat ttcactctca ccatcagcag cctgcagcct   240
```

```
gaagattttg caacttatta ctgccaacag tataatagtt accctcggac gttcggccaa    300
gggaccaagg tggaaatcaa a                                              321
```

<210> SEQ ID NO 2
<211> LENGTH: 107
<212> TYPE: PRT
<213> ORGANISM: Homo sapiens

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105
```

<210> SEQ ID NO 3
<211> LENGTH: 11
<212> TYPE: PRT
<213> ORGANISM: Homo sapiens

<400> SEQUENCE: 3

```
Arg Ala Ser Gln Gly Ile Ser Ser Trp Leu Ala
1               5                   10
```

<210> SEQ ID NO 4
<211> LENGTH: 7
<212> TYPE: PRT
<213> ORGANISM: Homo sapiens

<400> SEQUENCE: 4

```
Ala Ala Ser Ser Leu Gln Ser
1               5
```

<210> SEQ ID NO 5
<211> LENGTH: 9
<212> TYPE: PRT
<213> ORGANISM: Homo sapiens

<400> SEQUENCE: 5

```
Gln Gln Tyr Asn Ser Tyr Pro Arg Thr
1               5
```

<210> SEQ ID NO 6
<211> LENGTH: 366
<212> TYPE: DNA
<213> ORGANISM: Homo sapiens

<400> SEQUENCE: 6

```
caggtccagc tggtgcagtc tggggctgag gtgaagaagc ctgggtcctc ggtgaaggtc    60
tcctgcaagg cttctggagg caccttcagc agctatgctt tcagctgggt gcgacaggcc   120
```

```
cctggacaag gacttgagtg gatgggaagg gtcatccctt tccttggtat agcaaactcc    180
gcacagaaat tccagggcag agtcacaatt accgcggaca aatccacgag cacagcctac    240
atggacctga gcagcctgag atctgaggac acggccgtat attactgtgc gagagatgat    300
atagcagcac ttggtccttt tgactactgg ggccaggaa ccctggtcac cgtctcctca    360
gcctcc                                                                366
```

<210> SEQ ID NO 7
<211> LENGTH: 122
<212> TYPE: PRT
<213> ORGANISM: Homo sapiens

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Ala Ser
        115                 120
```

<210> SEQ ID NO 8
<211> LENGTH: 5
<212> TYPE: PRT
<213> ORGANISM: Homo sapiens

<400> SEQUENCE: 8

```
Ser Tyr Ala Phe Ser
1               5
```

<210> SEQ ID NO 9
<211> LENGTH: 17
<212> TYPE: PRT
<213> ORGANISM: Homo sapiens

<400> SEQUENCE: 9

```
Arg Val Ile Pro Phe Leu Gly Ile Ala Asn Ser Ala Gln Lys Phe Gln
1               5                   10                  15

Gly
```

<210> SEQ ID NO 10
<211> LENGTH: 11
<212> TYPE: PRT
<213> ORGANISM: Homo sapiens

<400> SEQUENCE: 10

```
Asp Asp Ile Ala Ala Leu Gly Pro Phe Asp Tyr
1               5                   10
```

<210> SEQ ID NO 11

```
<211> LENGTH: 321
<212> TYPE: DNA
<213> ORGANISM: Homo sapiens

<400> SEQUENCE: 11
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccgac gttcggccaa     300
gggaccaagg tggaaatcaa a                                              321
```

```
<210> SEQ ID NO 12
<211> LENGTH: 107
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

```
<210> SEQ ID NO 13
<211> LENGTH: 11
<212> TYPE: PRT
<213> ORGANISM: Homo sapiens

<400> SEQUENCE: 13

Arg Ala Ser Gln Ser Val Ser Ser Tyr Leu Ala
1               5                   10
```

```
<210> SEQ ID NO 14
<211> LENGTH: 7
<212> TYPE: PRT
<213> ORGANISM: Homo sapiens

<400> SEQUENCE: 14

Asp Ala Ser Asn Arg Ala Thr
1               5
```

```
<210> SEQ ID NO 15
<211> LENGTH: 10
<212> TYPE: PRT
<213> ORGANISM: Homo sapiens

<400> SEQUENCE: 15

Gln Gln Arg Ser Asn Trp Pro Pro Thr Phe
1               5                   10
```

<210> SEQ ID NO 16
<211> LENGTH: 372
<212> TYPE: DNA
<213> ORGANISM: Homo sapiens

<400> SEQUENCE: 16

```
gaggtgcagc tgttggagtc tgggggaggc ttggtacagc ctgggggtc cctgagactc      60
tcatgtgcag tctctggatt caccttaac agctttgcca tgagctgggt ccgccaggct     120
ccagggaagg ggctggagtg ggtctcagct attagtggta gtggtggtgg cacatactac    180
gcagactccg tgaagggccg gttcaccatc tccagagaca attccaagaa cacgctgtat    240
ctgcaaatga acagcctgag agccgaggac acggccgtat atttctgtgc gaaagataag    300
attctctggt tcggggagcc cgtctttgac tactggggcc agggaaccct ggtcaccgtc    360
tcctcagcct cc                                                        372
```

<210> SEQ ID NO 17
<211> LENGTH: 124
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser
        115                 120

<210> SEQ ID NO 18
<211> LENGTH: 5
<212> TYPE: PRT
<213> ORGANISM: Homo sapiens

<400> SEQUENCE: 18

Ser Phe Ala Met Ser
1               5

<210> SEQ ID NO 19
<211> LENGTH: 17
<212> TYPE: PRT
<213> ORGANISM: Homo sapiens

<400> SEQUENCE: 19

Ala Ile Ser Gly Ser Gly Gly Gly Thr Tyr Tyr Ala Asp Ser Val Lys
1               5                   10                  15

Gly

<210> SEQ ID NO 20
<211> LENGTH: 13
<212> TYPE: PRT
<213> ORGANISM: Homo sapiens

<400> SEQUENCE: 20

Asp Lys Ile Leu Trp Phe Gly Glu Pro Val Phe Asp Tyr
1               5                   10

<210> SEQ ID NO 21
<211> LENGTH: 321
<212> TYPE: DNA
<213> ORGANISM: Homo sapiens

<400> SEQUENCE: 21
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccgggctcct catctatgat gcttccaaca gggcctctgg catcccagcc   180
aggttcagtg gcagtgggtc tgggacagac ttcactctca ccatcagcag cctagagcct   240
gaagattttg cagtttatta ctgtcagcag cgtagcaact ggcctctcac tttcggcgga   300
gggaccaagg tggagatcaa a                                              321

<210> SEQ ID NO 22
<211> LENGTH: 107
<212> TYPE: PRT
<213> ORGANISM: Homo sapiens

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Gly Leu Leu Ile
        35                  40                  45

Tyr Asp Ala Ser Asn Arg Ala Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 23
<211> LENGTH: 11
<212> TYPE: PRT
<213> ORGANISM: Homo sapiens

<400> SEQUENCE: 23

Arg Ala Ser Gln Ser Val Ser Ser Tyr Leu Ala
1               5                   10

<210> SEQ ID NO 24
<211> LENGTH: 7
<212> TYPE: PRT
<213> ORGANISM: Homo sapiens

<400> SEQUENCE: 24

```
Asp Ala Ser Asn Arg Ala Ser
1               5

<210> SEQ ID NO 25
<211> LENGTH: 9
<212> TYPE: PRT
<213> ORGANISM: Homo sapiens

<400> SEQUENCE: 25

Gln Gln Arg Ser Asn Trp Pro Leu Thr
1               5

<210> SEQ ID NO 26
<211> LENGTH: 366
<212> TYPE: DNA
<213> ORGANISM: Homo sapiens

<400> SEQUENCE: 26
gaggtgcagc tggtgcagtc tggagcagag gtgaaaaagc ccggggagtc tctgaagatc      60
tcctgtaagg gttctggata cagcttttcc aactactgga tcggctgggt gcgccagatg     120
cccgggaaag gcctggagtg gatggggatc atctatcctc atgactctga tgccagatac     180
agcccgtcct tccaaggcca ggtcaccttc tcagccgaca gtccatcag caccgcctac     240 ctgcagtgga gcagcctgaa ggcctcggac accgccatgt attactgtgc gagacatgta     300
gggtggggat cgcggtactg gtacttcgat ctctggggcc gtggcaccct ggtcactgtc     360
tcctca                                                                366

<210> SEQ ID NO 27
<211> LENGTH: 122
<212> TYPE: PRT
<213> ORGANISM: Homo sapiens

<400> SEQUENCE: 27

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro His Asp Ser Asp Ala Arg Tyr Ser Pro Ser Phe
    50                  55                  60

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp
            100                 105                 110

Gly Arg Gly Thr Leu Val Thr Val Ser Ser
        115                 120

<210> SEQ ID NO 28
<211> LENGTH: 5
<212> TYPE: PRT
<213> ORGANISM: Homo sapiens

<400> SEQUENCE: 28

Asn Tyr Trp Ile Gly
1               5
```

```
<210> SEQ ID NO 29
<211> LENGTH: 17
<212> TYPE: PRT
<213> ORGANISM: Homo sapiens

<400> SEQUENCE: 29

Ile Ile Tyr Pro His Asp Ser Asp Ala Arg Tyr Ser Pro Ser Phe Gln
1               5                   10                  15
Gly

<210> SEQ ID NO 30
<211> LENGTH: 13
<212> TYPE: PRT
<213> ORGANISM: Homo sapiens

<400> SEQUENCE: 30

His Val Gly Trp Gly Ser Arg Tyr Trp Tyr Phe Asp Leu
1               5                   10

<210> SEQ ID NO 31
<211> LENGTH: 300
<212> TYPE: PRT
<213> ORGANISM: Homo sapiens

<400> SEQUENCE: 31

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
                20                  25                  30

Leu Ile Leu Val Val Val Leu Ala Val Val Pro Arg Trp Arg Gln
            35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
                100                 105                 110

Gly Thr Gln Thr Val Pro Cys Asn Lys Ile Leu Leu Trp Ser Arg Ile
            115                 120                 125

Lys Asp Leu Ala His Gln Phe Thr Gln Val Gln Arg Asp Met Phe Thr
            130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val His Val Met Leu
            195                 200                 205

Asn Gly Ser Arg Ser Lys Ile Phe Asp Lys Asn Ser Thr Phe Gly Ser
            210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
            245                 250                 255
```

```
Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
            290                 295                 300

<210> SEQ ID NO 32
<211> LENGTH: 300
<212> TYPE: PRT
<213> ORGANISM: Homo sapiens

<400> SEQUENCE: 32

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Leu Ala Val Val Pro Arg Trp Arg Gln
            35                  40                  45

Gln Trp Ser Gly Pro Gly Thr Thr Lys Arg Phe Pro Glu Thr Val Leu
50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
            85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
            115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
            165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
            195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Ala Leu Glu Ala
225                 230                 235                 240

Trp Val Ile His Gly Gly Arg Glu Asp Ser Arg Asp Leu Cys Gln Asp
            245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
            290                 295                 300

<210> SEQ ID NO 33
<211> LENGTH: 300
<212> TYPE: PRT
```

<213> ORGANISM: Homo sapiens

<400> SEQUENCE: 33

```
Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Pro Arg Trp Arg Gln
        35                  40                  45

Gln Trp Ser Gly Pro Gly Thr Thr Lys Arg Phe Pro Glu Thr Val Leu
50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Arg
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
290                 295                 300
```

<210> SEQ ID NO 34
<211> LENGTH: 300
<212> TYPE: PRT
<213> ORGANISM: Homo sapiens

<400> SEQUENCE: 34

```
Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Pro Arg Trp Arg Gln
        35                  40                  45

Gln Trp Ser Gly Pro Gly Thr Thr Lys Arg Phe Pro Glu Thr Val Leu
```

```
                50                  55                  60
Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
                 85                  90                  95

His Pro Cys Asn Ile Thr Glu Glu Asp Tyr Gln Pro Leu Met Lys Leu
                100                 105                 110

Gly Thr Gln Thr Val Pro Cys Asn Lys Ile Leu Leu Trp Ser Arg Ile
                115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
                180                 185                 190

Ser Arg Arg Phe Ala Glu Ala Ala Cys Asp Val Val His Val Met Leu
                195                 200                 205

Asn Gly Ser Arg Ser Lys Ile Phe Asp Lys Asn Ser Thr Phe Gly Ser
                210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
                260                 265                 270

Phe Phe Cys Lys Asn Ile Tyr Arg Pro Asp Lys Phe Leu Gln Cys Val
                275                 280                 285

Lys Asn Pro Glu Asp Ser Ser Cys Thr Ser Glu Ile
                290                 295                 300

<210> SEQ ID NO 35
<211> LENGTH: 14
<212> TYPE: PRT
<213> ORGANISM: Homo sapiens

<400> SEQUENCE: 35

Ser Lys Arg Asn Ile Gln Phe Ser Cys Lys Asn Ile Tyr Arg
1               5                   10

<210> SEQ ID NO 36
<211> LENGTH: 14
<212> TYPE: PRT
<213> ORGANISM: Homo sapiens

<400> SEQUENCE: 36

Glu Lys Val Gln Thr Leu Glu Ala Trp Val Ile His Gly Gly
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 37
```

His His His His His His
1               5

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tgaaagcttc taatacgact cactataggg c                               31

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaagatgaag acagatggtg cagccaccgt acg                             33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggagggtgcc aggggggaaga ccgatgggcc ctt                            33

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gggagtagag tcctgaggac tg                                         22

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggataacaat ttcacacagg                                            20

<210> SEQ ID NO 43
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tgaaagcttc taatacgact cactataggg caagcagtgg tatcaacgca gagt    54

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggtcagggcg cctgagttcc acg    23

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gataagcttg ccgccaccat ggactggacc tggaggttcc tc    42

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gataagcttg ccgccaccat ggagtttggg ctgagctggc tt    42

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gataagcttg ccgccaccat ggaagcccca gctcagcttc tc    42

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gataagcttg ccgccaccat gagggtcctc gctcagctcc tg    42

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

-continued gataagcttg ccgccaccat ggggtcaacc gccatcctcg cc                          42

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gataagcttg ccgccaccat ggaagcccca gctcagcttc tc                          42

<210> SEQ ID NO 51
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctgctgtggc ccatggtgtg ggcctaccct tacgacgtgc ctgactacgc caggtggcgc       60
cagacgtgga gc                                                           72

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aggtcaggta cctcagatct cagatgtgca ag                                     32

<210> SEQ ID NO 53
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tatagcccgg ggccgccacc atgtggtggc gcctgtggtg gctgctgctg ctgctgctgc       60
tgctgtggcc catggtgtgg gcc                                               83

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gaagacttaa ggcagcggca gaa                                               23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 55
gtagtctgag cagtactcgt tgc                                           23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgcattcatt ttatgtttca ggt                                           23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tcggacatct catgactttc ttt                                           23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aggacacgct gctaggctac ctt                                           23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtcctttctc cagtctgggc aag                                           23

<210> SEQ ID NO 60
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tccaccatgt atcacccagg cctctagagc ctgaaccttc tctggttg                48

<210> SEQ ID NO 61
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 61
caaccagaga aggttcaggc tctagaggcc tgggtgatac atggtgga                48

<210> SEQ ID NO 62
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gatattcttg caggaaaatc gaatattcct tttgcttat                           39

<210> SEQ ID NO 63
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ataagcaaaa ggaatattcg attttcctgc aagaatatc                           39

<210> SEQ ID NO 64
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tctgtagata ttcttgcaga aaaattgaat gttccttttg cttata                   46

<210> SEQ ID NO 65
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tataagcaaa aggaacattc aattttctg caagaatatc tacaga                    46

<210> SEQ ID NO 66
<211> LENGTH: 25
<212> TYPE: PRT
<213> ORGANISM: Homo sapiens

<400> SEQUENCE: 66

Lys Asn Ile Tyr Arg Pro Asp Lys Phe Leu Gln Cys Val Lys Asn Pro
1               5                   10                  15
Glu Asp Ser Ser Cys Thr Ser Glu Ile
            20                  25

<210> SEQ ID NO 67
<211> LENGTH: 21
<212> TYPE: PRT
<213> ORGANISM: Homo sapiens

<400> SEQUENCE: 67

Cys Val His Asn Leu Gln Pro Glu Lys Val Gln Thr Leu Glu Ala Trp

```
1               5                  10                 15
Val Ile His Gly Gly
            20

<210> SEQ ID NO 68
<211> LENGTH: 21
<212> TYPE: PRT
<213> ORGANISM: Homo sapiens

<400> SEQUENCE: 68

Cys Leu Glu Ser Ile Ile Ser Lys Arg Asn Ile Gln Phe Ser Ala Lys
1               5                   10                  15

Asn Ile Tyr Arg Cys
            20

<210> SEQ ID NO 69
<211> LENGTH: 5
<212> TYPE: PRT
<213> ORGANISM: Homo sapiens

<400> SEQUENCE: 69

Arg Asn Ile Gln Phe
1               5

<210> SEQ ID NO 70
<211> LENGTH: 4
<212> TYPE: PRT
<213> ORGANISM: Homo sapiens

<400> SEQUENCE: 70

Trp Val Ile His
1

<210> SEQ ID NO 71
<211> LENGTH: 4
<212> TYPE: PRT
<213> ORGANISM: Homo sapiens

<400> SEQUENCE: 71

Val Gln Thr Leu
1
```